(12) United States Patent
Sloan et al.

(10) Patent No.: US 12,202,885 B2
(45) Date of Patent: Jan. 21, 2025

(54) FORMULATIONS OF ANTIBODY MOLECULES TO INFLUENZA VIRUS

(71) Applicant: VISTERRA, INC., Waltham, MA (US)

(72) Inventors: Susan Sloan, Newton, MA (US); Bi Xu, Mission Viejo, CA (US)

(73) Assignee: VISTERRA, INC., Waltham, MA (US)

( * ) Notice: Subject to any disclaimer, the term of this patent is extended or adjusted under 35 U.S.C. 154(b) by 0 days.

(21) Appl. No.: 17/091,756

(22) Filed: Nov. 6, 2020

(65) Prior Publication Data

US 2021/0054053 A1 Feb. 25, 2021

Related U.S. Application Data

(63) Continuation of application No. 16/518,536, filed on Jul. 22, 2019, now abandoned, which is a continuation of application No. 15/440,381, filed on Feb. 23, 2017, now abandoned.

(60) Provisional application No. 62/299,162, filed on Feb. 24, 2016.

(51) Int. Cl.
| | |
|---|---|
| *C07K 16/10* | (2006.01) |
| *A61K 9/00* | (2006.01) |
| *A61K 39/00* | (2006.01) |
| *A61K 39/395* | (2006.01) |
| *A61K 47/02* | (2006.01) |
| *A61K 47/12* | (2006.01) |
| *A61K 47/18* | (2017.01) |
| *A61K 47/26* | (2006.01) |

(52) U.S. Cl.
CPC ........ *C07K 16/1018* (2013.01); *A61K 9/0019* (2013.01); *A61K 39/39591* (2013.01); *A61K 47/02* (2013.01); *A61K 47/12* (2013.01); *A61K 47/183* (2013.01); *A61K 47/26* (2013.01); *A61K 2039/505* (2013.01); *A61K 2039/54* (2013.01); *A61K 2039/545* (2013.01); *C07K 2317/56* (2013.01); *C07K 2317/565* (2013.01)

(58) Field of Classification Search
CPC ........... C07K 16/1018; C07K 2317/56; C07K 2317/565; A61K 9/0019; A61K 39/39591; A61K 47/02; A61K 47/12; A61K 47/183; A61K 47/26; A61K 2039/505; A61K 2039/54; A61K 2039/545; A61P 31/16
See application file for complete search history.

(56) References Cited

U.S. PATENT DOCUMENTS

| | | | |
|---|---|---|---|
| 4,474,757 A | 10/1984 | Arnon et al. | |
| 4,625,015 A | 11/1986 | Green et al. | |
| 5,589,174 A | 12/1996 | Okuno et al. | |
| 5,631,350 A | 5/1997 | Okuno et al. | |
| 5,684,146 A | 11/1997 | Okuno et al. | |
| 6,337,070 B1 | 1/2002 | Okuno et al. | |
| 6,720,409 B2 | 4/2004 | Okuno et al. | |
| 7,255,859 B1 | 8/2007 | Emrich et al. | |
| 7,527,800 B2 | 5/2009 | Yang et al. | |
| 7,537,768 B2 | 5/2009 | Luke et al. | |
| 7,566,454 B2 | 7/2009 | Lu et al. | |
| 7,566,458 B2 | 7/2009 | Yang et al. | |
| 7,572,620 B2 | 8/2009 | Olsen et al. | |
| 7,879,326 B2 | 2/2011 | Foung et al. | |
| 8,124,092 B2 | 2/2012 | Lanzavecchia | |
| 8,192,927 B2 | 6/2012 | Van Den Brink et al. | |
| 8,383,121 B2 | 2/2013 | Qian et al. | |
| 8,444,986 B2 | 5/2013 | Qian et al. | |
| 8,470,327 B2 | 6/2013 | Throsby et al. | |
| 8,486,406 B2 | 7/2013 | Burioni et al. | |
| 8,540,994 B2 | 9/2013 | Ho et al. | |
| 8,540,995 B2 | 9/2013 | Mookkan et al. | |
| 8,540,996 B2 | 9/2013 | Qian et al. | |
| 8,574,581 B2 | 11/2013 | Qian et al. | |
| 8,574,830 B2 | 11/2013 | Mookkan et al. | |
| 8,603,467 B2 | 12/2013 | Chen et al. | |
| 8,613,919 B1 * | 12/2013 | Ma ........................ | C07K 16/38 424/130.1 |
| 8,637,456 B2 | 1/2014 | Sasisekharan et al. | |
| 8,637,644 B2 | 1/2014 | Ho et al. | |
| 8,637,645 B2 | 1/2014 | Ho et al. | |
| 8,802,110 B2 | 8/2014 | Raman et al. | |
| 8,871,207 B2 | 10/2014 | Lanzavecchia | |
| 8,877,200 B2 | 11/2014 | Shriver et al. | |
| 9,096,657 B2 | 8/2015 | Shriver et al. | |
| 9,278,998 B2 | 3/2016 | Jayaraman et al. | |
| 9,334,309 B2 | 5/2016 | Sasisekharan et al. | |
| 9,572,861 B2 | 2/2017 | Sasisekharan et al. | |
| 9,587,010 B2 | 3/2017 | Lanzavecchia | |

(Continued)

FOREIGN PATENT DOCUMENTS

| | | |
|---|---|---|
| CA | 2872308 A1 | 11/2013 |
| CN | 102164613 A | 8/2011 |

(Continued)

OTHER PUBLICATIONS

Chavez BK, Agarabi CD, Read EK, Boyne MT 2nd, Khan MA, Brorson KA. Improved Stability of a Model IgG3 by DoE-Based Evaluation of Buffer Formulations. Biomed Res Int. 2016;2016:2074149. Epub Mar. 3, 2016. (Year: 2016).*

Wang S, Zhang N, Hu T, Dai W, Feng X, Zhang X, Qian F. Viscosity-Lowering Effect of Amino Acids and Salts on Highly Concentrated Solutions of Two IgG1 Monoclonal Antibodies. Mol Pharm. Dec. 7, 2015;12(12):4478-87. Epub Nov. 12, 2015. (Year: 2015).*

(Continued)

*Primary Examiner* — Rachel B Gill
(74) *Attorney, Agent, or Firm* — K&L Gates LLP

(57) ABSTRACT

This disclosure relates to formulations of peptide agents, e.g., antibodies and antigen-binding fragments thereof, that bind hemagglutinin protein of influenza viruses, and methods of their use.

6 Claims, 20 Drawing Sheets

Specification includes a Sequence Listing.

(56) References Cited

U.S. PATENT DOCUMENTS

| | | |
|---|---|---|
| 9,683,030 B2 | 6/2017 | Raguram et al. |
| 9,709,567 B2 | 7/2017 | Jayaraman et al. |
| 9,745,352 B2 | 8/2017 | Raman et al. |
| 9,969,794 B2 | 5/2018 | Shriver et al. |
| 9,982,037 B2 | 5/2018 | Raguram et al. |
| 10,226,527 B2 | 3/2019 | Tharakaraman et al. |
| 10,513,553 B2 | 12/2019 | Wollacott et al. |
| 10,538,578 B2 | 1/2020 | Raguram et al. |
| 10,800,835 B2 | 10/2020 | Shriver et al. |
| 11,230,593 B2 | 1/2022 | Narayan et al. |
| 2002/0054882 A1 | 5/2002 | Okuno et al. |
| 2005/0042229 A1 | 2/2005 | Yang et al. |
| 2005/0287172 A1 | 12/2005 | Yang et al. |
| 2006/0153871 A1 | 7/2006 | Olsen et al. |
| 2006/0217338 A1 | 9/2006 | Lu et al. |
| 2007/0286869 A1 | 12/2007 | Luke et al. |
| 2008/0014205 A1 | 1/2008 | Horowitz et al. |
| 2008/0241918 A1 | 10/2008 | Sasisekharan et al. |
| 2009/0060949 A1 | 3/2009 | Ho et al. |
| 2009/0081193 A1 | 3/2009 | Sasisekharan et al. |
| 2009/0092620 A1 | 4/2009 | Moste et al. |
| 2009/0106864 A1 | 4/2009 | Henry et al. |
| 2009/0136530 A1 | 5/2009 | Yang et al. |
| 2009/0234096 A1 | 9/2009 | Garry et al. |
| 2009/0264362 A1 | 10/2009 | Garry et al. |
| 2009/0269342 A1 | 10/2009 | Sasisekharan et al. |
| 2009/0291076 A1* | 11/2009 | Morichika ............ A61K 47/22 424/133.1 |
| 2009/0291472 A1 | 11/2009 | Lu et al. |
| 2009/0311265 A1 | 12/2009 | Van Den Brink et al. |
| 2010/0021489 A1 | 1/2010 | Amnon et al. |
| 2010/0036096 A1 | 2/2010 | Roosild et al. |
| 2010/0040635 A1 | 2/2010 | Horowitz et al. |
| 2010/0041740 A1 | 2/2010 | Wong et al. |
| 2010/0061990 A1 | 3/2010 | Sasisekharan et al. |
| 2010/0061995 A1 | 3/2010 | Carragher et al. |
| 2010/0080813 A1 | 4/2010 | Lanzavecchia |
| 2010/0086555 A1 | 4/2010 | Lanzavecchia |
| 2010/0145031 A1 | 6/2010 | Lanzavecchia et al. |
| 2010/0278834 A1 | 11/2010 | Lanzavecchia |
| 2010/0285011 A1* | 11/2010 | Morichika ......... A61K 39/3955 424/133.1 |
| 2010/0316654 A1 | 12/2010 | Horowitz et al. |
| 2011/0014187 A1 | 1/2011 | Burioni et al. |
| 2011/0033490 A1 | 2/2011 | Jayaraman et al. |
| 2011/0038935 A1 | 2/2011 | Marasco et al. |
| 2011/0065095 A1 | 3/2011 | Kida et al. |
| 2011/0201547 A1 | 8/2011 | Sasisekharan et al. |
| 2011/0274702 A1 | 11/2011 | Lanzavecchia |
| 2011/0319600 A1 | 12/2011 | Ikuta et al. |
| 2012/0020971 A1 | 1/2012 | Kauvar et al. |
| 2012/0039898 A1 | 2/2012 | Throsby et al. |
| 2012/0039899 A1 | 2/2012 | Olsen et al. |
| 2012/0058124 A1 | 3/2012 | Kurosawa et al. |
| 2012/0093823 A1 | 4/2012 | Van Den Brink et al. |
| 2012/0093834 A1 | 4/2012 | Horowitz et al. |
| 2012/0100142 A1 | 4/2012 | Crowe, Jr. et al. |
| 2012/0100150 A1 | 4/2012 | Jiang et al. |
| 2012/0107326 A1 | 5/2012 | Horowitz et al. |
| 2012/0114664 A1 | 5/2012 | Lanzavecchia |
| 2012/0128671 A1 | 5/2012 | Horowitz et al. |
| 2012/0128684 A1 | 5/2012 | Marasco et al. |
| 2012/0213819 A1 | 8/2012 | Tharakaraman et al. |
| 2012/0219585 A1 | 8/2012 | Raman et al. |
| 2012/0276115 A1 | 11/2012 | Van Den Brink et al. |
| 2012/0282273 A1 | 11/2012 | Wrammert et al. |
| 2013/0004505 A1 | 1/2013 | Chang et al. |
| 2013/0022608 A1 | 1/2013 | Burioni et al. |
| 2013/0022625 A1* | 1/2013 | Igawa .................. A61K 47/183 530/390.5 |
| 2013/0202608 A1 | 8/2013 | Mookkan et al. |
| 2013/0243792 A1 | 9/2013 | Vogels et al. |
| 2013/0280248 A1 | 10/2013 | Jeno et al. |
| 2013/0289246 A1 | 10/2013 | Crowe et al. |
| 2013/0302348 A1 | 11/2013 | Raguram et al. |
| 2013/0302349 A1 | 11/2013 | Shriver et al. |
| 2013/0309248 A1 | 11/2013 | Throsby et al. |
| 2014/0011982 A1 | 1/2014 | Marasco et al. |
| 2014/0046039 A1 | 2/2014 | Ahmed et al. |
| 2014/0148581 A1 | 5/2014 | Shriver et al. |
| 2014/0206603 A1 | 7/2014 | Sasisekharan et al. |
| 2014/0271655 A1 | 9/2014 | Lanzavecchia |
| 2014/0335504 A1 | 11/2014 | Sasisekharan et al. |
| 2015/0037352 A1 | 2/2015 | Shriver et al. |
| 2015/0147329 A1 | 5/2015 | Raman et al. |
| 2016/0257732 A1 | 9/2016 | Benjamin et al. |
| 2016/0266117 A1 | 9/2016 | Jayaraman et al. |
| 2016/0317612 A1 | 11/2016 | Sasisekharan et al. |
| 2017/0137498 A1 | 5/2017 | Wollacott et al. |
| 2017/0204167 A1 | 7/2017 | Lanzavecchia |
| 2017/0240617 A1 | 8/2017 | Sloan et al. |
| 2017/0306003 A1 | 10/2017 | Raguram et al. |
| 2018/0009850 A1 | 1/2018 | Raman et al. |
| 2018/0099040 A1 | 4/2018 | Marasco |
| 2019/0002536 A1 | 1/2019 | Shriver et al. |
| 2019/0062407 A1 | 2/2019 | Raguram et al. |
| 2019/0142931 A1 | 5/2019 | Tharakarman et al. |
| 2020/0181243 A1 | 6/2020 | Sloan et al. |
| 2020/0231657 A1 | 7/2020 | Wollacott et al. |
| 2020/0261481 A1 | 8/2020 | Shishido et al. |
| 2020/0308257 A1 | 10/2020 | Narayan et al. |
| 2022/0204592 A1 | 6/2022 | Shriver et al. |
| 2023/0257449 A1 | 8/2023 | Viswanathan et al. |

FOREIGN PATENT DOCUMENTS

| | | |
|---|---|---|
| CN | 104602709 A | 5/2015 |
| CN | 106470736 A | 3/2017 |
| CN | 108697715 A | 10/2018 |
| CN | 108948189 A | 12/2018 |
| EP | 0044710 A1 | 1/1982 |
| EP | 0417191 B1 | 3/1993 |
| EP | 2363415 A2 | 9/2011 |
| EP | 2846832 A1 | 3/2015 |
| EP | 3391888 | 10/2018 |
| JP | 62-051700 | 3/1987 |
| JP | 2008104450 A | 5/2008 |
| JP | 2011160681 A | 8/2011 |
| JP | 2011528901 A | 12/2011 |
| JP | 2015519052 A | 7/2015 |
| JP | 6363066 B2 | 7/2018 |
| WO | 198400687 A1 | 3/1984 |
| WO | 200246235 A1 | 6/2002 |
| WO | 2004029207 | 4/2004 |
| WO | 2004029207 A2 | 4/2004 |
| WO | 2007089753 A2 | 8/2007 |
| WO | 2007134327 A2 | 11/2007 |
| WO | 2007149715 A2 | 12/2007 |
| WO | 2008028946 A2 | 3/2008 |
| WO | 2008033105 A1 | 3/2008 |
| WO | 2008073161 A2 | 6/2008 |
| WO | 2008073161 | 7/2008 |
| WO | 2008091657 A1 | 7/2008 |
| WO | 2008110937 A2 | 9/2008 |
| WO | 2008118970 A2 | 10/2008 |
| WO | 2008140415 A1 | 11/2008 |
| WO | 2008143954 | 11/2008 |
| WO | 2008143954 A2 | 11/2008 |
| WO | 2008154813 A1 | 12/2008 |
| WO | 2009035412 A1 | 3/2009 |
| WO | 2009035420 A1 | 3/2009 |
| WO | 2009073163 A1 | 6/2009 |
| WO | 2009073330 A2 | 6/2009 |
| WO | 2009079259 A2 | 6/2009 |
| WO | 2009099394 A1 | 8/2009 |
| WO | 2009111865 A1 | 9/2009 |
| WO | 2009115972 A1 | 9/2009 |
| WO | 2009119722 A1 | 10/2009 |
| WO | 2009121004 A2 | 10/2009 |
| WO | 2009133249 A1 | 11/2009 |
| WO | 2009144667 A1 | 12/2009 |
| WO | 2009147248 A2 | 12/2009 |
| WO | 2010006144 A2 | 1/2010 |
| WO | 2010010466 A2 | 1/2010 |

(56) References Cited

FOREIGN PATENT DOCUMENTS

| | | |
|---|---|---|
| WO | 2010010467 A2 | 1/2010 |
| WO | 2010027818 A2 | 3/2010 |
| WO | 2010040281 A1 | 4/2010 |
| WO | 2010040572 A2 | 4/2010 |
| WO | 2010046775 A2 | 4/2010 |
| WO | 2010073647 A1 | 7/2010 |
| WO | 2010074656 A1 | 7/2010 |
| WO | 2010127252 A2 | 11/2010 |
| WO | 2010130636 A1 | 11/2010 |
| WO | 2010132604 A2 | 11/2010 |
| WO | 2010140114 A1 | 12/2010 |
| WO | 2011003100 A2 | 1/2011 |
| WO | 2011041391 A1 | 4/2011 |
| WO | 2011044570 A2 | 4/2011 |
| WO | 2011068143 A1 | 6/2011 |
| WO | 2011087092 A1 | 7/2011 |
| WO | 2011093217 A1 | 8/2011 |
| WO | 2011094445 A1 | 8/2011 |
| WO | 2011096302 A1 | 8/2011 |
| WO | 2011117848 A1 | 9/2011 |
| WO | 2011160083 A1 | 12/2011 |
| WO | 2012021786 A2 | 2/2012 |
| WO | 2012026878 A1 | 3/2012 |
| WO | 2012029997 A1 | 3/2012 |
| WO | 2012040406 A2 | 3/2012 |
| WO | 2012045001 A2 | 4/2012 |
| WO | 2012047941 A2 | 4/2012 |
| WO | 2012054745 A1 | 4/2012 |
| WO | 2012072788 A1 | 6/2012 |
| WO | 2012096994 A2 | 7/2012 |
| WO | 2013007770 A1 | 1/2013 |
| WO | 2013011347 A1 | 1/2013 |
| WO | 2013020074 A2 | 2/2013 |
| WO | 2013030604 A1 | 3/2013 |
| WO | 2013044840 A1 | 4/2013 |
| WO | 2013048153 A1 | 4/2013 |
| WO | 2013059524 A2 | 4/2013 |
| WO | 2013081371 A1 | 6/2013 |
| WO | 2013081463 A2 | 6/2013 |
| WO | 2013086052 A2 | 6/2013 |
| WO | 2013089496 A1 | 6/2013 |
| WO | 2013114885 A1 | 8/2013 |
| WO | 2013132007 A1 | 9/2013 |
| WO | 2013169377 A1 | 11/2013 |
| WO | 2013170139 A1 | 11/2013 |
| WO | 2014124319 A2 | 8/2014 |
| WO | 2015051010 A1 | 4/2015 |
| WO | 2015112994 A1 | 7/2015 |
| WO | 2016100807 A2 | 6/2016 |
| WO | 2017083627 A1 | 5/2017 |
| WO | 2017147248 A1 | 8/2017 |
| WO | 2020/198329 | 10/2020 |
| WO | 2020198329 A1 | 10/2020 |
| WO | 2021/119467 | 6/2021 |
| WO | 2021119467 A1 | 6/2021 |

OTHER PUBLICATIONS

Razinkov VI, Treuheit MJ, Becker GW. Accelerated formulation development of monoclonal antibodies (mAbs) and mAb-based modalities: review of methods and tools. J Biomol Screen. Apr. 2015;20(4):468-83. Epub Jan. 9, 2015. (Year: 2015).*
Wang W, Singh S, Zeng DL, King K, Nema S. Antibody structure, instability, and formulation. J Pharm Sci. Jan. 2007;96(1):1-26. (Year: 2007).*
Vidarsson G, Dekkers G, Rispens T. IgG subclasses and allotypes: from structure to effector functions. Front Immunol. Oct. 20, 2014;5:520. (Year: 2014).*
Baranovich et al. "The Hemagglutinin Stem-Binding Monoclonal Antibody VIS410 Controls Influenza Virus-Induced Acute Respiratory Distress Syndrome" Antimicrobial Agents and Chemotherapy (2016) vol. 60, No. 4, pp. 2118-2131.
Berg, J. K. A Study of VIS410 to Assess Safety and Pharmacokinetics. ClinicalTrials.gov Identifier: NCT02045472. Posted Jan. 24, 2014; Last updated May 14, 2015.

Berry, C.M., et al., "Passive Broad-Spectrum Influenza Immunoprophylaxis", Influenza Research and Treatment, vol. 2014, Article ID 267594, pp. 1-9; Published Sep. 22, 2014.
Boni et al., "Virulence attenuation during an influenza A/H5N1 pandemic," Phil Trans R Soc B (2012) 368(1614), 12 pages.
Chen et al. "Humanized antibodies with broad-spectrum neutralization to avian influenza virus H5N1", Antiviral Research, vol. 87, No. 1, Jul. 1, 2010 pp. 81-84.
Clementi et al. "Broad-range neutralizing anti-influenza A human monoclonal antibodies: new perspectives in therapy and prophylaxis" New Microbiologica (2012) vol. 35, pp. 399-406.
ClinicalTrials.gov Identifier: NCT02045472, "A Study of VIS410 to Assess Safety and Pharmacokinetics," ClinicalTrial.gov updated May 13, 2015, clinicaltrials.gov/ct2/show/record/NCT02045472.
ClinicalTrials.gov Identifier: NCT02468115, "Influenza Challenge Study of VIS410 in Healthy Volunteers," ClinicalTrial.gov updated Apr. 4, 2016, clinicaltrials_gov/ct2/show/record/NCT02468115.
Communication Made to Inventors Prior to Mar. 14, 2013.
Corti et al. "A Neutralizing Antibody Selected from Plasma Cells that Binds to Group 1 and Group 2 Influenza A Hemagglutinins", Science vol. 333, No. 6044, Aug. 2011, pp. 850-856.
Dreyfus et al. "Highly Conserved Protective Epitopes on Influenza B Viruses" Science (2012) vol. 337, pp. 1343-1348.
Ekiert et al., "A Highly Conserved Neutralizing Epitope on Group 2 Influenza A Viruses", Science, vol. 333, No. 6044, Aug. 2011 pp. 843-850.
Ekiert et al. "Broadly neutralizing antibodies against influenza virus and prospects for universal therapeies", Current Opinion in Virology, vol. 2, No. 2, Apr. 2012, pp. 134-141.
Ekiert et al., "Antibody recognition of a highly conserved influenza virus epitope" Science 324(5924):246-251 (2009).
Falconer et al., "Stabilization of a monoclonal antibody during purification and formulation by addition of basic amino acid excipients," J Chem Technol Biotechnol (2011) vol. 86, pp. 942-948.
Ferguson et al., "Strategiesfor containing an emerging influenza pandemic in Southeast Asia," Nature (2005) vol. 437(7056), pp. 209-214.
Gamblin and Skehel, "Influenza hemagglutinin and neuraminidase membrane glycoproteins." J Biol Chem (2010) vol. 285, No. 37, pp. 28403-28409.
Germann et al., "Mitigation strategies for pandemic influenza in the United States," PNAS (2006) vol. 103, No. 15, pp. 5935-5940.
Gershoni et al., "Epitope Mapping: The First Step in Developing Epitope-Based Vaccines," Biodrugs (2007) vol. 21, No. 3, pp. 145-156.
He et al., "Broadly Neutralizing Anti-Influenza Virus Antibodies: Enhancement of Neutralizing Potency in Polyclonal Mixtures and IgA Backbones," J Virol (2015) vol. 89, No. 7, pp. 3610-3618.
International Search Report and Written Opinion for International Application No. PCT/US2016/061501 mailed Feb. 8, 2017.
International Search Report and Written Opinion for PCT/US2013/040534 dated Sep. 2, 2013.
International Search Report and Written Opinion issued in International Application No. PCT/US2017/019053, mailed Jun. 13, 2017.
Jefferson et al., "Oseltamivir for influenza in adults and children: systematic review of clinical study reports and summary of regulatory comments," BMJ (2014) vol. 348, Article g2545, 18 pages.
Jorgensen et al., "Recent trends in stabilising peptides and proteins in pharmaceutical formulation—considerations In the choice of excipients," Expert Opinion on Drug Delivery (2009) vol. 6, No. 11, pp. 1219-1230.
Joshi et al., "Aggregation of Monoclonal Antibody Products: Formation and Removal," Biopharm International (2013) vol. 26, Issue 3, 5 pages.
Joshi et al., "Avoiding antibody aggregation during processing: Establishing hold times," Biotechnol J (2014) vol. 9, pp. 1195-1205.
Kalenik et al., "Influenza prevention and treatment by passive immunization," Acta Biochim Pol (2014) vol. 61, No. 3, pp. 573-87.
Krause et al. "A Broadly Neutralizing Human Monoclonal Antibody That Recognizes a Conserved, Novel Epitope on the Globular Head of the Influenza H1N1 Virus Hemagglutinin", Journal of Virology, vol. 85, No. 20, Oct. 15, 2011, pp. 10905-10908.

(56) References Cited

OTHER PUBLICATIONS

Kubota-Koketsu et al "Broad neutralizing human monoclonal antibodies against influenza virus from vaccinated healthy donors", Biochemical and Biophysical Research Communications, vol. 387, No. 1, Sep. 11, 2009 pp. 180-185.
Lachmann, P.J., "The Use of Antibodies in the Prophylaxis and Treatment of Infections", Emerging Microbes and Infections, Published Aug. 8, 2012, 1, e11, pp. 1-5.
Lambert et al., "Influenza Vaccines for the Future," N Engl J Med (2010) vol. 363, No. 21, pp. 2036-2044.
Laursen et al. "Broadly neutralizing antibodies against influenza viruses", Antiviral Research, vol. 98, No. 3, Jun. 2013, pp. 476-483.
Longini et al., "Containing Pandemic Influenza at the Source" Science (2005) vol. 39, pp. 1083-1087.
Okuno et al., "A common neutralizing epitope conserved between the hemagglutinins of influenza A virus H1 and H2 strains." J Virol. 67(5):2552-2558 (1993).
Opposition paper filed in Chilean Application 3051-2014 by AG Pharmaceutical Labs Industrial Association, dated Sep. 9, 2015.
Pedotti et al., "Computational Docking of Antibody-Antigen Complexes, Opportunities and Pitfalls Illustrated by Influenza Hemagglutinin," Int J Mol Sci (2011), vol. 12, pp. 226-251.
Plans-Rubio, "The vaccination coverage required to establish herd immunity against influenza viruses," Preventive Medicine (2012) vol. 55, pp. 72-77.
Rogers and Paulson "Receptor determinants of human and animal influenza virus isolates: differences in receptor specificity of the H3 hemagglutinin based on species of origin" Virology. 127(2):361-373 (1983).
Rogers et al. "Single amino acid substitutions in influenza haemagglutinin change receptor binding specificity" Nature. 304(5921):76-78 (1983).
Rudikoff et al., "Single Amino Acid Substitution Altering Antigen-Binding Specificity", Proc. Natl. Acad. Sci., vol. 79, pp. 1979-1983, Mar. 1982.
Saelens "One Against All: A Broadly Influenza Neutralizing Manmade Monoclonal Antibody Passes Phase I" EBioMedicine 5 (2016) pp. 16-17.
Sauter et al. "Binding of influenza virus hemagglutinin to analogs of its cell-surface receptor, sialic acid: analysis by proton nuclear magnetic resonance spectroscopy and X-ray crystallography" Biochemistry. 31(40):9609-9621 (1992).
Shaman et al., "Forecasting season outbreaks of influenza," PNAS (2012) vol. 109, No. 50, pp. 20425-20430.
Shaman et al., "Real-time influenza forecasts during the 2012-2013 season," Nature Communications (2013) vol. 4, Article 2837, 10 pages.
Shriver and Viswanathan, "Design of a Broadly Neutralizing Antibody Targeting Influenza A" Visterra Inc. (2012) Retrieved from the Internet Aug. 8, 2013; www.visterrainc.com/pdf/ICAAC-VIS410-Presentation-Final-10Sept2012.pdf.
Shriver et al. "Antibody-based strategies to preventand treat influenza" Frontiers in Immunology (2015) vol. 6, Article 315, 6 pages.
Skehel and Wiley "Receptor binding and membrane fusion in virus entry: the influenza hemagglutinin" Annu Rev Biochem. 69:531-569 (2000).
Smith, G.P., "Filamentous Fusion Phage: Novel Expression Vectors That Display Cloned Antigens on the Virion Surface", Science, 14:228(4705), pp. 1315-1317, 1985.
Soema et al., "Current and next generation influenza vaccines: Formulation and prouction strategies," Eur J Pharm Biopharm (2015) vol. 94, pp. 251-263.
Soundararajan et al. "Networks link antigenic and receptor-binding sites of influenza hemagglutinin: Mechanistic Insight into fitter strain propagation", Scientific Reports, vol. 1, Dec. 2011, pp. 1-7.
Sui et al., "Structural and functional bases for broad-spectrum neutralization of avian and human influenza A viruses" Nature Structural & Molecular Biology (2009) vol. 16, No. 3, pp. 265-273.
Sui et al., "Wide prevalence of heterosubtypic broadly neutralizing human anti-influenza A antibodies" Clin Infect Dis. 52(8):1003-1009 (2011).
Tan et al., "A pan-H1 anti-hemagglutinin monoclonal antibody with potent broad-spectrum efficacy in vivo" J Virol. 86(11):6179-6188 (2012).
Tharakaraman et al. "A broadly neutralizing human monoclonal antibody is effective against H7N9" PNAS (2015) vol. 112, No. 35, pp. 10890-10895.
Van Den Dool et al. "The Effects of Influenza Vaccination of Health Care Workers in Nursing Homes: Insights from a Mathematical Model," PLoS Medicine (2008) vol. 5, Issue 10, pp. 1453-1460.
Wang et al., "Antibody Structure, Instability, and Formulation," Journal of Pharmaceutical Sciences (2007) vol. 96, No. 1, pp. 1-26.
Wang et al., "Broadly protective monoclonal antibodies against H3 influenza viruses following sequential immunization with different hemagglutinins" PLoS Pathog. 6(2):e1000796 (2010).
Wang, "Instability, stabilization, and formulation of liquid protein pharmaceuticals," International Journal of Pharmaceutics (1999) vol. 185, pp. 129-188.
Warne et al., "Development of high concentration protein biopharmaceuticals: The use of platform approaches in formulation development," European Journal of Pharmaceutics and Biopharmaceutics (2011), vol. 78, No. 2, pp. 208-212.
Whittle et al. "Broadly neutralizing human antibody that recognizes the receptor-binding pocket of influenza virus hemagglutinin", National Academy of Sciences Proceedings, vol. 108, No. 34, Aug. 23, 2011, pp. 14216-14221.
Wollacott et al., "Safety and Upper Respiratory Pharmacokinetics of the Hemagglutinin Stalk-Binding Antibody VIS410 Support Treatment and Prophylaxis Based on Population Modeling of Seasonal Influenza A Outbreaks," EBioMedicine (2016) vol. 5, pp. 147-155.
Wrammert et al., "Broadly cross-reactive antibodies dominate the human B cell response against 2009 pandemic H1N1 influenza virus infection" J Exp Med. 208(1):181-193 (2011).
Nixon et al., "Fully human monoclonal antibody inhibitors of the neonatal Fc receptor reduce circulating IgG in non-human primates," Frontiers in Immunology (2015) vol. 6, Article 176, 13 pages.
Maggio, "Use of excipients to control aggregation in peptide and protein formulations," J Excipients and Food Chem (2010) vol. 1(2), pp. 40-49.
Gronvall et al., "Next-Generation Monoclonal Antibodies: Challenges and Opportunities," Center for Biosecurity of UPMC Final Report (2013) pp. 1-53.
Hershberger et al., "Safety and efficacy of monocolonal antibody VIS410 in adults with uncomplicated influenza A Infection: Results from a randomized, double-blind, phase-2, placebo-controlled study," EBioMedicine (2019) vol. 40, pp. 574-582.
Oh et al., "An Antibody against a Novel and Conserved Epitope in the Hemagglutinin 1 Subunit Neutralizes Numerous 15N1 Influenza Viruses," J Virol (2010) vol. 84, No. 16. pp. 8275-8286.
Sloan et al., "Clinical and virological responses to a broad-spectrum human monoclonal antibody in an influenza virus challenge study," Antiviral Research (2020) vol. 6, Article 104763.
Song et al., "Evaluation of a fully human monoclonal antibody against multiple influenza A viral strains in mice and a pandemic H1N1 strain in nonhuman primates," Antiviral Research (2014) vol. 111, pp. 60-68.
Ter Meulen, "Monoclonal antibodies for prophylaxis and therapy of infectious diseases," Expert Opin Emerging Drugs (2007) vol. 12, No. 4, pp. 525-540.
Vasquez et al., "Connecting the sequence dots: shedding light on the genesis of antibodies reported to be designed in silico," MABS (2019) vol. 11, No. 5, pp. 803-808.
Wu et al., "Logistical feasibility and potential benefits of a population-wide passive immunotherapy program during an influenza pandemic," Influenza Other Respi Viruses (2011) vol. 5, Supp. 1, pp. 226-229.
Wu et al., "Logistical feasibility and potential benefits of a population-wide passive-immunotherapy program during an influenza pandemic," PNAS (2010) vol. 107, No. 7, pp. 3269-3274.

(56) References Cited

OTHER PUBLICATIONS

Arnold et al., "The Swiss-Model Workspace: A web-based environment for protein structure homology modelling," Bioinformatics (2006) vol. 22, pp. 195-201.
Balazs et al., "Antibody-based Protection Against HIV Infection by Vectored Immunoprophylaxis," Nature (2011) vol. 481, pp. 81-84.
Bird et al., "Single-chain antigen-binding proteins", Science, 1988, vol. 242, pp. 423-426.
Booth et al., "Extending human IgG half-life using structure-guided design," MABS (2018) vol. 10, No. 7, pp. 1098-1110.
Carr et al., "Influenza hemagglutinin is spring-loaded by a metastable native conformation," Proc Natl Acad Sci USA (1997) vol. 94, pp. 14306-14313.
Chothia et al., "Canonical structures for the hypervariable regions of immunoglobulins", J. Mol. Biol., 1987, vol. 196, pp. 901-917.
Fukao et al., "Combination treatment with the cap-dependent endonuclease inhibitor baloxavir marboxil and a neuraminidase inhibitor in a mouse model of influenza A virus infection," J Antimicrob Chemother (2019) vol. 74, pp. 654-662.
Harper et al., "Seasonal Influenza in Adults and Children—Diagnosis, Treatment, Chemoprophylaxis, and Institutional Outbreak Management: Clinical Practice Guidelines of the Infection Diseases Society of America," Clin Infect Dis (2009) vol. 48, No. 8, pp. 1003-1032.
Huston et al., "Protein Engineering of Antibody Binding Sites: Recovery of Specific Activity in an Anti-Digoxin Single-Chain Fv Analogue Produced in *Escherichia coli*," Proc Natl Acad Sci USA (1988) vol. 85, pp. 5879-5883.
Kaufman and Sharp, "Amplification and Expression of Sequences Cotransfected With a Modular Dihydrofolate Reductase Complementary DNA Gene," Mol Biol (1982) vol. 159, pp. 601-621.
Kemble et al., "Intermonomer Disulfide Bonds Impair the Fusion Activity of Influenza Virus Hemagglutinin," J Virol (1992) vol. 66, pp. 4940-4950.
Kiefer et al., "The Swiss-Model Repository and associated resources," Nucleic Acids Research (2009) vol. 37, Database Issue, pp. D387-D392.
MacKenzie and Charlson, "Standards for the Use of Ordinal Scales in Clinical Trials," Br Med J (1986) vol. 292, pp. 40-43.
Mintseris et al., "Integrating Statistical Pair Potentials into Protein Complex Prediction," Proteins (2007) vol. 69, No. 3, pp. 511-520.
Peitsch, "Protein Modeling by E-mail," Nat Biotechnol (1995) vol. 13, pp. 658-660.
Pierce et al., "Accelerating Protein Docking in ZDOCK Using an Advanced 3D Convolution Library," PLoS One (2011) vol. 6, No. 99, Article e24657, 6 pages.
Pierce et al., "M-ZDOCK: a grid-based approach for Cn symmetric multimer docking," Bioinformatics (2005) vol. 21, No. 8, pp. 1472-1478.
Powers et al., "Expression of single-chain Fv-Fc fusions in Pichia pastoris", J. Immunol. Methods, 2001, vol. 251, pp. 123-135.
Smee et al., "Treatment of Oseltamivir-Resistant Influenza A (H1N1) Virus Infections in Mice With Antiviral Agents," Antiviral Res (2012) vol. 96, No. 1, pp. 13-20.
Urlaub and Chasin "Isolation of Chinese Hamster Cell Mutants Deficient in Dihydrofolate Reductase Activity," Proc Natl Acad Sci USA (1980) vol. 77, pp. 4216-4220.
Ward et al., "Binding activities of a repertoire of single immunoglobulin variable domains secreted from *Escherichia coli*", Nature, 1989, vol. 341, pp. 544-546.
Williams and Barclay, "The Immunoglobulin Superfamily—Domains for Cell Surface Recognition," Ann Rev Immunol (1988) vol. 6, pp. 381-405.
Throsby et al., "Hererosubtypic Neutralizing Monoclonal Antibodies Cross-Protective Against H5N1 and H1N1 Recovered From Human IgM+ Memory B Cells," (2008) PLoS One, vol. 3, Issue 12, Article e3942, 15 pages.
Chen et al., "ZDOCK: An Intitial-stage Protein Docking Algorithm," Proteins vol. 52, No. 1 (2003) pp. 80-87.
Extended European Search Report issued in EP Application No. 19217944.8, mailed Jun. 25, 2020, 12 pages.
International Search Report and Written Opinion in International Patent Application No. PCT/US2020/024664 dated Aug. 7, 2020.
International Search Report and Written Opinion in International Patent Application No. PCT/US2020/064573 dated Mar. 16, 2021.
Takashita, E. et al., "Susceptibility of Influenza Viruses to the Novel Cap-Dependent Endonuclease Inhibitor Baloxavir Marboxil," Frontiers in Microbiology vol. 9, Article 3026 (2018) 7 pages.
Duval, X. et al. "Efficacy of oseltamivir-zanamivir combination compared to each monotherapy for seasonal influenza: a randomized placebo-controlled trial." PLoS Medicine vol. 7,11 e1000362. Nov. 2, 2010.
Pardi, N. et al. "Nucleoside-modified mRNA immunization elicits influenza virus hemagglutinin stalk-specific antibodies." Nature Communications vol. 9,1 3361. Aug. 22, 2018.

\* cited by examiner

Heavy Chain

EVQLLESGGGLVKPGQSLKLSCAASGFTFTSYGMHWVRQPPGKGLEWVAVISYDGSYKYYADSVQG
RFTISRDNSKNTLYLQMNSLRAEDTAVYYCAKDSRLRSLLYFEWLSQGYFNPWGAGTTLTVSSAST
KGPSVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPPKSCDKTHTCPPCPGTELLGGPSVFLFPPKPKDTL
MISRTPEVTCVVVDVSHEDPEVKFNWYVDGVEVHNAKTKPREEQYNSTYRVVSVLTVLHQDWLNGK
EYKCKVSNKALPAPIEKTISKAKGEPREPQVYTLPPSRDELTKNQVSLTCLVKGFYPSDIAVEWES
NGQPENNYKTTPPVLDSDGSFFLYSKLTVDKSRWQQGNVFSCSVMHEALHNHYTQKSLSLSPGK
(SEQ ID NO: 94)

Light Chain

EIVMTQSPDSLAVSLGERATINCKSSQSVTYNYKNYLAWYQQKPGQPPKLLIYWASTRESGVPDRFSGSGSGT
DFTLTISSLQAEDVAVYYCQQYYRTPPTFGGGTKLDIKGSVAAPSVFIFPPSDEQLKSGTASVVCLLNNFYPREAK
VQWKVDNALQSGNSQESVTEQDSKDSTYSLSSTLTLSKADYEKHKVACEVTHQGLSSPVTKSFNRGEC
(SEQ ID NO: 95)

FIG. 1

|  | 10 | 20 | 30 | CDR-H1 | 40 | 50 | CDR-H2 | 60 | 70 | 80 | 90 | 100 | CDR-H3 | 110 | 120 | 129 |
|---|---|---|---|---|---|---|---|---|---|---|---|---|---|---|---|---|
| VH15 | EVQLLESGGG | LVKPGGSLKL | SCAASGFTFT | SYGMHWVRQP | PGKGLEWVAV | ISYDGSYKYY | ADSVQGRFTI | SRDNSKNTLY | LQMNSLRAED | TAVYYCAKDS | RLRSLLYFEW | LSQGYFNPWG | AGTTLTVSS |
| VH16 | EVQLLESGGG | LVKPGGSLKL | SCAASGFTFS | SYGMHWVRQP | PGKGLEWVAV | VSYDGSNKYY | ADSVQGRFTI | SRDNSKNTLY | LQMNSLRAED | TAVYYCAKDT | KLRSLLYFEW | LSSGLLDYWG | QGAMVTVSS |
| VH17 | EVQLLESGGG | LVKPGGSLKL | SCAASGFTFT | SYGMHWVRQP | PGKGLEWVAV | VSYDGSNKYY | ADSVQGRFTI | SRDNSKNTLY | LQMNSLRAED | TAVYYCAKDS | RLRSLLYFEW | LSQGYFNPWG | AGTTLTVSS |
| VH18 | EVQLLESGGG | LVKPGGSLKL | SCAASGFTFT | SYGMHWVRQP | PGKGLEWVAV | LSYDGNYKYY | ADSVQGRFTI | SRDNSKNTLY | LQMNSLRAED | TAVYYCAKDS | RLRSLLYFEW | LSQGYFNPWG | AGTTLTVSS |
| VH19 | EVQLLESGGG | LVKPGGSLKL | SCAASGFTFT | TTAMHWVRQP | PGKGLEWVAV | LSYDGNYKYY | ADSVQGRFTI | SRDNSKNTLY | LQMNSLRAED | TAVYYCAKDS | RLRSLLYFEW | LSQGYFNPWG | AGTTLTVSS |
| VH21 | EVQLLESGGG | LVKPGGSLKL | SCAASGFTFT | SYGMHWVRQP | PGKGLEWVAV | VSYDGNNKYY | ADSVQGRFTI | SRDNSKNTLY | LQMNSLRAED | TAVYYCAKDS | KLRSLLYFEW | LSSGLLDYWG | QGAMVTVSS |
| VH22 | EVQLLESGGG | LVKPGGSLKL | SCAASGFTFT | TTAMHWVRQP | PGKGLEWVAV | VSFDGNNRYY | ADSVQGRFTI | SRDNSKNTLY | LQMNSLRAED | TAVYYCAKDS | QLRSLLYFEW | LSSVLLDYWG | QGAMVTVSS |
| VH20 | EVQLLESGGG | LVKPGGSLKL | SCAASGFTFT | SYGMHWVRQP | PGKGLEWVAV | VSYDGSNKYY | ADSVQGRFTI | SRDNSKNTLY | LQMNSLRAED | TAVYYCAKDS | RLRSLLYFEW | LSQGYFNPWG | AGTTLTVSS |
| VH23 | EVQLLESGGG | LVKPGGSLKL | SCAASGFTFT | SYAMHWVRQP | PGKGLEWVAV | VSYDGNYKYY | ADSVQGRFTI | SRDNSKNTLY | LQMNSLRAED | TAVYYCAKDS | RLRSLLYFEW | LSQGYFNPWG | QGTTLTVSS |
| VH24 | EVQLLESGGG | LVKPGGSLKL | SCAASGFTFT | SYAMHWVRQP | PGKGLEWVAV | VSYDGNYKYY | ADSVQGRFTI | SRDNSKNTLY | LQMNSLRAED | TAVYYCAKDS | RLRSLLYFEW | LSQGYFNPWG | QGTTLTVSS |
| VH25 | QVQLLETGGG | LVKPGGSLKL | SCAASGFTFT | SYAMHWVRQP | PGKGLEWVAV | VSYDGNYKYY | ADSVQGRFTI | SRDNSKNTLY | LQMNSLRAED | TAVYYCAKDS | RLRSLLYFEW | LSQGYFNPWG | QGTTLTVSS |
| VH26 | EVQLLESGGG | LVKPGGSIKL | SCAASGFTFT | SYAMHWVRQP | PGKGLEWVAV | VSYDGNNKYY | ADSVQGRFTI | SRDNSKNTLY | LQMNSLRAED | TAVYYCAKDS | QLRTLLYFEW | LSQGYFNPWG | QGAMVTVSS |
| VH27 | EVQLLESGGG | LVKPGGSIKL | SCAASGFTFT | SYAMHWVRQP | PGKGLEWVAV | VSYDGNYKYY | ADSVQGRFTI | SRDNSKNTLY | LQMNSLRAED | TAVYYCAKDS | RLRTLLYFEW | LSQGYFDPWG | QGAMVTVSS |
| VH161 | EVQLLESGGG | LVKPGGSIKL | SCAASGFTFS | SYGMHWVRQP | PGKGLEWVAV | VSIDGNKRYY | ADSVQGRFTI | SRDNSKNTLY | LQMNSLRAED | TAVYYCAKDS | RLRSLLYFEW | LSSGLLDYWG | QGAMVTVSS |

FIG. 2

| | | 10 | 20 | CDR-L1 30 | 40 | 50 | CDR-L2 60 | 70 | 80 | 90 | CDR-L3 100 | 110 |
|---|---|---|---|---|---|---|---|---|---|---|---|---|
| VL28 | EIVMTQSPDS | LAVSLGERAT | INCKSSQSVT | FNYKNYLAWY | QQKPGQPPKL | LIYWASTRES | GVPDRFSGSG | SGTDFTLTIS | SLQAEDVAVY | YCQQYYRTPP | TFGGGTKLDI | K |
| VL29 | EIVMTQSPDS | LAVSLGERAT | INCKSSQSVT | FSYKNYLAWY | QQKPGQPPKL | LIYWASTRES | GVPDRFSGSG | SGTDFTLTIS | SLQAEDVAVY | YCQQYYRTPP | TFGGGTKLDI | K |
| VL30 | EIVMTQSPDS | LAVSLGERAT | INCKSSQSVT | FDYKNYLAWY | QQKPGQPPKL | LIYWASTRES | GVPDRFSGSG | SGTDFTLTIS | SLQAEDVAVY | YCQQYYRTPP | TFGGGTKLDI | K |
| VL35 | EIVMTQSPDS | LAVSLGERAT | INCKSSQSVT | WSYKNYLAWY | QQKPGQPPKL | LIYWASTRES | GVPDRFSGSG | SGTDFTLTIS | SLQAEDVAVY | YCQQYYRTPP | TFGGGTKLDI | K |
| VL31 | EIVMTQSPDS | LAVSLGERAT | INCKSSQTVT | FNYKNYLAWY | QQKPGQPPKL | LIYWASTRES | GVPDRFSGSG | SGTDFTLTIS | SLQAEDVAVY | YCQQHYRTPP | SFGGGTKLDI | K |
| VL32 | EIVMTQSPDS | LAVSLGERAT | INCKSSQTLS | FNYKNYLAWY | QQKPGQPPKL | LIYWASTRES | GVPDRFSGSG | SGTDFTLTIS | SLQAEDVAVY | YCQQHYRTPP | SFGGGTKLDI | K |
| VL33 | EIVMTQSPDS | LAVSLGERAT | INCKSSQTLS | FNYKNYLAWY | QQKPGQPPKL | LIYFASTRES | GVPDRFSGSG | SGTDFTLTIS | SLQAEDVAVY | YCQQHYRTPP | SFGGGTKLDI | K |
| VL34 | EIVMTQSPDS | LAVSLGERAT | INCKSSQTLS | FNYKNYLAWY | QQKPGQPPKL | LIYFASTRES | GVPDRFSGSG | SGTDFTLTIS | SLQAEDVAVY | YCQQHYRTPP | SFGGGTKLDI | K |
| VL36 | EIVMSQSPDT | LAVTLGERAS | INCKSSQSIT | FNYKNYLAWY | QQKPGQPPKV | LIYWASARET | GVPERFSGSG | SGTDFTLTIS | SLQPEDFATY | YCQQHYRTPP | SFGTGTKLDI | K |
| VL45 | DIQMTQSPSS | LSASVGDRVT | ITCRSSQSIT | FNYKNYLGWY | QQKPGKAPKL | LIYWGSYLES | GVPSRFSGSG | SGTDFTLTIS | SLQPEDFATY | YCQQHYRTPP | SFGSGTKLEI | K |
| VL46 | DIQMTQSPSS | LSASVGDRVT | ITCKSSQSIT | FNYKNYLGWY | QQKPGKAPKL | LIYWGSYLES | GVPSRFSGSG | SGTDFTLTIS | SLQPEDFATY | YCQQHYRTPP | SFGSGTKVEI | K |
| VL37 | EIVMTQSPDS | LAVSLGERAT | INCKSSQTLS | FNYKNYLAWY | QQKPGQPPKL | LIYWGSYLES | GVPDRFSGSG | SGTDFTLTIS | SLQAEDVAVY | YCQQHYRTPP | SFGTGTKLDI | K |
| VL38 | EIVMTQSPDS | LAVSLGERAT | INCKSSQTLS | FNYKNYLAWY | QQKPGQPPKL | LIYWASTRES | GVPDRFSGSG | SGTDFTLTIS | SLQAEDVAVY | YCQQHYRTPP | SFGSGTKLDI | K |
| VL39 | EIVMTQSPDS | LAVSLGERAT | INCKSSQTVT | FNYKNYLAWY | QQKPGQPPKL | LIYWASTRES | GVPDRFSGSG | SGTDFTLTIS | SLQAEDVAVY | YCQQHYRTPP | SFGSGTKLDI | K |
| VL40 | EIVMTQSPDS | LAVSLGERAT | INCKSSQTLS | FNYKNYLAWY | QQKPGQPPKL | LIYWASTRES | GVPDRFSGSG | SGTDFTLTIS | SLQAEDVAVY | YCQQHYRTPP | SFGNGTKLDI | K |
| VL41 | EIVMTQSPDS | LAVSLGERAT | INCKSSQTLS | FNYKNYLAWY | QQKPGQPPKL | LIYWASTRES | GVPDRFSGSG | SGTDFTLTIS | SLQAEDVAVY | YCQQHYRTPP | SFGTGTKLDI | K |
| VL42 | EIVMTQSPDS | LAVSLGERAT | INCKSSQTLS | FNYKNYLAWY | QQKPGQPPKL | LIYWASTRES | GVPDRFSGSG | SGTDFTLTIS | SLQAEDVAVY | YCQQHYRTPP | SFGSGTKLDI | K |
| VL43 | EIVMTQSPDS | LAVSLGERAT | INCKSSQTLS | FNYKNYLAWY | QQKPGQPPKL | LIYWASTRES | GVPDRFSGSG | SGTDFTLTIT | SLQAEDVAVY | YCQQHYRTPP | SFGQGTKLDI | K |
| VL44 | EIVMTQSPDS | LAVSLGERAT | INCKSSQTLS | FNYKNYLAWY | QQKPGQPPKL | LIYWASTRES | GVPDRFSGSG | SGTDFTLTIS | SLQAEDVAVY | YCQQHYRTPP | SFGNGTKLDI | K |
| VL47 | EIVMTQSPDT | LAVTLGERAT | IQCKSSQTLS | FNYKNYLAWY | QQKPGQPPKL | LIYWASTRES | GVPDRFSGSG | SGTDFTLTIS | SLQAEDVAVY | YCQQHYRTPP | SFGGGTKLDI | K |
| VL48 | EIVMTQSPDT | VAVTVGERAT | INCKSSQTVT | FNYKNYLAWY | QQKPGQPPKL | LIYWASTRES | GVPDRFSGSG | SGTDFTLTIS | SLQAEDVAVY | YCQQHYRTPP | SFGGGTKLDI | K |
| VL49 | DIVMTQSPDT | VAVTLGERAT | IDCKSSQTVT | FNYKNYLAWY | QQKPGQPPKL | LIYWASTRES | GVPDRFSGSG | SGTDFTLTIS | SLQAEDVAVY | YCQQHYRTPP | SFGGGTKLDI | K |
| VL50 | DIVMTQSPDT | LAVTVGERAT | IRCKSSQTVT | FNYKNYLAWY | QQKPGQPPKL | LIYWASTRES | GVPDRFSGSG | SGTDFTLTIS | SLQAEDVAVY | YCQQHYRTPP | SFGQGTKLDI | K |
| VL51 | DIVMTQSPDT | LAVSRGERAT | IDCKSSQTVT | FNYKNYLAWY | QQKPGQPPKL | LIYWASTRES | GVPDRFSGSG | SGTDFTLTIS | SLQAEDEAVY | YCQQHYRTPP | SFGQGTKLDI | K |

FIG. 3A

| | | | | | | | | | |
|---|---|---|---|---|---|---|---|---|---|
| VL52 | DIQMTQSPSS | LSASVGDRVT | ITCRSSQSIT | FDYKNYLAWY | QQKPGKAPKL | LIYWGSYLES | GVPSRFSGSG | SGTDFTLTIS | SLQPEDFATY | YCQQHYRTPP | SFGQGTKVEI K |
| VL53 | DIQMTQSPSS | LSASVGDRVT | ITCRSSQSIT | FNYKNYLAWY | QQKPGKAPKL | LIYWGSTLES | GVPSRFSGSG | SGTDFTLTIS | SLQPEDFATY | YCQQHYRTPP | SFGQGTKVEI K |
| VL54 | DIQMTQSPSS | LSASVGDRVT | ITCRSSQSIT | FNYKNYLAWY | QQKPGKAPKL | LIYWGSHLES | GVPSRFSGSG | SGTDFTLTIS | SLQPEDFATY | YCQQHYRTPP | SFGQGTKVEI K |
| VL55 | DIQMTQSPSS | LSASVGDRVT | ITCRSSQSIT | FNYKNYLAWY | QQKPGKAPKL | LIYWGSKLES | GVPSRFSGSG | SGTDFTLTIS | SLQPEDFATY | YCQQHYRTPP | SFGQGTKVEI K |
| VL56 | DIQMTQSPSS | LSASVGDRVT | ITCRSSQSIT | FNYKNYLAWY | QQKPGKAPKL | LIYWGSDLES | GVPSRFSGSG | SGTDFTLTIS | SLQPEDFATY | YCQQHYRTPP | SFGQGTKVEI K |
| VL57 | DIQMTQSPSS | LSASVGDRVT | ITCRSSQSIT | FNYKNYLAWY | QQKPGKAPKL | LIYWGSYLES | GVPSRFSGSG | SGTDFTLTIS | SLQPEDVATY | YCQQHYRTPP | SFGQGTKVEI K |
| VL58 | DIQMTQSPSS | LSASVGDRVT | ITCRSSQSIT | FNYKNYLAWY | QQKPGKAPKL | LIYWGSYLES | GVPSRFSGSG | SGTDFTLTIS | SLQPEDKATY | YCQQHYRTPP | SFGQGTKVEI K |
| VL59 | DIQMTQSPSS | LSASVGDRVT | ITCRSSQSIT | FNYKNYLAWY | QQKPGKAPKL | LIYWGSYLES | GVPSRFSGSG | SGTDFTLTIS | SLQPEDDATY | YCQQHYRTPP | SFGQGTKVEI K |
| VL60 | DIQMTQSPSS | LSASVGDRVT | ITCRSSQSIT | FNYKNYLAWY | QQKPGKAPKL | LIYWGSYLES | GVPSRFSGSG | SGTDFTLTIS | SLQPEDFATY | YCQQYYRTPP | SFGQGTKVEI K |
| VL61 | DIQMTQSPSS | LSASVGDRVT | ITCRSSQSIT | FNYKNYLAWY | QQKPGKAPKL | LIYWGSTRES | GVPSRFSGSG | SGTDFTLTIS | SLQPEDFATY | YCQQHYRTPP | SFGQGTKVEI K |
| VL153 | DIQMTQSPSS | LSASVGDRVT | ITCRSSQSIT | FQYKNYLAWY | QQKPGKAPKL | LIYWGSYLES | GVPSRFSGSG | SGTDFTLTIS | SLQPEDFATY | YCQQHYRTPP | SFGQGTKVEI K |
| VL154 | DIQMTQSPSS | LSASVGDRVT | ITCRSSQSIT | FRYKNYLAWY | QQKPGKAPKL | LIYWGSYLES | GVPSRFSGSG | SGTDFTLTIS | SLQPEDFATY | YCQQHYRTPP | SFGQGTKVEI K |
| VL155 | DIQMTQSPSS | LSASVGDRVT | ITCRSSQSIT | FEYKNYLAWY | QQKPGKAPKL | LIYWGSYLES | GVPSRFSGSG | SGTDFTLTIS | SLQPEDFATY | YCQQHYRTPP | SFGQGTKVEI K |
| VL156 | DIQMTQSPSS | LSASVGDRVT | ITCRSSQSIT | FDYKNYLAWY | QQKPGKAPKL | LIYWGSTLES | GVPSRFSGSG | SGTDFTLTIS | SLQPEDFATY | YCQQHYRTPP | SFGQGTKVEI K |
| VL62 | DIQMTQSPSS | LSASVGDRVT | ITCRSSQSIT | FNYKNYLAWY | QQKPGKAPKL | LIYWGSYLES | GVPSRFSGSG | SGTDFTLTIS | SLQPEDFATY | YCQQHYRTPP | SFGQGTKVEI K |

FIG. 3B

| | |
|---|---|
| FI6 VH | QVQLVQSGGGVVQPGRSLRLSCVASGFTFSTYAMHWVRQAPGRGLEWVAVISYDGNYKYYADSVKGRFSISRDNSNNTLHLEMNTLRTEDTALYYCAKDSQLRSLLYFEWLSQGYFDPWGQGTLVTVTS |
| FI370 VH | QVQLVQSGGGVVPPGRSLRLSCAASGFTFSTYGMHWVRQAPGKGLEWVAVISYDGNYKYYADSVRGRFTISRDNSKNTLNLDMNSLRTEDTALYYCAKDSQLRSLLYFDWLSQGYFDHWGQGTLVTVSS |
| FI6 VHv1 | QVQIVESGGGVVQPGRSLRLSCAASGFTFSSYGMHWVRQAPGKGLEWVAVISYDGSNKYYADSVKGRFTISRDNSKNTLYLQMNSLRAEDTAVYYCAKDSQLRSLLYFDWLSQGYFDYWGQGTLVTVSS |
| FI6 VHv3 | QVQLVESGGGVVQPGRSLRLSCAASGFTFSTYGMHWVRQAPGKGLEWVAVISYDANYKYYADSVKGRFTISRDNSKNTLLQMNSLRAEDTAVYYCAKDSQLRSLLYFEWLSQGYFDYWGQGTLVTVSS |
| FI6/370 VH | QVQLVQSGGGVVQPGRSLRLSCAASGFTFSTYAMHWVRQAPGKGLEWVAVISYDGNYKYYADSVKGRFTISRDNSKNTLYLEMNSLRTEDTALYYCAKDSQLRSLLYFDWLSQGYFDHWGQGTLVTVSS |
| FI6VK | DIQMTSQPDSLAVSLGARATINCKSSQSVTFNYIKNYLAWYQQKPGQPPKVLIYWASARESGVPDRFSGSGSGIDFTLTISSLQAEDVAVYYCQQHYRTPPTFGQGTKVEIK |

FIG. 4

|  | 10 | 20 | 30 | CDR-H1 40 | 50 | CDR-H2 60 | 70 | 80 | 90 | 100 | CDR-H3 110 | 120 | 130 |
|---|---|---|---|---|---|---|---|---|---|---|---|---|---|
| VH15-ID | IDEVQLLESG | GGLVKPGGSL | KLSCAASGFT | FTSYGMHWVR | QPPGKGLEWV | AVISVDGSYK | YYADSVQGRF | TISRDNSKNT | LYLQMNSLRA | EDTAVYYCAK | DSRLRSLLYF | EWLSQGYFNP | WGAGTHLTVS S |
| VH16-ID | IDEVQLLESG | GGLVKPGGSL | KLSCAASGFT | FSSYGMHWVR | QPPGKGLEWV | AVVSYDGSNK | YYADSVQGRF | TISRDNSKNT | LYLQMNSLRA | EDTAVYYCAK | DEKLRSLLYF | EWLSQGYFNP | WGQGAMVTVS S |
| VH17-ID | IDEVQLLESG | GGLVKPGGSL | KLSCAASGFT | FTSYGMHWVR | QPPGKGLEWV | AVVSYDGNYK | YYADSVQGRF | TISRDNSKNT | LYLQMNSLRA | EDTAVYYCAK | DSRLRSLLYF | EWLSQGYFNP | WGAGTHLTVS S |
| VH18-ID | IDEVQLLESG | GGLVKPGGSL | KLSCAASGFT | FTSYGMHWVR | QPPGKGLEWV | AVLSYDGNYK | YYADSVQGRF | TISRDNSKNT | LYLQMNSLRA | EDTAVYYCAK | DSRLRSLLYF | EWLSQGYFNP | WGAGTHLTVS S |
| VH19-ID | IDEVQLLESG | GGLVKPGGSL | KLSCAASGFT | FTTYAMHWVR | QPPGKGLEWV | AVLSYDGNYK | YYADSVQGRF | TISRDNSKNT | LYLQMNSLRA | EDTAVYYCAK | DSRLRSLLYF | EWLSQGYFNP | WGAGTHLTVS S |
| VH21-ID | IDEVQLLESG | GGLVKPGGSL | KLSCAASGFT | FSSYGMHWVR | QPPGKGLEWV | AVVSYDGNNK | YYADSVQGRF | TISRDNSKNT | LYLQMNSLRA | EDTAVYYCAK | DEKLRSLLYF | EWLSQGYFNP | WGQGAMVTVS S |
| VH22-ID | IDEVQLLESG | GGLVKPGGSL | KLSCAASGFT | FTTYAMHWVR | QPPGKGLEWV | AVVSYDGNNR | YYADSVQGRF | TISRDNSKNT | LYLQMNSLRA | EDTAVYYCAK | DSRLRSLLYF | EWLSSGLLDY | WGQGAMVTVS S |
| VH20-ID | IDEVQLLESG | GGLVKPGGSL | KLSCAASGFT | FTTYAMHWVR | QPPGKGLEWV | AVVSYDGNYK | YYADSVQGRF | TISRDNSKNT | LYLQMNSLRA | EDTAVYYCAK | DSQLRSLLYF | EWLSSGLLDY | WGQGAMVTVS S |
| VH23-ID | IDEVQLLESG | GGLVKPGGSL | KLSCAASGFT | FSSYGMHWVR | QPPGKGLEWV | AVVSYDGNYK | YYADSVQGRF | TISRDNSKNT | LYLQMNSLRA | EDTAVYYCAK | DSKLRSLLYF | EWLSQGYFNP | WGAGTHLTVS S |
| VH24-ID | IDEVQLLESG | GGLVKPGGSL | KLSCAASGFT | FTSYGMHWVR | QPPGKGLEWV | AVVSYDGNYK | YYADSVQGRF | TISRDNSKNT | LYLQMNSLRA | EDTAVYYCAK | DSRLRSLLYF | EWLSQGYFNP | WGAGTHLTVS S |
| VH25-ID | IDQVQLLESG | GGLVKPGGSL | KLSCAASGFT | FTSYGMHWVR | QPPGKGLEWV | AVVSYDGNYK | YYADSVQGRF | TISRDNSKNT | LYLQMNSLRA | EDTAVYYCAK | DSRLRSLLYF | EWLSQGYFNP | WGQGTHLTVS S |
| VH26-ID | IDEVQLLESG | GGLVKPGGSL | KLSCAASGFT | FTSYGMHWVR | QPPGKGLEWV | AVVSYDGNYK | YYADSVQGRF | TISRDNSKNT | LYLQMNSLRA | EDTAVYYCAK | DSQLRSLLYF | EWLSQGYFNP | WGQGTHLTVS S |
| VH27-ID | IDEVQLLESG | GGLVKPGGSL | KLSCAASGFT | FTSYGMHWVR | QPPGKGLEWV | AVVSYDGNYK | YYADSVQGRF | TISRDNSKNT | LYLQMNSLRA | EDTAVYYCAK | DSRLRSLLYF | EWLSQGYFDP | WGAGTHLTVS S |
| VH161-ID | IDEVQLLESG | GGLVKPGGSL | KLSCAASGFT | FSSYGMHWVR | QPPGKGLEWV | AVVSYDGSNK | YYADSVQGRF | TISRDNSKNT | LYLQMNSLRA | EDTAVYYCAK | DSKLRSLLYF | EWLSSGLLDY | WGQGAMVTVS S |

FIG. 5

|        |    |            |            |            | CDR-L1     |            |            | CDR-L2     |            |            |            |            | CDR-L3     |              |     |
|--------|----|------------|------------|------------|------------|------------|------------|------------|------------|------------|------------|------------|------------|--------------|-----|
|        |    | 10         | 20         | 30         | 40         | 50         | 60         | 70         | 80         | 90         | 100        | 110        |            |              |     |
| VL28-ID | ID | EIVMTQSP | DSLAVSLGER | ATINCKSSQS | VTYNYKNYLA | WYQQKPGQPP | KLLIYWASTR | ESGVPDRFSG | SGSGTDFTLT | ISSLQAEDVA | VYYCQQYYRT | PPTFGGGTKL | DIK |
| VL29-ID | ID | EIVMTQSP | DSLAVSLGER | ATINCKSSQS | VTFSYKNYLA | WYQQKPGQPP | KLLIYWASTR | ESGVPDRFSG | SGSGTDFTLT | ISSLQAEDVA | VYYCQQYYRT | PPTFGGGTKL | DIK |
| VL30-ID | ID | EIVMTQSP | DSLAVSLGER | ATINCKSSQS | VTFDYKNYLA | WYQQKPGQPP | KLLIYWASTR | ESGVPDRFSG | SGSGTDFTLT | ISSLQAEDVA | VYYCQQYYRT | PPTFGGGTKL | DIK |
| VL35-ID | ID | EIVMTQSP | DSLAVSLGER | ATINCKSSQS | VTWSYKNYLA | WYQQKPGQPP | KLLIYWASTR | ESGVPDRFSG | SGSGTDFTLT | ISSLQAEDVA | VYYCQQYYRT | PPTFGGGTKL | DIK |
| VL31-ID | ID | EIVMTQSP | DSLAVSLGER | ATINCKSSQT | VTFNYKNYLA | WYQQKPGQPP | KLLIYWASTR | ESGVPDRFSG | SGSGTDFTLT | ISSLQAEDVA | VYYCQQYYRT | PPSFGGGTKL | DIK |
| VL32-ID | ID | EIVMTQSP | DSLAVSLGER | ATINCKSSQT | LSFNYKNYLA | WYQQKPGQPP | KLLIYWASTR | ESGVPDRFSG | SGSGTDFTLT | ISSLQAEDVA | VYYCQQYYRT | PPSFGGGTKL | DIK |
| VL33-ID | ID | EIVMTQSP | DSLAVSLGER | ATINCKSSQT | VTFNYKNYLA | WYQQKPGQPP | KLLIYFASTR | ESGVPDRFSG | SGSGTDFTLT | ISSLQAEDVA | VYYCQQYYRT | PPSFGGGTKL | DIK |
| VL34-ID | ID | EIVMTQSP | DSLAVSLGER | ATINCKSSQT | VTFNYKNYLA | WYQQKPGQPP | KVLIYWASAR | ETGVPERFSG | SGSGTDFTLT | ISSLQAEDVA | VYYCQQYYRT | PPSFGGGTKL | EIK |
| VL36-ID | ID | EIVMSQSP | DTLAVILGER | ASINCKSSQT | LSFNYKNYLA | WYQQKPGKAP | KLLIYWGSYL | ESGVPSRFSG | SGSGTDFTLT | ISSLQEDDFA | TYYCQQYYRT | PPSFGTGTKL | EIK |
| VL45-ID | ID | IQMTQSP | SSLSASVGDR | VTITCRSSQS | ITFNYKNYLG | WYQQKPGKAP | KLLIYWGSYL | ESGVPSRFSG | SGSGTDFTLT | ISSLQEDFA | TYYCQQYYRT | PPSFGTGTKL | EIK |
| VL46-ID | ID | IQMTQSP | SSLSASVGDR | VTITCKSSQS | VTFNYKNYLA | WYQQKPGQPP | KLLIYWGSYL | ESGVPSRFSG | SGSGTDFTLT | ISSLQEDFA | TYYCQQYYRT | PPSFGGGTKV | EIK |
| VL37-ID | ID | EIVMTQSP | DSLAVSLGER | ATINCKSSQT | VTFNYKNYLA | WYQQKPGQPP | KLLIYWGSYL | ESGVPSRFSG | SGSGTDFTLT | ISSLQAEDVA | VYYCQQYYRT | PPSFGSGTKL | DIK |
| VL38-ID | ID | EIVMTQSP | DSLAVSLGER | ATINCKSSQT | VTFNYKNYLA | WYQQKPGQPP | KLLIYWASTR | ESGVPDRFSG | SGSGTDFTLT | ISSLQAEDVA | VYYCQQYYRT | PPSFGSGTKL | DIK |
| VL39-ID | ID | EIVMTQSP | DSLAVSLGER | ATINCKSSQT | VTFNYKNYLA | WYQQKPGQPP | KLLIYWASTR | ESGVPDRFSG | SGSGTDFTLT | ISSLQAEDVA | VYYCQQYYRT | PPSFGNGTKL | DIK |
| VL40-ID | ID | EIVMTQSP | DSLAVSLGER | ATINCKSSQT | VTFNYKNYLA | WYQQKPGQPP | KLLIYWASTR | ESGVPDRFSG | SGSGTDFTLT | ISSLQAEDVA | VYYCQQYYRT | PPSFGNGTKL | DIK |
| VL41-ID | ID | EIVMTQSP | DSLAVSLGER | ATINCKSSQT | VTFNYKNYLA | WYQQKPGQPP | KLLIYWASTR | ESGVPDRFSG | SGSGTDFTLT | ISSLQAEDVA | VYYCQQYYRT | PPSFGTGTKL | DIK |
| VL42-ID | ID | EIVMTQSP | DSLAVSLGER | ATINCKSSQT | LSFNYKNYLA | WYQQKPGQPP | KLLIYWASTR | ESGVPDRFSG | SGSGTDFTLT | ISSLQAEDVA | VYYCQQYYRT | PPSFGSGTKL | DIK |
| VL43-ID | ID | EIVMTQSP | DSLAVSLGER | ATINCKSSQT | LSFNYKNYLA | WYQQKPGQPP | KLLIYWASTR | ESGVPDRFSG | SGSGTDFTLT | ISSLQAEDVA | VYYCQQYYRT | PPSFGNGTKL | DIK |
| VL44-ID | ID | EIVMTQSP | DSLAVSLGER | ATINCKSSQT | LSFNYKNYLA | WYQQKPGQPP | KLLIYWASTR | ESGVPDRFSG | SGSGTDFTLT | ISSLQAEDVA | VYYCQQYYRT | PPSFGNGTKL | DIK |
| VL47-ID | ID | EIVMTQSP | DSLAVSRGER | ATIQCKSSQT | VTFNYKNYLA | WYQQKPGQPP | KLLIYWASTR | ESGVPDRFSG | SGSGTDFTLT | ITSLQAEDVA | VYYCQQHYRT | PPSFGGGTKL | DIK |
| VL48-ID | ID | DDIVMTQSP | ATINCKSSQT | LSFNYKNYLA | WYQQKPGQPP | KLLIYWASTR | ESGVPDRFSG | SGSGTDFTLT | ISSLQAEDVA | VYYCQQHYRT | PPSFGGGTKL | DIK |
| VL49-ID | ID | DDIVMTQSP | DTVAVTVGER | ATINCKSSQT | VTFNYKNYLA | WYQQKPGQPP | KLLIYWASTR | ESGVPDRFSG | SGSGTDFTLT | ISSLQAEDVA | VYYCQQHYRT | PPSFGGGTKL | DIK |
| VL50-ID | ID | DDIVMTQSP | DTVAVTVGER | ATIDCKSSQT | VTFNYKNYLA | WYQQKPGQPP | KLLIYWASTR | ESGVPDRFSG | SGSGTDFTLT | ISSLQAEDVA | VYYCQQHYRT | PPSFGGGTKL | DIK |
| VL51-ID | ID | DDIVMTQSP | DTLAVSRGER | ATIDCKSSQT | VTFNYKNYLA | WYQQKPGQPP | KLLIYWASTR | ESGVPDRFSG | SGSGTDFTLT | ISSLQAEDEA | VYYCQQHYRT | PPSFGGGTKL | DIK |

FIG. 6A

| | | | | | | | | |
|---|---|---|---|---|---|---|---|---|
| VL52-ID | IDDIQMTQSP | SSLSASVGDR | VTITCRSSQS | ITFDYKNYLA | WYQQKPGKAP | KLLIYWGSYL | ESGVPSRFSG | SGSGTDFTLT | ISSLQPEDFA | TYYCQQHYRT | PPSFGQGTKV EIK |
| VL53-ID | IDDIQMTQSP | SSLSASVGDR | VTITCRSSQS | ITFNYKNYLA | WYQQKPGKAP | KLLIYWGSTL | ESGVPSRFSG | SGSGTDFTLT | ISSLQPEDFA | TYYCQQHYRT | PPSFGQGTKV EIK |
| VL54-ID | IDDIQMTQSP | SSLSASVGDR | VTITCRSSQS | ITFNYKNYLA | WYQQKPGKAP | KLLIYWGSHL | ESGVPSRFSG | SGSGTDFTLT | ISSLQPEDFA | TYYCQQHYRT | PPSFGQGTKV EIK |
| VL55-ID | IDDIQMTQSP | SSLSASVGDR | VTITCRSSQS | ITFNYKNYLA | WYQQKPGKAP | KLLIYWGSKL | ESGVPSRFSG | SGSGTDFTLT | ISSLQPEDFA | TYYCQQHYRT | PPSFGQGTKV EIK |
| VL56-ID | IDDIQMTQSP | SSLSASVGDR | VTITCRSSQS | ITFNYKNYLA | WYQQKPGKAP | KLLIYWGSDL | ESGVPSRFSG | SGSGTDFTLT | ISSLQPEDFA | TYYCQQHYRT | PPSFGQGTKV EIK |
| VL57-ID | IDDIQMTQSP | SSLSASVGDR | VTITCRSSQS | ITFNYKNYLA | WYQQKPGKAP | KLLIYWGSYL | ESGVPSRFSG | SGSGTDFTLT | ISSLQPEDVA | TYYCQQHYRT | PPSFGQGTKV EIK |
| VL58-ID | IDDIQMTQSP | SSLSASVGDR | VTITCRSSQS | ITFNYKNYLA | WYQQKPGKAP | KLLIYWGSYL | ESGVPSRFSG | SGSGTDFTLT | ISSLQPEDKA | TYYCQQHYRT | PPSFGQGTKV EIK |
| VL59-ID | IDDIQMTQSP | SSLSASVGDR | VTITCRSSQS | ITFNYKNYLA | WYQQKPGKAP | KLLIYWGSYL | ESGVPSRFSG | SGSGTDFTLT | ISSLQPEDDA | TYYCQQHYRT | PPSFGQGTKV EIK |
| VL60-ID | IDDIQMTQSP | SSLSASVGDR | VTITCRSSQS | ITFNYKNYLA | WYQQKPGKAP | KLLIYWGSYL | ESGVPSRFSG | SGSGTDFTLT | ISSLQPEDFA | TYYCQQHYRT | PPSFGQGTKV EIK |
| VL61-ID | IDDIQMTQSP | SSLSASVGDR | VTITCRSSQS | ITFNYKNYLA | WYQQKPGKAP | KLLIYWGSTR | ESGVPSRFSG | SGSGTDFTLT | ISSLQPEDFA | TYYCQQHYRT | PPSFGQGTKV EIK |
| VL153-ID | IDDIQMTQSP | SSLSASVGDR | VTITCRSSQS | ITFQYKNYLA | WYQQKPGKAP | KLLIYWGSYL | ESGVPSRFSG | SGSGTDFTLT | ISSLQPEDFA | TYYCQQHYRT | PPSFGQGTKV EIK |
| VL154-ID | IDDIQMTQSP | SSLSASVGDR | VTITCRSSQS | ITFRYKNYLA | WYQQKPGKAP | KLLIYWGSYL | ESGVPSRFSG | SGSGTDFTLT | ISSLQPEDFA | TYYCQQHYRT | PPSFGQGTKV EIK |
| VL155-ID | IDDIQMTQSP | SSLSASVGDR | VTITCRSSQS | ITFEYKNYLA | WYQQKPGKAP | KLLIYWGSYL | ESGVPSRFSG | SGSGTDFTLT | ISSLQPEDFA | TYYCQQHYRT | PPSFGQGTKV EIK |
| VL156-ID | IDDIQMTQSP | SSLSASVGDR | VTITCRSSQS | ITFDYKNYLA | WYQQKPGKAP | KLLIYWGSTR | ESGVPSRFSG | SGSGTDFTLT | ISSLQPEDFA | TYYCQQHYRT | PPSFGQGTKV EIK |
| VL62-ID | IDDIQMTQSP | SSLSASVGDR | VTITCRSSQS | ITFNYKNYLA | WYQQKPGKAP | KLLIYWGSYL | ESGVPSRFSG | SGSGTDFTLT | ISSLQPEDFA | TYYCQQHYRT | PPSFGQGTKV EIK |

FIG. 6B

Additional Light Chain Variable Regions

VL165
DIQMTQSPSSLSASVGDRVTITCRSSQSITWNYKNYLAWYQQKPGKAPKLLIYWGSYLESGVPSRFSGSGSGTD
FTLTISSLQPEDFATYYCQQHYRTPPSFGQGTKVEIK

VL166
DIQMTQSPSSLSASVGDRVTITCRSSQSITWDYKNYLAWYQQKPGKAPKLLIYWGSYLESGVPSRFSGSGSGTD
FTLTISSLQPEDFATYYCQQHYRTPPSFGQGTKVEIK

VL167
DIQMTQSPSSLSASVGDRVTITCRSSQSITWQYKNYLAWYQQKPGKAPKLLIYWGSYLESGVPSRFSGSGSGTD
FTLTISSLQPEDFATYYCQQHYRTPPSFGQGTKVEIK

VL168
DIQMTQSPSSLSASVGDRVTITCRSSQSITWRYKNYLAWYQQKPGKAPKLLIYWGSYLESGVPSRFSGSGSGTD
FTLTISSLQPEDFATYYCQQHYRTPPSFGQGTKVEIK

VL169
DIQMTQSPSSLSASVGDRVTITCRSSQSITWEYKNYLAWYQQKPGKAPKLLIYWGSYLESGVPSRFSGSGSGTD
FTLTISSLQPEDFATYYCQQHYRTPPSFGQGTKVEIK

Additional Heavy Chain Variable Regions

VH164
QVQLLETGGGLVKPGQSLKLSCAASGFTFTSYAMHWVRQPPGKGLEWVAVVSYDGNYKYYADSVQGRFTISR
DNSKNTLYLQMNSLRAEDTAVYYCAKDSRLRSLLYFEWLSQGYFNPWGQGTTVTVSS

VH162
EVQLLESGGGLVKPGQSLKLSCAASGFSFSTYAMHWVRQPPGKGLEWVAVVSYDGNYKYADTVQGRFTISRD
NSKNTLYLQMNSLRAEDTAVYYCAKDSRLRSLLYFEWLSQGYFNPWGQGTTLTVSS

VH163
EVQLLESGGGLRKPGQSLKLSCAASGFSFSTYAMHWVRQPPGKGLEWVAVVSYDGNYKYYADSVQGRFTISR
DNSKNTLYLQMNSLRAEDTAVYYCAKDSRLRSLLYFEWLSQGYFNPWGQGTTLTVSS

FIG. 7

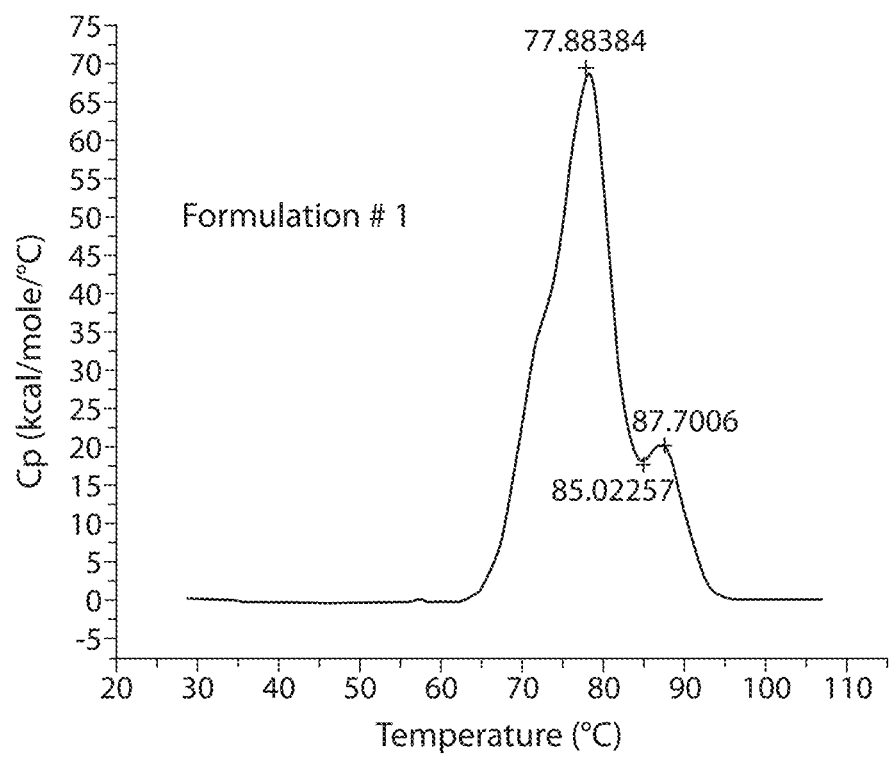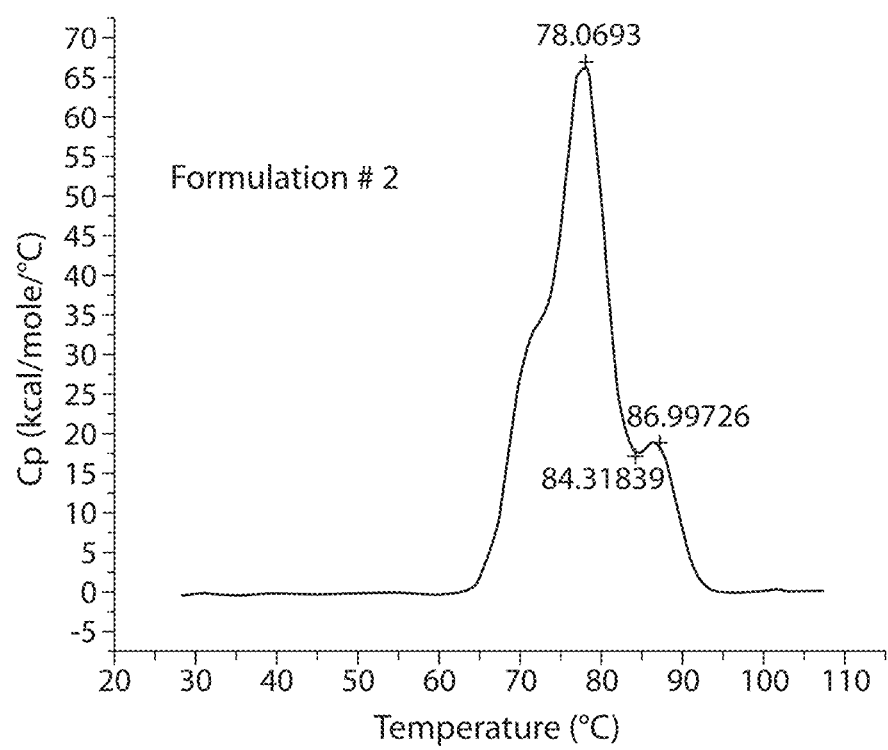
FIG. 8A

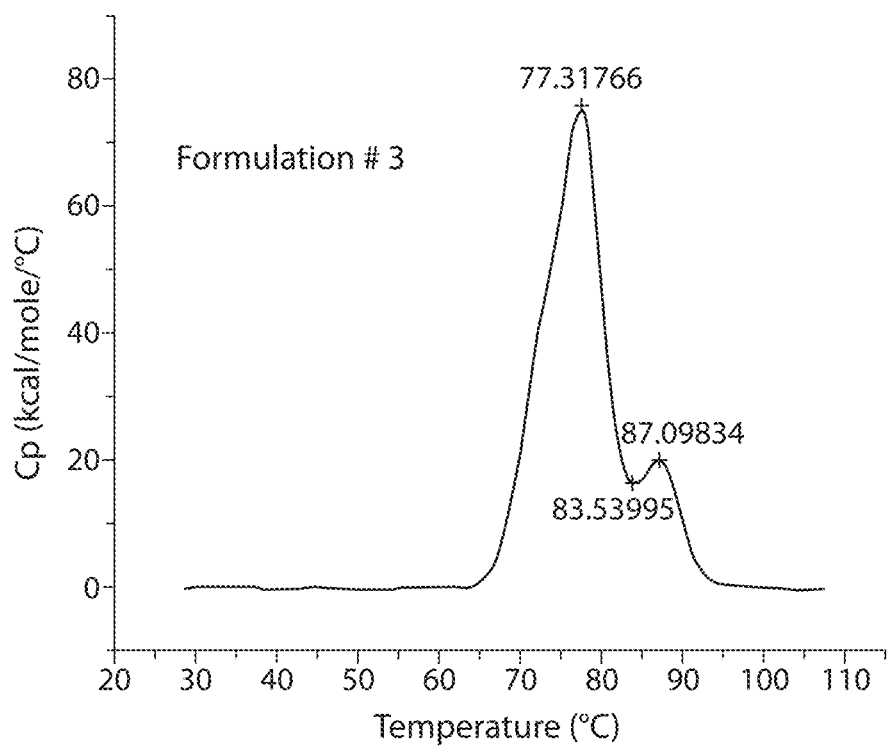
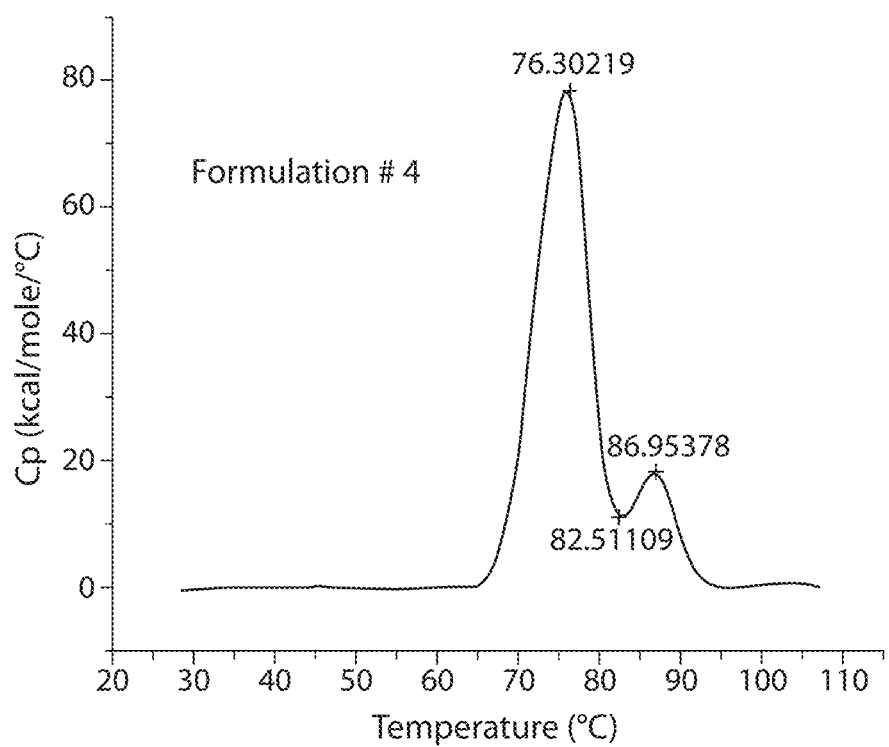
FIG. 8B

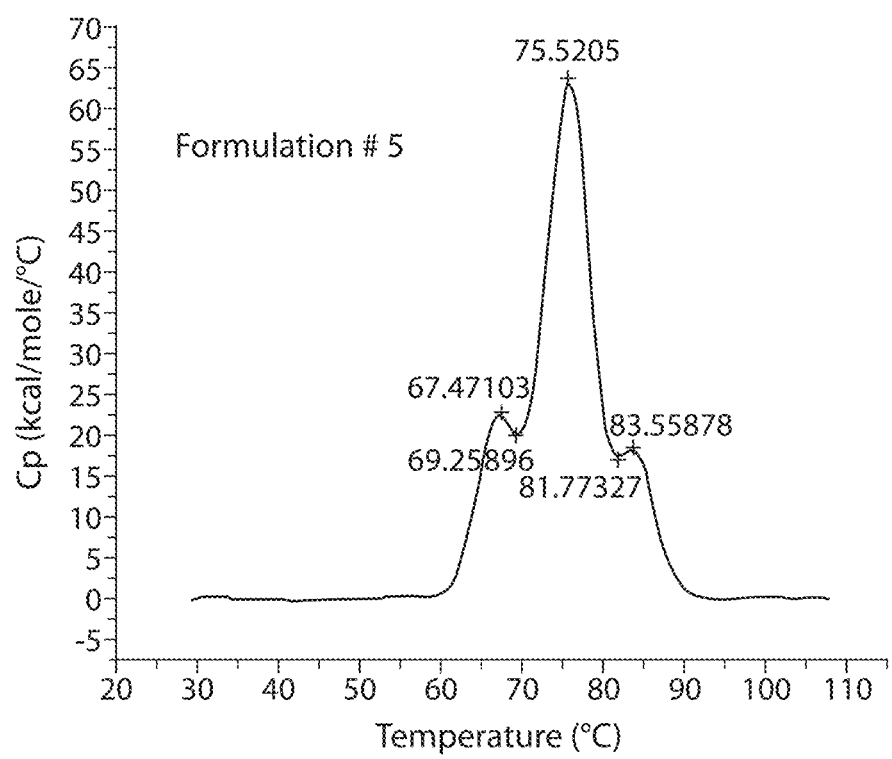
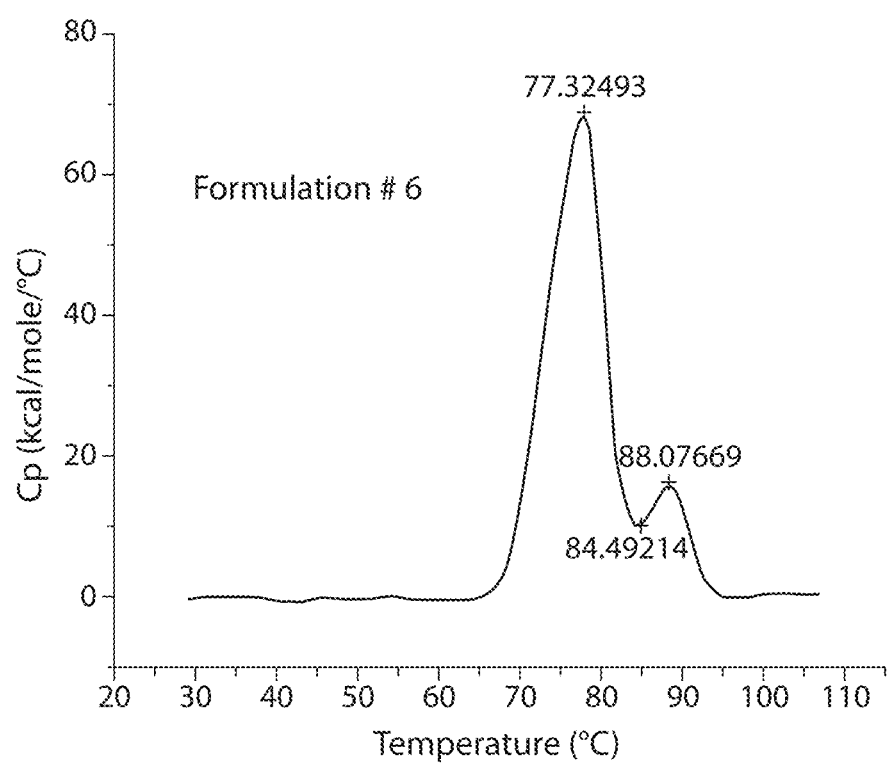
FIG. 8C

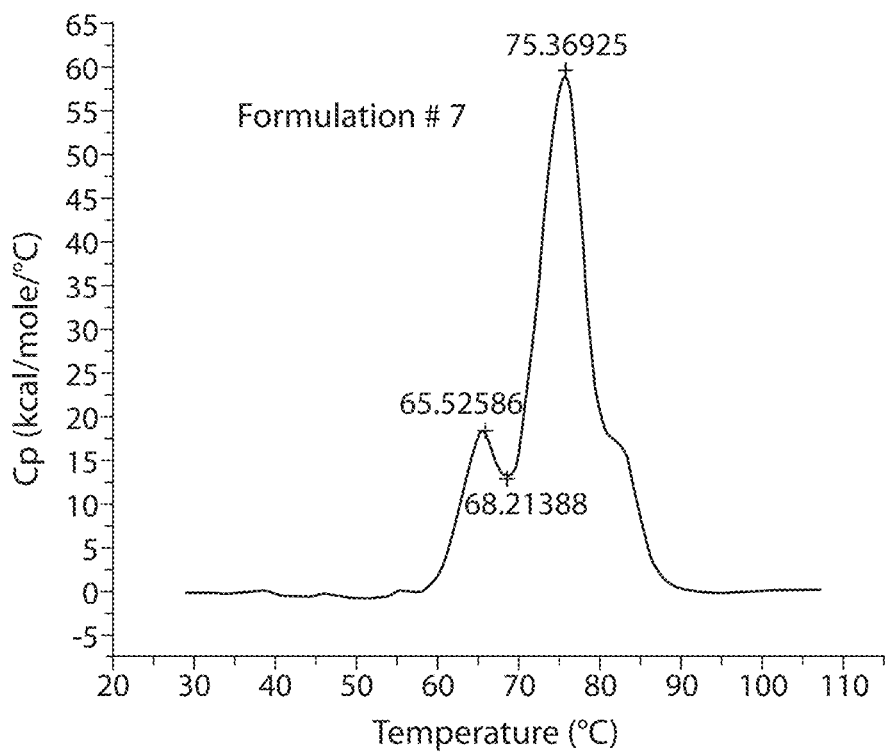
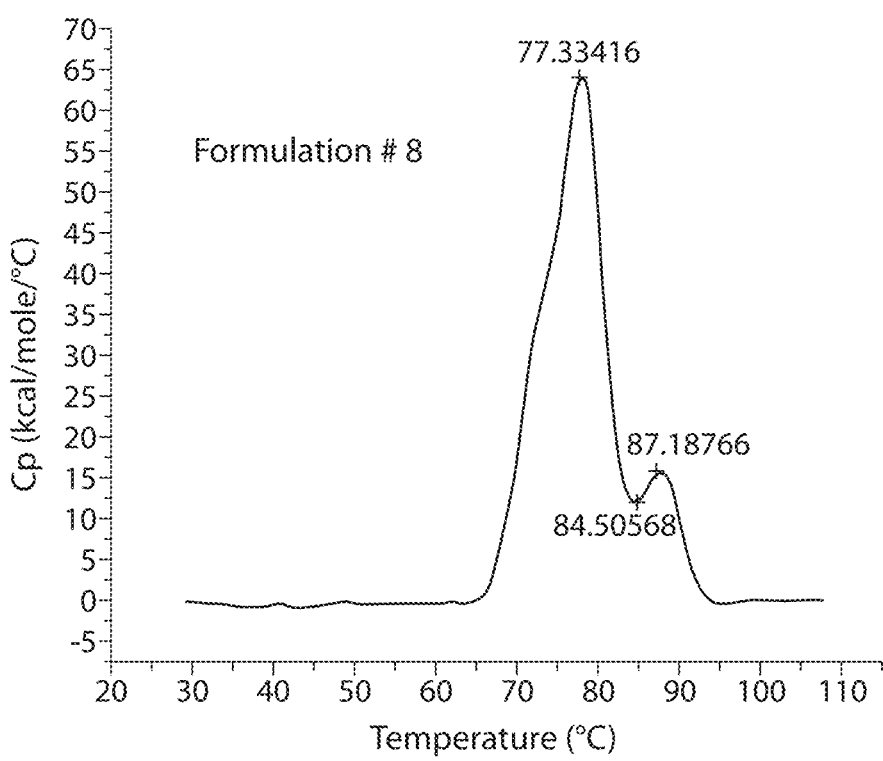
FIG. 8D

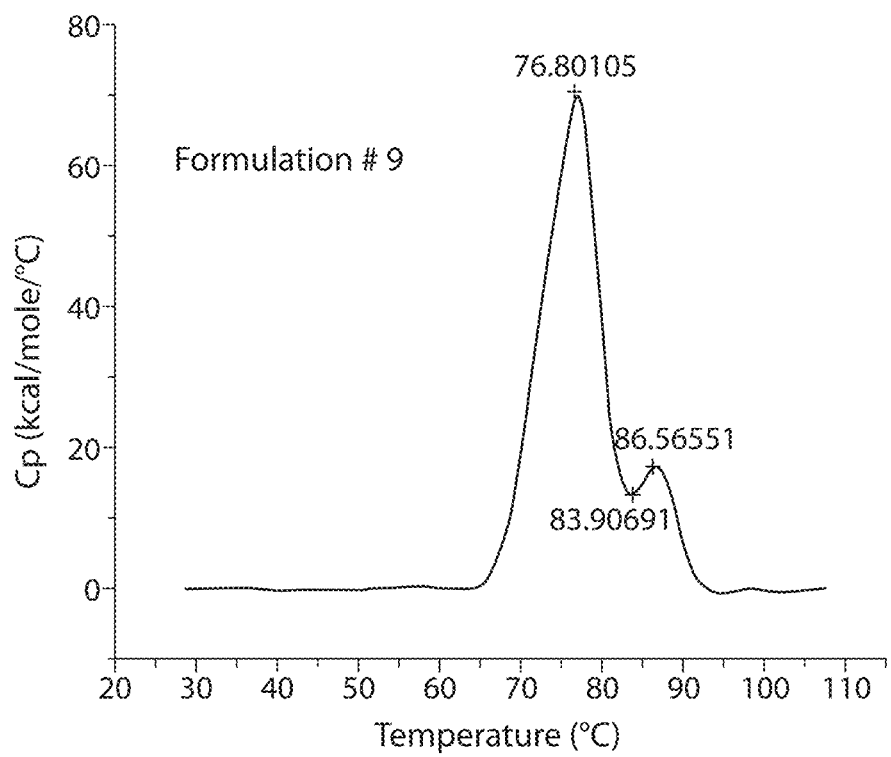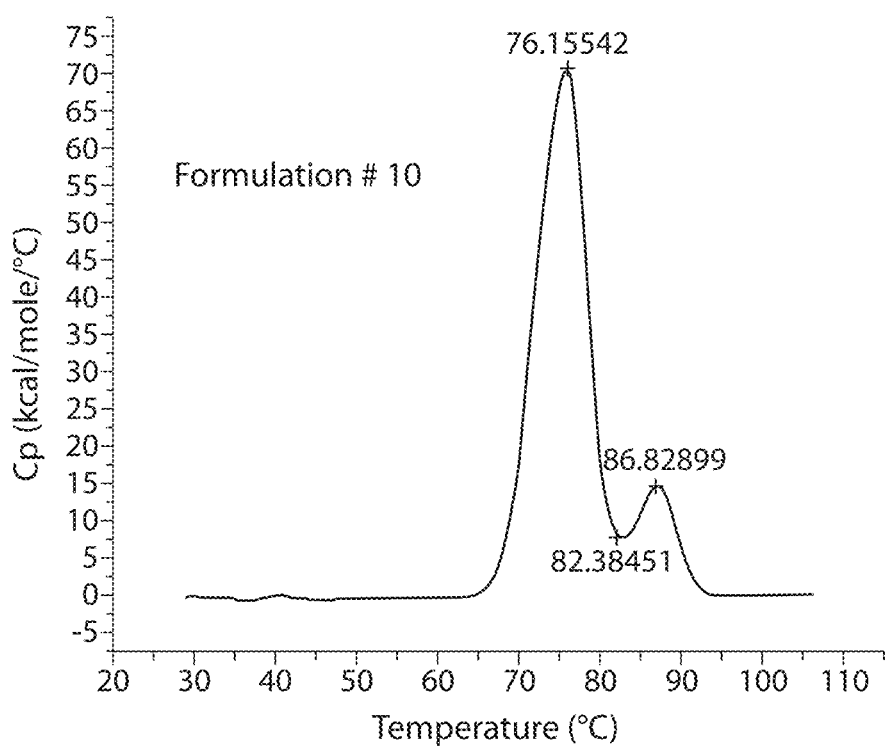
FIG. 8E

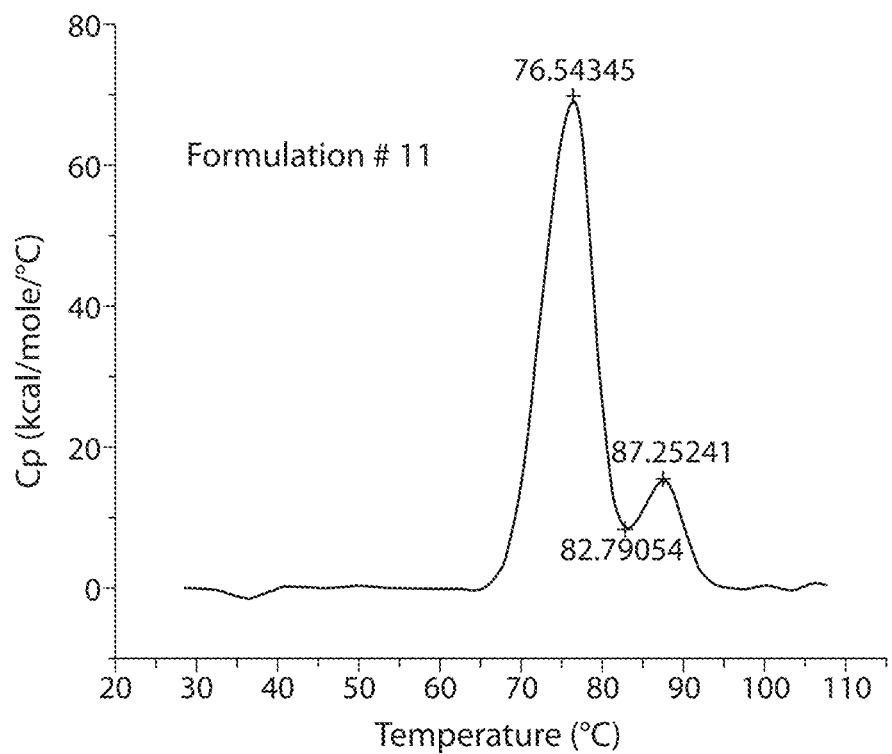
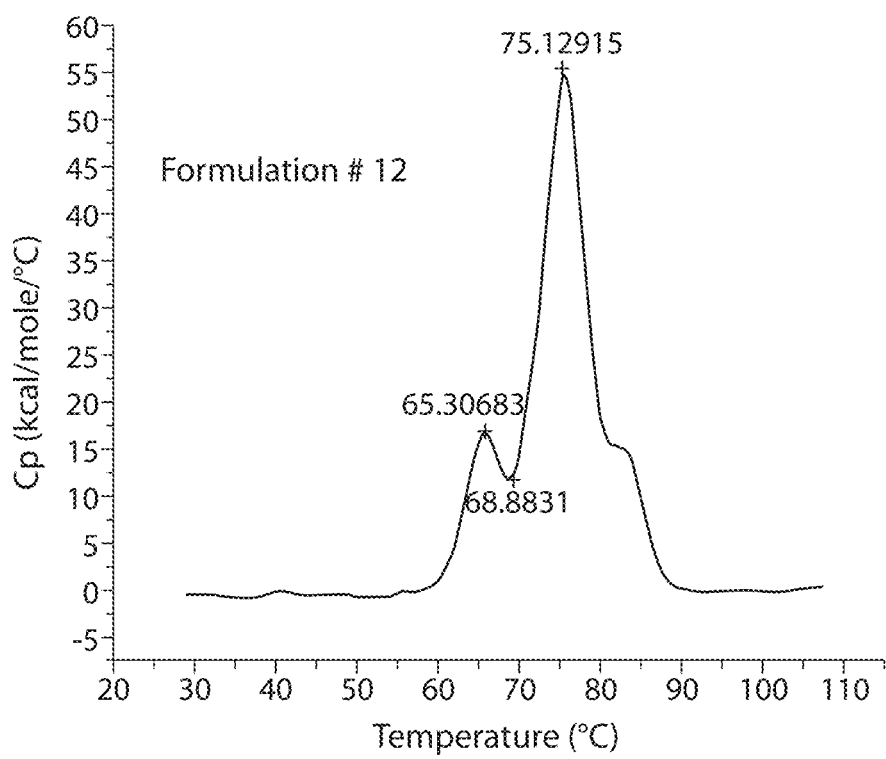
FIG. 8F

| Name | Migration Time | VC Area | Corrected Area Percent | Resolution (USP) | S/N (6 sigma) |
|---|---|---|---|---|---|
| | 14.4 | 25 | 0.2 | 0.00 | 0.1 |
| | 15.8 | 3696 | 32.9 | 5.89 | 649.3 |
| | 17.1 | 78 | 0.7 | 6.16 | 8.1 |
| | 18.2 | 40 | 0.4 | 3.58 | 4.1 |
| | 19.3 | 42 | 0.4 | 3.66 | 5.8 |
| | 19.7 | 7184 | 64.0 | 1.52 | 555.9 |
| | 22.5 | 109 | 1.0 | 8.08 | 16.9 |
| | 25.1 | 49 | 0.4 | 7.83 | 7.1 |
| Totals | | 11223 | 100.0 | | |

PDA – 220nm Results

| Name | Migration Time | VC Area | Corrected Area Percent | Resolution (USP) | S/N (6 sigma) |
|---|---|---|---|---|---|
| | 14.2 | 24 | 0.3 | 0.00 | 0.0 |
| | 15.6 | 103 | 1.1 | 6.95 | 12.7 |
| | 18.8 | 47 | 0.5 | 11.80 | 11.7 |
| | 22.4 | 32 | 0.3 | 10.35 | 10.4 |
| | 25.2 | 163 | 1.7 | 6.78 | 28.4 |
| | 26.8 | 238 | 2.5 | 3.84 | 17.7 |
| | 27.5 | 151 | 1.6 | 1.38 | 14.4 |
| | 27.9 | 8702 | 92.0 | 0.48 | 323.6 |
| Totals | | 9460 | 100.0 | | |

FORMULATIONS OF ANTIBODY MOLECULES TO INFLUENZA VIRUS

CROSS REFERENCE TO RELATED APPLICATIONS

This application is a continuation of U.S. patent application Ser. No. 16/518,536, filed Jul. 22, 2019, which is a continuation of U.S. patent application Ser. No. 15/440,381, filed Feb. 23, 2017, which claims the benefit of U.S. Provisional Application No. 62/299,162, filed Feb. 24, 2016. The contents of the aforementioned applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Feb. 20, 2017, is named P2029-701110_SL.txt and is 186,341 bytes in size.

BACKGROUND

Influenza is an infectious disease caused by RNA viruses of the family Orthomyxoviridae (the influenza viruses). Influenza viruses are classified based on core protein into three genera A, B and C that are further divided into subtypes determined by the viral envelope glycoproteins haemagglutinin (HA) and neuraminidase (NA). Influenza A viruses infect a range of mammalian and avian species, whereas type B and C infections are largely restricted to humans. Only types A and B cause human disease of any concern.

High mutation rates and frequent genetic reassortments of the influenza viruses contribute to great variability of the HA and NA antigens. Minor point mutations causing small changes ("antigenic drift") occur relatively often. Antigenic drift enables the virus to evade immune recognition, resulting in repeated influenza outbreaks during interpandemic years. Major changes in the HA antigen ("antigenic shift") are caused by reassortment of genetic material from different influenza A subtypes. Antigenic shifts resulting in new pandemic strains are rare events, occurring through reassortment between animal and human subtypes, for example in co-infected pigs.

Influenza A spreads around the world in seasonal epidemics, resulting in the deaths of between 250,000 and 500,000 people every year, and up to millions in some pandemic years. On average 41,400 people died each year in the United States between 1979 and 2001 from influenza.

SUMMARY

The disclosure is based, at least in part, on the discovery of human anti-HA antibodies comprising functional and structural properties disclosed herein, e.g., antibodies that bind a conserved region or epitope on influenza virus and uses thereof.

Accordingly, the disclosure features formulations comprising binding agents, e.g., antibody molecules, or preparations, or isolated preparations thereof, that bind hemagglutinin (HA) from influenza viruses. In an embodiment, a binding agent, e.g., an antibody molecule, is broad spectrum, and binds more than one HA, e.g., an HA from one or both of Group 1 or Group 2 strains of influenza A viruses and/or one or more strains of influenza B viruses. Therefore, in an embodiment, a binding agent, e.g., an antibody molecule, disclosed herein can treat or prevent infection by a Group 1 influenza virus and a Group 2 influenza virus. In another embodiment, a binding agent, e.g., an antibody molecule, disclosed herein can treat or prevent infection by an influenza A virus and an influenza B virus. The binding agents, e.g., antibody molecules, share sufficient structural similarity with antibodies or variable regions disclosed herein, such that they possess functional attributes of the antibodies disclosed herein. In an embodiment, the structural similarity can be in terms of a three dimensional structure or a linear amino acid sequence, or both.

In an aspect, the disclosure features a formulation, e.g., a pharmaceutical formulation, comprising an anti-HA antibody molecule described herein, e.g., an antibody molecule comprising one, two, or three heavy chain (HC) CDRs and/or one, two, or three light chain (LC) CDRs of Ab 044, a buffering agent, and a tonicity agent.

In an embodiment, the antibody molecule is present at a concentration of about 5 mg/mL to about 150 mg/mL, e.g., about 10 mg/mL to about 100 mg/mL, about 15 mg/mL to about 75 mg/mL, about 20 mg/mL to about 60 mg/mL, about 20 mg/mL to about 50 mg/mL, about 20 mg/mL to about 30 mg/mL, about 15 mg/mL to about 25 mg/mL, about 25 mg/mL to about 35 mg/mL, about 25 mg/mL to about 50 mg/mL, about 5 mg/mL to about 20 mg/mL, about 8 mg/mL to about 16 mg/mL, about 5 mg/mL to about 50 mg/mL, about 50 mg/mL to about 100 mg/mL, about 40 mg/mL to about 110 mg/mL, about 100 mg/mL to about 150 mg/mL, about 5 mg/mL to about 25 mg/mL, about 10 mg/mL to about 30 mg/mL, about 20 mg/mL to about 40 mg/mL, about 30 mg/mL to about 50 mg/mL, about 40 mg/mL to about 60 mg/mL, about 50 mg/mL to about 70 mg/mL, about 60 mg/mL to about 80 mg/mL, about 70 mg/mL to about 90 mg/mL, about 80 mg/mL to about 100 mg/mL, about 90 mg/mL to about 110 mg/mL, or about 100 mg/mL to about 120 mg/mL, e.g., about 150 mg/mL or less, about 100 mg/mL or less, about 50 mg/mL or less, about 25 mg/mL or less, about 20 mg/mL or less, about 16 mg/mL or less, about 10 mg/mL or less, about 8 mg/mL or less, e.g., about 5 mg/mL, about 8 mg/mL, about 10 mg/mL, about 15 mg/mL, about 16 mg/mL, about 20 mg/mL, about 25 mg/mL, about 30 mg/mL, about 35 mg/mL, about 40 mg/mL, about 45 mg/mL, about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, or about 150 mg/mL.

In an embodiment, the antibody molecule is present at a concentration of about 10 to about 40 mg/mL, e.g., about 20 mg/mL to about 30 mg/mL, e.g., about 25 mg/mL. In an embodiment, the antibody molecule is present at a concentration of about 25 mg/mL. In another embodiment, the antibody molecule is present at a concentration of about 40 mg/mL to about 60 mg/mL, e.g., about 50 mg/mL. In an embodiment, the antibody molecule is present at a concentration of about 50 mg/mL. In another embodiment, the antibody molecule is present at a concentration of about 20 mg/mL to about 60 mg/mL, e.g., about 25 mg/mL to about 50 mg/mL.

In an embodiment, the antibody molecule is present at a concentration of about 5 to about 10 mg/mL, e.g., about 8 mg/mL. In an embodiment, the antibody molecule is present at a concentration of about 8 mg/mL. In another embodiment, the antibody molecule is present at a concentration of about 10 mg/mL to about 20 mg/mL, e.g., about 16 mg/mL. In an embodiment, the antibody molecule is present at a concentration of about 16 mg/mL. In another embodiment, the antibody molecule is present at a concentration of about 5 mg/mL to about 20 mg/mL, e.g., about 8 mg/mL to about 16 mg/mL.

In an embodiment, the antibody molecule is present at a concentration of about 25 to about 150 mg/mL, e.g., about 50 mg/mL to about 100 mg/mL, e.g., about 50 mg/mL.

In an embodiment, the antibody molecule comprises a heavy chain immunoglobulin variable region segment comprising:
an HC CDR1 comprising the sequence S-Y-A-M-H (SEQ ID NO: 68);
an HC CDR2 comprising the sequence V-V-S-Y-D-G-N-Y-K-Y-Y-A-D-S-V-Q-G (SEQ ID NO: 69); and
an HC CDR3 comprising the sequence D-S-R-L-R-S-L-L-Y-F-E-W-L-S-Q-G-Y-F-N-P (SEQ ID NO: 70).

In an embodiment, the antibody molecule comprises a light chain immunoglobulin variable region segment comprising:
an LC CDR1 comprising the sequence Q-S-I-T-F-D-Y-K-N-Y-L-A (SEQ ID NO: 145);
an LC CDR2 comprising the sequence W-G-S-Y-L-E-S (SEQ ID NO: 72); and an LC CDR3 comprising the sequence Q-Q-H-Y-R-T-P-P-S (SEQ ID NO: 73).

In an embodiment, the antibody molecule comprises:
(a) a heavy chain immunoglobulin variable region segment comprising:
an HC CDR1 comprising the sequence S-Y-A-M-H (SEQ ID NO: 68);
an HC CDR2 comprising the sequence V-V-S-Y-D-G-N-Y-K-Y-Y-A-D-S-V-Q-G (SEQ ID NO: 69); and
an HC CDR3 comprising the sequence D-S-R-L-R-S-L-L-Y-F-E-W-L-S-Q-G-Y-F-N-P (SEQ ID NO: 70); and
(b) a light chain immunoglobulin variable region segment comprising:
an LC CDR1 comprising the sequence Q-S-I-T-F-D-Y-K-N-Y-L-A (SEQ ID NO: 145);
an LC CDR2 comprising the sequence W-G-S-Y-L-E-S (SEQ ID NO: 72); and
an LC CDR3 comprising the sequence Q-Q-H-Y-R-T-P-P-S (SEQ ID NO: 73).

In an embodiment, the antibody molecule comprises a heavy chain immunoglobulin variable region segment that comprises SEQ ID NO: 25, or an amino acid sequence that differs by no more than 1, 2, 3, 4, or 5 amino acids therefrom.

In an embodiment, the antibody molecule comprises a light chain immunoglobulin variable region segment that comprises SEQ ID NO: 52, or an amino acid sequence that differs by no more than 1, 2, 3, 4, or 5 amino acids therefrom.

In an embodiment, the antibody molecule comprises:
(a) a heavy chain immunoglobulin variable region segment that comprises SEQ ID NO: 25, or an amino acid sequence that differs by no more than 1, 2, 3, 4, or 5 amino acids therefrom; and
(b) a light chain immunoglobulin variable region segment that comprises SEQ ID NO: 52, or an amino acid sequence that differs by no more than 1, 2, 3, 4, or 5 amino acids therefrom.

In an embodiment, the antibody molecule comprises:
(a) a heavy chain immunoglobulin variable region segment that comprises SEQ ID NO: 25; and
(b) a light chain immunoglobulin variable region segment that comprises SEQ ID NO: 52.

In an embodiment, the buffering agent is present at a concentration of about 5 mM to about 150 mM, e.g., about 10 mM to about 100 mM, about 20 mM to about 75 mM, about 30 mM to about 50 mM, about 10 mM to about 50 mM, about 50 mM to about 100 mM, about 100 mM to about 150 mM, about 10 mM to about 30 mM, about 20 mM to about 40 mM, about 30 mM to about 50 mM, about 40 mM to about 60 mM, about 50 mM to about 70 mM, about 60 mM to about 80 mM, about 70 mM to about 90 mM, or about 80 mM to about 100 mM, e.g., about 150 mM or less, about 100 mM or less, about 75 mM or less, about 50 mM or less, about 25 mM or less, or about 10 mM or less, e.g., about 5 mM, about 10 mM, about 20 mM, about 30 mM, about 40 mM, about 50 mM, about 60 mM, about 70 mM, about 80 mM, about 90 mM, about 100 mM, about 110 mM, about 120 mM, about 130 mM, about 140 mM, or about 150 mM.

In an embodiment, the buffering agent is present at a concentration of about 20 mM to about 60 mM, e.g., about 30 to about 50 mM, e.g., about 40 mM. In an embodiment, the buffering agent is present at a concentration of about 40 mM.

In an embodiment, the buffering agent is a citrate buffer, a phosphate buffer, or a citrate-phosphate buffer. In an embodiment, the buffering agent comprises citrate-sodium phosphate. In an embodiment, the formulation comprises citrate-sodium phosphate at a concentration of about 20 mM to about 60 mM, e.g., about 30 to about 50 mM, e.g., about 40 mM.

In an embodiment, the buffering agent provides a pH of about 5.5 to about 7, e.g., about 6 to about 6.5, e.g., about 5.5, about 6, about 6.5, or about 7. In an embodiment, the buffering agent comprises citrate-sodium phosphate and provides a pH of about 6 to about 6.5, e.g., about 6 or about 6.5.

In an embodiment, the tonicity agent is present at a concentration of about 10 mM to about 500 mM, about 50 mM to about 200 mM, e.g., about 60 mM to about 190 mM, about 70 mM to about 180 mM, about 80 mM to about 170 mM, about 90 mM to about 160 mM, about 100 mM to about 150 mM, about 145 mM to about 155 mM, about 140 mM to about 160 mM, about 135 mM to about 165 mM, about 130 mM to about 170 mM, about 120 mM to about 180 mM, about 110 mM to about 190 mM, about 100 mM to about 200 mM, about 50 mM to about 100 mM, about 100 mM to about 150 mM, or about 150 mM to about 120 mM, e.g., about 200 mM or less, about 150 mM or less, about 100 mM or less, or about 75 mM or less, e.g., about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, or about 200 mM.

In an embodiment, the tonicity agent is present at a concentration of about 50 to about 200 mM, about 75 mM to about 150 mM, about 120 mM to about 180 mM, e.g., about 140 to about 160 mM, e.g., about 150 mM.

In an embodiment, the tonicity agent comprises sodium chloride. In an embodiment, the tonicity agent comprises sodium chloride and is present at a concentration of about 140 to about 160 mM, e.g., about 150 mM.

In an embodiment, the tonicity agent provides a tonicity (or osmolarity) of about 250 mOsm/L to about 350 mOsm/L, about 260 mOsm/L to about 340 mOsm/L, about 270 mOsm/L to about 330 mOsm/L, about 280 mOsm/L to about 320 mOsm/L, about 285 mOsm/L to about 310 mOsm/L, or about 290 mOsm/L to about 300 mOsm/L, e.g., about 250 mOsm/L, about 260 mOsm/L, about 270 mOsm/L, about 280 mOsm/L, about 290 mOsm/L, about 300 mOsm/L, about 310 mOsm/L, about 320 mOsm/L, about 330 mOsm/L, about 340 mOsm/L, or about 350 mOsm/L.

In an embodiment, the formulation has a pH of about 5.5 to about 7, e.g., about 6 to about 6.5, e.g., about 5.5, about 6, about 6.5, or about 7.

In an embodiment, the formulation comprises:
(a) an antibody molecule described herein at a concentration about 10 to about 40 mg/mL, e.g., about 20 to about 30 mg/mL, e.g., a concentration of about 25 mg/mL;
(b) a buffering agent, e.g., citrate-sodium phosphate, at a concentration about 20 mM to 60 mM, e.g., about 30 to about 50 mM, e.g., about 40 mM; and
(c) a tonicity agent, e.g., sodium chloride, at a concentration of about 75 to about 150 mM, about 120 mM to about 180 mM, e.g., about 140 to about 160 mM, e.g., a concentration of about 150 mM,
wherein the pH of the formulation is about 5.5 to about 6.5, e.g., about 6 or about 6.5.

In an embodiment, the formulation comprises: about 25 mg/mL of an antibody molecule described herein, about 40 mM citrate-sodium phosphate, about 150 mM sodium chloride, at a pH of about 6.

In an embodiment, the formulation further comprises a surfactant, e.g., a nonionic surfactant.

In an embodiment, the surfactant is present at a concentration of about 0.005% to about 0.1% (w/v), e.g., about 0.01% to about 0.05%, about 0.015% to about 0.04%, about 0.02% to about 0.03%, about 0.01% to about 0.03%, about 0.02% to about 0.04%, about 0.01% to about 0.025%, about 0.025% to about 0.1%, about 0.005% to about 0.05%, or about 0.05% to about 0.1%, e.g., about 0.1% or less, about 0.075% or less, about 0.05% or less, about 0.025% or less, or about 0.01% or less, e.g., about 0.005%, about 0.01%, about 0.015%, about 0.02%, about 0.025%, about 0.03%, about 0.035%, about 0.04%, about 0.05%, about 0.06%, about 0.07%, about 0.08%, about 0.09%, or about 0.1%.

In an embodiment, the surfactant is present at a concentration of about 0.01% to about 0.05%, e.g., about 0.025%.

In an embodiment, the surfactant is polysorbate 80 (TWEEN® 80). In an embodiment, the surfactant is polysorbate 80 and is present a concentration of about 0.01% and about 0.05%, e.g., about 0.025%.

In an embodiment, the formulation comprises:
(a) an antibody molecule described herein at a concentration of about 10 to about 40 mg/mL, e.g., about 20 to about 30 mg/mL, e.g., about 25 mg/mL;
(b) a buffering agent, e.g., citrate-sodium phosphate, at a concentration of about 20 mM to about 60 mM, e.g., about 30 to about 50 mM, e.g., a concentration of about 40 mM;
(c) a tonicity agent, e.g., sodium chloride, at a concentration of about 75 mM to about 150 mM, about 120 mM to 180 mM, e.g., about 140 to about 160 mM, e.g., a concentration of about 150 mM; and
(d) a surfactant, e.g., polysorbate 80, at a concentration of about 0.01% to about 0.04%, e.g., about 0.025%,
wherein the pH of the pharmaceutical composition is about 5.5 to about 6.5, e.g., about 6 or about 6.5.

In an embodiment, the formulation comprises about 25 mg/mL of an antibody molecule described herein, about 40 mM citrate-sodium phosphate, about 150 mM sodium chloride, about 0.025% polysorbate 80, at a pH of about 6.

In an embodiment, the formulation comprises about 25 mg/mL of an antibody molecule described herein, about 40 mM citrate-sodium phosphate, about 150 mM sodium chloride, about 0.025% polysorbate 80, at a pH of about 6.5.

In an embodiment, the formulation comprises about 25 mg/mL of an antibody molecule described herein, about 40 mM citrate-sodium phosphate, about 75 mM sodium chloride, about 0.025% polysorbate 80, at a pH of about 6.5.

In an embodiment, the formulation further comprises a stabilizing agent.

In an embodiment, the stabilizing agent is present at a concentration of about 0.1% to about 10% (w/v), e.g., about 0.2% to about 5%, about 0.5% to about 1.5%, about 0.5% to about 1%, about 1% to about 2%, e.g., about 5% or less, about 4% or less, about 3% or less, about 2% or less, about 1% or less, about 0.5% or less, or about 0.2% or less, e.g., about 0.6%, about 0.8%, about 1%, about 1.5%, about 2%, about 3%, about 4%, or about 5%.

In an embodiment, the stabilizing agent is an amino acid. In an embodiment, the amino acid is glycine, histidine, arginine, methionine, proline, lysine, glutamic acid, or a combination thereof. In an embodiment, the formulation comprises one, two or all of: glycine, histidine, or arginine. In an embodiment, the amino acid is glycine. In an embodiment, the formulation comprises glycine, which is present at a concentration of about 0.5% to about 2%, e.g., about 1%.

In an embodiment, the formulation comprises:
(a) an antibody molecule described herein at a concentration of about 10 to about 40 mg/mL, e.g., about 20 to about 30 mg/mL, e.g., about 25 mg/mL;
(b) a buffering agent, e.g., citrate-sodium phosphate, at a concentration of about 20 mM to about 60 mM, e.g., about 30 to about 50 mM, e.g., about 40 mM;
(c) a tonicity agent, e.g., sodium chloride, at a concentration of about 75 mM to about 150 mM, about 120 mM to about 180 mM, e.g., about 140 to about 160 mM, e.g., about 150 mM;
(d) a surfactant, e.g., polysorbate 80, at a concentration of about 0.01% to about 0.04%, e.g., about 0.025%; and
(c) a stabilizing agent, e.g., glycine, at a concentration of about 0.5% to about 2%, e.g., about 1%,
wherein the pH of the pharmaceutical composition is about 5.5 to about 6.5, e.g., about 6 or about 6.5.

In an embodiment, the formulation comprises about 25 mg/mL of an antibody molecule described herein, about 40 mM citrate-sodium phosphate, about 150 mM sodium chloride, about 0.025% polysorbate 80, about 1% glycine, at a pH of about 6.

In an embodiment, the formulation further comprises a carbohydrate, e.g., a polyol or a sugar.

In an embodiment, the carbohydrate is sucrose, trehalose, mannitol, dextran, sorbitol, inositol, glucose, fructose, lactose, xylose, mannose, maltose, raffinose, a combination thereof.

In an embodiment, the formulation further comprises further comprising a polymer, e.g., a hydrophilic polymer. In an embodiment, the polymer is a polyethylene glycol (PEG), dextran, hydroxyl ethyl starch (HETA), or gelatin.

In an embodiment, the formulation further comprises a preservative. In an embodiment, the preservative is benzyl alcohol, m-cresol, or phenol.

In an embodiment, the level of high molecular weight (HMW) species in the formulation is less than about 5%, less than about 4%, less than about 3%, less than about 2%, or less than 1%, e.g., before storage, or after storage for at least about 1 week at 4° C., at least about 1 week at 45° C., at least about 2 weeks at 4° C., at least about 2 weeks at 45° C., at least about 3 weeks at 4° C., at least about 3 weeks at 45° C., at least about 4 weeks at 4° C., or at least about 4 weeks at 45° C. In an embodiment, the level of HMW species is less than about 2% before storage. In an embodiment, the level of HMW species is less than about 2% after storage for 2 weeks at 4° C. In an embodiment, the level of HMW species is less than about 5% after storage for 2 weeks at 45° C.

In an embodiment, the level of low molecular weight (LMW) species in the formulation is less than about 5%, less than about 4%, less than about 3%, less than about 2%, or less than 1%, e.g., before storage or after storage for at least about 1 week at 4° C., at least about 1 week at 45° C., at least about 2 weeks at 4° C., at least about 2 weeks at 45° C., at least about 3 weeks at 4° C., at least about 3 weeks at 45° C., at least about 4 weeks at 4° C., or at least about 4 weeks at 45° C. In an embodiment, the level of LMW species is less than about 1% before storage. In an embodiment, the level of LMW species is less than about 1% after storage for 2 weeks at 4° C. In an embodiment, the level of LMW species is less about 2% after storage for 2 weeks at 45° C.

In an embodiment, the level of HMW and LMW species in the formulation is less than about 8%, less than about 7%, less than about 6%, less than about 5%, less than about 4%, less than about 3%, less than about 2%, or less than 1%, e.g., before storage, or after storage for at least about 1 week at 4° C., at least about 1 week at 45° C., at least about 2 weeks at 4° C., at least about 2 weeks at 45° C., at least about 3 weeks at 4° C., at least about 3 weeks at 45° C., at least about 4 weeks at 4° C., or at least about 4 weeks at 45° C. In an embodiment, the level of HMW and LMW species is less than about 2% before storage. In an embodiment, the level of HMW and LMW species is less than about 2% after storage for 2 weeks at 4° C. In an embodiment, the level of LMW species is less than about 6% after storage for 2 weeks at 45° C.

In an embodiment, about 90% or more, about 92% or more, about 94% or more, about 95% or more, about 96% or more, about 97% or more, about 98% or more, or about 99% or more of the antibody molecules in the formulation are present as monomers, e.g., before storage, or after storage for at least about 1 week at 4° C., at least about 1 week at 45° C., at least about 2 weeks at 4° C., at least about 2 weeks at 45° C., at least about 3 weeks at 4° C., at least about 3 weeks at 45° C., at least about 4 weeks at 4° C., or at least about 4 weeks at 45° C. In an embodiment, about 98% or more of the antibody molecules in the formulation are present as monomers before storage. In an embodiment, about 98% or more of the antibody molecules in the formulation are present as monomers after storage for 2 weeks at 4° C. In an embodiment, about 94% or more of the antibody molecules in the formulation are present as monomers after storage for 2 weeks at 45° C.

In an embodiment, the level of monomers, HMW species, or LMW species is determined by size exclusion chromatography (SEC), e.g., size exclusion-high performance liquid chromatography (SEC-HPLC). In another embodiment, the monomeric nature of the antibody molecule is determined by a binding assay, a surface charge assay, a bioassay, or the ratio of HMW species to LMW species.

In an embodiment, the purity of the antibody molecule in the formulation, e.g., after storage for two 2 weeks at 4° C., is at least about 96%, at least about 97%, at least about 98%, or at least about 99%. In an embodiment, the purity of the antibody molecule in the formulation, e.g., after storage for two 2 weeks at 45° C., is at least about 90%, at least about 92%, at least about 94%, at least about 96%, at least about 97%, at least about 98%, or at least about 99%. In an embodiment, the purity (or heterogeneity) of the antibody molecule is determined by detecting the intact heavy and light chains (e.g., in a reduced sample) or intact immunoglobulins (e.g., in a non-reduced sample) in the formulation.

In an embodiment, the purity (or heterogeneity) of the antibody molecule in the formulation is determined by capillary electrophoresis-sodium dodecyl sulfate (CE-SDS) in a reduced sample. In an embodiment, the purity (or heterogeneity) of the antibody molecule in the formulation is determined by CE-SDS in a non-reduced sample. In an embodiment, the purity of the antibody molecule in the formulation, e.g., after storage for two 2 weeks at 4° C., is at least about 98% as determined by CE-SDS in a reduced sample. In an embodiment, the purity of the antibody molecule in the formulation, e.g., after storage for two 2 weeks at 45° C., is at least about 96% as determined by CE-SDS in a reduced sample. In an embodiment, the purity of the antibody molecule in the formulation, e.g., after storage for two 2 weeks at 4° C., is at least about 97% as determined by CE-SDS in a non-reduced sample. In an embodiment, the purity of the antibody molecule in the formulation, e.g., after storage for two 2 weeks at 45° C., is at least about 92% as determined by CE-SDS in a non-reduced sample.

In an embodiment, the activity of the antibody molecule is decreased by less than about 25%, less than about 20%, less than about 15%, less than about 10%, less than about 5%, or less than about 2%, after storage, e.g., for at least about 1 week, at least about 2 weeks, or at least about 3 weeks, e.g., at 4° C. or 45° C. In an embodiment, the activity of the antibody molecule is decreased by less than about 25% after storage for about 2 weeks at 45° C. In an embodiment, the activity of the antibody molecule is determined by a hemagglutinin (HA) binding assay, e.g., an HA-binding ELISA.

In an embodiment, the formulation is a liquid formulation (e.g., a frozen or non-frozen liquid formulation). In an embodiment, the formulation is stored as a frozen liquid. In another embodiment, the formulation is a lyophilized formulation.

In an embodiment, the formulation is for use in treating or preventing influenza in a subject. In an embodiment, the formulation is for use in treating a subject having influenza. In another embodiment, the formulation is for use in preventing a subject from having influenza. In an embodiment, the formulation is for intravenous administration.

In another aspect, the disclosure features a device, e.g., an injection device, comprising a formulation described herein, e.g., a pharmaceutical formulation described herein.

In yet another aspect, the disclosure features a kit, comprising one or more containers comprising a formulation described herein, e.g., a pharmaceutical formulation described herein, and instructions for use of the formulation, e.g., for administration of the formulation to a subject, or for making a solution for administration to a subject.

In another aspect, the disclosure features a container (e.g., a vial or an intravenous (IV) solution bag) comprising an anti-HA antibody molecule described herein or a formulation (e.g., a pharmaceutical formulation described herein) comprising an anti-HA antibody molecule described herein.

In an embodiment, the container is a vial, e.g., a glass vial. In an embodiment, the container (e.g., vial) comprises about 10 mg/mL to about 100 mg/mL, e.g., about 20 mg/mL to about 60 mg/mL (e.g., about 25 mg/mL to about 50 mg/mL) of the antibody molecule. In an embodiment, the container (e.g., vial) comprises about 10 mL to about 60 mL, e.g., about 20 mL to about 40 mL, of the formulation. In an embodiment, the container (e.g., vial) is a first (or primary) container, e.g., for storing the antibody molecule or formulation.

The antibody molecule or formulation can be transferred into a second (or secondary) container before use. In an embodiment, the second (or secondary) container is suitable, or includes a solution that is suitable, for administration, e.g., intravenous administration. In an embodiment, the second (or secondary) container includes a solution suitable for intravenous administration. In an embodiment, the solution comprises saline, optionally, further comprises dextrose. In an embodiment, the solution (e.g., saline) does not comprise dextrose. For example, an amount equal to one dose of the antibody molecule can be transferred into a container suitable for IV administration.

In an embodiment, 1 to 10 vials (e.g., 1 to 8 vials, 1 to 6 vials, 1 to 4 vials, 1 to 2 vials, 6 to 8 vials, 4 to 8 vials, or 2 to 8 vials) of the formulation are transferred (e.g., diluted) into an IV solution bag, e.g., containing saline with or without dextrose.

In an embodiment, the container is a container suitable for IV administration (e.g., an IV solution bag). In an embodiment, the amount of the antibody molecules in the container (e.g., IV solution bag) equals to the amount of the antibody molecules in 1 to 10 vials (e.g., 1 to 8 vials, 1 to 6 vials, 1 to 4 vials, 1 to 2 vials, 6 to 8 vials, 4 to 8 vials, or 2 to 8 vials) of the formulation as described above. In an embodiment, the container (e.g., IV solution bag) comprises about 2000 mg to about 5000 mg, e.g., about 2300 mg to about 4600 mg, of the antibody molecule, e.g., in a solution suitable for IV administration (e.g., saline with or without dextrose).

In an embodiment, the container suitable for IV administration (e.g., IV solution bag) is not a second (or secondary) container (e.g., is a first (or primary) container, e.g., where the antibody molecule is stored), and comprises about 5 mg/mL to about 25 mg/mL, e.g., about 8 mg/mL to about 16 mg/mL of the antibody molecule. In an embodiment, the container (e.g., IV solution bag) comprises about 100 mL to about 400 mL (e.g., about 200 mL to about 300 mL) of a solution (e.g., a solution suitable for IV administration) comprising the antibody molecule. In an embodiment, the container (e.g., IV solution bag) comprises about 2000 mg to about 5000 mg, e.g., about 2000 mg to about 4000 mg or about 2300 mg to about 4600 mg, of the antibody molecule.

In another aspect, the disclosure features a method of preparing a composition (e.g., a solution) for administration to a subject. The method comprises combining a formulation described herein with a solution suitable for intravenous administration.

In an embodiment, the solution comprises saline, optionally, further comprises dextrose. In an embodiment, the solution does not comprise dextrose. In an embodiment, about 2000 mg to about 5000 mg of the antibody molecule is combined with the solution. In another embodiment, about 2300 mg to about 4600 mg of the antibody molecule is combined with the solution. In yet another embodiment, about 2000 mg to about 4000 mg of the antibody molecule is combined with the solution. In an embodiment, the formulation is combined with the solution in an intravenous (IV) solution bag.

In still another aspect, the disclosure features a method of treating or preventing influenza, the method comprising administering to a subject having influenza, or at risk of having influenza, an effective amount of a formulation described herein, e.g., a pharmaceutical formulation described herein, thereby treating or preventing influenza.

In an aspect, the disclosure features a formulation described herein, e.g., a pharmaceutical formulation described herein, for use in treating or preventing influenza in a subject.

Anti-HA Antibody Molecules

Various anti-HA antibody molecules, or preparations, or isolated preparations thereof, can be included in a formulation (e.g., pharmaceutical formulation) described herein.

In an embodiment, the antibody molecule comprises one or more (e.g., 2, 3, 4, 5, 6, 7, 8, 9, 10, 11, 12, 13, 14, 15, 16, 17, 18, or all) of the following properties:
(a) it fails to produce any escape mutants as determined by the failure of a viral titer to recover following at least 10, 9, 8, 7, 6, or 5 rounds of serial infections in cell culture with a mixture of the antibody molecule and an influenza A virus, e.g., a Group 1 strain, e.g., an H1N1 strain, e.g., A/South Carolina/1/1918, A/Puerto Rico/08/1934, or A/California/04/2009, an H5N1 strain, e.g., A/Indonesia/5/2005 or A/Vietnam/1203/2004, or an H7N9, e.g., A/Anhui/1/2013 or A/Shanghai/1/2013;
(b) it produces fewer escape mutants than does a reference anti-HA antibody molecule, e.g., Ab 67-11, F16, F128, C179, F10, CR9114, or CR6261, e.g., when tested by the method described in (a);
(c) it binds with high affinity to an HA of at least 1, 2, 3, 4, or 5 influenza subtypes of Group 1 and at least 1, 2, 3, 4, or 5 influenza subtypes of Group 2;
(d) it prevents infection by at least 1, 2, 3, 4 or 5 influenza subtypes of Group 1, and by at least 1, 2, 3, 4 or 5 influenza subtypes of Group 2;
(e) it inhibits fusogenic activity of the targeted HA;
(f) it treats or prevents infection by a Group 1 virus, such as where the virus is an H1, H5, or H9 virus; and it treats or prevents infection by a Group 2 virus, such as where the virus is an H3 or H7 virus;
(g) it treats or prevents infection by an influenza A H1N1 strain, an influenza A H3N2 strain, or both;
(h) it is effective for prevention or treatment of infection, e.g., in humans or mice, with H1N1 or H3N2 when administered at 50 mg/kg, 25 mg/kg, 10 mg/kg, 6 mg/kg, 5 mg/kg, 4 mg/kg, 3 mg/kg, 2 mg/kg, or 1 mg/kg;
(i) it treats or prevents infection by an influenza A H5N1 strain, an influenza A H7N9 strain, or both;
(j) it is effective for prevention or treatment of infection, e.g., in humans or mice, with H5N1 or H7N9 when administered at 50 mg/kg, 25 mg/kg, 10 mg/kg, 6 mg/kg, 5 mg/kg, 4 mg/kg, 3 mg/kg, 2 mg/kg, or 1 mg/kg;
(k) the concentration of antibody molecule required for 50% neutralization of influenza A virus is less than 10 µg/mL;
(l) it treats or prevents infection by an influenza B virus, e.g., B/Wisconsin/1/2010;
(m) it is effective for prevention or treatment of infection, e.g., in humans or mice, with an influenza B virus, e.g., B/Wisconsin/1/2010, when administered at 10 mg/kg, 6 mg/kg, 4 mg/kg, 3 mg/kg, 2 mg/kg, or 1 mg/kg;
(n) the concentration of antibody molecule required for 50% neutralization of influenza B virus, e.g., B/Wisconsin/1/2010, virus is less than 10 µg/mL;
(o) it prevents or minimizes a secondary infection (e.g., secondary bacterial infection) or an effects thereof on a subject;
(p) it is effective for preventing or minimizing secondary infection (e.g., secondary bacterial infection) or effects thereof on a subject when administered at 50 mg/kg, 25 mg/kg, 10 mg/kg, 6 mg/kg, 5 mg/kg, 4 mg/kg, 3 mg/kg, 2 mg/kg, or 1 mg/kg;
(q) it binds an epitope which comprises or consists of the hemagglutinin trimer interface; and (r) it binds an epitope other than that bound by a reference anti-HA antibody molecule, e.g., Ab 67-11, FI6, FI28, C179, F10, CR9114, or CR6261, e.g., as determined by a method described herein, e.g., a structural analysis (e.g., by X-ray crystallography or NMR spectroscopy) or a competition assay (e.g., by ELISA); or (s) it binds to an epitope, e.g., it has an epitope that overlaps with or is the same as, of an antibody disclosed herein, e.g., as determined by a method described herein (e.g., a mutational analysis or a crystal structure analysis).

In an embodiment, the antibody molecule has one, two, or all of the following characteristics: (i) the antibody molecule prevents infection by at least 1, 2, 3, 4 or 5 influenza subtypes of Group 1, and by at least 1, 2, 3, 4 or 5 influenza subtypes of Group 2; (ii) the concentration of the antibody molecule required for 50% neutralization of influenza A virus is less than 10 µg/mL; or (iii) the antibody molecule binds an epitope that comprises or consists of the hemagglutinin trimer interface.

In an embodiment, the antibody molecule treats or prevents infection by a Group 1 virus, such as where the virus is an H1, H2, H5, H6, H8, H9, H12, H11, H13, H16, or H17 virus; and treats or prevents infection by a Group 2 virus, such as where the virus is an H3, H4, H7, H10 or H15 virus. In an embodiment, the antibody molecule prevents infection by at least 1, 2, 3, 4, 5, 6, 7, 8, 9, 10 or 11 influenza subtypes of Group 1, and by at least 1, 2, 3, 4, 5 or 6 influenza subtypes of Group 2. In an embodiment, the antibody molecule treats or prevents infection by one or more of H1N1, H2N2, H5N1, or H9N2, and also treats or prevents infection by one or more of H3N2, H7N7, or H7N9.

In an embodiment, the antibody molecule binds, and in an embodiment, neutralizes: at least one strain from the Group 1 H1, e.g., H1a or H1b, cluster and at least one strain from the Group 2 H3 or H7 cluster. In an embodiment, the antibody molecule, binds, and in an embodiment, neutralizes: at least one strain from the Group 1 H1, e.g., H1a or H1b, cluster and at least one influenza B strain, e.g., B/Wisconsin/1/2010. In an embodiment, the antibody molecule binds, and in an embodiment, neutralizes: at least one strain from the Group 2 H3 or H7 cluster and at least one influenza B strain, e.g., B/Wisconsin/1/2010. In an embodiment, the antibody molecule binds, and in an embodiment, neutralizes: at least one strain from the Group 1 H1, e.g., H1a or H1b, cluster, at least one strain from the Group 2 H3 or H7 cluster, and at least one influenza B strain, e.g., B/Wisconsin/1/2010. In an embodiment, the antibody molecule treats or prevents infection by one or more of influenza B viruses, e.g., B/Wisconsin/1/2010.

In an embodiment, the antibody molecule is not an anti-HA antibody molecule previously described in the art. For example, the antibody molecule is other than one or more or all of Ab 67-11 (U.S. Provisional Application No. 61/645,453, U.S. Application Publication No. 2013/0302348, and International Application Publication No. WO 2013/169377), FI6 (FI6, as used herein, refers to any specifically disclosed FI6 sequence in U.S. Application Publication Nos. 2010/0080813 or 2011/0274702, International Application Publication No. WO2013/011347, or Corti et al., *Science* 333:850-856, 2011; FIG. 4), F128 (U.S. Application Publication No. 2010/0080813), C179 (Okuno et al., *J. Virol.* 67:2552-1558, 1993), F10 (Sui et al., *Nat. Struct. Mol. Biol.* 16:265, 2009), CR9114 (Dreyfus et al., *Science* 337(6100):1343-1348, 2012), or CR6261 (Ekiert et al., *Science* 324:246-251, 2009).

In an embodiment, the antibody molecule neutralizes infection with H1N1 and H3N2 in vitro. In another embodiment, the antibody molecule neutralizes infection with H1N1 and H3N2 in vivo. In an embodiment, the antibody molecule neutralizes infection with H5N1 in vitro. In another embodiment, the antibody molecule neutralizes infection with H5N1 in vivo. In an embodiment, the antibody molecule neutralizes infection with H7N9 in vitro. In another embodiment, the antibody molecule neutralizes infection with H7N9 in vivo. In an embodiment, the antibody molecule neutralizes infection with an influenza B virus, e.g., B/Wisconsin/1/2010, in vitro. In another embodiment, the antibody molecule neutralizes infection with an influenza B virus, e.g., B/Wisconsin/1/2010, in vivo.

In another embodiment, the concentration of the antibody molecule required for 50% neutralization of influenza A virus is 10 µg/mL or less, such as 9 µg/mL or less, 8 µg/mL or less, 7 µg/mL or less, 6 µg/mL or less, or 5 µg/mL or less. In another embodiment, the concentration of the antibody molecule required for 60% neutralization of influenza A virus, 50% neutralization of influenza A virus, or 40% neutralization of influenza A virus is 10 µg/mL or less, such as 9 µg/mL or less, 8 µg/mL or less, 7 µg/mL or less, 6 µg/mL or less, or 5 µg/mL or less.

In yet another embodiment, the antibody molecule is effective for prevention or treatment of infection, e.g., in humans or mice, with H1N1 or H3N2, such as when administered at 50 mg/kg, 25 mg/kg, 10 mg/kg, 6.0 mg/kg, 5.0 mg/kg, 4.0 mg/kg, 3.0 mg/kg, 2.0 mg/kg, 1.0 mg/kg or less. In still another embodiment, the antibody molecule is effective for prevention or treatment of infection, e.g., in humans or mice, with H5N1 or H7N9, such as when administered at 50 mg/kg, 25 mg/kg, 10 mg/kg, 6.0 mg/kg, 5.0 mg/kg, 4.0 mg/kg, 3.0 mg/kg, 2.0 mg/kg, 1.0 mg/kg or less. In another embodiment, the antibody molecule is effective for the treatment or prevention of a Group 1 virus, where the Group 1 virus is H1, H5, or H9, and in another embodiment, the anti-HA antibody molecule, is effective for the treatment or prevention of a Group 2 virus, where the Group 2 virus is H3 or H7.

In another embodiment, the concentration of the antibody molecule required for 50% neutralization of influenza B virus, e.g., B/Wisconsin/1/2010, is 10 µg/mL or less, such as 9 µg/mL or less, 8 µg/mL or less, 7 µg/mL or less, 6 µg/mL or less, or 5 µg/mL or less. In another embodiment, the concentration of the antibody molecule required for 60% neutralization of influenza B virus, e.g., B/Wisconsin/1/2010, 50% neutralization of influenza B virus, e.g., B/Wisconsin/1/2010, or 40% neutralization of influenza B virus, e.g., B/Wisconsin/1/2010, is 10 µg/mL or less, such as 9 µg/mL or less, 8 µg/mL or less, 7 µg/mL or less, 6 µg/mL or less, or 5 µg/mL or less.

In an embodiment, the antibody molecule comprises one or both of the following properties: (i) it fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); or (ii) it produces fewer escape mutants than does a reference anti-HA antibody molecule, such as Ab 67-11, F16, F128, C179, F10, CR9114, or CR6261, such as when tested by the method described in (i).

In another embodiment, the antibody molecule is a full length tetrameric antibody, a single chain antibody (scFv), a F(ab')$_2$ fragment, a Fab fragment, or an Fd fragment. In another embodiment, the heavy chain of the antibody molecule is a γ1 heavy chain, and in yet another embodiment, the light chain of the antibody molecule is a κ light chain or a λ light chain. In yet another embodiment, the antibody molecule is an IgG1 antibody.

In an embodiment, the antibody molecule binds an epitope that has one, two, three, four, five, or all of, the following properties a)-f): a) it includes one, two, or all of, H3 HA1 residues N38, I278, and D291; b) it includes H3 HA2 residue N12; c) it does not include one, two or all of, H3 HA1 residues Q327, T328, and R329; d) it does not include one, two, three, four, or all of, H3 HA2 residues G1, L2, F3, G4, and D46; e) it includes one, two, or all of, H3 HA1 residues T318, R321, and V323; or f) it includes 1, 2, 3, 4, 5, 6, 7, 8, 9, 10, 11, 12, 13, 14, 15, 16, 17, or all of, H3 HA2 residues A7, E11, I18, D19, G20, W21, L38, K39, T41, Q42, A43, I45, I48, N49, L52, N53, I56, and E57.

In an embodiment the antibody molecule has properties: a) and b). In an embodiment the antibody molecule has properties: c) and d). In an embodiment the antibody molecule has properties: a); and c) or d). In an embodiment the antibody molecule has properties: b); and c) or d). In an embodiment the antibody molecule has properties: c); and a) or b). In an embodiment the antibody molecule has properties: d); and a) or b). In an embodiment the antibody molecule has properties: a), b), c) and d). In an embodiment the antibody molecule has properties: a), b), c), d), e), and f).

In an embodiment, the antibody molecule has a $K_D$ for H3 of equal to or less than $10^{-6}$ nM, wherein said $K_D$ is increased by at least 2, 5, 10, or 100 fold, by a mutation or mutations in any of: a) H3 HA1 residues N38, I278, or D291; b) H3 HA2 residue N12; c) H3 HA1 residues T318, R321, or V323; or d) H3 HA2 residues A7, E11, I18, D19, G20, W21, L38, K39, T41, Q42, A43, I45, I48, N49, L52, N53, I56, or E57. In an embodiment, the antibody molecule has a $K_D$ for H3 of equal to or less than $10^{-6}$ nM, wherein said $K_D$ is increased by no more than 2, or 5 fold, by a mutation or mutations in any of: e) H3 HA1 residues Q327, T328, or R329; or f) H3 HA2 residues G1, L2, F3, G4, or D46.

In an embodiment, the antibody molecule binds an epitope that has one, two, three, four, five, or all of, the following properties aa)-ff): aa) it includes one, two, or all of, H1 HA1 residues H31, N279, and S292; bb) it includes H1 HA2 residue G12; cc) it does not include one or both of H1 HA1 residues Q328 and S329; dd) it does not include one, two, three, four, or all of, H1 HA2 residues G1, L2, F3, G4, and D46; ee) it includes one, two, or all of, H1 HA1 residues T319, R322, and 1324 are bound by both Ab 044 and FI6; or ff) it includes 1, 2, 3, 4, 5, 6, 7, 8, 9, 10, 11, 12, 13, 14, 15, 16, 17, or all of, H1 HA2 residues A7, E11, I18, D19, G20, W21, Q38, K39, T41, Q42, N43, I45, I48, T49, V52, N53, I56, and E57. In an embodiment, the antibody molecule has properties: aa) and bb). In an embodiment, the antibody molecule has properties: cc) and dd). In an embodiment, the antibody molecule has properties: aa); and cc) or dd). In an embodiment, the antibody molecule has properties: bb); and cc) or dd). In an embodiment, the antibody molecule has properties: cc); and aa) or bb). In an embodiment, the antibody molecule has properties: dd); and aa) or bb). In an embodiment, the antibody molecule has properties: aa), bb), cc) and dd). In an embodiment, the antibody molecule has properties: aa), bb), cc), dd), ee), and ff).

In an embodiment, the antibody molecule has a $K_D$ for H1 of equal to or less than $10^{-6}$ nM, wherein said $K_D$ is increased by at least 2, 5, 10, or 100 fold, by a mutation or mutations in any of: aa) H1 HA1 residues H31, N279, and S292; bb) H1 HA2 residue G12; cc) H1 HA1 residues T319, R322, and 1324; or dd) H1 HA2 residues A7, E11, I18, D19, G20, W21, Q38, K39, T41, Q42, N43, I45, I48, T49, V52, N53, I56, and E57. In an embodiment, the antibody molecule has a $K_D$ for H1 of equal to or less than $10^{-6}$ nM, wherein said $K_D$ is increased by no more than 2, or 5 fold, by a mutation or mutations in any of: ee) H1 HA1 residues Q328 and S329; or ff) H1 HA2 residues G1, L2, F3, G4, and D46.

In an embodiment, the antibody molecule has one, two, three or all of the following properties: a) and aa); b) and bb); c) and cc); or d) and dd), as described above. In an embodiment, the antibody molecule has properties c), cc), d), and dd), as described above.

In an embodiment, the antibody molecule comprises one or both of: a heavy chain variable region comprising at least, or more than, 60, 65, 70, 75, 80, 85, 87, 90, 95, 98 or 99 percent homology with a heavy chain variable region from Table 3, Table 4A, Table 4B, FIG. 2, FIG. 5 or FIG. 7; and a light chain variable region comprising at least, or more than, 60, 65, 70, 75, 80, 85, 87, 90, 95, 98 or 99 percent homology with light chain variable region from Table 3, Table 4A, Table 4B, FIGS. 3A-3B, FIGS. 6A-6B or FIG. 7.

In an embodiment, the antibody molecule comprises a heavy chain variable region 25 (SEQ ID NO: 25), or a structurally or functionally related variable heavy chain region as described herein.

In an embodiment, the antibody molecule comprises a light chain variable region 52 (SEQ ID NO: 52), 155 (SEQ ID NO: 155), or 45 (SEQ ID NO: 45), or a structurally or functionally related variable light chain region as described herein. In an embodiment, the antibody molecule comprises a heavy chain variable region 25 (SEQ ID NO: 25), or a structurally or functionally related variable heavy chain region as described herein; and a light chain variable region 52 (SEQ ID NO: 52), 155 (SEQ ID NO: 155), or 45 (SEQ ID NO: 45), or a structurally or functionally related variable light chain region as described herein.

In an embodiment, the antibody molecule comprises a heavy chain variable region comprising one, two, or all of CDR1, CDR2, and CDR3, from heavy chain variable region 25 (SEQ ID NO: 25), or a structurally or functionally related variable heavy chain region as described herein. In an embodiment, the antibody molecule comprises a light chain variable region comprising one, two, or all of CDR1, CDR2, and CDR3, from light chain variable region 52 (SEQ ID NO: 52), 155 (SEQ ID NO:155), or 45 (SEQ ID NO:45), or a structurally or functionally related sequence as described herein. In an embodiment, the antibody molecule comprises a heavy chain variable region comprising one, two, or all of CDR1, CDR2, and CDR3, from heavy chain variable region 25 (SEQ ID NO: 25), or a structurally or functionally related variable heavy chain region as described herein; and a light chain variable region comprising one, two, or all of CDR1, CDR2, and CDR3, from light chain variable region 52 (SEQ ID NO: 52), 155 (SEQ ID NO: 155), or 45 (SEQ ID NO: 45), or a structurally or functionally related variable light chain region as described herein.

In an embodiment, the antibody molecule comprises a heavy chain variable region from FIG. 2 or FIG. 5 or a structurally or functionally related variable heavy chain region as described herein. In an embodiment, the antibody molecule comprises a light chain variable region from FIGS.

3A-3B or FIGS. 6A-6B or a structurally or functionally related variable light chain region as described herein.

In an embodiment, the antibody molecule comprises one, two, or all of, a CDR1, CDR2, and CDR3 from a heavy chain variable region from FIG. 2 or FIG. 5, or a structurally or functionally related sequences as described herein. In an embodiment, the antibody molecule comprises one, two, or all of, a CDR1, CDR2, and CDR3 from a light chain variable region from FIGS. 3A-3B or FIGS. 6A-6B, or a structurally or functionally related sequences as described herein.

In an embodiment the antibody molecule comprises one, two or all of, HC CDR1, HC CDR2, and HC CDR3 and one, two or all of, LC CDR1, LC CDR2, and LC CDR3 from an antibody disclosed in Table 3, or a structurally or functionally related sequence as described herein.

In another embodiment, the antibody molecule comprises the light chain LC45 (SEQ ID NO: 45). In yet another embodiment, the antibody comprises the light chain LC45, and the heavy chain HC25 (SEQ ID NO: 25) or HC24 (SEQ ID NO: 24). In an embodiment, the antibody molecule comprises the light chain LC45 (SEQ ID NO: 45) and the heavy chain HC25 (SEQ ID NO: 25). In yet another embodiment, the antibody molecule comprises light chain LC52 (SEQ ID NO: 52) and heavy chain HC25 (SEQ ID NO: 25).

In an embodiment the antibody molecule comprises one or both of: a) one or more framework regions (FRs) from heavy chain disclosed herein, e.g., one or more or all of FR1, FR2, FR3, or FR4, or FR sequences that differ individually, or collectively, by no more than 1, 2, 3, 4, of 5 amino acid residues, e.g., conservative residues, from a heavy chain disclosed herein; and b) one or more framework regions (FRs) from light chain disclosed herein, e.g., one or more or all of FR1, FR2, FR3, or FR4, or FR sequences that differ individually, or collectively, by no more than 1, 2, 3, 4, of 5 amino acid residues, e.g., conservative residues, from a light chain disclosed herein.

In an embodiment, the antibody molecule comprises: (a) a heavy chain immunoglobulin variable domain comprising a sequence at least 60, 70, 80, 85, 87, 90, 95, 97, 98, or 99, e.g., 90%, homologous, to a heavy chain consensus sequence provided herein, e.g., the heavy chain consensus sequence provided in FIG. 2 or FIG. 5, e.g., the heavy chain consensus sequence provided in FIG. 2, SEQ ID NO: 161; and (b) a light chain immunoglobulin variable domain comprising a sequence at least 60, 70, 80, 85, 87, 90, 95, 97, 98, or 99, e.g., 95%, homologous, to a light chain consensus sequence provided herein, e.g., the light chain consensus sequence provided in FIGS. 3A-3B or FIG. 6, e.g., the light chain consensus sequence provided in FIGS. 3A-3B, SEQ ID NO: 62.

For example, in an embodiment, the antibody molecule disclosed herein comprises one or both of: (a) a heavy chain immunoglobulin variable domain comprising the sequence of SEQ ID NO: 161, or a sequence at least 87% identical to SEQ ID NO: 161; and (b) a light chain immunoglobulin variable domain comprising the sequence SEQ ID NO: 62, or a sequence at least 95% identical to SEQ ID NO: 62.

In another embodiment, the antibody molecule comprises: (a) a heavy chain immunoglobulin variable domain comprising the sequence of SEQ ID NO:161, or a sequence at least 87% identical to SEQ ID NO: 161; and (b) a light chain immunoglobulin variable domain comprising the sequence SEQ ID NO: 62, or a sequence at least 95% identical to SEQ ID NO: 62, wherein said antibody molecule: (i) fails to produce any escape mutants as determined by the failure of a viral titer to recover following at least 10, 9, 8, 7, 6, or 5 rounds of serial infections in cell culture with a mixture of the antibody molecule and an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010); and (ii) produces fewer escape mutants than does a reference anti-HA antibody molecule, e.g., Ab 67-11, F16, F128, C179, F10, CR9114, or CR6261, such as when tested by the method described in (i).

In an embodiment, the antibody molecule comprises one or both of: (a) a heavy chain immunoglobulin variable region comprising the sequence of SEQ ID NO: 161, or a sequence that differs from SEQ ID NO: 161 by not more than 1, 2, 3, 4, 5, 6, 8, 10, 11, 12, 13, 14, 15 or 16, e.g., by no more than 2, 3, 4, or 5 amino acids, e.g., conservative amino acids; and (b) a light chain immunoglobulin variable domain comprising the sequence SEQ ID NO: 62, or a sequence that differs from SEQ ID NO: 62 that differs by no more than 1, 2, 3, 4 or 5 amino acids, e.g., conservative amino acids.

In an embodiment, the 1, 2, 3, 4, 5, 6, 8, 10, 11, 12, 13, 14, 15 or 16 amino acid differences, e.g., conservative amino acid differences, in the heavy chain immunoglobulin variable region are in the FR regions of the heavy chain immunoglobulin variable domain. In another embodiment, the 1, 2, 3, 4 or 5 amino acid differences, e.g., conservative amino acid differences, in the light chain immunoglobulin variable domain are in the FR regions of the light chain immunoglobulin variable domain. In an embodiment, the amino acid differences in the heavy chain immunoglobulin variable region, or in the light chain immunoglobulin variable region, are conservative amino acid changes.

In an embodiment, the antibody molecule comprises one or both of: a) one or more framework regions (FRs) from heavy chain consensus sequence disclosed herein, e.g., one or more or all of FR1, FR2, FR3, or FR4, or sequences that differ individually, or collectively, by no more than 1, 2, 3, 4, of 5 amino acid residues, e.g., conservative residues, from a heavy chain variable region consensus sequence disclosed herein; and b) one or more framework regions (FRs) from light chain consensus sequence disclosed herein, e.g., one or more or all of FR1, FR2, FR3, or FR4, or sequences that differ individually, or collectively, by no more than 1, 2, 3, 4, of 5 amino acid residues, e.g., conservative residues, from a light chain variable region consensus disclosed herein.

In an embodiment, the antibody molecule binds to an epitope, e.g., an epitope that overlaps with or is the same as, of an antibody disclosed herein, e.g., as determined by mutational analysis or crystal structure analysis.

In an embodiment, the antibody molecule competes with a reference antibody molecule, e.g., an antibody molecule described herein, for binding to a substrate, e.g., an HA.

The HA can be from a Group 1 strain, e.g., HA1 or HA5, e.g., from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004Binding to the same epitope, or a portion thereof, can be shown by one or more of: a) mutational analysis, e.g., binding to HA, or binding affinity for HA, is decreased or abolished if a residue is mutated; b) analysis, e.g., comparison, of the crystal structure of the antibody molecule and HA and the crystal structure of a reference antibody and HA, e.g., to determine the touch points of each; c) competition of the two antibodies for binding to HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/ 2004; or d) (c) and one or both of (a) and (b).

Competition between the antibody molecule and a reference antibody molecule can be determined by evaluating the ability of the antibody molecule or the reference antibody molecule to decrease binding of the other to a substrate, e.g., HA, e.g., HA1 or HA5, from, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004. Reduction of the ability to bind can be evaluated by methods in the art. Reduction of the ability to bind can be evaluated, e.g., by one or more of: a) BIAcore analysis; b) ELISA assay; or c) flow cytometry. The antibody molecule can compete with the reference antibody such that binding of the reference antibody is decreased by 50% or more.

In an embodiment, the antibody molecule binds to the same epitope, or a portion thereof, which the reference antibody molecule binds. In an embodiment, the antibody molecule does not bind to the same epitope, or a portion thereof, which the reference antibody molecule binds.

In an embodiment, the antibody molecule comprises a structural or functional property of Ab 044.

In an embodiment, the antibody molecule competes with a reference antibody molecule, e.g., an antibody molecule described herein, for binding to a substrate, e.g., an HA. The reference antibody molecule can be: a) an antibody molecule comprising: i) a heavy chain immunoglobulin variable region segment comprising a CDR1 comprising the sequence S-Y-A-M-H (SEQ ID NO: 68); a CDR2 comprising the sequence V-V-S-Y-D-G-N-Y-K-Y-Y-A-D-S-V-Q-G (SEQ ID NO: 69); and a CDR3 comprising the sequence D-S-R-L-R-S-L-L-Y-F-E-W-L-S-Q-G-Y-F-N-P (SEQ ID NO:70); and ii) a light chain variable region segment comprising: a CDR1 comprising the sequence Q-S-I-T-F-D-Y-K-N-Y-L-A (SEQ ID NO:145); a CDR2 comprising the sequence W-G-S-Y-L-E-S (SEQ ID NO:72); and a CDR3 comprising the sequence Q-Q-H-Y-R-T-P-P-S (SEQ ID NO:73); b) an antibody molecule comprises one or both of: (i) a heavy chain immunoglobulin variable region segment comprising SEQ ID NO: 25; and (ii) a light chain variable region segment comprising SEQ ID NO: 52; or c) Ab 044.

In an embodiment, the antibody molecule binds to the same epitope, or a portion thereof, on HA, as does a reference antibody molecule, e.g., an antibody molecule disclosed herein. The reference antibody molecule can be: a) an antibody molecule comprising: i) a heavy chain immunoglobulin variable region segment comprising a CDR1 comprising the sequence S-Y-A-M-H (SEQ ID NO: 68); a CDR2 comprising the sequence V-V-S-Y-D-G-N-Y-K-Y-Y-A-D-S-V-Q-G (SEQ ID NO: 69); and a CDR3 comprising the sequence D-S-R-L-R-S-L-L-Y-F-E-W-L-S-Q-G-Y-F-N-P (SEQ ID NO: 70); and ii) a light chain variable region segment comprising: a CDR1 comprising the sequence Q-S-I-T-F-D-Y-K-N-Y-L-A (SEQ ID NO: 145); a CDR2 comprising the sequence W-G-S-Y-L-E-S (SEQ ID NO: 72); and a CDR3 comprising the sequence Q-Q-H-Y-R-T-P-P-S (SEQ ID NO: 73); b) an antibody molecule comprises one or both of: (i) a heavy chain immunoglobulin variable region segment comprising SEQ ID NO: 25; and (ii) a light chain variable region segment comprising SEQ ID NO:52; or c) Ab 044.

In an embodiment, the an antibody molecule comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 52.

In an embodiment, the antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 52, wherein, each HC CDR differs by no more than 1, 2, 3, 4 or 5 amino acids, e.g., 1 or 2, e.g., conservative amino acids, from the corresponding CDR of SEQ ID NO: 25 and each LC CDR differs by no more than 1, 2, 3, 4 or 5 amino acids, e.g., 1 or 2, e.g., conservative amino acids, from the corresponding CDR of SEQ ID NO: 52.

In an embodiment, the antibody molecule comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 52, wherein the antibody molecule comprises 1, 2, 3, 4, 5, or all of: (i) a HC CDR1 comprising: S at the 1st position and A at the $3^{rd}$ position in HC CDR1; (ii) a HC CDR2 comprising one or both, e.g., one of: V at the $2^{nd}$ position; or N at the $7^{th}$ position and Q at the $16^{th}$ position in HC CDR2; (iii) a HC CDR3 comprising: R at the $3^{rd}$ position (and optionally, L at the $3^{rd}$ position); (iv) a LC CDR1 comprising one or both of, e.g., one of: I at the $3^{rd}$ position; or D at the 6th position in LC CDR1; (v) a LC CDR2 comprising one, two, or three of, e.g., one of: G at the $2^{nd}$ position; Y at the $4^{th}$ position; or L at the $5^{th}$ position in LC CDR2; (vi) a LC CDR3 comprising: S at the $9^{th}$ position in LC CDR3.

In an embodiment, the antibody molecule, comprises: (a) a heavy chain immunoglobulin variable region segment comprising SEQ ID NO: 25 (or a sequence that differs by no more than 1, 2, 3, 4 or 5 amino acids, e.g., conservative amino acids, therefrom); and (b) a light chain variable region segment comprising SEQ ID NO: 52 (or a sequence that differs by no more than 1, 2, 3, 4 or 5 amino acids, e.g., conservative amino acids, therefrom).

In an embodiment, the antibody molecule comprises one or both of: (a) a heavy chain immunoglobulin variable region segment comprising a CDR1 comprising the sequence S-Y-A-M-H (SEQ ID NO: 68) (or a sequence that differs by no more than, 1, 2, 3, 4, or 5, e.g., 1 or 2 amino acids, e.g., conservative amino acids, therefrom); a CDR2 comprising the sequence V-V-S-Y-D-G-N-Y-K-Y-Y-A-D-S-V-Q-G (SEQ ID NO: 69) (or a sequence that differs by no more than, 1, 2, 3, 4, or 5, e.g., 1 or 2 amino acids, e.g., conservative amino acids, therefrom); a CDR3 comprising the sequence D-S-R-L-R-S-L-L-Y-F-E-W-L-S-Q-G-Y-F-N-P (SEQ ID NO: 70) (or a sequence that differs by no more than, 1, 2, 3, 4, or 5, e.g., 1 or 2 amino acids, e.g., conservative amino acids, therefrom); and (b) a light chain variable region segment comprising a CDR1 comprising the sequence: Q-S-I-T-F-D-Y-K-N-Y-L-A (SEQ ID NO: 145) (or a sequence that differs by no more than, 1, 2, 3, 4, or 5, e.g., 1 or 2 amino acids, e.g., conservative amino acids, therefrom); a CDR2 comprising the sequence W-G-S-Y-L-E-S (SEQ ID NO: 72) (or a sequence that differs by no more than, 1, 2, 3, 4, or 5, e.g., 1 or 2 amino acids, e.g., conservative amino acids, therefrom); a CDR3 comprising the sequence Q-Q-H-Y-R-T-P-P-S (SEQ ID NO: 73) (or a sequence that differs by no more than, 1, 2, 3, 4, or 5, e.g., 1 or 2 amino acids, e.g., conservative amino acids, therefrom).

In an embodiment, the antibody molecule comprises one or both of: a) LC CDR1-3, that collectively, differ from the Ab 044 LC CDR1-3 by no more than, 1, 2, 3, 4, 5, 6, 7, 8, 9, or 10, e.g., 1, 2, 3, or 4, amino acids, e.g., conservative amino acids; and b) HC CDR1-3, that collectively, differ from the Ab 044 HC CDR1-3 by no more than, 1, 2, 3, 4, 5, 6, 7, 8, 9, or 10, e.g., 1, 2, 3, or 4, amino acids, e.g., conservative amino acids.

In an embodiment, the antibody molecule comprises one or both of: (a) a heavy chain immunoglobulin variable region segment comprising SEQ ID NO: 25; and (b) a light chain variable region segment comprising SEQ ID NO: 52.

In an embodiment, the antibody molecule comprises one or both of: (a) a heavy chain immunoglobulin variable region segment comprising a CDR1 comprising the sequence S-Y-A-M-H (SEQ ID NO: 68) (or a sequence that differs by no more than, 1, 2, or 3, e.g., 1 or 2, amino acids, e.g., conservative amino acids, there from, optionally provided that at least 1 or 2 of the highlighted residue are not changed, e.g., both S and A are not changed); a CDR2 comprising the sequence V-V-S-Y-D-G-N-Y-K-Y-A-D-S-V-Q-G (SEQ ID NO: 69) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., V or both N and Q or all three of V, N, and Q are not changed); a CDR3 comprising the sequence D-S-R-L-R-S-L-L-Y-F-E-W-L-S-Q-G-Y-F-N-P (SEQ ID NO: 70) (or a sequence that differs by no more than, 1, 2, 3, 4, or 5, e.g., 1 or 2 amino acids, e.g., conservative amino acids, therefrom, optionally provided that R is not changed); and (b) a light chain variable region segment comprising a CDR1 comprising the sequence: Q-S-I-T-F-D-Y-K-N-Y-L-A (SEQ ID NO: 145) (or a sequence that differs by no more than, 1, 2, 3, 4, or 5, e.g., 1 or 2, amino acids, e.g., conservative amino acids, therefrom, optionally provided that at least 1 or 2 of the highlighted residues are not changed, e.g., I or D is not changed); a CDR2 comprising the sequence W-G-S-Y-L-E-S (SEQ ID NO: 72) (or a sequence that differs by no more than, 1, 2, 3, 4, or 5, e.g., 1 or 2, amino acids, e.g., conservative amino acids, therefrom, optionally provided that at least 1, 2 or 3 of the highlighted residues are not changed, e.g., 1, 2 or all of G, Y, and L are not changed); a CDR3 comprising the sequence Q-Q-H-Y-R-T-P-P-S (SEQ ID NO: 73) (or a sequence that differs by no more than, 1, 2, 3, 4, or 5, e.g., 1 or 2 amino acids, e.g., conservative amino acids, therefrom, optionally provided that at least 1 or both of the highlighted residues are not changed, e.g., S is not changed). In an embodiment, a CDR of the light or heavy chain includes one of the highlighted residues, or one of the highlighted combinations of residues, for that CDR, (e.g., while other residues in that CDR might be changed, the highlighted residue or combination of residues, are not changed). For example, in an embodiment, V or both N and Q, for heavy chain CDR2 are not changed.

In an embodiment, a CDR of the light chain and a CDR of the heavy chain each includes one of the highlighted residues, or one of the highlighted combinations of residues, for that CDR. In an embodiment, each of two CDRs in the antibody molecule includes one of the highlighted residues, or one of the highlighted combinations of residues, for that CDR. In an embodiment, both are in the light chain. In an embodiment, both are in the heavy chain. In an embodiment, each of the three CDRs in the heavy chain includes one of the highlighted residues, or one of the highlighted combinations of residues, for that CDR. In an embodiment, each of the three CDRs in the light chain includes one of the highlighted residues, or one of the highlighted combinations of residues, for that CDR. In an embodiment, each of the six CDRs in the heavy and light chain includes one of the highlighted residues, or one of the highlighted combinations of residues, for that CDR.

In an embodiment, the antibody molecule comprises one or more (e.g., 2, 3, 4, 5, or all) of the following properties: (a) both S and A in HC CDR1 are unchanged; (b) V or both N and Q or all three of V, N, and Q in HC CDR2 are unchanged; (c) R in HC CDR3 is unchanged; (d) One or both of I and D in LC CDR1 are unchanged; (e) 1, 2 or 3 of G, Y, and L in LC CDR2 are unchanged; or (f) S in LC CDR3 is unchanged. In an embodiment, the antibody molecule comprises 1, 2, 3, 4, 5, or all 6 properties selected from (a) to (f). In an embodiment, the antibody molecule comprises a heavy chain having a one or more properties selected from (a), (b), and (c) and a light chain having one or more properties selected from (d), (e), and (f).

In an embodiment, the antibody molecule comprises one or both of: (a) a heavy chain immunoglobulin variable region segment comprising: a CDR1 comprising the sequence S-Y-A-M-H (SEQ ID NO: 68); a CDR2 comprising the sequence V-V-S-Y-D-G-N-Y-K-Y-A-D-S-V-Q-G (SEQ ID NO: 69); a CDR3 comprising the sequence D-S-R-L-R-S-L-L-Y-F-E-W-L-S-Q-G-Y-F-N-P (SEQ ID NO: 70); and (b) a light chain variable region segment comprising a CDR1 comprising the sequence Q-S-I-T-F-D-Y-K-N-Y-L-A (SEQ ID NO: 145); a CDR2 comprising the sequence W-G-S-Y-L-E-S (SEQ ID NO:72); and a CDR3 comprising the sequence Q-Q-H-Y-R-T-P-P-S (SEQ ID NO: 73).

In an embodiment, the antibody molecule comprises one or both of: a) one or more framework regions (FRs) from SEQ ID NO: 25 e.g., the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 25; and b) one or more framework regions (FRs) from SEQ ID NO: 52. For example, the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 52.

In an embodiment, the antibody molecule comprises: (a) a heavy chain immunoglobulin variable region segment that further comprises one or more or all of: an FR1 comprising the sequence Q-V-Q-L-L-E-T-G-G-G-L-V-K-P-G-Q-S-L-K-L-S-C-A-A-S-G-F-T-F-T (SEQ ID NO: 74) (or a sequence that differs by no more than, 1, 2, 3, 4, or 5, e.g., 1 or 2, amino acids, e.g., conservative amino acids, therefrom, optionally provided that T is not changed); an FR2 comprising the sequence W-V-R-Q-P-P-G-K-G-L-E-W-V-A (SEQ ID NO: 75) (or a sequence that differs by no more than, 1, 2, 3, 4, or 5, e.g., 1 or 2, amino acids, e.g., conservative amino acids, therefrom, optionally provided that W is not changed, or that if changed, is other than R); an FR3 comprising the sequence R-F-T-I-S-R-D-N-S-K-N-T-L-Y-L-Q-M-N-S-L-R-A-E-D-T-A-V-Y-Y-C-A-K (SEQ ID NO: 76) (or a sequence that differs by no more than, 1, 2, 3, 4, or 5, e.g., 1 or 2, amino acids, e.g., conservative amino acids, therefrom, optionally provided that one, two or three of I, R, or L is not changed, or that if I is changed it is other than G, if R is changed it is other than P. or if L is changed it is other than A); and an FR4 comprising the sequence W-G-Q-G-T-T-L-T-V-S-S (SEQ ID NO: 77) (or a sequence that differs by no more than, 1, 2, 3, 4, or 5, e.g., 1 or 2, amino acids, e.g., conservative amino acids, therefrom) or W-G-Q-G-T-T-V-T-V-S-S (SEQ ID NO: 171) (or a sequence that differs by no more than, 1, 2, 3, 4, or 5, e.g., 1 or 2, amino acids, e.g., conservative amino acids, therefrom); and (b) a light chain immunoglobulin variable region segment comprising one or more or all of: an FR1 comprising the sequence D-I-Q-M-T-Q-S-P-S-S-L-S-A-S-V-G-D-R-V-T-I-T-C-R-S-S (SEQ ID NO: 78) (or a sequence that differs by no more than, 1, 2, 3, 4, or 5, e.g., 1 or 2, amino acids, e.g., conservative amino acids, therefrom, optionally provided that R is not changed); an FR2 comprising the sequence W-Y-Q-Q-K-P-G-K-A-P-K-L-L-I-Y (SEQ ID NO: 79) (or a sequence that differs by no more than, 1, 2, 3, 4, or 5, e.g., 1 or 2 amino acids, e.g., conservative amino acids, therefrom); an FR3 comprising the sequence G-V-P-S-R-F-S-G-S-G-S-G-T-D-F-T-L-T-I-S-S-L-Q-P-E-D-F-A-T-Y-Y-C (SEQ ID NO: 80) (or a sequence that differs by no more than, 1, 2, 3, 4, or 5, e.g., 1 or 2 amino acids, e.g., conservative amino acids, therefrom, optionally provided that C is not changed, or if changed, is other than P); and an FR4 comprising the sequence F-G-Q-G-T-K-V-E-I-K (SEQ ID NO: 81) (or a sequence that differs by no more than, 1, 2, 3, 4, or 5, e.g., 1 or 2 amino acids, e.g., conservative amino acids, therefrom). In an embodiment, a FR of the light or heavy chain includes one of the highlighted residues, or one of the highlighted combinations of residues, for that FR, (e.g., while other residues in that FR might be changed, the highlighted residue or combination of residues, are not changed). For example, in an embodiment, one, two or three of I, R, or L for heavy chain FR3 is not changed.

In an embodiment, a FR of the light chain and a FR of the heavy chain each includes one of the highlighted residues, or one of the highlighted combinations of residues, for that FR. In an embodiment, each of two FRs in the antibody molecule includes one of the highlighted residues, or one of the highlighted combinations of residues, for that FR. In an embodiment, both are in the light chain. In an embodiment, both are in the heavy chain. In an embodiment, each of FR2 and FR3 in the heavy chain includes one of the highlighted residues, or one of the highlighted combinations of residues, for that FR. In an embodiment, each of FR1 and FR2 in the heavy and light chain includes one of the highlighted residues for that FR. In an embodiment, all of the highlighted residues in heavy chain FR1-4 are unchanged. In an embodiment, all of the highlighted residues in light chain FR1-4 are unchanged. In an embodiment, all of the highlighted residues in both heavy and light chain FR1-4 are unchanged.

In an embodiment, sequence of FR1 of the heavy chain variable region segment is Q-V-Q-L-L-E-T-G-G-G-L-V-K-P-G-Q-S-L-K-L-S-C-A-A-S-G-F-T-F-T (SEQ ID NO: 74). In an embodiment, sequence of FR1 of the heavy chain variable region segment is E-V-Q-L-L-E-S-G-G-G-L-V-K-P-G-Q-S-L-K-L-S-C-A-A-S-G-F-T-F-T (SEQ ID NO: 183).

In another embodiment, the antibody molecule comprises a structural or functional property of Ab 069.

In an embodiment, the antibody molecule competes with a reference antibody molecule, e.g., an antibody molecule described herein, for binding to a substrate, e.g., an HA. The reference antibody molecule can be: a) an antibody molecule comprising: i) a heavy chain immunoglobulin variable region segment comprising a CDR1 comprising the sequence S-Y-A-M-H (SEQ ID NO: 68); a CDR2 comprising the sequence V-V-S-Y-D-G-N-Y-K-Y-Y-A-D-S-V-Q-G (SEQ ID NO: 69); and a CDR3 comprising the sequence D-S-R-L-R-S-L-L-Y-F-E-W-L-S-Q-G-Y-F-N-P (SEQ ID NO: 70); and ii) a light chain variable region segment comprising: a CDR1 comprising the sequence Q-S-I-T-F-E-Y-K-N-Y-L-A (SEQ ID NO:172); a CDR2 comprising the sequence W-G-S-Y-L-E-S (SEQ ID NO:72); and a CDR3 comprising the sequence Q-Q-H-Y-R-T-P-P-S (SEQ ID NO: 73); b) an antibody molecule comprises one or both of: (i) a heavy chain immunoglobulin variable region segment comprising SEQ ID NO: 25; and (ii) a light chain variable region segment comprising SEQ ID NO:155; or c) Ab 069.

In an embodiment, the antibody molecule binds to the same epitope, or a portion thereof, on HA, as does a reference antibody molecule, e.g. an antibody molecule disclosed herein. The reference antibody molecule can be: a) an antibody molecule comprising: i) a heavy chain immunoglobulin variable region segment comprising a CDR1 comprising the sequence S-Y-A-M-H (SEQ ID NO: 68); a CDR2 comprising the sequence V-V-S-Y-D-G-N-Y-K-Y-Y-A-D-S-V-Q-G (SEQ ID NO: 69); and a CDR3 comprising the sequence D-S-R-L-R-S-L-L-Y-F-E-W-L-S-Q-G-Y-F-N-P (SEQ ID NO: 70); and ii) a light chain variable region segment comprising: a CDR1 comprising the sequence Q-S-I-T-F-E-Y-K-N-Y-L-A (SEQ ID NO: 172); a CDR2 comprising the sequence W-G-S-Y-L-E-S (SEQ ID NO:72); and a CDR3 comprising the sequence Q-Q-H-Y-R-T-P-P-S (SEQ ID NO: 73); b) an antibody molecule comprises one or both of: (i) a heavy chain immunoglobulin variable region segment comprising SEQ ID NO: 25; and (ii) a light chain variable region segment comprising SEQ ID NO: 155; or c) Ab 069.

In an embodiment the antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 155.

In an embodiment the antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 155, wherein each HC CDR differs by no more than 1, 2, 3, 4 or 5 amino acids, e.g., 1 or 2, e.g., conservative amino acids, from the corresponding CDR of SEQ ID NO: 25 and each LC CDR differs by no more than 1, 2, 3, 4 or 5 amino acids, e.g., 1 or 2, e.g., conservative amino acids, from the corresponding CDR of SEQ ID NO: 155.

In an embodiment the antibody molecule, comprises one or both of: a heavy chain variable region comprising at least 60, 70, 80, 85, 90, 95, 98 or 99 percent homology with SEQ ID NO: 25; and a light chain variable region comprising at least 60, 70, 80, 85, 90, 95, 98 or 99 percent homology with SEQ ID NO: 155, wherein the antibody molecule comprises 1, 2, 3, 4, 5, or all of: (i) a HC CDR1 comprising: S at the 1st position and A at the $3^{rd}$ position in HC CDR1; (ii) a HC CDR2 comprising one or both, e.g., one of: V at the 2nd position; or N at the $7^{th}$ position and Q at the $16^{th}$ position in HC CDR2; (iii) a HC CDR3 comprising: R at the $3^{rd}$ position (and optionally, L at the $3^{rd}$ position); (iv) a LC CDR1 comprising one or both of, e.g., one of: I at the $3^{rd}$ position; or E at the $6^{th}$ position in LC CDR1; (v) a LC CDR2 comprising one, two or three of, e.g., one of: G at the $2^{nd}$ position; Y at the $4^{th}$ position; or L at the $5^{th}$ position in LC CDR2; (vi) a LC CDR3 comprising: S at the $9^{th}$ position in LC CDR3.

In an embodiment, the antibody molecule, comprises one or both of: (a) a heavy chain immunoglobulin variable region segment comprising SEQ ID NO: 25 (or a sequence that differs by no more than 1, 2, 3, 4 or 5 amino acids, e.g., conservative amino acids, therefrom); and (b) a light chain variable region segment comprising SEQ ID NO: 155 (or a sequence that differs by no more than 1, 2, 3, 4 or 5 amino acids, e.g., conservative amino acids, therefrom).

In an embodiment, the antibody molecule comprises one or both of: (a) a heavy chain immunoglobulin variable region segment comprising SEQ ID NO: 25; and (b) a light chain variable region segment comprising SEQ ID NO: 155.

In an embodiment, the antibody molecule comprises one or both of: (a) a heavy chain immunoglobulin variable region segment comprising a CDR1 comprising the sequence S-Y-A-M-H (SEQ ID NO: 68) (or a sequence that differs by no more than, 1, 2, 3, 4, or 5, e.g., 1 or 2 amino acids, e.g., conservative amino acids, therefrom); a CDR2 comprising the sequence V-V-S-Y-D-G-N-Y-K-Y-Y-A-D-S-V-Q-G (SEQ ID NO: 69) (or a sequence that differs by no more than, 1, 2, 3, 4, or 5, e.g., 1 or 2 amino acids, e.g., conservative amino acids, therefrom); a CDR3 comprising the sequence D-S-R-L-R-S-L-L-Y-F-E-W-L-S-Q-G-Y-F-N-P (SEQ ID NO: 70) (or a sequence that differs by no more than, 1, 2, 3, 4, or 5, e.g., 1 or 2 amino acids, e.g., conservative amino acids, therefrom); and (b) a light chain variable region segment comprising a CDR1 comprising the sequence: Q-S-I-T-F-E-Y-K-N-Y-L-A (SEQ ID NO: 172) or a sequence that differs by no more than, 1, 2, 3, 4, or 5, e.g., 1 or 2 amino acids, e.g., conservative amino acids, therefrom); a CDR2 comprising the sequence W-G-S-Y-L-E-S (SEQ ID NO: 72) (or a sequence that differs by no more than, 1, 2, 3, 4, or 5, e.g., 1 or 2 amino acids, e.g., conservative amino acids, therefrom); a CDR3 comprising the sequence Q-Q-H-Y-R-T-P-P-S (SEQ ID NO: 73) (or a sequence that differs by no more than, 1, 2, 3, 4, or 5, e.g., 1 or 2 amino acids, e.g., conservative amino acids, therefrom).

In an embodiment, the antibody molecule comprises one or both of: a) LC CDR1-3, that collectively, differ from the Ab 069 LC CDR1-3 by no more than, 1, 2, 3, 4, 5, 6, 7, 8, 9, or 10, e.g., 1, 2, 3, or 4, amino acids, e.g., conservative amino acids; and b) HC CDR1-3, that collectively, differ from the Ab 069 HC CDR1-3 by no more than, 1, 2, 3, 4, 5, 6, 7, 8, 9, or 10, e.g., 1, 2, 3, or 4, amino acids, e.g., conservative amino acids.

In an embodiment, the antibody molecule comprises one or both of: (a) a heavy chain immunoglobulin variable region segment comprising a CDR1 comprising the sequence S̲-Y-A̲-M-H (SEQ ID NO: 68) (or a sequence that differs by no more than, 1, 2, or 3, e.g., 1 or 2 amino acids, e.g., conservative amino acids, therefrom, optionally provided that at least 1 or 2 of the highlighted residues are not changed, e.g., both S̲ and A̲ are not changed); a CDR2 comprising the sequence V-V̲-S-Y-D-G-N̲-Y-K-Y-Y-A-D-S-V-Q-G (SEQ ID NO: 69) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., V̲ or both N̲ and Q or all three of V̲, N̲, and Q are not changed); a CDR3 comprising the sequence D-S-R̲-L-R-S-L-L-Y-F-E-W-L-S-Q-G-Y-F-N-P (SEQ ID NO: 70) (or a sequence that differs by no more than, 1, 2, 3, 4, or 5, e.g., 1 or 2 amino acids, e.g., conservative amino acids, therefrom optionally provided that, R̲ is not changed); and (b) a light chain variable region segment comprising a CDR1 comprising the sequence: Q-S-I̲-T-F-E̲-Y-K-N-Y-L-A (SEQ ID NO: 172) or a sequence that differs by no more than, 1, 2, 3, 4, or 5, e.g., 1 or 2 amino acids, e.g., conservative amino acids, therefrom, optionally provided that at least 1 or 2 of the highlighted residues are not changed, e.g., I̲ or E̲ is not changed); a CDR2 comprising the sequence W-G̲-S-Y̲-L-E-S (SEQ ID NO: 72) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., 1, 2 or all of G̲, Y̲, and L̲ are not changed); a CDR3 comprising the sequence Q-Q-H̲-Y-R-T-P-P-S̲ (SEQ ID NO: 73) (or a sequence that differs by no more than, 1, 2, 3, 4, or 5, e.g., 1 or 2 amino acids, e.g., conservative amino acids, therefrom, optionally provided that, at least one or both of the highlighted residues are not changed, e.g., S is not changed).

In an embodiment, a CDR of the light or heavy chain includes one of the highlighted residues, or one of the highlighted combinations of residues, for that CDR (e.g., while other residues in that CDR might be changed, the highlighted residue or combination of residues, are not changed). In an embodiment, a CDR of the light and a CDR of the heavy chain each includes one of the highlighted residues, or one of the highlighted combinations of residues, for that CDR. In an embodiment, each of two CDRs in the antibody molecule includes one of the highlighted residues, or one of the highlighted combinations of residues, for that CDR. In an embodiment, both are in the light chain. In an embodiment, both are in the heavy chain. In an embodiment, each of the three CDRs in the heavy chain includes one of the highlighted residues, or one of the highlighted combinations of residues, for that CDR. In an embodiment, each of the three CDRs in the light chain includes one of the highlighted residues, or one of the highlighted combinations of residues, for that CDR. In an embodiment, each of the six CDRs in the heavy and light chain includes one of the highlighted residues, or one of the highlighted combinations of residues, for that CDR.

In an embodiment, the antibody molecule comprises one or more (e.g., 2, 3, 4, 5, or all) of the following properties: (a) both S̲ and A̲ in HC CDR1 are unchanged; (b) V̲ or both N̲ and Q̲ or all three of V̲, N̲, and Q in HC CDR2 are unchanged; (c) R̲ in HC CDR3 is unchanged; (d) one or both of I̲ and E̲ in LC CDR1 are unchanged; (e) 1, 2 or 3 of G̲, Y̲, and L̲ in LC CDR2 are unchanged; or (f) S in LC CDR3 is unchanged. In an embodiment the antibody molecule comprises 1, 2, 3, 4, 5, or all 6 properties selected from (a) to (f). In an embodiment, the antibody molecule comprises a heavy chain having a one or more properties selected from (a), (b), and (c) and a light chain having one or more properties selected from (d), (e), and (f).

In an embodiment, the antibody molecule comprises one or both of: (a) a heavy chain immunoglobulin variable region segment comprising: a CDR1 comprising the sequence S-Y-A-M-H (SEQ ID NO: 68); a CDR2 comprising the sequence V-V-S-Y-D-G-N-Y-K-Y-Y-A-D-S-V-Q-G (SEQ ID NO: 69); a CDR3 comprising the sequence D-S-R-L-R-S-L-L-Y-F-E-W-L-S-Q-G-Y-F-N-P (SEQ ID NO: 70); and (b) a light chain variable region segment comprising a CDR1 comprising the sequence Q-S-I-T-F-E-Y-K-N-Y-L-A (SEQ ID NO: 172); a CDR2 comprising the sequence W-G-S-Y-L-E-S (SEQ ID NO: 72); and a CDR3 comprising the sequence Q-Q-H-Y-R-T-P-P-S (SEQ ID NO: 73).

In an embodiment, the antibody molecule comprises one or both of: a) one or more framework regions (FRs) from SEQ ID NO: 25, e.g., one or more or all of FR1, FR2, FR3, or FR4, or sequences that differ individually, or collectively, by no more than 1, 2, 3, 4, of 5 amino acid residues, e.g., conservative residues, from SEQ ID NO: 25; and b) one or more framework regions (FRs) from SEQ ID NO: 155, e.g., one or more or all of FR1, FR2, FR3, or FR4, or sequences that differ individually, or collectively, by no more than 1, 2, 3, 4, of 5 amino acid residues, e.g., conservative residues, from SEQ ID NO: 155.

In an embodiment, the antibody molecule comprises: (a) a heavy chain immunoglobulin variable region segment that further comprises one or more or all of: an FR1 comprising the sequence Q-V-Q-L-L-E-T-G-G-G-L-V-K-P-G-Q-S-L-K-L-S-C-A-A-S-G-F-T-F-T̲ (SEQ ID NO:74) (or a sequence that differs by no more than, 1, 2, 3, 4, or 5, e.g., 1 or 2, amino acids, e.g., conservative amino acids, therefrom, optionally provided that T̲ is not changed); an FR2 comprising the sequence W̲-V-R-Q-P-P-G-K-G-L-E-W̲-V-A (SEQ ID NO: 75) (or a sequence that differs by no more than, 1, 2, 3, 4, or 5, e.g., 1 or 2, amino acids, e.g., conservative amino acids, therefrom, optionally provided that W̲ is not changed, or that if changed, is other than R); an FR3 comprising the sequence R-F-T-I̲-S-R̲-D-N-S-K-N-T-L̲-Y-L-Q-M-N-S-L-R-A-E-D-T-A-V-Y̲-Y-C̲-A-K (SEQ ID NO: 76) (or a sequence that differs by no more than, 1, 2, 3, 4, or 5, e.g., 1 or 2, amino acids, e.g., conservative amino acids, therefrom, optionally provided that one, two or three of I̲, R̲, or L̲ is not changed, or that if I̲ is changed is other than G, if R is changed it is other than P. or if L̲ is changed it is other than A); and (b) the light chain immunoglobulin variable region segment comprises one or more or all of an FR1 comprising the sequence D-I-Q-M-T-Q-S-P-S-S-L-S-A-S-V-G-D-R-V-T-I-T-C-R̲-S-S (SEQ ID NO: 78) (or a sequence that differs by no more than, 1, 2, 3, 4, or 5, e.g., 1 or 2 amino acids, e.g., conservative amino acids, therefrom, optionally provided that R̲ is not changed); an FR2 comprising the sequence W-Y-Q̲-Q-K-P-G-K-A-P-K-L-L-I-Y (SEQ ID NO: 79) (or a sequence that differs by no more than, 1, 2, 3, 4, or 5, e.g., 1 or 2, amino acids, e.g., conservative amino acids, therefrom); an FR3 comprising the sequence G-V-P-S-R-F-S-G-S-G-S-G-T-D-F-T-L-T-I-S-S-L-Q-P-E-D-F-A-T-Y-Y-C̲ (SEQ ID NO: 80) (or a sequence that differs by no more than, 1, 2, 3, 4, or 5, e.g., 1 or 2 amino acids, e.g., conservative amino acids, therefrom, optionally provided that C̲ is not changed, or if changed, is other than P); and an FR4 comprising the sequence F-G-Q-G-T-K-V-E-I-K (SEQ ID NO: 81) (or a sequence that differs by no more than, 1, 2, 3, 4, or 5, e.g., 1 or 2 amino acids, e.g., conservative amino acids, therefrom).

In an embodiment a FR of the light or heavy chain includes one of the highlighted residues, or one of the highlighted combinations of residues, for that FR (e.g., while other residues in that FR might be changed, the highlighted residue or combination of residues, are not changed). For example, in an embodiment, one, two or three of I̲, R̲, or L̲ for heavy chain FR3 is not changed.

In an embodiment, a FR of the light chain and a FR of the heavy chain each includes one of the highlighted residues, or one of the highlighted combinations of residues, for that FR. In an embodiment, each of two FRs in the antibody molecule includes one of the highlighted residues, or one of the highlighted combinations of residues, for that FR. In an embodiment, both are in the light chain. In an embodiment, both are in the heavy chain. In an embodiment, each of FR2 and FR3 in the heavy chain includes one of the highlighted residues, or one of the highlighted combinations of residues, for that FR. In an embodiment, each of FR1 and FR2 in the heavy and light chain includes one of the highlighted residues for that FR. In an embodiment, all of the highlighted residues in heavy chain FR1-4 are unchanged. In an embodiment, all of the highlighted residues in light chain FR1-4 are unchanged. In an embodiment, all of the highlighted residues in both heavy and light chain FR1-4 are unchanged.

In another embodiment, the antibody molecule comprises a structural or functional property of Ab 032.

In an embodiment, the antibody molecule competes with a reference antibody molecule, e.g., an antibody molecule described herein, for binding to a substrate, e.g., an HA. The reference antibody molecule can be: a) an antibody molecule comprising: i) a heavy chain immunoglobulin variable region segment comprising a CDR1 comprising the sequence S-Y-A-M-H (SEQ ID NO: 68); a CDR2 comprising the sequence V-V-S-Y-D-G-N-Y-K-Y-Y-A-D-S-V-Q-G (SEQ ID NO: 69); and a CDR3 comprising the sequence D-S-R-L-R-S-L-L-Y-F-E-W-L-S-Q-G-Y-F-N-P (SEQ ID NO: 70); and ii) a light chain variable region segment comprising: a CDR1 comprising the sequence Q-S-I-T-F-N-Y-K-N-Y-L-A (SEQ ID NO: 71); a CDR2 comprising the sequence W-G-S-Y-L-E-S (SEQ ID NO: 72); and a CDR3 comprising the sequence Q-Q-H-Y-R-T-P-P-S (SEQ ID NO: 73); b) an antibody molecule comprises one or both of: (i) a heavy chain immunoglobulin variable region segment comprising SEQ ID NO: 25; and (ii) a light chain variable region segment comprising SEQ ID NO:45; or c) Ab 032.

In an embodiment, the antibody molecule binds to the same epitope, or a portion thereof, on HA, as does a reference antibody molecule, e.g. an antibody molecule disclosed herein. The reference antibody molecule can be: a) an antibody molecule comprising: i) a heavy chain immunoglobulin variable region segment comprising a CDR1 comprising the sequence S-Y-A-M-H (SEQ ID NO: 68); a CDR2 comprising the sequence V-V-S-Y-D-G-N-Y-K-Y-Y-A-D-S-V-Q-G (SEQ ID NO: 69); and a CDR3 comprising the sequence D-S-R-L-R-S-L-L-Y-F-E-W-L-S-Q-G-Y-F-N-P (SEQ ID NO: 70); and ii) a light chain variable region segment comprising: a CDR1 comprising the sequence Q-S-I-T-F-N-Y-K-N-Y-L-A (SEQ ID NO: 71); a CDR2 comprising the sequence W-G-S-Y-L-E-S (SEQ ID NO: 72); and a CDR3 comprising the sequence Q-Q-H-Y-R-T-P-P-S (SEQ ID NO: 73); b) an antibody molecule comprises one or both of: (i) a heavy chain immunoglobulin variable region segment comprising SEQ ID NO: 25; and (ii) a light chain variable region segment comprising SEQ ID NO: 45; or c) Ab 032.

In an embodiment, the antibody molecule comprises one or both of: a heavy chain variable region comprising least 60, 70, 80, 85, 90, 95, 98 or 99 percent homology with SEQ ID NO: 25; or a light chain variable region comprising least 60, 70, 80, 85, 90, 95, 98 or 99 percent homology with SEQ ID NO: 45.

In an embodiment, the antibody molecule comprises one or both of: a heavy chain variable region comprising least 60, 70, 80, 85, 90, 95, 98 or 99 percent homology with SEQ ID NO: 25; and a light chain variable region comprising least 60, 70, 80, 85, 90, 95, 98 or 99 percent homology with SEQ ID NO: 45, wherein each HC CDR differs by no more than 1, 2, 3, 4 or 5 amino acids, e.g., 1 or 2, e.g., conservative amino acids, from the corresponding CDR of SEQ ID NO: 25 and each LC CDR differs by no more than 1, 2, 3, 4 or 5 amino acids, e.g., 1 or 2, e.g., conservative amino acids, from the corresponding CDR of SEQ ID NO: 45.

In an embodiment, the antibody molecule comprises one or both of: a heavy chain variable region comprising least 60, 70, 80, 85, 90, 95, 98 or 99 percent homology with SEQ ID NO: 25; and a light chain variable region comprising least 60, 70, 80, 85, 90, 95, 98 or 99 percent homology with SEQ ID NO: 45, wherein the antibody molecule comprises 1, 2, 3, 4, 5, or all of: (i) a HC CDR1 comprising: S at the 1$^{st}$ position and A at the 3$^{rd}$ position in HC CDR1; (ii) a HC CDR2 comprising one or both, e.g., one of: V at the 2$^{nd}$ position; or N at the 7$^{th}$ position and Q at the 16 position in HC CDR2; (iii) a HC CDR3 comprising: R at the 3$^{rd}$ position (and optionally, L at the 3$^{rd}$ position); (iv) a LC CDR1 comprising: I at the 3$^{rd}$ position; (v) a LC CDR2 comprising one, two, or three of, e.g., one of: Gat the 2$^{nd}$ position; Y at the 4$^{th}$ position; or L at the 5$^{th}$ position in LC CDR2; (vi) a LC CDR3 comprising: S at the 9$^{th}$ position in LC CDR3.

In an embodiment, the antibody molecule comprises one or both of: (a) a heavy chain immunoglobulin variable region segment comprising SEQ ID NO:25 (or a sequence that differs by no more than 1, 2, 3, 4 or 5 amino acids, e.g., conservative amino acids, therefrom); and (b) a light chain variable region segment comprising SEQ ID NO:155 (or a sequence that differs by no more than 1, 2, 3, 4 or 5 amino acids, e.g., conservative amino acids, therefrom).

In an embodiment, the antibody molecule comprises one or both of: (a) a heavy chain immunoglobulin variable region segment comprising SEQ ID NO: 25; and (b) a light chain variable region segment comprising SEQ ID NO: 155.

In an embodiment, the antibody molecule comprises one or both of: (a) a heavy chain immunoglobulin variable region segment comprising a CDR1 comprising the sequence S-Y-A-M-H (SEQ ID NO: 68) (or a sequence that differs by no more than, 1, 2, 3, 4, or 5, e.g., 1 or 2 amino acids, e.g., conservative amino acids, therefrom); a CDR2 comprising the sequence V-V-S-Y-D-G-N-Y-K-Y-Y-A-D-S-V-Q-G (SEQ ID NO: 69) (or a sequence that differs by no more than, 1, 2, 3, 4, or 5, e.g., 1 or 2 amino acids, e.g., conservative amino acids, therefrom); a CDR3 comprising the sequence D-S-R-L-R-S-L-L-Y-F-E-W-L-S-Q-G-Y-F-N-P (SEQ ID NO: 70) (or a sequence that differs by no more than, 1, 2, 3, 4, or 5, e.g., 1 or 2 amino acids, e.g., conservative amino acids, therefrom); and (b) a light chain variable region segment comprising a CDR1 comprising the sequence: Q-S-I-T-F N-Y-K-N-Y-L-A (SEQ ID NO: 71) (or a sequence that differs by no more than, 1, 2, 3, 4, or 5, e.g., 1 or 2 amino acids, e.g., conservative amino acids, therefrom); a CDR2 comprising the sequence W-G-S-Y-L-E-S (SEQ ID NO: 72) (or a sequence that differs by no more than, 1, 2, 3, 4, or 5, e.g., 1 or 2 amino acids, e.g., conservative amino acids, therefrom); a CDR3 comprising the sequence Q-Q-H-Y-R-T-P-P-S (SEQ ID NO: 73) (or a sequence that differs by no more than, 1, 2, 3, 4, or 5, e.g., 1 or 2 amino acids, e.g., conservative amino acids, therefrom).

In an embodiment, the antibody molecule comprises one or both of: a) LC CDR1-3, that collectively, differ from the Ab 032 LC CDR1-3 by no more than, 1, 2, 3, 4, 5, 6, 7, 8, 9, or 10, e.g., 1, 2, 3, or 4, amino acids, e.g., conservative amino acids; and b) HC CDR1-3, that collectively, differ from the Ab 032 HC CDR1-3 by no more than, 1, 2, 3, 4, 5, 6, 7, 8, 9, or 10, e.g., 1, 2, 3, or 4, amino acids, e.g., conservative amino acids.

In an embodiment, the antibody molecule comprises one or both of: (a) a heavy chain immunoglobulin variable region segment comprising a CDR1 comprising the sequence S-Y-A-M-H (SEQ ID NO: 68) (or a sequence that differs by no more than, 1, 2, or 3, e.g., 1 or 2 amino acids, e.g., conservative amino acids, therefrom, optionally provided that at least 1 or 2 of the highlighted residues are not changed, e.g., both S and A are not changed); a CDR2 comprising the sequence V-V-S-Y-D-G-N-Y-K-Y-Y-A-D-S-V-Q-G (SEQ ID NO: 69) (or a sequence that differs by no more than, 1, 2, 3, 4, or 5, e.g., 1 or 2 amino acids, e.g., conservative amino acids, therefrom, provided that, e.g., at least 1, 2, or 3 of the highlighted residues are not changed, e.g., V or both N and Q or all three of V, N, and Q are not changed); a CDR3 comprising the sequence D-S-R-L-R-S-L-L-Y-F-E-W-L-S-Q-G-Y-F-N-P (SEQ ID NO: 70) (or a sequence that differs by no more than, 1, 2, 3, 4, or 5, e.g., 1 or 2 amino acids, e.g., conservative amino acids, therefrom, optionally provided that R is not changed); and (b) a light chain variable region segment comprising a CDR1 comprising the sequence: Q-S-I-T-F-N-Y-K-N-Y-L-A (SEQ ID NO: 71) or a sequence that differs by no more than, 1, 2, 3, 4, or 5, e.g., 1 or 2 amino acids, e.g., conservative amino acids, therefrom, optionally provided that at least 1 or 2 of the highlighted residues are not changed, e.g., I is not changed); a CDR2 comprising the sequence W-G-S-Y-L-E-S (SEQ ID NO:72) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., 1, 2 or all of G Y, and L are not changed); a CDR3 comprising the sequence Q-Q-_I-Y-R-T-P-P (SEQ ID NO: 73) (or a sequence that differs by no more than, 1, 2, 3, 4, or 5, e.g., 1 or 2 amino acids, e.g., conservative amino acids, therefrom, optionally provided that at least one or both of the highlighted residues are not changed, e.g., Sis not changed).

In an embodiment, a CDR of the light or heavy chain includes one of the highlighted residues, or one of the highlighted combinations of residues, for that CDR (e.g., while other residues in that CDR might be changed, the highlighted residue or combination of residues, are not changed). In an embodiment, a CDR of the light and a CDR of the heavy chain each includes one of the highlighted residues, or one of the highlighted combinations of residues, for that CDR. In an embodiment, each of two CDRs in the antibody molecule includes one of the highlighted residues, or one of the highlighted combinations of residues, for that CDR. In an embodiment, both are in the light chain. In an embodiment, both are in the heavy chain. In an embodiment each of the three CDRs in the heavy chain includes one of the highlighted residues, or one of the highlighted combinations of residues, for that CDR. In an embodiment, each of the three CDRs in the light chain includes one of the highlighted residues, or one of the highlighted combinations of residues, for that CDR. In an embodiment, each of the six CDRs in the heavy and light chain includes one of the highlighted residues, or one of the highlighted combinations of residues, for that CDR.

In an embodiment, the antibody molecule comprises one or more (e.g., 2, 3, 4, 5, or all) of the following properties: (a) both S and A in HC CDR1 are unchanged; (b) V or both N and Q or all three of V, N, and Q in HC CDR2 are unchanged; (c) R in HC CDR3 is unchanged; (d) I in LC CDR1 is unchanged; (e) 1, 2 or 3 of G Y and L in LC CDR2 are unchanged; or (f) in LC CDR3 is unchanged. In an embodiment, the antibody molecule comprises 1, 2, 3, 4, 5, or all 6 properties selected from (a) to (f). In an embodiment, the antibody molecule comprises a heavy chain having a one or more properties selected from (a), (b), and (c) and a light chain having one or more properties selected from (d), (e), and (f).

In an embodiment, the antibody molecule comprises one or both of: (a) a heavy chain immunoglobulin variable region segment comprising: a CDR1 comprising the sequence S-Y-A-M-H (SEQ ID NO: 68); a CDR2 comprising the sequence V-V-S-Y-D-G-N-Y-K-Y-Y-A-D-S-V-Q-G (SEQ ID NO: 69); a CDR3 comprising the sequence D-S-R-L-R-S-L-L-Y-F-E-W-L-S-Q-G-Y-F-N-P (SEQ ID NO: 70); and (b) a light chain variable region segment comprising a CDR1 comprising the sequence Q-S-I-T-F-N-Y-K-N-Y-L-A (SEQ ID NO: 71); a CDR2 comprising the sequence W-G-S-Y-L-E-S (SEQ ID NO:72); and a CDR3 comprising the sequence Q-Q-H-Y-R-T-P-P-S (SEQ ID NO:73).

In an embodiment, the antibody molecule comprises one or both of: a) one or more framework regions (FRs) from SEQ ID NO: 25. For example, the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 25; and b) one or more framework regions (FRs) from SEQ ID NO: 45. For example, the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 45.

In an embodiment, the antibody molecule comprises: (a) a heavy chain immunoglobulin variable region segment that further comprises one or more or all of: an FR1 comprising the sequence Q-V-Q-L-L-E-T-G-G-G-L-V-K-P-G-Q-S-L-K-L-S-C-A-A-S-G-F-T-F-T (SEQ ID NO: 74) (or a sequence that differs by no more than, 1, 2, 3, 4, or 5, e.g., 1 or 2, amino acids, e.g., conservative amino acids, therefrom, optionally provided that T is not changed); an FR2 comprising the sequence W-V-R-Q-P-P-G-K-G-L-E-W-V-A (SEQ ID NO: 75) (or a sequence that differs by no more than, 1, 2, 3, 4, or 5, e.g., 1 or 2, amino acids, e.g., conservative amino acids, therefrom, optionally provided that W is not changed, or that if changed, is other than R); an FR3 comprising the sequence R-F-T-I-S-R-D-N-S-K-N-T-L-Y-L-Q-M-N-S-L-R-A-E-D-T-A-V-Y-Y-C-A-K (SEQ ID NO: 76) (or a sequence that differs by no more than, 1, 2, 3, 4, or 5, e.g., 1 or 2, amino acids, e.g., conservative amino acids, therefrom, optionally provided that one, two or three of I, R, or L is not changed, or that if I is changed it is other than G, if R is changed it is other than P. or if L is changed it is other than A); and an FR4 comprising the sequence W-G-Q-G-T-T-L-T-V-S-S (SEQ ID NO: 77) (or a sequence that differs by no more than, 1, 2, 3, 4, or 5, e.g., 1 or 2 amino acids, e.g., conservative amino acids, therefrom) or W-G-Q-G-T-T-V-T-V-S-S (SEQ ID NO:171) (or a sequence that differs by no more than, 1, 2, 3, 4, or 5, e.g., 1 or 2 amino acids, e.g., conservative amino acids, therefrom); and (b) the light chain immunoglobulin variable region segment comprises one or more or all of an FR1 comprising the sequence D-I-Q-M-T-Q-S-P-S-S-L-S-A-S-V-G-D-R-V-T-I-T-C-R-S-S (SEQ ID NO:78) (or a sequence that differs by no more than, 1, 2, 3, 4, or 5, e.g., 1 or 2 amino acids, e.g., conservative amino acids, therefrom, optionally provided that R is not changed); an FR2 comprising the sequence W-Y-Q-Q-K-P-G-K-A-P-K-L-L-I-Y (SEQ ID NO:79) (or a sequence that differs by no more than, 1, 2, 3, 4, or 5, e.g., 1 or 2 amino acids, e.g., conservative amino acids, therefrom); an FR3 comprising the sequence G-V-P-S-R-F-S-G-S-G-S-G-T-D-F-T-L-T-I-S-S-L-Q-P-E-D-F-A-T-Y-Y-C (SEQ ID NO:80) (or a sequence that differs by no more than, 1, 2, 3, 4, or 5, e.g., 1 or 2 amino acids, e.g., conservative amino acids, therefrom, optionally provided that C is not changed, or if changed, is other than P); and an FR4 comprising the sequence F-G-Q-G-T-K-V-E-I-K (SEQ ID NO:81) (or a sequence that differs by no more than, 1, 2, 3, 4, or 5, e.g., 1 or 2 amino acids, e.g., conservative amino acids, therefrom).

In an embodiment a FR of the light or heavy chain includes one of the highlighted residues, or one of the highlighted combinations of residues, for that FR (e.g., while other residues in that FR might be changed, the highlighted residue or combination of residues, are not changed). For example, in an embodiment, one, two or three of I, R, or L for heavy chain FR3 is not changed.

In an embodiment, a FR of the light chain and a FR of the heavy chain each includes one of the highlighted residues, or one of the highlighted combinations of residues, for that FR. In an embodiment, each of two FRs in the antibody molecule includes one of the highlighted residues, or one of the highlighted combinations of residues, for that FR. In an embodiment, both are in the light chain. In an embodiment, both are in the heavy chain. In an embodiment, each of FR2 and FR3 in the heavy chain includes one of the highlighted residues, or one of the highlighted combinations of residues, for that FR. In an embodiment, each of FR1 and FR2 in the heavy and light chain includes one of the highlighted residues for that FR. In an embodiment, all of the highlighted residues in heavy chain FR1-4 are unchanged. In an embodiment, all of the highlighted residues in light chain FR1-4 are unchanged. In an embodiment, all of the highlighted residues in both heavy and light chain FR1-4 are unchanged.

In another embodiment, the antibody molecule comprises a structural or functional property of Ab 031.

In an embodiment, the antibody molecule competes with a reference antibody molecule, e.g., an antibody molecule described herein, for binding to a substrate, e.g., an HA. The reference antibody molecule can be: a) an antibody molecule comprising: i) a heavy chain immunoglobulin variable region segment comprising a CDR1 comprising the sequence S-Y-A-M-H (SEQ ID NO: 68); a CDR2 comprising the sequence V-V-S-Y-D-G-N-Y-K-Y-Y-A-D-S-V-Q-G (SEQ ID NO: 69); and a CDR3 comprising the sequence D-S-R-L-R-S-L-L-Y-F-E-W-L-S-Q-G-Y-F-N-P (SEQ ID NO: 70); and ii) a light chain variable region segment comprising: a CDR1 comprising the sequence Q-S-I-T-F-N-Y-K-N-Y-L-A (SEQ ID NO:71); a CDR2 comprising the sequence W-G-S-Y-L-E-S (SEQ ID NO:72); and a CDR3 comprising the sequence Q-Q-H-Y-R-T-P-P-S (SEQ ID NO:73); b) an antibody molecule comprises one or both of: (i) a heavy chain immunoglobulin variable region segment comprising SEQ ID NO: 24; and (ii) a light chain variable region segment comprising SEQ ID NO:45; or c) Ab 031.

In an embodiment, the antibody molecule binds to the same epitope, or a portion thereof, on HA, as does a reference antibody molecule, e.g. an antibody molecule disclosed herein. The reference antibody molecule can be: a) an antibody molecule comprising: i) a heavy chain immunoglobulin variable region segment comprising a CDR1 comprising the sequence S-Y-A-M-H (SEQ ID NO: 68); a CDR2 comprising the sequence V-V-S-Y-D-G-N-Y-K-Y-Y-A-D-S-V-Q-G (SEQ ID NO: 69); and a CDR3 comprising the sequence D-S-R-L-R-S-L-L-Y-F-E-W-L-S-Q-G-Y-F-N-P (SEQ ID NO: 70); and ii) a light chain variable region segment comprising: a CDR1 comprising the sequence Q-S-I-T-F-N-Y-K-N-Y-L-A (SEQ ID NO: 71); a CDR2 comprising the sequence W-G-S-Y-L-E-S (SEQ ID NO:72); and a CDR3 comprising the sequence Q-Q-H-Y-R-T-P-P-S (SEQ ID NO: 73); b) an antibody molecule comprises one or both of: (i) a heavy chain immunoglobulin variable region segment comprising SEQ ID NO: 24; and (ii) a light chain variable region segment comprising SEQ ID NO: 45; or c) Ab 031.

In an embodiment, the antibody molecule comprises one or both of: a heavy chain variable region comprising least 60, 70, 80, 85, 90, 95, 98 or 99 percent homology with SEQ ID NO: 24; and a light chain variable region comprising least 60, 70, 80, 85, 90, 95, 98 or 99 percent homology with SEQ ID NO: 45.

In an embodiment, the antibody molecule comprises one or both of: a heavy chain variable region comprising least 60, 70, 80, 85, 90, 95, 98 or 99 percent homology with SEQ ID NO: 24; and a light chain variable region comprising least 60, 70, 80, 85, 90, 95, 98 or 99 percent homology with SEQ ID NO: 45, wherein, optionally, each HC CDR differs by no more than 1, 2, 3, 4 or 5 amino acids, e.g., 1 or 2, e.g., conservative amino acids, from the corresponding CDR of SEQ ID NO: 24 and each LC CDR differs by no more than 1, 2, 3, 4 or 5 amino acids, e.g., 1 or 2, e.g., conservative amino acids, from the corresponding CDR of SEQ ID NO: 45.

In an embodiment, the antibody molecule comprises one or both of: a heavy chain variable region comprising least 60, 70, 80, 85, 90, 95, 98 or 99 percent homology with SEQ ID NO: 25; and a light chain variable region comprising least 60, 70, 80, 85, 90, 95, 98 or 99 percent homology with SEQ ID NO: 45, wherein the antibody molecule comprises 1, 2, 3, 4, 5, or all of: (i) a HC CDR1 comprising: S at the $1^{st}$ position and A at the $3^{rd}$ position in HC CDR1; (ii) a HC CDR2 comprising one or both, e.g., one of: V at the $2^{nd}$ position; or N at the $7^{th}$ position and Q at the $16^{th}$ position in HC CDR2; (iii) a HC CDR3 comprising: R at the $3^{rd}$ position (and optionally, L at the $3^{rd}$ position); (iv) a LC CDR1 comprising: I at the $3^{rd}$ position; (v) a LC CDR2 comprising one, two, or three of, e.g., one of: G at the $2^{nd}$ position; Y at the $4^{th}$ position; or L at the $5^{th}$ position in LC CDR2; (vi) a LC CDR3 comprising: S at the $9^{th}$ position in LC CDR3.

In an embodiment, the antibody molecule comprises: (a) a heavy chain immunoglobulin variable region segment comprising SEQ ID NO: 24 (or a sequence that differs by no more than 1, 2, 3, 4 or 5 amino acids, e.g., conservative amino acids, therefrom); and (b) a light chain variable region segment comprising SEQ ID NO: 45 (or a sequence that differs by no more than 1, 2, 3, 4 or 5 amino acids, e.g., conservative amino acids, therefrom).

In an embodiment, the antibody molecule comprises one or both of: (a) a heavy chain immunoglobulin variable region segment comprising SEQ ID NO: 24; and (b) a light chain variable region segment comprising SEQ ID NO: 45.

In an embodiment, the antibody molecule comprises one or both of: (a) a heavy chain immunoglobulin variable region segment comprising a CDR1 comprising the sequence S-Y-A-M-H (SEQ ID NO: 68) (or a sequence that differs by no more than, 1, 2, 3, 4, or 5, e.g., 1 or 2 amino acids, e.g., conservative amino acids, therefrom); a CDR2 comprising the sequence V-V-S-Y-D-G-N-Y-K-Y-Y-A-D-S-V-Q-G (SEQ ID NO: 69) (or a sequence that differs by no more than, 1, 2, 3, 4, or 5, e.g., 1 or 2 amino acids, e.g., conservative amino acids, therefrom); and a CDR3 comprising the sequence D-S-R-L-R-S-L-L-Y-F-E-W-L-S-Q-G-Y-F-N-P (SEQ ID NO: 70) (or a sequence that differs by no more than, 1, 2, 3, 4, or 5, e.g., 1 or 2 amino acids, e.g., conservative amino acids, therefrom); and (b) a light chain variable region segment comprising a CDR1 comprising the sequence Q-S-I-T-F-N-Y-K-N-Y-L-A (SEQ ID NO: 71) (or a sequence that differs by no more than, 1, 2, 3, 4, or 5, e.g., 1 or 2 amino acids, e.g., conservative amino acids, therefrom); a CDR2 comprising the sequence W-G-S-Y-L-E-S (SEQ ID NO: 72) (or a sequence that differs by no more than, 1, 2, 3, 4, or 5, e.g., 1 or 2 amino acids, e.g., conservative amino acids, therefrom); and a CDR3 comprising the sequence Q-Q-H-Y-R-T-P-P-S (SEQ ID NO: 73) (or a sequence that differs by no more than, 1, 2, 3, 4, or 5, e.g., 1 or 2 amino acids, e.g., conservative amino acids, therefrom).

In an embodiment, the antibody molecule comprises one or both of: a) LC CDR1-3, that collectively, differ from the Ab 031 LC CDR1-3 by no more than, 1, 2, 3, 4, 5, 6, 7, 8, 9, or 10, e.g., 1, 2, 3, or 4, amino acids, e.g., conservative amino acids; and b) HC CDR1-3, that collectively, differ from the Ab 031 HC CDR1-3 by no more than, 1, 2, 3, 4, 5, 6, 7, 8, 9, or 10, e.g., 1, 2, 3, or 4, amino acids, e.g., conservative amino acids.

In an embodiment, the antibody molecule comprises one or both of: (a) a heavy chain immunoglobulin variable region segment comprising a CDR1 comprising the sequence S-Y-A-M-H (SEQ ID NO: 68) (or a sequence that differs by no more than, 1, 2, or 3, e.g., 1 or 2 amino acids, e.g., conservative amino acids, therefrom, optionally provided that at least 1 or 2 of the highlighted residues are not changed, e.g., both S and A are not changed); a CDR2 comprising the sequence V-V-S-Y-D-G-N-Y-K-Y-Y-A-D-S-V-Q-G (SEQ ID NO: 69) (or a sequence that differs by no more than, 1, 2, 3, 4, or 5, e.g., 1 or 2 amino acids, e.g., conservative amino acids, therefrom, provided that, e.g., at least 1, 2, or 3 of the highlighted residues are not changed, e.g., V or both N and Q or all three of V, N, and Q are not changed); a CDR3 comprising the sequence D-S-R-L-R-S-L-L-Y-F-E-W-L-S-Q-G-Y-F-N-P (SEQ ID NO: 70) (or a sequence that differs by no more than, 1, 2, 3, 4, or 5, e.g., 1 or 2 amino acids, e.g., conservative amino acids, therefrom optionally provided that, e.g., R is not changed); and (b) a light chain variable region segment comprising a CDR1 comprising the sequence Q-S-I-T-F-N-Y-K-N-Y-L-A (SEQ ID NO: 71) or a sequence that differs by no more than, 1, 2, 3, 4, or 5, e.g., 1 or 2 amino acids, e.g., conservative amino acids, therefrom, optionally provided that at least 1 or 2 of the highlighted residues are not changed, e.g., I is not changed); a CDR2 comprising the sequence W-G-S-Y-L-E-S (SEQ ID NO:72) (or a sequence that differs by no more than, 1, 2, 3, 4, or 5, e.g., 1 or 2 amino acids, e.g., conservative amino acids, therefrom, optionally provided that at least 1, 2, or 3 of the highlighted residues are not changed, e.g., 1, 2 or all of G, Y, and L are not changed); a CDR3 comprising the sequence Q-Q-H-Y-R-T-P-P-S (SEQ ID NO:73) (or a sequence that differs by no more than, 1, 2, 3, 4, or 5, e.g., 1 or 2 amino acids, e.g., conservative amino acids, therefrom, optionally provided that at least one or both of the highlighted residues are not changed, e.g., S is not changed).

In an embodiment, a CDR of the light or heavy chain includes one of the highlighted residues, or one of the highlighted combinations of residues, for that CDR (e.g., while other residues in that CDR might be changed, the highlighted residue or combination of residues, are not changed). In an embodiment, a CDR of the light and a CDR of the heavy chain each includes one of the highlighted residues, or one of the highlighted combinations of residues, for that CDR. In an embodiment, each of two CDRs in the antibody molecule includes one of the highlighted residues, or one of the highlighted combinations of residues, for that CDR. In an embodiment, both are in the light chain. In an embodiment, both are in the heavy chain. In an embodiment, each of the three CDRs in the heavy chain includes one of the highlighted residues, or one of the highlighted combinations of residues, for that CDR. In an embodiment, each of the three CDRs in the light chain includes one of the highlighted residues, or one of the highlighted combinations of residues, for that CDR. In an embodiment, each of the six CDRs in the heavy and light chain includes one of the highlighted residues, or one of the highlighted combinations of residues, for that CDR.

In an embodiment, the antibody molecule comprises one or more (e.g., 2, 3, 4, 5, or all) of the following properties: (a) both S and A in HC CDR1 are unchanged; (b) V or both N and Q or all three of V, N, and Q in HC CDR2 are unchanged; (c) R in HC CDR3 is unchanged; (d) I in LC CDR1 is unchanged; (e) 1, 2 or 3 of G, Y, and L in LC CDR2 are unchanged; (f) S in LC CDR3 is unchanged.

In an embodiment, the antibody molecule comprises 1, 2, 3, 4, 5, or all 6 properties selected from (a) to (f). In an embodiment, the antibody molecule comprises a heavy chain having a one or more properties selected from (a), (b), and (c) and a light chain having one or more properties selected from (d), (e), and (f). In the embodiment, the antibody molecule comprises one or both of: (a) a heavy chain immunoglobulin variable region segment comprising a CDR1 comprising the sequence S-Y-A-M-H (SEQ ID NO: 68); a CDR2 comprising the sequence V-V-S-Y-D-G-N-Y-K-Y-Y-A-D-S-V-Q-G (SEQ ID NO: 69); and a CDR3 comprising the sequence D-S-R-L-R-S-L-L-Y-F-E-W-L-S-Q-G-Y-F-N-P (SEQ ID NO:70); and (b) a light chain variable region segment comprising a CDR1 comprising the sequence Q-S-I-T-F-N-Y-K-N-Y-L-A (SEQ ID NO: 71); a CDR2 comprising the sequence W-G-S-Y-L-E-S (SEQ ID NO: 72); and a CDR3 comprising the sequence Q-Q-H-Y-R-T-P-P-S (SEQ ID NO: 73).

In an embodiment, the antibody molecule comprises one or both of: a) one or more framework regions (FRs) from SEQ ID NO: 24. For example, the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 24; and b) one or more framework regions (FRs) from SEQ ID NO: 45. For example, the antibody molecule comprises one or more or all of FR1, FR2, FR3, or FR4, or sequences that differ individually, or collectively, by no more than 1, 2, 3, 4, of 5 amino acid residues, e.g., conservative residues, from SEQ ID NO: 45.

In an embodiment, the antibody molecule comprises: (a) a heavy chain immunoglobulin variable region segment that further comprises one or more or all of: an FR1 comprising the sequence E-V-Q-L-L-E-S-G-G-G-L-V-K-P-G-Q-S-L-K-L-S-C-A-A-S-G-F-T-F-T (SEQ ID NO:82) (or a sequence that differs by no more than, 1, 2, 3, 4, or 5, e.g., 1 or 2 amino acids, e.g., conservative amino acids, therefrom, optionally provided that T is not changed); an FR2 comprising the sequence W-V-R-Q-P-P-G-K-G-L-E-W-V-A (SEQ ID NO:75) (or a sequence that differs by no more than, 1, 2, 3, 4, or 5, e.g., 1 or 2 amino acids, e.g., conservative amino acids, therefrom, optionally provided that W is not changed, or that if changed, is other than R); an FR3 comprising the sequence R-F-T-I-S-R-D-N-S-K-N-T-L-Y-L-Q-M-N-S-L-R-A-E-D-T-A-V-Y-Y-C-A-K (SEQ ID NO:76) (or a sequence that differs by no more than, 1, 2, 3, 4, or 5, e.g., 1 or 2 amino acids, e.g., conservative amino acids, therefrom, optionally provided that one, two or three of I, R, or L is not changed, or that if I is changed it is other than G, if R is changed it is other than P. or if L is changed it is other than A); and an FR4 comprising the sequence W-G-Q-G-T-T-L-T-V-S-S (SEQ ID NO:77) (or a sequence that differs by no more than, 1, 2, 3, 4, or 5, e.g., 1 or 2 amino acids, e.g., conservative amino acids, therefrom) or W-G-Q-G-T-T-V-T-V-S-S (SEQ ID NO:171) (or a sequence that differs by no more than, 1, 2, 3, 4, or 5, e.g., 1 or 2 amino acids, e.g., conservative amino acids, therefrom); and (a) a light chain immunoglobulin variable region segment further comprises one or more or all of: an FR1 comprising the sequence D-I-Q-M-T-Q-S-P-S-S-L-S-A-S-V-G-D-R-V-T-I-T-C-R-S-S (SEQ ID NO:78) (or a sequence that differs by no more than, 1, 2, 3, 4, or 5, e.g., 1 or 2 amino acids, e.g., conservative amino acids, therefrom, optionally provided that R is not changed); an FR2 comprising the sequence W-Y-Q-Q-K-P-G-K-A-P-K-L-L-I-Y (SEQ ID NO:79) (or a sequence that differs by no more than, 1, 2, 3, 4, or 5, e.g., 1 or 2 amino acids, e.g., conservative amino acids, therefrom); an FR3 comprising the sequence G-V-P-S-R-F-S-G-S-G-S-G-T-D-F-T-L-T-I-S-S-L-Q-P-E-D-F-A-T-Y-Y-C (SEQ ID NO:80) (or a sequence that differs by no more than, 1, 2, 3, 4, or 5, e.g., 1 or 2 amino acids, e.g., conservative amino acids, therefrom, optionally provided that C is not changed, or if changed, is other than P); and an FR4 comprising the sequence F-G-Q-G-T-K-V-E-I-K (SEQ ID NO:81) (or a sequence that differs by no more than, 1, 2, 3, 4, or 5, e.g., 1 or 2 amino acids, e.g., conservative amino acids, therefrom).

In an embodiment, a FR of the light or heavy chain includes one of the highlighted residues, or one of the highlighted combinations of residues, for that FR (e.g., while other residues in that FR might be changed, the highlighted residue or combination of residues, are not changed). For example, in an embodiment, one, two or three of I, R, or L for heavy chain FR3 is not changed.

In an embodiment, a FR of the light chain and a FR of the heavy chain each includes one of the highlighted residues, or one of the highlighted combinations of residues, for that FR. In an embodiment, each of two FRs in the antibody molecule includes one of the highlighted residues, or one of the highlighted combinations of residues, for that FR. In an embodiment, both are in the light chain. In an embodiment, both are in the heavy chain. In an embodiment each of FR2 and FR3 in the heavy chain includes one of the highlighted residues, or one of the highlighted combinations of residues, for that FR. In an embodiment, each of FR1 and FR2 in the heavy and light chain includes one of the highlighted residues for that FR. In an embodiment, all of the highlighted residues in heavy chain FR1-4 are unchanged. In an embodiment, all of the highlighted residues in light chain FR1-4 are unchanged. In an embodiment, all of the highlighted residues in both heavy and light chain FR1-4 are unchanged.

In an embodiment, the antibody molecule comprises: (a) the heavy chain immunoglobulin variable region segment comprises one or more or all of an FR1 comprising the sequence E-V-Q-L-L-E-S-G-G-G-L-V-K-P-G-Q-S-L-K-L-S-C-A-A-S-G-F-T-F-T (SEQ ID NO: 82); an FR2 comprising the sequence W-V-R-Q-P-P-G-K-G-L-E-W-V-A (SEQ ID NO: 75); an FR3 comprising the sequence R-F-T-I-S-R-D-N-S-K-N-T-L-Y-L-Q-M-N-S-L-R-A-E-D-T-A-V-Y-Y-C-A-K (SEQ ID NO: 76); and an FR4 comprising the sequence W-G-Q-G-T-T-L-T-V-S-S (SEQ ID NO: 77) or W-G-Q-G-T-T-V-T-V-S-S (SEQ ID NO: 171); and (b) the light chain immunoglobulin variable region segment comprising one or more or all of an FR1 comprising the sequence D-I-Q-M-T-Q-S-P-S-S-L-S-A-S-V-G-D-R-V-T-I-T-C-R-S-S (SEQ ID NO: 78); an FR2 comprising the sequence W-Y-Q-Q-K-P-G-K-A-P-K-L-L-I-Y (SEQ ID NO: 79); an FR3 comprising the sequence G-V-P-S-R-F-S-G-S-G-S-G-T-D-F-T-L-T-I-S-

S-L-Q-P-E-D-F-A-T-Y-Y-C (SEQ ID NO: 80); and an FR4 comprising the sequence F-G-Q-G-T-K-V-E-I-K (SEQ ID NO: 81).

In another embodiment, the antibody molecule comprises: (a) a heavy chain immunoglobulin variable region segment comprising SEQ ID NO: 24 (or a sequence that differs by no more than 1, 2, 3, 4 or 5 amino acids, e.g., conservative amino acids, therefrom); and (b) a light chain variable region segment comprising SEQ ID NO:45 (or a sequence that differs by no more than 1, 2, 3, 4 or 5 amino acids, e.g., conservative amino acids, therefrom).

In another embodiment, the antibody molecule comprises a structural or functional property of one or both a heavy chain variable region and a light chain variable region disclosed herein.

In an embodiment, the antibody molecule competes with a reference antibody molecule, e.g., an antibody molecule described herein, for binding to a substrate, e.g., an HA. The reference antibody molecule can be: a) an antibody molecule comprising the heavy and light CDRs from: a heavy chain variable region from Table 3, Table 4A, Table 4B, FIG. 2, FIG. 5, or FIG. 7; and a light chain variable region from Table 3, Table 4A, Table 4B, FIGS. 3A-3B, FIGS. 6A-6B, or FIG. 7; b) an antibody molecule that comprises: (i) a heavy chain immunoglobulin variable region segment from Table 3, Table 4A, Table 4B, FIG. 2, FIG. 5, or FIG. 7; and (ii) a light chain variable region segment from Table 3, Table 4A, Table 4B, FIGS. 3A-3B, FIGS. 6A-6B, or FIG. 7; or c) an antibody disclosed herein.

In an embodiment the antibody molecule binds to the same epitope, or a portion thereof, on HA, as does a reference antibody molecule, e.g. an antibody molecule disclosed herein. The reference antibody molecule can be: a) an antibody molecule comprising the heavy and light CDRs from: a heavy chain variable region from Table 3, Table 4A, Table 4B, FIG. 2, FIG. 5, or FIG. 7; and a light chain variable region from Table 3, Table 4A, Table 4B, FIGS. 3A-3B, FIGS. 6A-6B, or FIG. 7; b) an antibody molecule that comprises: (i) a heavy chain immunoglobulin variable region segment from Table 3, Table 4A, Table 4B, FIG. 2, FIG. 5, or FIG. 7; and (ii) a light chain variable region segment from Table 3, Table 4A, Table 4B, FIGS. 3A-3B, FIGS. 6A-6B, or FIG. 7; or c) an antibody disclosed herein.

In an embodiment, the antibody molecule comprises one or both of: a heavy chain variable region comprising least 60, 70, 80, 85, 90, 95, 98 or 99 percent homology with a reference heavy chain from Table 3, Table 4A, Table 4B, FIG. 2, FIG. 5 or FIG. 7; and a light chain variable region comprising least 60, 70, 80, 85, 90, 95, 98 or 99 percent homology with reference light chain from Table 3, Table 4A, Table 4B, FIGS. 3A-3B, FIGS. 6A-6B or FIG. 7, wherein, optionally, each HC CDR differs by no more than 1, 2, 3, 4 or 5 amino acids, e.g., 1 or 2, e.g., conservative amino acids, from the corresponding HC CDR from its reference heavy chain and each LC CDR differs by no more than 1, 2, 3, 4 or 5 amino acids, e.g., 1 or 2, e.g., conservative amino acids, from the corresponding CDR in its reference light chain.

In an embodiment, the antibody molecule comprises: a heavy chain variable region comprising least 60, 70, 80, 85, 90, 95, 98 or 99 percent homology with a heavy chain from Table 3 and a light chain variable region comprising least 60, 70, 80, 85, 90, 95, 98 or 99 percent homology with the corresponding light chain from Table 3.

In an embodiment, the antibody molecule comprises: a heavy chain variable region comprising least 60, 70, 80, 85, 90, 95, 98 or 99 percent homology with a heavy chain from Table 4A and a light chain variable region comprising least 60, 70, 80, 85, 90, 95, 98 or 99 percent homology with the corresponding light chain from Table 4A.

In an embodiment the antibody molecule comprises: a heavy chain variable region comprising least 60, 70, 80, 85, 90, 95, 98 or 99 percent homology with a heavy chain from Table 4B and a light chain variable region comprising least 60, 70, 80, 85, 90, 95, 98 or 99 percent homology with the corresponding light chain from Table 4B.

In an embodiment the antibody molecule comprises one or both of: a heavy chain variable region from Table 3, Table 4A, Table 4B, FIG. 2, FIG. 5, or FIG. 7; and a light chain variable region from Table 3, Table 4A, Table 4B, FIGS. 3A-3B, FIGS. 6A-6B, or FIG. 7.

In an embodiment the antibody molecule comprises: a heavy chain variable region from Table 3 and the corresponding light chain from Table 3; a heavy chain from Table 4A and the corresponding light chain from Table 4A; or a heavy chain from Table 4B and the corresponding light chain from Table 4B.

In an embodiment, the antibody molecule comprises one or both of: (a) a heavy chain immunoglobulin variable region segment comprising a CDR1, a CDR2 and a CDR3 from a heavy chain sequence of Table 3, Table 4A, Table 4B, FIG. 2, FIG. 5, or FIG. 7 (or CDRs that, individually or collectively, differ therefrom by no more than, 1, 2, 3, 4, or 5, e.g., 1 or 2 amino acids, e.g., conservative amino acids)); and (b) a light chain immunoglobulin variable region segment comprising a CDR1, a CDR2 and a CDR3 from a light chain sequence of Table 3, Table 4A, Table 4B, FIGS. 3A-3B, FIGS. 6A-6B, or FIG. 7 (or CDRs that, individually or collectively, differ therefrom by no more than, 1, 2, 3, 4, or 5, e.g., 1 or 2 amino acids, e.g., conservative amino acids).

In an embodiment, the antibody molecule comprises one or both of: CDRs from a heavy chain of Table 3 and the light chain CDRs from the corresponding light chain from Table 3. In an embodiment, the antibody molecule comprises one or both of: CDRs from a heavy chain of Table 4A and the light chain CDRs from the corresponding light chain from Table 4A. In an embodiment, the antibody molecule comprises one or both of: CDRs from a heavy chain of Table 4B and the light chain CDRs from the corresponding light chain from Table 4B.

In an embodiment, the antibody molecule comprises one or both of: (a) a heavy chain immunoglobulin variable region segment comprising a CDR1, a CDR2; and a CDR3 from a heavy chain sequence of FIG. 2, FIG. 5, or FIG. 7; and (b) a light chain immunoglobulin variable region segment comprising a CDR1, a CDR2 and a CDR3 from a light chain sequence of FIGS. 3A-3B, FIGS. 6A-6B, or FIG. 7. In an embodiment, the antibody molecule comprises: (a) a heavy chain immunoglobulin variable region segment from FIG. 2 or FIG. 7; and (b) a light chain immunoglobulin variable region segment from FIGS. 3A-3B or FIG. 7.

In an embodiment, the heavy chain immunoglobulin variable region further comprises an Isoleucine-Aspartate (Ile-Asp) dipeptide at the N-terminus. In another embodiment, the light chain immunoglobulin variable region further comprises an Ile-Asp dipeptide at the N-terminus. In yet another embodiment, both the heavy chain immunoglobulin variable region and the light chain immunoglobulin variable region or an antibody featured in the disclosure further comprises an Ile-Asp dipeptide at the N-terminus. In other embodiment the Ile-Asp dipeptide is absent from one or both the heavy and light chain.

In an embodiment, the antibody molecule comprises one or both of: a) one or more framework regions (FRs) from heavy chain disclosed herein. E.g., the antibody molecule comprises one or more or all of FR1, FR2, FR3, or FR4, or sequences that differ individually, or collectively, by no more than 1, 2, 3, 4, of 5 amino acid residues, e.g., conservative residues, from heavy chain disclosed herein; and b) one or more framework regions (FRs) from light chain disclosed herein. E.g., the antibody molecule comprises one or more or all of FR1, FR2, FR3, or FR4, or sequences that differ individually, or collectively, by no more than 1, 2, 3, 4, of 5 amino acid residues, e.g., conservative residues, from light chain disclosed herein.

In an embodiment, the antibody molecule comprises:
(a) a heavy chain immunoglobulin variable region segment comprising one or more or all of a CDR1 comprising the sequence G-F-T-F-[S/T]-[S/T]-Y-[A/G]-M-H (SEQ ID NO: 184), or a sequence that differs from SEQ ID NO: 184 by no more than 1 or 2 residues; a CDR2 comprising the sequence V-[I/V/L]-S-[Y/F]-D-G-[S/N]-[Y/N]-[K/R]-Y-Y-A-D-S-V-Q-G (SEQ ID NO: 2) or a sequence that differs from SEQ ID NO: 2 by no more than 1 or 2 residues; or a CDR3 comprising the sequence D-[S/T]-[R/K/Q]-L-R-[S/T]-L-L-Y-F-E-W-L-S-[Q/S]-G-[Y/L/V]-[F/L]-[N/D]-[P/Y] (SEQ ID NO: 3), or a sequence that differs from SEQ ID NO:3 by no more than 1 or 2 residues; and
(b) a light chain variable region segment comprising one or more or all of a CDR1 comprising the sequence [K/R]-S-S-Q-[S/T]-[V/L/I]-[T/S]-[Y/F/W]-[N/S/D]-Y-K-N-Y-L-A (SEQ ID NO: 185) or a sequence that differs from SEQ ID NO: 185 by no more than 1 or 2 residues, or comprising the sequence [K/R]-S-S-Q-[S/T]-[V/L/I]-[T/S]-[Y/F/W]-[N/S/D/Q/R/E]-Y-K-N-Y-L-A (SEQ ID NO: 186) or a sequence that differs from SEQ ID NO: 186 by no more than 1 or 2 residues or [K/R]-S-S-Q-[S/T]-[V/L/I]-[T/S]-[Y/F/W]-[N/S/D/E]-Y-K-N-Y-L-A (SEQ ID NO: 185) or a sequence that differs from SEQ ID NO: 186 by no more than 1 or 2 residues; a CDR2 comprising the sequence W-[A/G]-S-[T/A/Y/H/K/D]-[R/L]-E-[S/T] (SEQ ID NO: 5) or a sequence that differs from SEQ ID NO:5 by no more than 1 or 2 residues; or a CDR3 comprising the sequence Q-Q-[Y/H]-Y-R-T-P-P-[T/S] (SEQ ID NO: 6) or a sequence that differs from SEQ ID NO:6 by no more than 1 or 2 residues;
optionally, provided that,
if the light chain variable region segment comprises: a CDR 1 comprising the sequence K-S-S-Q-S-V-T-Y-N-Y-K-N-Y-L-A (SEQ ID NO:83); a CDR2 comprising the sequence W-A-S-T-R-E-S (SEQ ID NO: 84); and a CDR3 comprising the sequence Q-Q-Y-Y-R-T-P-P-T (SEQ ID NO: 85);
then the heavy chain variable region segment comprises one or more of the following: (a) CDRs other than the following: a CDR1 comprising the sequence S-Y-G-M-H (SEQ ID NO: 86); a CDR2 comprising the sequence V-I-S-Y-D-G-S-Y-K-Y-Y-A-D-S-V-Q-G (SEQ ID NO: 87); or a CDR3 comprising the sequence D-S-E-L-R-S-L-L-Y-F-E-W-L-S-Q-G-Y-F-N-P (SEQ ID NO:88); or (b) FRs other than the following: an FR1 other than E-V-Q-L-L-E-S-G-G-G-L-V-K-P-G-Q-S-L-K-L-S-C-A-A-S-G-F-T-F-T (SEQ ID NO: 82); an FR2 other than W-V-R-Q-P-P-G-K-G-L-E-W-V-A (SEQ ID NO:75); an FR3 other than R-F-T-I-S-R-D-N-S-K-N-T-L-Y-L-Q-M-N-S-L-R-A-E-D-T-A-V-Y-Y-C-A-K (SEQ ID NO: 76); or an FR4 other than W-G-A-G-T-T-L-T-V-S-S (SEQ ID NO: 89); (c) a CDR1 where the amino residue at position 5 of SEQ ID NO: 184 is an S, the amino acid residue at position 6 of SEQ ID NO: 184 is a T, or the amino acid residue at position 8 of SEQ ID NO: 184 is an A; (d) a CDR2 wherein the amino residue at position 2 of SEQ ID NO: 2 is a V or an L, the amino acid at position 4 is an F, the amino acid at position 7 is an N, the amino acid at position 8 is a Y, or the amino acid at position 9 is a R; (e) a CDR3 wherein the amino residue at position 2 of SEQ ID NO:3 is a T, the amino acid residue at position 3 of SEQ ID NO:3 is an R, a K, or a Q, the amino acid residue at position 6 of SEQ ID NO: 3 is a T, the amino acid residue at position 15 of SEQ ID NO: 3 is an S, the amino acid residue at position 17 of SEQ ID NO:3 is an L, or a V, the amino acid residue at position 18 of SEQ ID NO:3 is an L, the amino acid residue at position 19 of SEQ ID NO:3 is a D, or the amino acid residue at position 20 of SEQ ID NO:3 is a Y; (f) an FR1 wherein the amino residue at position 11 of SEQ ID NO: 7 is a Q, or the amino acid residue at position 7 of SEQ ID NO: 7 is a T; (g) an FR4 wherein the amino residue at position 3 of SEQ ID NO:10 is a Q, the amino acid residue at position 5 of SEQ ID NO: 10 is an A; the amino acid residue at position 6 of SEQ ID NO: 10 is an M, or the amino acid residue at position 7 of SEQ ID NO:10 is a V; or (h) it produces fewer escape mutants than does a reference anti-HA antibody molecule, e.g., Ab 67-11, F16, F128, C179, F10, CR9114, or CR6261, e.g., when tested by a method disclosed herein, and also provided that, if the heavy chain immunoglobulin variable region segment comprises: a CDR1 comprising the sequence S-Y-G-M-H (SEQ ID NO: 86); a CDR2 comprising the sequence V-I-S-Y-D-G-S-Y-K-Y-Y-A-D-S-V-Q-G (SEQ ID NO:87); and a CDR3 comprising the sequence D-S-E-L-R-S-L-L-Y-F-E-W-L-S-Q-G-Y-F-N-P (SEQ ID NO: 88), then the light chain variable region segment comprises one of more of the following: (a) CDRs other than the following: CDR1 KSSQSVTYNYKNYLA (SEQ ID NO: 83); CDR2 WASTRES (SEQ ID NO:84); or CDR3 QQYYRTPPT (SEQ ID NO: 85); (b) FRs other than the following: FR comprising the sequence EIVMTQSPDSLAVSLGERATINC (SEQ ID NO: 90); FR2 comprising the sequence WYQQKPGQPPKLLIY (SEQ ID NO: 91); FR3 comprising the sequence GVPDRFSGSGSGTDFTLTISSLQAEDVAVYYC (SEQ ID NO: 92); or FR4 comprising the sequence FGGGTKLDIK (SEQ ID NO: 93); (c) a CDR1 wherein the amino residue at position 1 of SEQ ID NO: 185 is an R, the amino residue at position 5 of SEQ ID NO:4 is a T, the amino residue at position 6 of SEQ ID NO:4 is an L or an I, the amino residue at position 7 of SEQ ID NO: 185 is an S, the amino residue at position 8 of SEQ ID NO: 185 is an F or a W, or the amino residue at position 9 of SEQ ID NO: 185 is an S or a D; (d) a CDR2 wherein the amino residue at position 2 of SEQ ID NO: 5 is a G, the amino residue at position 4 of SEQ ID NO: 5 is an A, a Y, an H, a K, or a D, the amino residue at position 5 of SEQ ID NO: 5 is an L, the amino residue at position 7 of SEQ ID NO: 5 is a T; (e) a CDR3 wherein the amino residue at position 3 of SEQ ID NO: 6 is an H; the amino acid residue at position 9 of SEQ ID NO: 6 is an S; (f) an FR1 wherein the amino residue at position 1 of SEQ ID NO: 11 is a D; the amino residue at position 3 of SEQ ID NO: 11 is a Q, the amino residue at position 9 of SEQ ID NO: 11 is an S, the amino residue at position 10 of SEQ ID NO: 11 is a T, the amino residue at position 11 of SEQ ID NO: 11 is a V, the amino residue at position 12 of SEQ ID NO:11 is an S, the amino residue at position 13 of SEQ ID NO: 11 is an A, the amino residue at position 14 of SEQ ID NO:11 is a T, the amino residue at position 15 of SEQ ID NO:11 is a V or an R, the amino residue at position 17 of SEQ ID NO: 11 is a D, the amino residue at position 20 of SEQ ID NO:11 is an S, the amino residue at position 22 of SEQ ID NO:11 is a T, a Q, a D, or an R; (g) an FR2 wherein the amino residue at position 8 of SEQ ID NO:12 is a K; or the amino residue at position 9 of SEQ ID NO: 12 is an A; (h) an FR3 wherein the amino residue at position 4 of SEQ ID NO: 13 is an E or an S; the amino residue at position 24 of SEQ ID NO: 13 is a P, the amino residue at position 27 of SEQ ID NO: 13 is an F, a K, or a D, the amino residue at position 29 of SEQ ID NO: 13 is a T; (i) an FR4 wherein the amino residue at position 3 of SEQ ID NO:14 is a Q, a T, an S, or an N, the amino residue at position 7 of SEQ ID NO:14 is a V, or the amino residue at position 8 of SEQ ID NO:14 is an E; or (j) it produces fewer escape mutants than does a reference anti-HA antibody molecule, e.g., Ab 67-11, F16, F128, C179, F10, CR9114, or CR6261, e.g., when tested by a method disclosed herein; and further provided that if the light chain variable region segment comprises: a CDR 1 comprising the sequence K-S-S-Q-S-V-T-F-N-Y-K-N-Y-L-A (SEQ ID NO: 146); a CDR2 comprising the sequence W-A-S-A-R-E-S (SEQ ID NO: 147); and a CDR3 comprising the sequence Q-Q-H-Y-R-T-P-P-T (SEQ ID NO: 148); then the heavy chain variable region segment comprises one or more of the following: CDRs other than the CDR's described at FIG. 4; or FRs other than the FRs described at FIG. 4.

In an embodiment, the heavy chain CDR sequences, collectively, differ from the recited sequences by no more than 5, 4, 3, 2 or 1 amino acid residues; and the light chain CDR sequences, collectively, differ from the recited sequences by no more than 5, 4, 3, 2 or 1 amino acid residues.

In an embodiment, the antibody molecule comprises:
(a) a heavy chain (HC) immunoglobulin variable region segment comprising:
   an HC CDR1 comprising the sequence S-Y-A-M-H (SEQ ID NO:68), or a sequence that differs therefrom at the $3^{rd}$ position (A to G substitution);
   an HC CDR2 comprising the sequence V-V-S-Y-D-G-N-Y-K-Y-Y-A-D-S-V-Q-G (SEQ ID NO:69) or a sequence that differs therefrom at the 2 position (V to I substitution), the $7^{th}$ residue (N to S substitution), the $8^{th}$ position (Y to N substitution), or a combination thereof;
   an HC CDR3 comprising the sequence D-S-R-L-R-S-L-L-Y-F-E-W-L-S-Q-G-Y-F-N-P (SEQ ID NO:70), or a sequence that differs therefrom at the $2^{nd}$ position (S to T substitution), the $3^{rd}$ position (R to K substitution), the $15^{th}$ position (Q to S substitution), the 17 position (Y to L substitution), the $18^{th}$ position (F to L substitution), the 19 position (N to D substitution), the 20 position (P to Y substitution), or a combination thereof; and
(b) a light chain (LC) immunoglobulin variable region segment comprising:
   an LC CDR1 comprising the sequence Q-S-I-T-F-N-Y-K-N-Y-L-A (SEQ ID NO:71), or a sequence that differs therefrom at the $2^{nd}$ position (S to T substitution), the $3^{rd}$ position (I to V substitution), the $5^{th}$ position (F to Y substitution), the $6^{th}$ position (N to S or N to D substitution), the $12^{th}$ position (A to G substitution), or a combination thereof;
   an LC CDR2 comprising the sequence W-G-S-Y-L-E-S (SEQ ID NO:72), or a sequence that differs therefrom at the $2^{nd}$ position (G to A substitution), the $4^{th}$ position (Y to T substitution), the $5^{th}$ position (L to R substitution), or a combination thereof;
   an LC CDR3 comprising the sequence Q-Q-H-Y-R-T-P-P-S (SEQ ID NO:73), or a sequence that differs therefrom at the $3^{rd}$ position (H to Y substitution), the $9^{th}$ position (S to T substitution), or both.

In an embodiment, the HC CDR1-3 and LC CDR1-3, collectively, comprise sequences that differ by 0, 1 or 2 amino acids from SEQ ID NOS: 68-73.

In an embodiment, the antibody molecule comprises a heavy chain immunoglobulin variable region segment encoded by a nucleotide sequence described herein. In another embodiment, the antibody molecule comprises a light chain immunoglobulin variable region segment encoded by a nucleotide sequence described herein. In yet another embodiment, the antibody molecule comprises a heavy chain immunoglobulin variable region segment encoded by a nucleotide sequence described herein and a light chain immunoglobulin variable region segment encoded by a nucleotide sequence described herein.

In an embodiment, the heavy chain immunoglobulin variable region segment is expressed from a recombinant vector, such as an expression vector, that comprises a nucleotide sequence that encodes a heavy chain immunoglobulin variable region segment. In another embodiment, the light chain immunoglobulin variable segment is expressed from a recombinant vector, such as an expression vector, that comprises a nucleotide sequence that encodes a light chain immunoglobulin variable region segment. In yet another embodiment, the heavy chain immunoglobulin variable region segment and light chain immunoglobulin variable region segment are expressed from a recombinant vector, such as an expression vector, that comprises a nucleotide sequence that encodes a heavy chain immunoglobulin variable region segment and a nucleotide sequence that encodes a light chain immunoglobulin variable region segment.

In an embodiment, the nucleotide sequence encodes (a) a heavy chain immunoglobulin variable region segment comprising the amino acid sequence of: S-Y-A-M-H (SEQ ID NO: 68) in CDR1; V-V-S-Y-D-G-N-Y-K-Y-Y-A-D-S-V-Q-G (SEQ ID NO: 69) in CDR2; and D-S-R-L-R-S-L-L-Y-F-E-W-L-S-Q-G-Y-F-N-P (SEQ ID NO: 70) in CDR3; and (b) a light chain immunoglobulin variable region segment comprising the amino acid sequence of: Q-S-I-T-F-D-Y-K-N-Y-L-A (SEQ ID NO: 145) in CDR1; W-G-S-Y-L-E-S (SEQ ID NO: 72) in CDR2; and Q-Q-H-Y-R-T-P-P-S (SEQ ID NO: 73) in CDR3.

In an embodiment, the heavy chain immunoglobulin variable region segment is expressed from a cell (e.g., a host cell) containing a recombinant vector described herein, such as a recombinant vector comprising a nucleic acid sequence that encodes a heavy chain immunoglobulin variable region. In another embodiment, the light chain immunoglobulin variable region segment is expressed from a cell (e.g., a host cell) containing a recombinant vector described herein, such as a recombinant vector comprising a nucleic acid sequence that encodes a light chain immunoglobulin variable region.

In yet another embodiment, the cell (e.g., a host cell) contains a recombinant vector comprising a nucleic acid sequence that encodes a heavy chain immunoglobulin variable region, and a nucleic acid sequence that encodes a light chain immunoglobulin variable region.

In an embodiment, the antibody molecule is made by a method comprising providing a cell (e.g., a host cell) comprising a nucleotide sequence expressing a heavy chain variable region segment and a nucleotide sequence expressing a light chain variable region segment, and expressing the nucleic acids in the cell.

In an embodiment, the nucleotide sequence expressing the heavy chain variable region segment and the nucleotide sequence expressing the light chain variable region segment are on the same recombinant vector (e.g., expression vector). In another embodiment, the nucleotide sequence expressing the heavy chain variable region segment and the nucleotide sequence expressing the light chain variable region segment are on separate recombinant vectors (e.g., expression vectors).

In an embodiment, the antibody molecule is present in a pharmaceutical composition containing a pharmaceutically acceptable carrier. In an embodiment, the pharmaceutical composition is present in a container as described herein.

METHODS OF USE

In another aspect, the disclosure features a method of treating or preventing infection with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010), in a subject, e.g., a human subject. The method includes administering a formulation described herein, e.g., a pharmaceutical formulation described herein, to a subject, e.g., human subject, in need thereof.

In an embodiment, the influenza A virus is an H1, H5, H9, H3 or H7 strain, such as an H1N1 strain, an H3N2 strain, an H5N1 strain, or an H7N9 strain of influenza A virus.

In an embodiment, the formulation is administered at dose of about 2000 mg to about 5000 mg, e.g., about 2300 mg to about 4600 mg, about 2000 mg to about 2500 mg, about 2500 mg to about 3000 mg, about 3000 mg to about 3500 mg, about 3500 mg to about 4000 mg, about 4000 mg to about 4500 mg, about 4500 to about 5000 mg, of the antibody molecule. In an embodiment, the formulation is administered at a dose about 2300 mg or about 4600 mg, of the antibody molecule. In an embodiment, the formulation is administered intravenously, e.g., by infusion.

In an embodiment, the administration results in, or correlates with, one or more of a reduction in the incidence or severity of a symptom or manifestation of an influenza infection, or the delay or onset of a symptom or manifestation of an influenza infection. In an embodiment, the administration results in, or correlates with, one or more of a reduction in the incidence or severity of a symptom or manifestation of a secondary infection, or the delay or onset of a symptom or manifestation of a secondary infection.

In an embodiment, the subject, e.g., a human subject, has been administered, or the method comprises, administering, or recommending the administration of, a second or additional therapy. In an embodiment, the antibody molecule is administered in combination with a second or additional agent or therapy.

In an embodiment, the second or additional therapy comprises administration of a vaccine or an anti-viral therapy, e.g., an anti-NA or an anti-M2 therapy. In an embodiment the second or additional therapy comprises a administration of a vaccine, e.g., a vaccine described herein or a mixture (a.k.a. a cocktail) of influenza peptides to stimulate the patient's immune system to prevent infection with particular strains of influenza A. In an embodiment the second or additional agent comprises administering an antiviral agent, a pain reliever, an anti-inflammatory, an antibiotic, a steroidal agent, a second therapeutic antibody molecule (e.g., an anti-HA antibody), an adjuvant, a protease or glycosidase (e.g., sialidase). In an embodiment the second or additional agent comprises, acyclovir, ribavirin, amantadine, remantidine, a neuraminidase inhibitor (e.g., zanamivir (Relenza®), oseltamivir (Tamiflu®), laninamivir, peramivir), or rimantadine.

In an embodiment the second or additional agent comprises a second antibody molecule, e.g., Ab 67-11 (U.S. Provisional application No. 61/645,453, U.S. Application Publication No. 2013/0302348, and International Application Publication No. WO 2013/169377), F16 (U.S. Application Publication No. 2010/0080813), F128 (U.S. Application Publication No. 2010/0080813), C179 (Okuno et al., *J. Virol.* 67:2552-8, 1993), F10 (Sui et al., *Nat. Struct. Mol. Biol.* 16:265, 2009), CR9114 (Dreyfus et al., *Science* 337: 1343, 2012), or CR6261 (Ekiert et al., *Science* 324:246, 2009). Thus, the formulation described herein (e.g., a formulation comprising Ab 044) can be used in combination of any of those antibodies.

In an embodiment the second or additional agent comprises a second or additional antibody molecule, e.g., an anti-HA antibody, e.g., an anti-HA antibody disclosed herein. For example, two or more of Ab 044, Ab 069, Ab 032, and Ab 031 can be administered. For example, Ab 044 can be administered in combination with Ab 069 or Ab 032.

In the case of combinations, two agents can be administered as part of the same dosage unit or administered separately. Other exemplary agents useful for treating the symptoms associated with influenza infection are acetaminophen, ibuprofen, aspirin, and naproxen.

In an embodiment the formulation, e.g., pharmaceutical formulation, is administered to a human subject suffering from or susceptible to an influenza infection. In an embodiment, the formulation, e.g., pharmaceutical formulation, is administered prior to known exposure to influenza, or to particular influenza subtypes or strains. In an embodiment, the formulation, e.g., pharmaceutical formulation, is administered prior to manifestation of effects or symptoms of influenza infection, or to one or more particular effects manifestation of effects or symptoms of influenza infection. In an embodiment, the formulation, e.g., pharmaceutical formulation, is administered after known exposure to influenza, or to particular influenza subtypes or strains. In an embodiment, the formulation, e.g., pharmaceutical formulation, is administered after manifestation of effects or symptoms of influenza infection, or after observation of one or more particular effects manifestation of effects or symptoms of influenza infection. In an embodiment, the formulation, e.g., pharmaceutical formulation, is administered in response to, or to treat or prevent, a manifestation of an effect or a symptom of influenza infection, e.g., inflammation, fever, nausea, weight loss, loss of appetite, rapid breathing, increase heart rate, high blood pressure, body aches, muscle pain, eye pain, fatigue, malaise, dry cough, runny nose, and/or sore throat.

In an embodiment, the method further comprises, testing the subject, e.g., human subject, for the influenza virus, e.g., with a method disclosed herein. In an embodiment, the administration is responsive to a positive test for influenza.

In yet another aspect, the disclosure features a method of treating a subject, e.g., a human subject, infected with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010) by administering a formulation, e.g., pharmaceutical formulation, described herein. For example, the influenza A virus is an H1, H5, H9, H3 or H7 strain, such as an H1N1 strain, an H3N2 strain, an H5N1 strain, or an H7N9 strain of influenza A virus.

In an embodiment, the formulation, e.g., pharmaceutical formulation, is administered instead of a vaccine for prevention of influenza. In another embodiment, the formulation, e.g., pharmaceutical formulation, is administered in combination with (simultaneously or sequentially with) a vaccine for prevention of the influenza.

In yet another aspect, the disclosure features a method of detecting influenza (e.g., influenza A or influenza B) virions in a biological sample, such as by contacting the sample with a formulation, e.g., pharmaceutical formulation, comprising an anti-HA antibody molecule described herein, and then detecting the binding of the antibody molecule to the sample. In an embodiment, the method of detecting the influenza virus (e.g., influenza A or influenza B virus) is performed in vitro.

In one aspect, the disclosure features a method of (a) providing a sample from a patient; (b) contacting the sample with a formulation, e.g., pharmaceutical formulation, comprising an anti-HA antibody molecule described herein, and (c) determining whether the antibody molecule binds a polypeptide in the sample, where if the antibody molecule binds a polypeptide in the sample, then the patient is determined to be infected with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010). In an embodiment, the patient is determined to be infected with an influenza virus (e.g., an influenza A virus, e.g., a Group 1 strain, e.g., an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, or an influenza B virus, e.g., B/Wisconsin/1/2010), and the patient is further administered a formulation or an antibody molecule, disclosed herein, with which the test was performed.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments featured in the disclosure are set forth in the accompanying drawings and the description below. Other features, objects, and advantages featured in the disclosure will be apparent from the description and drawings, and from the claims.

BRIEF DESCRIPTION OF THE DRAWINGS

FIG. 1 is the heavy and light chain amino acid sequences (SEQ ID NOs:94 and 95, respectively) of the anti-HA antibody A18. The constant domain sequence is indicated by italics. The CDRs are indicated by underlining.

FIG. 2 is the variable heavy chain domain sequence of exemplary anti-HA antibodies. The SEQ ID NOs for sequences shown are as follows: VH15 is SEQ ID NO: 15; VH16 is SEQ ID NO: 16; VH17 is SEQ ID NO: 17; VH18 is SEQ ID NO: 18; VH19 is SEQ ID NO: 19; VH21 is SEQ ID NO: 21; VH22 is SEQ ID NO: 22; VH20 is SEQ ID NO: 20; VH23 is SEQ ID NO: 23; VH24 is SEQ ID NO: 24; VH25 is SEQ ID NO: 25; VH26 is SEQ ID NO: 26; VH27 is SEQ ID NO: 27; and VH161 is SEQ ID NO: 161.

FIGS. 3A-3B depict the variable light chain domain sequence of exemplary anti-HA antibodies. The SEQ ID NOs for sequences shown are as follows: VL28 is SEQ ID NO: 28; VL29 is SEQ ID NO: 29; VL30 is SEQ ID NO: 30; VL35 is SEQ ID NO: 35; VL31 is SEQ ID NO: 31; VL32 is SEQ ID NO: 32; VL33 is SEQ ID NO: 33; VL34-ID is SEQ ID NO: 34; VL36 is SEQ ID NO: 36; VL45 is SEQ ID NO: 45; VL46 is SEQ ID NO: 46; VL37 is SEQ ID NO: 37; VL38 is SEQ ID NO: 38; VL39 is SEQ ID NO: 39; VL40 is SEQ ID NO: 40; VL41 is SEQ ID NO: 41; VL42 is SEQ ID NO: 42; VL43 is SEQ ID NO: 43; VL44 is SEQ ID NO: 44; VL47 is SEQ ID NO: 47; VL48 is SEQ ID NO: 48; VL49 is SEQ ID NO: 49; VL50 is SEQ ID NO: 50; VL51 is SEQ ID NO: 51; VL52 is SEQ ID NO: 52; VL53 is SEQ ID NO: 53; VL54 is SEQ ID NO: 54; VL55 is SEQ ID NO: 55; VL56 is SEQ ID NO: 56; VL57 is SEQ ID NO: 57; VL58 is SEQ ID NO: 58; VL59 is SEQ ID NO: 59; VL60 is SEQ ID NO: 60; VL61 is SEQ ID NO: 61; VL153 is SEQ ID NO: 153; VL154 is SEQ ID NO: 154; VL155 is SEQ ID NO: 155; VL156 is SEQ ID NO: 156; and VL62 is SEQ ID NO: 62.

FIG. 4 shows the amino acid sequences of the heavy chain variable regions of FI6 (SEQ ID NO: 175), F1370 (SEQ ID NO: 176), F16 variant 1 (SEQ ID NO: 177), F16 variant 3 (SEQ ID NO: 178), FI6/370 (SEQ ID NO: 179) and the amino acid sequence of kappa light chain variable region of F16 (SEQ ID NO: 180).

FIG. 5 is the variable heavy chain domain sequence of exemplary anti-HA antibodies as shown in FIG. 2 and including an N-terminal ID dipeptide. The SEQ ID NOs. for sequences shown are as follows: VH15-ID is SEQ ID NO: 96; VH16-ID is SEQ ID NO: 97; VH17-ID is SEQ ID NO: 98; VH18-ID is SEQ ID NO: 99; VH19-ID is SEQ ID NO: 100; VH21-ID is SEQ ID NO: 101; VH22-ID is SEQ ID NO: 102; VH20-ID is SEQ ID NO: 103; VH23-ID is SEQ ID NO: 104; VH24-ID is SEQ ID NO: 105; VH25-ID is SEQ ID NO: 106; VH26-ID is SEQ ID NO: 107; VH27-ID is SEQ ID NO: 108; and VH161-ID is SEQ ID NO: 109.

FIGS. 6A-6B depict the variable light chain domain sequence of exemplary anti-HA antibodies as shown in FIGS. 3A-3B and including an N-terminal ID dipeptide. The SEQ ID NOs for sequences shown are as follows: VL28-ID is SEQ ID NO: 110; VL29-ID is SEQ ID NO: 111; VL30-ID is SEQ ID NO: 112; VL35-ID is SEQ ID NO: 113; VL31-ID is SEQ ID NO: 114; VL32-ID is SEQ ID NO: 115; VL33-ID is SEQ ID NO: 116; VL34-ID is SEQ ID NO: 117; VL36-ID is SEQ ID NO: 118; VL45-ID is SEQ ID NO: 119; VL46-ID is SEQ ID NO: 120; VL37-ID is SEQ ID NO: 121; VL38-ID is SEQ ID NO: 122; VL39-ID is SEQ ID NO: 123; VL40-ID is SEQ ID NO: 124; VL41-ID is SEQ ID NO: 125; VL42-ID is SEQ ID NO: 126; VL43-ID is SEQ ID NO: 127; VL44-ID is SEQ ID NO: 128; VL47-ID is SEQ ID NO: 129; VL48-ID is SEQ ID NO: 130; VL49-ID is SEQ ID NO: 131; VL50-ID is SEQ ID NO: 132; VL51-ID is SEQ ID NO: 133; VL52-ID is SEQ ID NO: 134; VL53-ID is SEQ ID NO: 135; VL54-ID is SEQ ID NO: 136; VL55-ID is SEQ ID NO: 137; VL56-ID is SEQ ID NO: 138; VL57-ID is SEQ ID NO: 139; VL58-ID is SEQ ID NO: 140; VL59-ID is SEQ ID NO: 141; VL60-ID is SEQ ID NO: 142; VL61-ID is SEQ ID NO: 143; VL153-ID is SEQ ID NO: 157; VL154-ID is SEQ ID NO: 158; VL155-ID is SEQ ID NO: 159; VL156-ID is SEQ ID NO: 160; and VL62-ID is SEQ ID NO: 144.

FIG. 7 shows the variable light and heavy chain sequences of additional exemplary anti-HA antibodies. The SEQ ID NOs for sequences shown are as follows: VL165 is SEQ ID NO: 165; VL166 is SEQ ID NO: 166; VL167 is SEQ ID NO: 167; VL168 is SEQ ID NO: 168; VL169 is SEQ ID NO: 169; VH164 is SEQ ID NO: 164; VH162 is SEQ ID NO: 162; VH163 is SEQ ID NO: 163.

FIGS. 8A-8G show the DSC profile for all of the 14 formulation samples tested in Example 2.

DETAILED DESCRIPTION

Figure 8G:
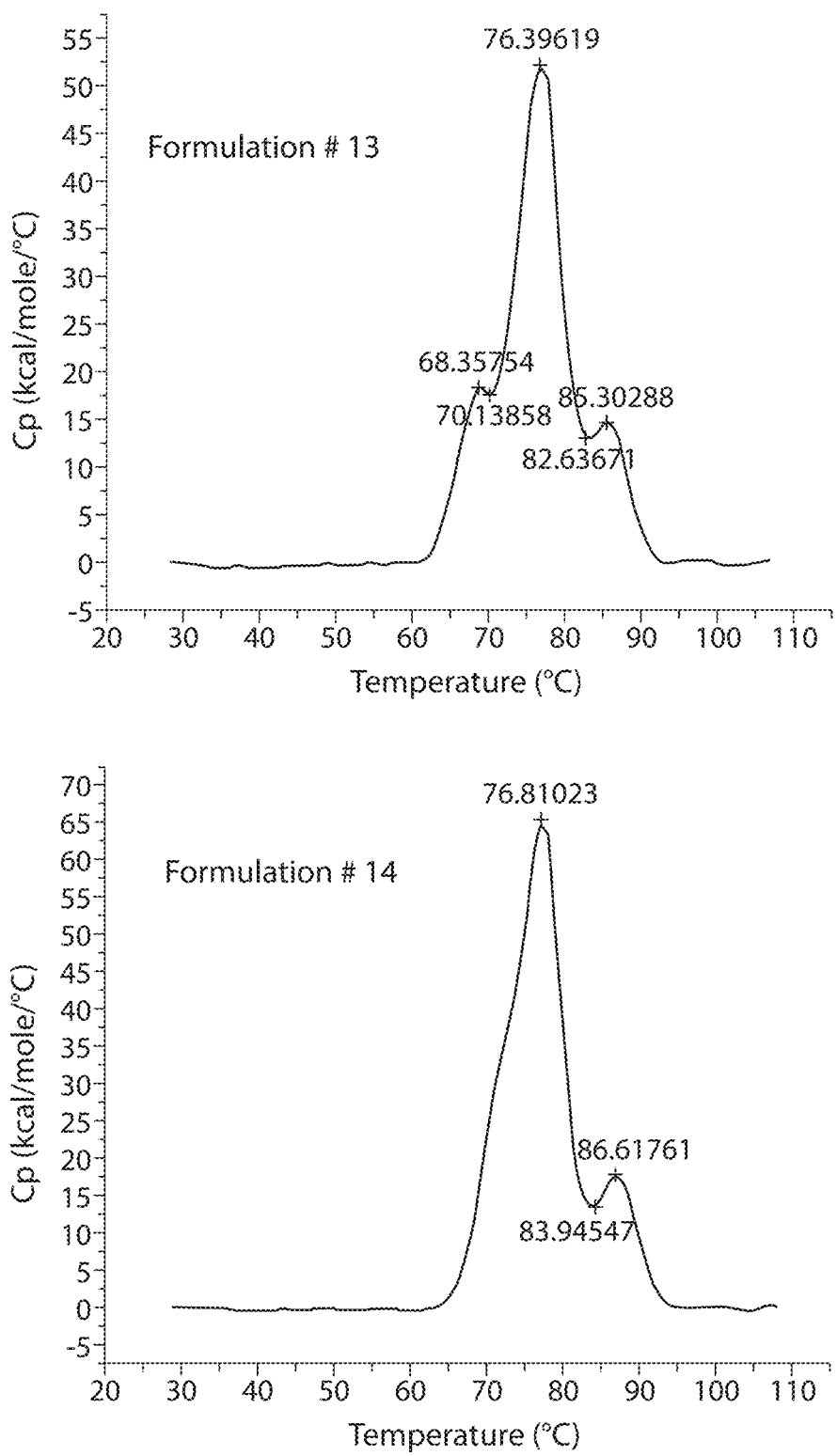

The disclosure is based, at least in part, on the design and synthesis of antibody molecules that can bind an epitope that is conserved across multiple hemagglutinin subtypes of influenza viruses (e.g., influenza A and influenza B viruses). For example, formulations (e.g., pharmaceutical formulations) comprising the antibody molecules described herein are useful as broad spectrum therapy against disease caused by at least one influenza A strain belonging to Group 1 and one influenza A strain belonging to Group 2 to neutralize infectivity of viruses belonging to both Group 1 and Group 2 (at least one subtype of each). Without wishing to be bound by theory, it is believed that the formulations (e.g., pharmaceutical formulations) described herein are suitable for use in treating or preventing influenza viruses, at least in part, because the formulations (e.g., pharmaceutical formulations) have one or more desired properties such as improved stability (e.g., low degradation and/or aggregation) and maintained potency (e.g., HA binding).

The antibody molecules were designed by a rational structure-based approach to target a region on the virus that is not fully accessible to the human immune system and, therefore, not amenable to antibody selection through more classical screening approaches. This rational-based approach to the design and development of broad-spectrum antibody molecules allows for the development of more efficacious vaccines for pandemic and seasonal influenza. This approach also allows for the advance preparation of pandemic vaccines so that they are ready to be employed against specific virus subtypes (e.g., avian virus subtypes) that may mutate to become human-adapted and highly transmissible. Vaccines (e.g., seasonal vaccines) that utilize the approach described herein can generate a more potent immune response without the use of adjuvants and provide broad protection against viral strain variation.

Definitions

As used herein, the term "antibody molecule" refers to a polypeptide that comprises sufficient sequence from an immunoglobulin heavy chain variable region and/or sufficient sequence from an immunoglobulin light chain variable region, to provide antigen specific binding. It comprises full length antibodies as well as fragments thereof, e.g., Fab fragments, that support antigen binding. Typically an antibody molecule will comprise heavy chain CDR1, CDR2, and CDR3 and light chain CDR1, CDR2, and CDR3 sequence. Antibody molecules include human, humanized, CDR-grafted antibodies and antigen binding fragments thereof. In an embodiment, an antibody molecule comprises a protein that comprises at least one immunoglobulin variable region segment, e.g., an amino acid sequence that provides an immunoglobulin variable domain or immunoglobulin variable domain sequence.

The VH or VL chain of the antibody molecule can further include all or part of a heavy or light chain constant region, to thereby form a heavy or light immunoglobulin chain, respectively. In an embodiment, the antibody molecule is a tetramer of two heavy immunoglobulin chains and two light immunoglobulin chains.

An antibody molecule can comprise one or both of a heavy (or light) chain immunoglobulin variable region segment. As used herein, the term "heavy (or light) chain immunoglobulin variable region segment," refers to an entire heavy (or light) chain immunoglobulin variable region, or a fragment thereof, that is capable of binding antigen. The ability of a heavy or light chain segment to bind antigen is measured with the segment paired with a light or heavy chain, respectively. In some embodiment, a heavy or light chain segment that is less than a full length variable region will, when paired with the appropriate chain, bind with an affinity that is at least 20, 30, 40, 50, 60, 70, 80, 90, or 95% of what is seen when the full length chain is paired with a light chain or heavy chain, respectively.

An immunoglobulin variable region segment may differ from a reference or consensus sequence. As used herein, to "differ," means that a residue in the reference sequence or consensus sequence is replaced with either a different residue or an absent or inserted residue.

An antibody molecule can comprise a heavy (H) chain variable region (abbreviated herein as VH), and a light (L) chain variable region (abbreviated herein as VL). In another example, an antibody comprises two heavy (H) chain variable regions and two light (L) chain variable regions or antibody binding fragments thereof. The light chains of the immunoglobulin may be of types kappa or lambda. In an embodiment, the antibody molecule is glycosylated. An antibody molecule can be functional for antibody dependent cytotoxicity and/or complement-mediated cytotoxicity, or may be non-functional for one or both of these activities. An antibody molecule can be an intact antibody or an antigen-binding fragment thereof.

Antibody molecules include "antigen-binding fragments" of a full length antibody, e.g., one or more fragments of a full-length antibody that retain the ability to specifically bind to an HA target of interest. Examples of binding fragments encompassed within the term "antigen-binding fragment" of a full length antibody include (i) a Fab fragment, a monovalent fragment consisting of the VL, VH, CL and CH1 domains; (ii) a F(ab') or $F(ab')_2$ fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) *Science* 242:423-426; and Huston et al. (1988) *Proc. Natl. Acad. Sci. USA* 85:5879-5883. Antibody molecules include diabodies.

As used herein, an antibody refers to a polypeptide, e.g., a tetrameric or single chain polypeptide, comprising the structural and functional characteristics, particularly the antigen binding characteristics, of an immunoglobulin. Typically, a human antibody comprises two identical light chains and two identical heavy chains. Each chain comprises a variable region.

The variable heavy (VH) and variable light (VL) regions can be further subdivided into regions of hypervariability, termed "complementarity determining regions" ("CDR"), interspersed with regions that are more conserved, termed "framework regions" (FR). Human antibodies have three VH CDRs and three VL CDRs, separated by framework regions FR1-FR4. The extent of the FRs and CDRs has been precisely defined (see, Kabat, E. A., et al. (1991) Sequences of Proteins of Immunological Interest, Fifth Edition, U.S. Department of Health and Human Services, NIH Publication No. 91-3242; and Chothia, C. et al. (1987) *J. Mol. Biol.* 196:901-917). Kabat definitions are used herein. Each VH and VL is typically composed of three CDRs and four FRs, arranged from amino-terminus to carboxyl-terminus in the following order: FR1, CDR1, FR2, CDR2, FR3, CDR3, FR4.

The heavy and light immunoglobulin chains can be connected by disulfide bonds. The heavy chain constant region typically comprises three constant domains, CH1, CH2 and CH3. The light chain constant region typically comprises a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

The term "immunoglobulin" comprises various broad classes of polypeptides that can be distinguished biochemically. Those skilled in the art will appreciate that heavy chains are classified as gamma, mu, alpha, delta, or epsilon ($\gamma, \mu, \alpha, \delta, \epsilon$) with some subclasses among them (e.g., $\gamma 1$-$\gamma 4$). It is the nature of this chain that determines the "class" of the antibody as IgG, IgM, IgA IgD, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure. Light chains are classified as either kappa or lambda ($\kappa, \lambda$). Each heavy chain class may be bound with either a kappa or lambda light chain.

Suitable antibodies include, but are not limited to, monoclonal, monospecific, polyclonal, polyspecific, human antibodies, primatized antibodies, chimeric antibodies, bi-specific antibodies, humanized antibodies, conjugated antibodies (e.g., antibodies conjugated or fused to other proteins, radiolabels, or cytotoxins), Small Modular ImmunoPharmaceuticals ("SMIPs"), single chain antibodies, cameloid antibodies, and antibody fragments.

In an embodiment, an antibody is a humanized antibody. A humanized antibody refers to an immunoglobulin comprising a human framework region and one or more CDR's from a non-human, e.g., mouse or rat, immunoglobulin. The immunoglobulin providing the CDR's is often referred to as the "donor" and the human immunoglobulin providing the framework often called the "acceptor," though in an embodiment, no source or no process limitation is implied. Typically a humanized antibody comprises a humanized light chain and a humanized heavy chain immunoglobulin.

An "immunoglobulin domain" refers to a domain from the variable or constant domain of immunoglobulin molecules. Immunoglobulin domains typically contain two $\beta$-sheets formed of about seven $\beta$-strands, and a conserved disulfide bond (see e.g., A. F. Williams and A. N. Barclay (1988) *Ann. Rev. Immunol.* 6:381-405).

As used herein, an "immunoglobulin variable domain sequence" refers to an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In an embodiment, a polypeptide that comprises an immunoglobulin variable domain sequence can associate with another immunoglobulin variable domain sequence to form a target binding structure (or "antigen binding site"), e.g., a structure that interacts with the target antigen.

As used herein, the term antibodies comprises intact monoclonal antibodies, polyclonal antibodies, single domain antibodies (e.g., shark single domain antibodies (e.g., IgNAR or fragments thereof)), multispecific antibodies (e.g., bi-specific antibodies) formed from at least two intact antibodies, and antibody fragments so long as they exhibit the desired biological activity. Antibodies for use herein may be of any type (e.g., IgA, IgD, IgE, IgG, or IgM).

The antibody or antibody molecule can be derived from a mammal, e.g., a rodent, e.g., a mouse or rat, horse, pig, or goat. In an embodiment, an antibody or antibody molecule is produced using a recombinant cell. In some embodiments an antibody or antibody molecule is a chimeric antibody, for example, from mouse, rat, horse, pig, or other species, bearing human constant and/or variable regions domains.

A binding agent, as used herein, is an agent that bind, e.g., specifically binds, a target antigen, e.g., HA. Binding agents of the invention share sufficient structural relationship with anti-HA antibody molecules disclosed herein to support specific binding to HA, and in an embodiment, other functional properties of an anti-HA antibody molecule disclosed herein. In an embodiment, a binding agent will exhibit a binding affinity at of at least 10, 20, 30, 40, 50, 60, 70, 80, or 90% of an antibody molecule disclosed herein, e.g., an antibody molecule with which it shares, significant structural homology, e.g., CDR sequences. Binding agents can be naturally occurring, e.g., as are some antibodies, or synthetic. In an embodiment a binding agents is a polypeptide, e.g., an antibody molecule, e.g., an antibody. While some binding agents are antibody molecules, other molecules, e.g., other polypeptides, can also function as binding agents. Polypeptide binding agents can be monomeric or multimeric, e.g., dimeric, trimeric, or tetrameric and can be stabilized by intra- or interchain bonds, e.g., disulfide bonds. They can contain natural or non-naturally occurring amino acid residues. In an embodiment, binding agents are antibody molecules, or other polypeptides, that present one or more CDRs of antibody molecules disclosed herein or that otherwise mimic the structure of an antibody molecule disclosed herein. Binding agents can also comprise aptomers, nucleic acids or other molecular entities. A binding agent can be developed in a variety of ways, e.g., by immunization, by rational design, screening of random structures, or a combination of those or other approaches. Typically a binding agent will act by making contact with substantially the same epitope as an antibody molecule disclosed herein, e.g., an antibody molecule with which it shares, significant structural homology, e.g., CDR sequences. A binding agent can interact with amino acids, saccharides, or combinations thereof. Polypeptides other than antibodies can be used as a scaffold to present sequence, e.g., one or more, or a complete set of heavy chain and/or light chain CDRs, disclosed herein. Exemplary scaffolds include adnectin, zinc finger DNA-binding proteins. protein A, lipoclins, ankryin consensus repeat domain, thioredoxin, anticalins, centyrin, avimer domains, ubiquitin, peptidomimetics, stapled peptides, cystine-knot miniproteins, and IgNARs. In some embodiments, a binding agent is or comprises a nucleic acid, e.g., DNA, RNA or mixtures thereof. In an embodiment, a binding agent, e.g., a nucleic acid, shows secondary, tertiary, or quaternary structure. In some embodiments a binding agent, e.g., a nucleic acid, forms a structure that mimics the structure of an antibody molecule disclosed herein.

A broad spectrum binding agent, e.g., antibody molecule, as used herein, binds, a plurality of different HA molecules, and optionally neutralizes viruses comprising the different HA molecules. In an embodiment it binds a first HA and binds a second HA from influenza A Group 1, and optionally neutralizes viruses comprising the first or second HA molecules. In an embodiment, it binds a first HA from an influenza A Group 1 virus, and binds a second HA from an influenza A Group 2 virus, and optionally neutralizes viruses comprising the different HA molecules. In an embodiment it binds a first HA from an influenza A Group 1 or 2 virus and binds a HA from an influenza B virus, and optionally neutralizes viruses comprising the different HA molecules. In an embodiment, it binds, and in an embodiment neutralizes, at least two different clades or clusters of virus, e.g., from different Groups. In an embodiment, it binds, and in an embodiment neutralizes, all or substantially all strains of Group 1 and/or Group 2 disclosed herein. In an embodiment, a binding agent, e.g., antibody molecule, binds, and in an embodiment, neutralizes: at least one strain from the Group 1 H1, e.g., H1a or H1b, cluster and at least one strain from the Group 2 H3 or H7 cluster. In an embodiment, a binding agent, e.g., antibody molecule, binds, and in an embodiment, neutralizes: at least one strain from the Group 1 H1, e.g., H1a or H1b, cluster and at least one influenza B strain. In an embodiment, a binding agent, e.g., antibody molecule, binds, and in an embodiment, neutralizes: at least one strain from the Group 2 H3 or H7 cluster and at least one influenza B strain. In an embodiment, a binding agent, e.g., antibody molecule, binds, and in an embodiment, neutralizes: at least one strain from the Group 1 H1, e.g., H1a or H1b, cluster, at least one strain from the Group 2 H3 or H7 cluster, and at least one influenza B strain. In some embodiments, binding agent, e.g., antibody molecule, binds, and optionally neutralizes or mediate infection of particular hosts, e.g., avian, camel, canine, cat, civet, equine, human, mouse, swine, tiger, or other mammal or bird.

The term "combination therapy", as used herein, refers to administration of a plurality of agents, e.g., wherein at least one binding agent, e.g., antibody molecule, disclosed herein is administered to a subject, e.g., a human subject. The introduction of the agents into the subject can be at different times. In an embodiment, the agents are administered in overlapping regimens, or such that the subject is simultaneously exposed to both agents, or such that the response of the subject is better than would be seen with either agent administered alone.

As used herein, an "escape mutant" is a mutated influenza strain that is resistant to neutralization by an anti-HA antibody molecule described herein. In an embodiment, an escape mutant is resistant to neutralization with a binding agent, e.g., antibody molecule, but its parent strain is neutralized by the binding agent, e.g., antibody molecule.

As used herein, "pandemic influenza" refers to a new viral strain that arises due to human adaptation of an influenza strain by mutation or by emergence of a strain by reassortment of different strains of influenza A. The resulting pandemic strain is significantly different from previous strains and most people will have little or no pre-existing immunity. Symptoms and complications may be more severe and more frequent than those typical of seasonal influenza. Examples of past pandemic flu viruses include, e.g., the 2009 H1N1 'swine flu,' the 1957-58 H2N2 'Asian flu' and the 1968 H3N2 influenza strains.

The terms "purified" and "isolated" as used herein in the context of an antibody molecule, e.g., a antibody, a immunogen, or generally a polypeptide, obtained from a natural source, refers to a molecule which is substantially free of contaminating materials from the natural source, e.g., cellular materials from the natural source, e.g., cell debris, membranes, organelles, the bulk of the nucleic acids, or proteins, present in cells. Thus, a polypeptide, e.g., an antibody molecule, that is isolated includes preparations of a polypeptide having less than about 30%, 20%, 10%, 5%, 2%, or 1% (by dry weight) of cellular materials and/or contaminating materials. The terms "purified" and "isolated" when used in the context of a chemically synthesized species, e.g., an antibody molecule, or immunogen, refers to the species which is substantially free of chemical precursors or other chemicals which are involved in the syntheses of the molecule.

A preparation of binding agents, e.g., antibody molecules, as used herein, comprises a plurality of molecules of a binding agent, e.g., antibody molecule, described herein. In an embodiment, that binding agent, e.g., antibody molecule, makes up at least 60, 70, 80, 90, 95, 98, 99, 99.5 or 99.9%, of the preparation, or of the active ingredients of the preparation, by weight or number. In an embodiment, that binding agent is an antibody molecule which makes up at least 60, 70, 80, 90, 95, 98, 99, 99.5 or 99.9%, of the preparation, or of the active ingredients, or polypeptide ingredients, or antibody molecules, of the preparation, by weight or number. In an embodiment, the binding agent is an antibody molecule and the preparation contains no more than 30, 20, 10, 5, 2, 1, or 0.5%, by weight or number, of a contaminant, e.g., a reactant, solvent, precursor or other species, from the source, or used in the preparation, of the antibody molecule, e.g., a species from a cell, reaction mixture, or other system used to produce the antibody molecule.

As used herein, the term "prevent infection" means that a subject (e.g., a human) is less likely to be infected by influenza if the subject receives the antibody prior to (e.g., 1 day, 2 days, 1 week, 2 weeks, 3 weeks, or 1 month of more) before being exposed to influenza.

As used herein, "seasonal influenza" is a strain that is identical or closely related to strains that have been circulating in the human population in recent years and therefore most people are at least partially immune to it. Such a strain is not likely to cause severe disease. Symptoms can include fever, cough, runny nose, and muscle pain, and in rare cases, death can result from complications, such as pneumonia. Outbreaks follow predictable seasonal patterns, annually, and usually in fall and winter and in temperate climates. Infection due to seasonal influenza is commonly referred to as the flu.

As used herein, specific binding, means that a binding agent, e.g., an antibody molecule, binds its antigen with a $K_D$ of equal to or less than $10^{-5}$ nM. In an embodiment, the antibody binds it's antigen with a $K_D$ of equal to or less than $10^{-6}$, $10^{-7}$, $10^{-8}$, $10^{-9}$, $10^{-10}$, $10^{-11}$, or $10^{-12}$ nM.

As used herein, the term "therapeutically effective amount" refers to an amount of a therapeutic agent, e.g., a binding agent, e.g., an antibody molecule, which results in a positive outcome for the subject. In an embodiment, it can be statistically correlated with therapeutic effect or benefit, e.g., the lessening or prevention of a manifestation of an effect or a symptom, when administered to a population of subjects. In an embodiment, it is an amount that also provides a preselected, or reasonable, benefit/risk ratio. In an embodiment, it is an amount effective to reduce the incidence and/or severity of and/or to delay onset of one or more features, symptoms, or characteristics of a disease, disorder, or condition. A therapeutically effective amount is can be administered in a dosing regimen that may comprise one or multiple unit doses.

As used herein, the term "treat infection" means that a subject (e.g., a human) who has been infected with an influenza and experiences symptoms of the influenza (e.g., the flu), will In an embodiment, suffer less severe symptoms and/or will recover faster when the antibody molecule is administered than if the antibody is never administered. In an embodiment, when an infection is treated, an assay to detect virus in the subject will detect less virus after effective treatment for the infection. For example, a diagnostic assay using an antibody molecule, such as an antibody molecule described herein, will detect less or no virus in a biological sample of a patient after administration of an antibody molecule for the effective treatment of the viral infection. Other assays, such as PCR (e.g., qPCR) can also be used to monitor treatment in a patient, to detect the presence, e.g., decreased presence (or absence) after treatment of viral infection in the patient. Treatment can, e.g., partially or completely alleviate, ameliorate, relive, inhibit, reduce the severity of, and/or reduces incidence and optionally, delay onset of, one or more manifestations of the effects or symptoms, features, and/or causes of a particular disease, disorder, and/or condition (e.g., influenza). In an embodiment, treatment is of a subject who does not exhibit signs of the relevant disease, disorder and/or condition and/or of a subject who exhibits only early signs of the disease, disorder, and/or condition. In an embodiment, treatment is of a subject who exhibits one or more established signs of the relevant disease, disorder and/or condition. In an embodiment, treatment is of a subject diagnosed as suffering from influenza.

Calculations of "homology" or "sequence identity" or "identity" between two sequences (the terms are used interchangeably herein) can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences.

Formulations

The binding agents, e.g., antibody molecules, described herein can be formulated, e.g., as pharmaceutical compositions, such as for the treatment or prevention of influenza.

Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible.

A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The compositions comprising the antibody molecules described herein can be formulated according to methods known in the art. Pharmaceutical formulation is a well-established art, and is further described in Gennaro (ed.), Remington: The Science and Practice of Pharmacy, $20^{th}$ ed., Lippincott, Williams & Wilkins (2000) (ISBN: 0683306472); Ansel et al., Pharmaceutical Dosage Forms and Drug Delivery Systems, $7^{th}$ Ed., Lippincott Williams & Wilkins Publishers (1999) (ISBN: 0683305727); and Kibbe (ed.), Handbook of Pharmaceutical Excipients American Pharmaceutical Association, $3^{rd}$ ed. (2000) (ISBN: 091733096X).

Pharmaceutical compositions may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Typically, compositions for the agents described herein are in the form of injectable or infusible solutions.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular (IM), intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and by intrasternal injection or by infusion.

Pharmaceutical compositions may be provided in a sterile injectable form (e.g., a form that is suitable for subcutaneous injection or intravenous infusion). In an embodiment, the pharmaceutical composition is provided in a liquid dosage form that is suitable for injection or topical application. In some embodiments, pharmaceutical compositions are provided as in dry form, e.g., as powders (e.g. lyophilized and/or sterilized preparations). The Pharmaceutical composition can be provided under conditions that enhance stability, e.g., under nitrogen or under vacuum. Dry material can be reconstituted with an aqueous diluent (e.g., water, buffer, salt solution, etc.) prior to injection.

In an embodiment, the pharmaceutical composition containing an anti-HA antibody is administered intranasally. In another embodiment, the pharmaceutical composition containing an anti-HA antibody is administered by inhalation, such as by oral or by nasal inhalation.

In an embodiment, the pharmaceutical composition is suitable for buccal, oral or nasal delivery, e.g., as a liquid, spray, or aerosol, e.g., by topical application, e.g., by a liquid or drops, or by inhalation). In an embodiment, a pharmaceutical preparation comprises a plurality of particles, suitable, e.g., for inhaled or aerosol delivery. In an embodiment, the mean particle size of 4, 5, 6, 7, 8, 9, 10, 11, 12, or 13 microns. In an embodiment, a pharmaceutical preparation is formulated as a dry powder, suitable, e.g., for inhaled or aerosol delivery. In an embodiment, a pharmaceutical preparation is formulated as a wet powder, through inclusion of a wetting agent, e.g., water, saline, or other liquid of physiological pH. In an embodiment, a pharmaceutical preparation is provided as drops, suitable, e.g., for delivery to the nasal or buccal cavity.

In an embodiment, the pharmaceutical composition is disposed in a delivery device, e.g., a syringe, a dropper or dropper bottle, an inhaler, or a metered dose device, e.g., an inhaler. In an embodiment, the pharmaceutical composition is disposed in a container, e.g., an intravenous (IV) solution bag.

In an embodiment, a pharmaceutical composition contains a vector, such as an adenovirus-associated virus (AAV)-based vector, that encodes a heavy chain of an anti-HA antibody molecule, and a light chain of an anti-HA antibody molecule, described herein. The composition containing the vector can be administered to a subject, such as a patient, such as by injection, e.g., IM injection. Genes encoding the anti-HA antibody under control of, for example, cytomegalovirus (CMV) promoters, are expressed in the body, and the recombinant anti-HA antibody molecule is introduced into the circulation. See e.g., Balazs et al., *Nature* 30:481:81-84, 2011.

Pharmaceutical compositions typically should be sterile and stable under the conditions of manufacture and storage. A pharmaceutical composition can also be tested to insure it meets regulatory and industry standards for administration.

The composition can be formulated as a solution, microemulsion, dispersion, liposome, or other ordered structure suitable to high drug concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, typical methods of preparation are vacuum drying and freeze-drying that yields a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

A pharmaceutical composition may be provided, prepared, packaged, and/or sold in bulk, as a single unit dose, and/or as a plurality of single unit doses. Typically a bulk preparation will contain at least 2, 5, 10, 20, 50, or 100 unit doses. A unit dose is typically the amount introduced into the patient in a single administration. In an embodiment, only a portion of a unit dose is introduced. In an embodiment, a small multiple, e.g., as much as 1.5, 2, 3, 5, or 10 times a unit dose is administered. The amount of the active ingredient is generally equal to a dose which would be administered to a subject and/or a convenient fraction of such a dose such as, for example, one-half or one-third of such a dose.

A formulation of a binding agent, e.g., an antibody molecule, can include, e.g., an anti-HA antibody molecule described herein, a buffer, and a tonicity agent. The pH of the formulation is generally pH 5.5-7.0.

In some embodiments, the formulation is a liquid formulation. In some embodiments, the formulation is stored as a liquid. In other embodiments, the formulation is a lyophilized formulation. In certain embodiments, the formulation is prepared as a liquid and then is dried, e.g., by lyophilization or spray-drying, prior to storage. A dried formulation can be used as a dry compound, e.g., as an aerosol or powder, or reconstituted to its original or another concentration, e.g., using water, a buffer, or other appropriate liquid.

A "reconstituted" formulation is one which has been prepared by dissolving a lyophilized protein formulation in a diluent such that the protein is dispersed in the reconstituted formulation. The reconstituted formulation in suitable for administration (e.g. parenteral administration) to a patient to be treated with the protein of interest and, in certain embodiments of the invention, may be one which is suitable for subcutaneous administration. The "diluent" of interest herein is one which is pharmaceutically acceptable (safe and non-toxic for administration to a human) and is useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

A "lyoprotectant" is a molecule which, when combined with a protein of interest, significantly prevents or reduces chemical and/or physical instability of the protein upon lyophilization and subsequent storage. Exemplary lyoprotectants include sugars such as sucrose or trehalose; an amino acid such as monosodium glutamate or histidine; a methylamine such as betaine; a lyotropic salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; pluronics; and combinations thereof. Typically, the lyoprotectant is a non-reducing sugar, such as trehalose or sucrose. The lyoprotectant is added to the pre-lyophilized formulation in a "lyoprotecting amount" which means that, following lyophilization of the protein in the presence of the lyoprotecting amount of the lyoprotectant, the protein essentially retains its physical and chemical stability and integrity upon lyophilization and storage.

A "bulking agent" is a compound which adds mass to the lyophilized mixture and contributes to the physical structure of the lyophilized cake (e.g. facilitates the production of an essentially uniform lyophilized cake which maintains an open pore structure). Exemplary bulking agents include mannitol, glycine, polyethylene glycol and xorbitol.

In some embodiments, the anti-HA antibody molecule purification process is designed to permit transfer of an anti-HA antibody molecule into a formulation suitable for storage as a liquid. In other embodiments, the anti-HA antibody molecule purification process is designed to permit transfer of an anti-HA antibody molecule into a formulation for long-term storage as a frozen liquid and subsequently for freeze-drying.

In some embodiments, the formulation is lyophilized with the protein at a specific concentration. The lyophilized formulation can then be reconstituted as needed with a suitable diluent (e.g., water) to resolubilize the original formulation components to a desired concentration, generally the same or higher concentration compared to the concentration prior to lyophilization. The lyophilized formulation may be reconstituted to produce a formulation that has a concentration that differs from the original concentration (e.g., before lyophilization), depending upon the amount of water or diluent added to the lyophilate relative to the volume of liquid that was originally freeze-dried. Suitable formulations can be identified by assaying one or more parameters of antibody integrity. The assayed parameters are generally the percentage of HMW species or the percentage of LMW species.

The percentage of HMW species or LMW species is determined either as a percentage of the total protein content in a formulation or as a change in the percentage increase over time (e.g., during storage). The total percentage of HMW species in an acceptable formulation is not greater than 10% (e.g., not greater than 5%, not greater than 4%, not greater than 3%, not greater than 2%, or not greater than 1%) HMW species after storage as a lyophilate or liquid at 2° C. to 50° C. (e.g., at 4° C. to 45° C., at 4° C. to 25° C., at 4° C. to 15° C., at about 4° C., at about 25° C., or at about 45° C.) for at least one week, two weeks, one month, three months, six months, nine months, or one year or not greater than about 10% LMW species after storage as a lyophilate or liquid at 2° C. to 50° C. (e.g., at 4° C. to 45° C., at 4° C. to 25° C., at 4° C. to 15° C., at about 4° C., at about 25° C., or at about 45° C.) for at least one week, two weeks, one month, three months, six months, nine months, or one year. In an embodiment, the total percentage of HMW species is not greater than 5%. In another embodiment, the total percentage of HMW species is not greater than 3%. By "about" is meant ±20% of a cited numerical value. Thus, for example, "about 20° C." means 16° C. to 24° C.

Typically, the stability profile is less than 10% HMW/LMW at 2°-8° C. for a refrigerated product, and 25° C. for a room-temperature product. HMW species or LMW species are assayed in a formulation stored as a lyophilate after the lyophilate is reconstituted. 45° C. is an accelerated condition that is generally used for testing stability and determining stability for short-term exposures to non-storage conditions, e.g., as may occur during transfer of a product during shipping.

When the assayed parameter is the percentage change in HMW species or LMW species, the percent of total protein in one or both species after storage is compared to the percent total protein in one or both species prior to storage (e.g., upon preparation of the formulation). The difference in the percentages is determined. In general, the change in the percentage of protein in HMW species or LMW species in liquid formulations is not greater than 10%, e.g., not greater than about 8%, not greater than about 7%, not greater than about 6%, not greater than about 5%, not greater than about 4%, or not greater than about 3% after storage at 2° C.-8° C. (e.g., 4° C.) or 25° C., for about one week, two weeks, one month, three months, six months, nine months, or twelve months, eighteen, or twenty-four months. In an embodiment, the increase of HMW species is not more than 2%, typically not more than 1%, per year. By "about" is meant ±20% of a cited numerical value. Thus, about 10% means 8% to 12%. Formulations stored as lyophilized product generally have less than about 5%, less than about 4%, less than about 3%, or less than about 2% HMW species or less than about 5%, less than about 4%, less than about 3%, or less than about 2% LMW species after reconstitution following storage at 2° C.-8° C. (e.g., 4° C.) or 25° C. for about for about one week, two weeks, one month, three months, six months, nine months, or twelve months, eighteen, or twenty-four months.

Formulations of anti-HA antibody molecules can be stored as a liquid for, e.g., at least two weeks, at least one month, at least two months, at least three months, at least four months, at least six months, at least nine months, at least one year, or at least two years. Formulations of anti-HA antibody molecules can be stored as a lyophilate for, e.g., at least two years, at least three years, at least four years, or at least five years. In an embodiment, the formulation is in a form of, or is stored as, a frozen lipid.

Additional details related to components of formulations and methods of assaying the integrity of the anti-HA antibody molecule, e.g., the anti-HA antibody molecule described herein, in a formulation are provided infra.

Anti-HA antibody molecule concentrations in formulations are generally between about 0.1 mg/mL and about 250 mg/mL, e.g., between about 0.5 mg/mL and about 100 mg/mL, about 0.5 mg/mL and about 1.0 mg/mL, about 0.5 mg/mL and about 45 mg/mL, about 1 mg/mL and about 10 mg/mL, about 5 mg/mL and 20 mg/mL, about 8 mg/mL and about 16 mg/mL, about 10 mg/mL and about 40 mg/mL, about 10 mg/mL and about 50 mg/mL, about 20 mg/mL and 60 mg/mL, about 25 mg/mL and 50 mg/mL, about 50 mg/mL and about 100 mg/mL, about 100 mg/mL and about 200 mg/mL, or about 200 mg/mL and about 250 mg/mL. In the context of ranges, "about" means −20% of the lower-cited numerical value of the range and +20% of the upper-cited numerical value of the range. In the context of ranges, e.g., about 10 mg/mL to about 100 mg/mL, this means, between 8 mg/mL to 120 mg/mL. In some cases, antibody concentrations in formulations can be, for example, between 1 mg/mL and 100 mg/mL, e.g., 2 mg/mL and 80 mg/mL, 5 mg/mL and 60 mg/mL, 10 mg/mL and 50 mg/mL, 15 mg/mL and 40 mg/mL, 20 mg/mL and 30 mg/mL anti-HA antibody molecule described herein, e.g., Ab 044. Such antibody formulations can be used as therapeutic agents. Accordingly, the concentration of anti-HA antibody molecule in a formulation is sufficient to provide such dosages in a volume of the formulation that is tolerated by a subject being treated and is appropriate for the method of administration. In one non-limiting example, to supply a high dosage subcutaneously, in which the volume limitation is small (e.g., about 1 ml to 1.2 ml per injection), the concentration of antibody is generally at least 25 mg/mL or greater, e.g., 100 mg/mL or greater, e.g., 100 mg/mL to 500 mg/mL, 100 mg/mL to 250 mg/mL, or 100 mg/mL to 150 mg/mL. Such high concentrations can be achieved, for example, by reconstituting a lyophilized formulation in an appropriate volume of diluent (e.g., sterile water for injection, buffered saline). In some cases, the reconstituted formulation has a concentration of between 25 mg/mL and 500 mg/mL, e.g., between about 100 mg/mL and 500 mg/mL (e.g., 100 mg/mL, 125 mg/mL, 150 mg/mL, 175 mg/mL, 200 mg/mL, 250 mg/mL, 275 mg/mL, 300 mg/mL, 350 mg/mL, 375 mg/mL, 400 mg/mL, 425 mg/mL, 450 mg/mL, 475 mg/mL and 500 mg/mL). For delivery via inhalation, the formulation is generally somewhat concentrated (e.g., between about 25 mg/mL and 500 mg/mL, e.g., between about 100 mg/mL and 500 mg/mL) so as to provide a sufficient dose in a limited volume of aerosol for inspiration. In some cases, low concentrations (e.g., between about 0.05 mg/mL and 1 mg/mL) are used. Methods are known in the art to adapt the dosage delivered to the method of delivery, e.g., a jet nebulizer or a metered aerosol.

Buffers

The pH of a formulation as described herein is generally between about pH 5.0 to about 7.0, for example, about pH 5.5 to about 6.5, about pH 5.5 to about 6.0, about pH 6.0 to about 6.5, pH 5.5, pH 6.0, or pH 6.5. In general, a buffer that can maintain a solution at pH 5.5 to 6.5 is used to prepare a formulation, e.g., a buffer having a pKa of about 6.0. Suitable buffers include, without limitation, 2-morpholino-ethanesulfonic acid (MES), phosphate, and citrate (e.g., citrate-sodium phosphate). The concentration of the buffer is between about 5 mM and about 100 mM, e.g., about 25 mM to about 50 mM. In some cases, citrate-sodium phosphate buffer is used at a concentration of about 40 nM. Other buffers can include, histidine buffer, acetate, or succinate, e.g., for a desired pH other than about 6.0, e.g., below 6.0. In other cases, histidine buffer is used at a concentration of up to 60 nM, e.g., about 5 mM or about 10 mM. In other cases, acetate or succinate buffer is used at a concentration of about 5 mM or about 10 mM.

Tonicity Agents

Tonicity agents are known in the art and include, e.g., sodium chloride, potassium chloride, or dextrose.

The tonicity agent is generally used at a concentration of about 50 mM to about 200 mM. For example, the tonicity agent can be used at a concentration of about 50 mM to about 200 mM, e.g., about 60 mM to about 190 mM, about 70 mM to about 180 mM, about 80 mM to about 170 mM, about 90 mM to about 160 mM, about 100 mM to about 150 mM, about 145 mM to about 155 mM, about 140 mM to about 160 mM, about 135 mM to about 165 mM, about 130 mM to about 170 mM, about 120 mM to about 180 mM, about 110 mM to about 190 mM, about 100 mM to about 200 mM, about 50 mM to about 100 mM, about 100 mM to about 150 mM, or about 150 mM to about 120 mM, e.g., about 200 mM or less, about 150 mM or less, about 100 mM or less, or about 75 mM or less, e.g., about 50 mM, about 60 mM, about 70 mM, about 80 mM, about 90 mM, about 100 mM, about 110 mM, about 120 mM, about 130 mM, about 140 mM, about 150 mM, about 160 mM, about 170 mM, about 180 mM, about 190 mM, or about 200 mM.

In an embodiment, the tonicity agent is used at a concentration of about 50 to about 200 nM, about 75 mM to about 150 mM, about 120 mM to about 180 mM, e.g., about 140 to about 160 mM, e.g., about 150 mM. In an embodiment, the tonicity agent comprises sodium chloride. In an embodiment, the tonicity agent comprises sodium chloride and is used at a concentration of about 140 to about 160 mM, e.g., about 150 mM.

The tonicity agent used in the formulation can generally provide a tonicity (or osmolarity) of about 250 mOsm/L to about 350 mOsm/L, about 260 mOsm/L to about 340 mOsm/L, about 270 mOsm/L to about 330 mOsm/L, about 280 mOsm/L to about 320 mOsm/L, about 285 mOsm/L to about 310 mOsm/L, or about 290 mOsm/L to about 300 mOsm/L, e.g., about 250 mOsm/L, about 260 mOsm/L, about 270 mOsm/L, about 280 mOsm/L, about 290 mOsm/L, about 300 mOsm/L, about 310 mOsm/L, about 320 mOsm/L, about 330 mOsm/L, about 340 mOsm/L, or about 350 mOsm/L.

In an embodiment, the tonicity agent provides a tonicity (or osmolality) of about 240 mOsm/kg to about 340 mOsm/kg, about 250 mOsm/kg to about 330 mOsm/kg, about 260 mOsm/kg to about 320 mOsm/kg, about 270 mOsm/kg to about 310 mOsm/kg, about 280 mOsm/kg to about 300 mOsm/kg, or about 285 mOsm/kg to about 295 mOsm/kg, e.g., about 240 mOsm/kg, about 250 mOsm/kg, about 260 mOsm/kg, about 270 mOsm/kg, about 280 mOsm/kg, about 290 mOsm/kg, about 300 mOsm/kg, about 310 mOsm/kg, about 320 mOsm/kg, about 330 mOsm/kg, or about 340 mOsm/kg.

By "isotonic" is meant that the formulation of interest has essentially the same osmotic pressure as human blood. Isotonic formulations will generally have an osmotic pressure, e.g., from about 250 to 350 mOsm/L. Isotonicity can be measured using a vapor pressure or ice-freezing type osmometer, for example.

Surfactants

In certain embodiments, a surfactant is included in the formulation. Examples of surfactants include, without limitation, nonionic surfactants such as polysorbates (e.g., polysorbate-20, polysorbate-40, polysorbate-60, polysorbate-65, polysorbate-80, or polysorbate-85); poloxamers (e.g., poloxamer 188); Triton™; sodium dodecyl sulfate (SDS); sodium laurel sulfate; sodium octyl glycoside; lauryl-sulfobetaine, myristyl-sulfobetaine, linoleyl-sulfobetaine, stearyl-sulfobetaine, lauryl-sarcosine, myristyl-sarcosine, linoleyl-sarcosine, stearyl-sarcosine, linoleyl-betaine, myristyl-betaine, cetyl-betaine, lauroamidopropyl-betaine, cocamidopropyl-betaine, linoleamidopropyl-betaine, myristamidopropyl-betaine, palmidopropyl-betaine, isostearamidopropyl-betaine (e.g. lauroamidopropyl), myristarnidopropyl-, palmidopropyl-, or isostearamidopropyl-dimethylamine; sodium methyl cocoyl-, or disodium methyl ofeyl-taurate; and the Monaquat™ series (Mona Industries, Inc., Paterson, N.J.), polyethyl glycol, polypropyl glycol, and copolymers of ethylene and propylene glycol (e.g. pluronics, PF68).

The amount of surfactant added is such that it reduces aggregation of the reconstituted protein to an acceptable level as assayed using, e.g., SEC-HPLC of HMW species or LMW species, and minimizes the formation of particulates after reconstitution of a lyophilate of an anti-HA antibody molecule formulation. The addition of surfactant has also been shown to reduce the reconstitution time of a lyophilized formulation of anti-HA antibody molecules, and aid in de-gassing the solution. For example, the surfactant can be present in the formulation (liquid or prior to lyophilization) in an amount from about 0.001% to 0.5%, e.g., from about 0.005% to 0.05%, about 0.005% to about 0.2%, and about 0.01% to 0.2%.

Cryoprotectants

Cryoprotectants are known in the art and include, e.g., sucrose, trehalose, and glycerol. A cryoprotectant exhibiting low toxicity in biological systems is generally used. The cryoprotectant is included in the formulation at a concentration of about 0.5% to 15%, about 0.5% to 2%, about 2% to 5%, about 5% to 10%, about 10% to 15%, and about 5% (weight/volume).

Histidine buffer, which can be used as a buffer in an anti-HA antibody molecule formulation, may have cryoprotectant properties. In some embodiments of the invention, a histidine buffer is used in conjunction with a cryoprotectant such as a sugar, e.g., sucrose. A formulation of the invention can specifically exclude the use of histidine in any substantial amount, e.g., neither the buffer nor the cryoprotectant component of the formulation is a histidine.

The viscosity of a formulation is generally one that is compatible with the route of administration of the formulation. In some embodiments, the viscosity of the formulation is between 1 cP and 2 cP, or similar to water (about 1 cP). In other embodiments, the viscosity of the formulation is between about 5 cP and about 40 cP. In specific embodiments, the viscosity of the formulation is 1 cP, 2 cP, 3 cP, 4 cP, 5 cP, 10 cP, 15 cP, 20 cP, 25 cP, 30 cP, 35 cP, or 40 cP.

Additions to Formulations

Formulations are stored as sterile solutions or sterile lyophilates. Prevention of the action of microorganisms in formulations can also be achieved by including at least one antibacterial and/or antifungal agent in a formulation, for example, parabens, chlorobutanol, phenol, ascorbic acid, thimerosal, and the like. In some cases, a lyophilate is reconstituted with bacteriostatic water (e.g., water containing 0.9% benzyl alcohol). Considerations for the inclusion of a preservative in a formulation are known in the art as are methods of identifying preservatives that are compatible with a specific formulation and method of delivery (e.g., see Gupta, et al. (2003), AAPS Pharm. Sci. 5:article 8, p. 1-9). A "preservative" is a compound which can be added to the diluent to essentially reduce bacterial action in the reconstituted formulation, thus facilitating the production of a multi-use reconstituted formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol.

In some cases, the formulation is isotonic. In general, any component known in the art that contributes to the solution osmolarity/tonicity can be added to a formulation (e.g., salts, sugars, polyalcohols, or a combination thereof). Isotonicity is generally achieved using either a component of a basic formulation (such as sucrose) in an isotonic concentration or by adding an additional component such as, a sugar, a polyalcohol such as manitol or sorbitol, or a salt such as sodium chloride.

In some cases, a salt is used in an anti-HA antibody molecule formulation, e.g., to achieve isotonicity or to increase the integrity of the anti-HA antibody molecule of the formulation. Salts suitable for use are discussed, supra. The salt concentration can be from 0 mM to about 300 mM. In one example, the salt is used at a concentration of 150 nM in the formulation.

In certain cases, the formulation is prepared with Tween (e.g., Tween® 20, Tween® 80) to decrease interfacial degradation. The Tween concentration can be from about 0.001% to about 0.05%. In one example, Tween-80 is used at a concentration of 0.025% in the formulation.

In certain other cases, the formulation is prepared with glycine. The glycine concentration in the formulation can be from about 0.01% to about 5%. In one example, glycine is used at a concentration of 1% in the formulation. In another example, glycine is used at a concentration of 2% in the formulation. In some cases both Tween and arginine are added to the anti-HA antibody molecule formulations described herein.

In yet other cases, the formulation may be prepared with at least one of: sucrose, histidine, or arginine. If sucrose is included in the formulation, it can be added to a concentration of between about 1% and about 10%. In one example, sucrose is found in the formulation at a concentration of 2%. If histidine is included in the formulation, it can be added to a concentration of between about 0.5% to about 5%. In one example, histidine is found in the formulation at a concentration of 1%. In another example, histidine is found in the formulation at a concentration of 2%. If arginine is included in the formulation, it can be added to a concentration of between about 0.5% to about 5%. In one example, arginine is found in the formulation at a concentration of 1%. In another example, arginine is found in the formulation at a concentration of 2%.

Exemplary Formulations

Exemplary anti-HA antibody molecule formulations are described in Table 7. In an embodiment, an anti-HA antibody molecule formulation comprises 25 mg/mL anti-HA antibody molecule described herein (e.g., Ab 044), 40 mM citrate-sodium phosphate, 150 mM sodium chloride, 0.025% Tween-80, at pH 6.0. In another embodiment, an anti-HA antibody molecule formulation comprises 25 mg/mL anti-HA antibody molecule described herein (e.g., Ab 044), 40 mM citrate-sodium phosphate, 150 mM sodium chloride, 0.025% Tween-80, at pH 6.5. In another embodiment, an anti-HA antibody molecule formulation comprises 25 mg/mL anti-HA antibody molecule described herein (e.g., Ab 044), 40 mM citrate-sodium phosphate, 1% glycine, 75 mM sodium chloride, 0.025% Tween-80, at pH6.5. In another embodiment, an anti-HA antibody molecule formulation comprises 25 mg/mL anti-HA antibody molecule described herein (e.g., Ab 044), 40 mM citrate-sodium phosphate, 150 mM sodium chloride, at pH 6.0. In another embodiment, an anti-HA antibody molecule formulation comprises 25 mg/mL anti-HA antibody molecule described herein (e.g., Ab 044), 40 mM citrate-sodium phosphate, 75 mM sodium chloride, 0.025% Tween-80, at pH 6.5.

Additional exemplary anti-HA antibody molecule formulations are described in Table 5.

Storage and Preparation Methods

Liquid

In some cases, formulations containing antibodies are stored as liquid. Accordingly, it is desirable that the formulation be relatively stable under such conditions, including, at 4° C. or in room temperature. One method of determining the suitability of a formulation is to subject a sample formulation to agitation or storage (e.g., at 4° C., 25° C., or 45° C.) for a period of time (e.g., one week, two weeks, or four weeks), determining the amount of LMW species and/or HMW species that accumulate after the agitation or storage and comparing it to the amount of LMW species or HMW species present in the sample prior to the agitation or storage procedure. An increase in the LMW or HMW species indicates decreased stability.

Freezing

In some cases, formulations containing antibodies are frozen for storage. Accordingly, it is desirable that the formulation be relatively stable under such conditions, including, under freeze-thaw cycles. One method of determining the suitability of a formulation is to subject a sample formulation to at least two, e.g., three, four, five, eight, ten, or more cycles of freezing (at, for example −20° C. or −80° C.) and thawing (for example by fast thaw in a 37° C. water bath or slow thaw at 2°–8° C.), determining the amount of LMW species and/or HMW species that accumulate after the freeze-thaw cycles and comparing it to the amount of LMW species or HMW species present in the sample prior to the freeze-thaw procedure. An increase in the LMW or HMW species indicates decreased stability.

Lyophilization

Formulations can be stored after lyophilization. Therefore, testing a formulation for the stability of the protein component of the formulation after lyophilization is useful for determining the suitability of a formulation. The method is similar to that described, supra, for freezing, except that the sample formulation is lyophilized instead of frozen, reconstituted to its original volume, and tested for the presence of LMW species and/or HMW species. The lyophilized sample formulation is compared to a corresponding sample formulation that was not lyophilized. An increase in LMW or HMW species in the lyophilized sample compared to the corresponding sample indicates decreased stability in the lyophilized sample.

In general, a lyophilization protocol includes loading a sample into a lyophilizer, a pre-cooling period, freezing, vacuum initiation, ramping to the primary drying temperature, primary drying, ramping to the secondary drying temperature, secondary drying, and stoppering the sample. Additional parameters that can be selected for a lyophilization protocol include vacuum (e.g., in microns) and condenser temperature. Suitable ramp rates for temperature are between about 0.1° C./min. to 2° C./min., for example 0.1° C./min. to 1.0° C./min., 0.1° C./min. to 0.5° C./min., 0.2° C./min. to 0.5° C./min., 0.1° C./min., 0.2° C./min., 0.3° C./min., 0.4° C./min., 0.5° C./min., 0.6° C./min., 0.7° C./min., 0.8° C./min., 0.9° C./min., and 1.0° C./min. Suitable shelf temperatures during freezing for a lyophilization cycle are generally from about −55° C. to −5° C., −25° C. to −5° C., −20° C. to −5° C., −15° C. to −5° C., −10° C. to −5° C., −10° C., −11° C., −12° C., −13° C., −14° C., −15° C., −16° C., −17° C., −18° C., −19° C., −20° C., −21° C., −22° C., −23° C., −24° C., or −25° C. Shelf temperatures can be different for primary drying and secondary drying, for example, primary drying can be performed at a lower temperature than secondary drying. In a non-limiting example, primary drying can be executed at 0° C. and secondary drying at 25° C.

In some cases, an annealing protocol is used during freezing and prior to vacuum initiation. In such cases, the annealing time must be selected and the temperature is generally above the glass transition temperature of the composition. In general, the annealing time is about 2 to 15 hours, about 3 to 12 hours, about 2 to 10 hours, about 3 to 5 hours, about 3 to 4 hours, about 2 hours, about 3 hours, about 5 hours, about 8 hours, about 10 hours, about 12 hours, or about 15 hours. The temperature for annealing is generally from about −35° C. to about −5° C., for example from about −25° C. to about −8° C., about −20° C. to about −10° C., about −25° C., about −20° C., about −15° C., about 0° C., or about −5° C. In some cases, the annealing temperature is generally from −35° C. to 5° C., for example from 25° C. to −8° C., −20° C. to −10° C., −25° C., −20° C., −15° C., 0° C., or 5° C.

In general, a lyophilization cycle can run from 10 hours to 100 hours, e.g., 20 hours to 80 hours, 30 hours to 60 hours, 40 hours to 60 hours, 45 hours to 50 hours, 50 hours to 65 hours.

Non-limiting examples of the temperature range for storage of an antibody formulation are about −20° C. to about 50° C., e.g., about −15° C. to about 30° C., about −15° C. to about 20° C., about 5° C. to about 25° C., about 5° C. to about 20° C., about 5° C. to about 15° C., about 2° C. to about 12° C., about 2° C. to about 10 C, about 2° C. to about 8° C., about 2° C. to about 6° C., 2 C, 3° C., 4° C., 5° C., 6° C., 7° C., 8° C., 10° C., 15° C., or 25° C. Notwithstanding the storage temperatures, in certain cases, samples are stable under temperature changes that may transiently occur during storage and transportation conditions that can be anticipated for such compositions.

Spray-Drying

In some cases, a formulation is spray-dried and then stored. Spray-drying is conducted using methods known in the art, and can be modified to use liquid or frozen spray-drying (e.g., using methods such as those from Niro Inc. (Madison, WI), Upperton Particle Technologies (Nottingham, England), or Buchi (Brinkman Instruments Inc., Westbury, NY), or U.S. Application Publication Nos. 2003/0072718 and 2003/0082276).

Determination of Antibody Molecule Integrity

The accumulation of LMW species and HMW species are useful measures of antibody stability. Accumulation of either LMW or HMW in a formulation is indicative of instability of a protein stored as part of the formulation. Size exclusion chromatography with HPLC can be used to determine the presence of LMW and HMW species. Suitable systems for such measurements are known in the art, e.g., HPLC systems (Waters, Milford, MA). Other systems known in the art can be used to evaluate the integrity of antibody in a formulation, for example, SDS-PAGE (to monitor HMW and LMW species), bioassays of antibody activity, enzyme-linked immunosorbent assay, ability to bind purified target protein (e.g., HA), and cation exchange-HPLC (CEX-HPLC; to detect variants and monitor surface charge). In one example, a bioassay is a cell-based assay in which inhibition of an HA-dependent activity is examined in the presence of different concentrations of formulated nanobody molecule to demonstrate biological activity.

Articles of Manufacture

The present application also provides an article of manufacture that includes a formulation as described herein and provides instructions for use of the formulation. The article of manufacture can include a container suitable for containing the formulation. A suitable container can be, without limitation, a bottle, vial, syringe, test tube, nebulizer (e.g., ultrasonic or vibrating mesh nebulizers), i.v. solution bag, or inhaler (e.g., a metered dose inhaler (MDI) or dry powder inhaler (DPI)). The container can be formed of any suitable material such as glass, metal, or a plastic such as polycarbonate, polystyrene, or polypropylene. In general, the container is of a material that does not absorb significant amounts of protein from the formulation and is not reactive with components of the formulation. In some embodiments, the container is a clear glass vial with a West 4432/50 1319 siliconized gray stopper or a West 4023 Durafluor stopper. In some embodiments, the container is a syringe. In specific embodiments, the formulation comprises about 25 mg/mL of an antibody molecule described herein, about 40 mM citrate-sodium phosphate, about 150 mM sodium chloride, and about 0.025% polysorbate 80, at a pH of about 6, in a pre-filled syringe. In certain embodiments, the syringe is suitable for use with an auto-injector device.

In an embodiment, the container is a container suitable for storage of the formulation or antibody molecule, e.g., a vial. In another embodiment, the container is a container suitable for administration of the formulation or antibody molecule, e.g., an intravenous (IV) bag. In an embodiment, the antibody molecule or formulation in a first container (e.g., suitable for storage) is transferred to a second container (e.g., suitable for administration) before use. In an embodiment, transfer includes dilution of the antibody molecule or formulation. In an embodiment, transfer occurs less than 4 hours, e.g., less than 3, 2, or 1 hours, prior to administration of the antibody molecule or formulation to a subject.

In an embodiment, the container suitable for administration (e.g., an IV solution bag) is a primary container and ready to use for administration (e.g., IV administration). For example, in one configuration, it is typically not necessary, or there is no need, to transfer the antibody molecule or formulation, e.g., from a vial (e.g., a storage vial) to an IV solution bag, or to dilute the antibody molecule or formulation, e.g., into an IV solution, before administration (e.g., on the same day of administration). In an embodiment, the container is a vial, e.g., a glass vial. In an embodiment, the container (e.g., vial) comprises about 10 mg/mL to about 100 mg/mL, e.g., about 20 mg/mL to about 60 mg/mL (e.g., about 25 mg/mL to about 50 mg/mL) of the antibody molecule. In an embodiment, the container (e.g., vial) comprises about 10 mL to about 60 mL, e.g., about 20 mL to about 40 mL, of the antibody molecule or formulation. In an embodiment, the container (e.g., vial) is a first (or primary) container, e.g., for storing the antibody molecule or formulation.

The antibody molecule or formulation can be transferred into a second container before use. In an embodiment, the second container is suitable, or includes a solution that is suitable, for administration, e.g., intravenous administration. In an embodiment, the second container includes a solution suitable for intravenous administration. In an embodiment, the solution comprises saline, optionally, further comprises dextrose. In an embodiment, the solution (e.g., saline) does not comprise dextrose. For example, an amount equal to one dose of the antibody molecule can be transferred into a container suitable for IV administration. In an embodiment, 1 to 10 vials (e.g., 1 to 8 vials, 1 to 6 vials, 1 to 4 vials, 1 to 2 vials, 6 to 8 vials, 4 to 8 vials, or 2 to 8 vials) of the antibody molecule or formulation are diluted into an IV solution bag, e.g., containing saline with or without dextrose.

In an embodiment, the container is a container suitable for IV administration (e.g., an IV solution bag). In an embodiment, the amount of the antibody molecule in the container (e.g., IV solution bag) equals to 1 to 10 vials (e.g., 1 to 8 vials, 1 to 6 vials, 1 to 4 vials, 1 to 2 vials, 6 to 8 vials, 4 to 8 vials, or 2 to 8 vials) of the antibody molecule as described above. In an embodiment, the container (e.g., IV solution bag) comprises about 500 mg to about 16000 mg, e.g., about 500 mg to about 8000 mg, about 500 mg to about 5000 mg/mL, about 1000 mg to about 5000 mg, about 2000 mg to about 4000 mg, or about 2300 mg to about 4600 mg, e.g., about 2300 mg or about 4600 mg, of the antibody molecule or formulation. In an embodiment, the container (e.g., IV solution bag) further comprises saline. In an embodiment, the container further comprises dextrose. In another embodiment, the container does not comprise dextrose.

In an embodiment, the container suitable for IV administration (e.g., IV solution bag) is not a second (or secondary) container (e.g., is a first (or primary) container, e.g., where the antibody molecule is stored), and comprises about 5 mg/mL to about 25 mg/mL, e.g., about 8 mg/mL to about 16 mg/mL of the antibody molecule. In an embodiment, the container (e.g., IV solution bag) comprises about 100 mL to about 400 mL, e.g., about 200 mL to about 300 mL, of antibody molecule. In an embodiment, the container (e.g., IV solution bag) comprises about 2000 mg to about 5000 mg, e.g., about 2300 mg to about 4600 mg, of the antibody molecule.

In an embodiment, the antibody molecule is administered from the container (e.g., IV solution bag) to the subject through an IV line.

Disclosed herein are also methods of preparing a composition (e.g., a solution) or a container for administration (e.g., intravenous administration). In an embodiment, the method comprises transferring an antibody molecule or a formulation disclosed herein to a container suitable for administration (e.g., an intravenous (IV) solution bag). In an embodiment, the method comprises contacting, e.g., combining (e.g., mixing or diluting) an antibody molecule or a formulation disclosed herein with a solution suitable for administration. In an embodiment, the container suitable for administration is an IV solution bag. In an embodiment, the solution suitable for administration is an IV solution, e.g., saline with or without dextrose. In an embodiment, about 2000 mg to about 5000 mg of the antibody molecule is contacted (e.g., combined) with the solution. In an embodiment, about 2300 mg to about 4600 mg or about 2000 mg to about 4000 mg of the antibody molecule is contacted (e.g., combined) with the solution.

Examples of nebulizers include, in non-limiting examples, jet nebulizers, ultrasonic nebulizers, and vibrating mesh nebulizers. These classes use different methods to create an aerosol from a liquid. In general, any aerosol-generating device that can maintain the integrity of the protein in these formulations is suitable for delivery of formulations as described herein.

Formulations to be used for administration to a subject, e.g., as a pharmaceutical, must be sterile. This is accomplished using methods known in the art, e.g., by filtration through sterile filtration membranes, prior to, or following, formulation of a liquid or lyophilization and reconstitution. Alternatively, when it will not damage structure, components of the formulation can be sterilized by autoclaving and then combined with filter or radiation sterilized components to produce the formulation.

Hemagglutinin (HA) Polypeptides and Influenza

Influenza viruses are negative sense, single-stranded, segmented RNA envelope viruses. Two glycoproteins, a hemagglutinin (HA) polypeptide and a neuraminidase (NA) polypeptide, are displayed on the outer surface of the viral envelope. There are several Influenza A subtypes, labeled according to an H number (for the type of hemagglutinin) and an N number (for the type of neuraminidase). There are 17 different H antigens (H1 to H17) and nine different N antigens (N1 to N9). Influenza strains are identified by a nomenclature based on the number of the strain's HA polypeptide and NA polypeptide subtypes, for example, H1N1, H1N2, H1N3, H1N4, H1N5, and the like.

HA is the major viral surface glycoprotein that mediates binding and entry of the virus into host cells and is a primary target of neutralizing antibody responses. HA is a trimer of three identical monomers. Each monomer is synthesized as a precursor, $HA_0$, that is proteolytically processed into two disulfide-bonded polypeptide chains, $HA_1$ and $HA_2$. The ectodomain of this protein has (i) a globular head domain possessing receptor binding activity and major antigenic determinants, (ii) a hinge region, and (iii) a stem region where a sequence critical for fusion, the fusion peptide, is located. The viral replication cycle is initiated when the virion attaches via its surface hemagglutinin proteins to sialylated glycan receptors on the host cell and enters the cell by endocytosis. The acidic environment in the endosome induces conformational changes in HA that expose the fusion peptide hidden within the stem region of the trimer. The exposed fusion peptide mediates the fusion of the viral and target cell membranes resulting in the release of the viral ribonucleoprotein into the cell cytoplasm.

Influenza A hemagglutinin subtypes have been divided into two main groups and four smaller clades, and these are further divided into clusters. Group 1 influenza A strains are divided into 3 clades: (i) H8, H9 and H12 ("the H9 cluster"); (ii) H1, H2, H5, H6 and H17 ("the H1a cluster"); and (iii) H11, H13 and H16 ("the H1b cluster"). Group 2 strains are divided into 2 clades: (i) H3, H4 and H14 ("the H3 cluster"); and (ii) H7, H10 and H15 ("the H7 cluster"). The H1b and the H1a clusters are classified together as the H1 cluster. The different HA subtypes do not necessarily share strong amino acid sequence identity, but their overall 3D structures are similar.

Of the 17 HA polypeptide subtypes, only 3 (H1, H2 and H3) have adapted for human infection. These subtypes have in common an ability to bind alpha 2,6 sialylated glycans. In contrast, their avian counterparts preferentially bind to alpha 2,3 sialylated glycans. HA polypeptides that have adapted to infect humans (e.g., of HA polypeptides from the pandemic H1N1 (1918) and H3N2 (1967-68) influenza subtypes) have been characterized by an ability to preferentially bind to α2,6 sialylated glycans in comparison with their avian progenitors that preferentially bind to α2,3 sialylated glycans (see e.g., Skehel & Wiley, *Annu Rev Biochem,* 69:531, 2000; Rogers, & Paulson, *Virology,* 127:361, 1983; Rogers et al., *Nature,* 304:76, 1983; Sauter et al., *Biochemistry,* 31:9609, 1992).

Further, HA polypeptides that mediate infection of humans preferentially bind to umbrella topology glycans over cone topology glycans (see e.g., U.S. 2011/0201547). Without wishing to be bound by any particular theory, it has been proposed that the ability to infect human hosts correlates less with binding to glycans of a particular linkage, and more with binding to glycans of a particular topology, even though cone-topology glycans may be α2,6 sialylated glycans. In has been demonstrated that HA polypeptides that mediate infection of humans bind to umbrella topology glycans, often showing preference for umbrella topology glycans over cone topology glycans (see, for example, U.S. Ser. No. 12/348,266 filed Jan. 2, 2009, U.S. Ser. No. 12/301,126, filed Nov. 17, 2008, U.S. Ser. No. 61/018,783, filed Jan. 3, 2008, U.S. Ser. No. 11/969,040, filed Jan. 3, 2008, U.S. Ser. No. 11/893,171, filed Aug. 14, 2007, U.S. Ser. No. 60/837,868, filed on Aug. 14, 2006, U.S. Ser. No. 60/837,869, filed on August 14, and to PCT application PCT/US07/18160, filed Aug. 14, 2007).

Mature HA polypeptides include three domains, (i) a globular domain (a.k.a., the head domain) consists mainly of the HA1 peptide and contains the receptor (sialylated glycoproteins)-binding region, (ii) a stalk domain (HA1 and HA2) where the membrane fusion peptide resides, and (iii) a transmembrane domain (HA2) that anchors hemagglutinin to the viral envelope. A set of amino acids in the interface of the HA1 and HA2 peptides is highly conserved across all influenza subtypes. The HA1/HA2 membrane proximal region (MPER), including a canonical alpha-helix, is also highly conserved across influenza subtypes.

HA polypeptides interact with the surface of cells by binding to a glycoprotein receptor, known as the HA receptor. Binding of an HA polypeptide to an HA receptor is predominantly mediated by N-linked glycans on the HA receptors. HA polypeptides on the surface of flu virus particles recognize sialylated glycans that are associated with HA receptors on the surface of the cellular host. Following replication of viral proteins and genome by the cellular machinery, new viral particles bud from the host to infect neighboring cells.

Currently, vaccines are administered to subjects, e.g., humans, to prevent the flu, e.g., to prevent infection or to minimize the effects of an infection with influenza virus. Traditional vaccines contain a cocktail of antigens from various strains of influenza and are administered to humans to prevent the human from getting infected with the virus. HA is the main target of influenza A-neutralizing antibodies, and HA undergoes continuous evolution driven by the selective pressure of the antibody response, which is primarily directed against the membrane-distal receptor-binding subdomain of the HA polypeptide. The subject, however, is protected only from strains that are identical to, or closely related to, the strains from which the antigens in the cocktail were derived. The human is still most vulnerable to infection by other strains of the flu that were not included in the cocktail. One of the advantages of the antibodies provided herein is their ability to bind an epitope of HA that is conserved across multiple strains of influenza A, and in an embodiment, influenza B. Thus, administration of an anti-HA antibody described herein will be more effective to protect an individual from infection from a broader spectrum of influenza (e.g., influenza A and, in an embodiment, influenza B) and conditions associate thereof (e.g., secondary infections, e.g., secondary bacterial infections). Further, the antibodies are effective in treating a subject after infection has occurred.

Epitope

HAs exist in nature as homotrimers of proteolytically processed mature subunits. Each subunit of the trimer is synthesized as a precursor. A precursor molecule is proteolytically processed into two disulfide bonded polypeptide chains to form a mature HA polypeptide. The mature HA polypeptide includes two domains: (1) a core HA-1 domain that extends from the base of the molecule through the fibrous stem to the membrane distal head region that contains the glycan receptor binding domain, returning to fibrous region ending in the cleavage site, and (2) HA-2 domain that includes the stem region and the transmembrane domain of HA. HA-1 includes a glycan binding site. The glycan binding site may be responsible for mediating binding of HA to the HA-receptor. The HA-2 domain acts to present the HA-1 domain. The HA trimer can be stabilized by polar and non-polar interactions between the three long HA alpha-helices of the stem of HA monomers.

HA sequences from all influenza subtypes share a set of amino acids in the interface of the HA-1 and HA-2 domains that are well conserved. The HA-1/HA-2 interface membrane proximal epitope region (MPER) that includes the canonical α-helix and residues in its vicinity are also conserved across a broad spectrum of subtypes. (Ekiert et al., *Science,* 324(5924):246, 2009; Sui et al., *Nat Struct Mol Biol.* 16(3):265, 2009).

Ab 044 has high affinity for HA's from Group 1 and Group 2. It binds a conformational epitope that is broadly conserved across a plurality of influenza strains. Numerous amino acid residues distributed along the linear sequences of HA from different strains/subtypes contribute the Ab 044 conformational epitope. The interaction of Ab044 with H3 was analyzed by docking studies and residues bound by (or not bound by) Ab 044 were identified.

The Fv of Ab 044 was docked against HA of group I and II strains using ZDOCK. The structure of the HA antigen was modeled using the SWISS MODEL homology modeling server keeping the solved crystal structure of H1N1 as the template. ZDOCK uses shape complementarity along with desolvation and electrostatic energy terms ('ZRANK') to rank docked poses. To ensure the docked poses do not deviate significantly from the native complex, mapped epitope and paratope residues by alanine scanning are forced to be included in the binding interface.

For comparison studies, amino acids that bind (or do not bind) FI6 were taken from published US patent application US 2011/0274702 A1, Neutralizing Anti-Influenza A Virus Antibodies and Uses Thereof, filed Jul. 18, 2011.

ZDOCK is a Fast Fourier Transform based protein docking program. It was developed by Zhiping Weng at the University of Massachusetts Medical School. In ZDOCK, two PDB files are input and the output is the predicted structure of their complex. The program searches all possible binding modes in the translational and rotational space between the two proteins and evaluates each by an energy scoring function. The protein's structure is converted to a digital signal and a Fast Fourier Transform technique used to reduce computational time. ZDOCK is discussed in Pierce B G, Hourai Y, Weng Z. (2011) Accelerating Protein Docking in ZDOCK Using an Advanced 3D Convolution Library. PLoS One 6(9): e24657, Pierce B, Tong W, Weng Z. (2005) M-ZDOCK: A Grid-based Approach for $C_n$ Symmetric Multimer Docking. Bioinformatics 21(8): 1472-1476; Mintseris J, Pierce B, Wiehe K, Anderson R, Chen R, Weng Z. (2007) Integrating Statistical Pair Potentials into Protein Complex Prediction. Proteins 69(3): 511-520; and Chen R, Li L, Weng Z. (2003) ZDOCK: An Initial-stage Protein Docking Algorithm. Proteins 52(1): 80-7.

SWISS-MODEL is a fully automated protein structure homology-modeling server. It is accessible via the ExPASy web server, or from the program DeepView (Swiss Pdb-Viewer). Swiss-Model is discussed in Arnold K., Bordoli L., Kopp J., and Schwede T. (2006). The SWISS-MODEL Workspace: A web-based environment for protein structure homology modelling. Bioinformatics, 22, 195-201; Kiefer F, Arnold K, Kunzli M, Bordoli L, Schwede T (2009). The SWISS-MODEL Repository and associated resources. Nucleic Acids Research. 37, D387-D392; and Peitsch, M. C. (1995) Protein modeling by E-mail Bio/Technology 13: 658-660.

H3 residues that bind Ab 044 and H3 residues that bind FI6 are discussed below.

H3 HA1

The amino acid sequence of H3 HA1 is provided below, as SEQ ID NO: 173. Residues N38, 1278, and D291 shown in dashed boxes, are bound by Ab 044 but not by FI6; Residues Q327, T328, and R329 shown in dotted boxes, are bound by FI6 but not by Ab 044; residues T318, R321, and V323 shown in solid boxes, are bound by both Ab 044 and FI6.

```
                                                            (SEQ ID NO: 173)
QDLPGNDNST ATLCLGHHAV PNGTLVKTIT DDQIEVTNAT ELVQSSSTGK

ICNNPHRILD GIDCTLIDAL LGDPHCDVFQ NETWDLFVER SKAFSNCYPY DVPDYASLRS

LVASSGTLEF ITEGFTWTGV TQNGGSNACK RGPGSGFFSR LNWLTKSGST YPVLNVTMPN

NDNFDKLYIW GIHHPSTNQE QTSLYVQASG RVTVSTRRSQ QTIIPNIGSR PWVRGLSSRI

SIYWTIVKPG DVLVINSNGN LIAPRGYFKM RTGKSSIMRS DAPIDTCISE CITPNGSIPN

DKPFQNVNKI TYGACPKYVK QNTLKLATGM RNVPEKQTR
```

H3 HA2

The amino acid sequence of H3 HA21 is provided below, as SEQ ID NO: 174 Residue N12 shown in a dash box, is bound by Ab 044 but not by FI6; Residues G1, L2, F3, G4, and D46 shown in dotted boxes, are bound by FI6 but not by Ab 044; residues A7, E11, I18, D19, G20, W21, L38, K39, T41, Q42, A43, I45, I48, N49, L52, N53, I56, and E57, shown in solid boxes, are bound by both Ab 044 and FI6.

(SEQ ID NO: 174)

GLFGAIAGFI ENGWEGMIDG WYGFRHQNSE GTGQAADLKS TQAAIDQING

KLNRVIEKTN EKFHQIEKEF SEVEGRIQDL EKYVEDTKID LWSYNAELLV ALENQHTIDL

TDSEMNKLFE KTRRQLRENA EEMGNGCFKI YHKCDNACIE SIRNGTYDHD VYRDEALNNR

FQIKG

H1 residues that bind Ab 044 and H1 residues that bind FI6 are discussed below.

H1 HA1

The amino acid sequence of H1 HA1 is provided below, as SEQ ID NO: 181. Residues H31, N279, and S292 shown in dashed boxes, are bound by Ab 044 but not by FI6. Residues Q328 and S329 shown in dotted boxes, are bound by FI6 but not by Ab 044. Residues T319, R322, and I324 shown in solid boxes, are bound by both Ab 044 and FI6.

highlighted amino acids are unique to Ab044's epitope) is shown in FIG. 26 of International Application Publication No. WO2013/170139. A three dimensional representation of H3 HA with the amino acid residues that are part of FI6's epitope but not predicted to be part of Ab044's epitope highlighted is shown in FIG. 27 of International Application Publication No. WO2013/170139. The content of International Application Publication No. WO2013/170139 is incorporated by reference in its entirety.

(SEQ ID NO: 181)

TNADTI CIGYHANNST DTVDTVLEKN VTVTHSVNLL

EDSHNGKLCK LKGIAPLQLG KCNIAGWLLG NPECDLLLTA SSWSYIVETS

NSENGTCYPG DFIDYEELRE QLSSVSSFEK FEIFPKTSSW PNHETTKGVT

AACSYAGASS FYRNLLWLTK KGSSYPKLSK SYVNNKGKEV LVLWGVHHPP

TGTDQQSLYQ NADAYVSVGS SKYNRRFTPE IAARPKVRDQ AGRMNYYWTL

LEPGDTITFE ATGNLIAPWY AFALNRGSGS GIITSDAPVH DCNTKCQTPH

GAINSSLPFQ NIHPVTIGEC PKYVRSTKLR MATGLRNIPS IQS

H1 HA2

The amino acid sequence of H1 HA2 is provided below, as SEQ ID NO: 182. Residues G12 shown in a dashed box, is bound by Ab 044 but not by FI6. Residues G1, L2, F3, G4, and D46 shown in dotted boxes, are bound by FI6 but not by Ab 044. Residues A7, E11, I18, D19, G20, W21, Q38, K39, T41, Q42, N43, I45, I48, T49, V52, N53, I56, and E57 shown in solid boxes, are bound by both Ab 044 and FI6.

Binding Agents, e.g., Anti-HA Antibody Molecules

Formulations (e.g., pharmaceutical formulations) described herein include binding agents, e.g., antibody molecules, described herein.

Binding agents, and in particular, the antibody molecules described herein, can bind to influenza A viruses from both Group 1 and Group 2, and in an embodiment also bind influenza B viruses. For example, the antibody molecules (SEQ ID NO: 182)

GLFGAIAGF IEGGWTGMID GWYGYHHQNE QGSGYAADQK STQNAIDGIT

NKVNSVIEKM NTQFTAVGKE FNNLERRIEN LNKKVDDGFL DIWTYNAELL

VLLENERTLD FHDSNVRNLY EKVKSQLKNN AKEIGNGCFE FYHKCDDACM

ESVRNGTYDY PKYSEESKLN REEIDGVKLE SMGVYQILAI YSTVASSLVL

LVLSLGAISFW MCSNGSLQCR ICI

A three dimensional representation of H3 HA with the amino acids residues that are predicted to be part of Ab044 epitope but not part of FI6's epitope highlighted (that is, the described herein can bind to an HA polypeptide on at least 1, 2, 3, 4, 5, 6, 7, 8, 9, 10 or 11 strains from Group 1, and can also bind to an HA polypeptide on at least 1, 2, 3, 4, 5, or 6 strains from Group 2. In another example, the antibody molecules described herein can bind to an HA polypeptide on an influenza strain from at least 1, 2 or 3 clades from Group 1, and can also bind to an HA polypeptide on an influenza strain from one or both clades of Group 2. The antibody molecules described herein inhibit cell entry and thus targeting an early step in the infection process.

The binding agents, and in particular, the antibody molecules disclosed herein, can be effective to treat or prevent infection by seasonal or pandemic influenza strains. The binding agents, and in particular the antibody molecules described herein, can be characterized by their ability to prevent or treat a Group 1 or a Group 2 strain of influenza A viruses or, in an embodiment, a strain of influenza B viruses. The binding agents, and in particular the antibody molecules disclosed herein, are effective to prevent or treat infection by one or more strains of Group 1, one or more strains of Group 2, and also one or more strains of influenza B viruses.

The binding agents, and in particular the antibody molecules can be effective to treat the infection when administered the same day as the subject is exposed, or when administered, e.g., 1 day, 2 days, 3 days, 4 days or later after infection, or upon a first symptom experienced by the patient.

Strains

The antibody molecules described herein are effective to treat one or more influenza strains of Group 1, one or more influenza strains of Group 2, and also one or more influenza B strains, and specific isolates within these strains. Certain antibody molecules may be more effective for treatment of certain isolates than other isolates. Exemplary influenza strains and isolates are described in the below Table 1.

TABLE 1

Exemplary influenza strains and Isolates

| Type | Group | HA type | Isolate |
|---|---|---|---|
| A | 1 | H1N1 | A/PR/8/34 (aka PR-8) |
|   |   |   | A/Solomon Islands/03/06 |
|   |   |   | A/Solomon Islands/20/1999 |
|   |   |   | A/California/07/2009 |
|   |   |   | A/New Caledonia/20/99 |
|   |   |   | A/Bangkok/10/83 |
|   |   |   | A/Yamagata/120/86 |
|   |   |   | A/Osaka/930/88 |
|   |   |   | A/Suita/1/89 |
|   |   |   | A/California/04/2009 |
| A | 1 | H2N2 | A/Okuda/57 |
|   |   |   | A/Adachi/2/57 |
|   |   |   | A/Kumamoto/1/65 |
|   |   |   | A/Kaizuka/2/65 |
|   |   |   | A/Izumi/5/65 |
|   |   |   | A/Chicken/PA/2004 |
| A | 1 | H5N1 | A/Vietnam/1203/04 |
|   |   |   | A/Duck/Singapore/3/97 |
|   |   |   | A/Duck/MN/1525/81 |
| A | 1 | H9N2 | A/Hong Kong/1073/2004 |
|   |   |   | A/Swine/Hong Kong/9/98 |
|   |   |   | A/Guinea fowl/HK/WF10/99 |
| A | 1 | H16N3 | A/black headed gull/Mongolia/1756/2006 |
| A | 2 | H3N2 | X-31 |
|   |   |   | A/Victoria/3/75 |
|   |   |   | A/Wyoming/03/2003 |
|   |   |   | A/Wisconsin/67/2005 |
|   |   |   | A/Brisbane/10/2007 |
|   |   |   | A/California/7/2004 |
|   |   |   | A/New York/55/2004 |
|   |   |   | A/Moscow/10/1999 |
|   |   |   | A/Aichi/2/68 |
|   |   |   | A/Beijing/32/92/X-117 |
|   |   |   | A/Fukuoka/C29/85 |
|   |   |   | A/Sichuan/2/87 |
|   |   |   | A/Ibaraki/1/90 |
|   |   |   | A/Suita/1/90 |
|   |   |   | A/Perth/16/2009 |
|   |   |   | A/Uruguay/716/2007 |
|   |   |   | A/Fujian/411/2003 |
|   |   |   | A/Panama/2007/99 |
|   |   |   | A/Shangdong/09/93 |
| A | 2 | H7N7 | A/Netherlands/219/2003 |
| A | 2 | H7N9 | A/Anhui/1/2013 |
|   |   |   | A/Shanghai/1/2013 |
| B |   |   | B/Wisconsin/1/2010 |

Affinity can also be in reference to a particular isolate of a given Group 1 or Group 2 strain for influenza A viruses or a strain for influenza B viruses. Exemplary isolates are as provided in the above Table 1.

Mechanisms of Inhibition

While not being limited by a specific mechanism, HA specific antibodies can inhibit infection by numerous methods, such as by blocking viral attachment to sialic acid residues on surface proteins on host cells, by interfering with the structural transition of HA that triggers fusion activity in the endosome, or by simultaneously inhibiting attachment and virus-cell fusion.

In an embodiment, antibody molecules disclosed herein bind an epitope at the HA trimer interface. Structural changes at the trimer interface are important for fusion of the viral membrane and the endocytic membrane, and the antibody molecules described herein interfere with this critical step of infection. Assays to measure fusogenic activity of HA are known in the art. For example, one fusion assay measures syncytia formation, which occurs in cell-cell fusion events. Cells that express and display an influenza viral strain HA can be used in the assay. Membrane-anchored hemagglutinin in these cells is induced to convert to the fusion conformation by a brief (e.g., 3 minute) exposure to low pH (e.g., pH 5). A 2-3-hour incubation period follows to allow the cells to recover and fuse to form syncytia. A nuclear stain can be used to aid in the visualization of these fusion products, and their count is used as a gauge of fusion activity. A candidate anti-HA antibody can be added either before or after the low pH treatment to determine at which stage of the fusion process the antibody interferes.

Another type of fusion assay monitors content mixing. To measure content mixing, host cells (e.g., erythrocytes) are loaded with a dye (e.g., Lucifer yellow) to determine whether the contents of HA-bound host cells could be delivered to HA-expressing cells after exposure to fusion-inducing conditions (e.g., low pH, such as pH less than 6 or pH less than 5). If the dye fails to mix with the contents of the host cells, then the conclusion can be made that fusion is inhibited. See e.g., Kemble et al., *J. Virol.* 66:4940-4950, 1992.

In another example, a fusion assay is performed by monitoring lipid mixing. The lipid mixing assay can be performed by labeling host cells (e.g., erythrocytes) with a fluorescent dye (e.g., R18 (octadecylrhodamine)) or dye pairs (e.g., CPT-PC/DABS-PC) (for fluorescence resonance energy transfer), exposing the host cells and HA-expressing cells to fusion-inducing conditions, and assaying for fluorescence dequenching (FDQ). Lipid mixing leads to dilution of the label into the viral envelope and a consequent dequenching. A lag in dequenching or the absence of dequenching is indicative of membrane fusion inhibition. See e.g., Kemble et al., *J. Virol.* 66:4940-4950, 1992; and Carr et al., *Proc. Natl. Acad. Sci.* 94:14306-14313, 1997.

Escape Mutants

In an embodiment, influenza strains will rarely if ever produce escape mutants when contacted with the formulations (e.g., pharmaceutical formulations) described herein.

Escape mutants can be identified by methods known in the art. For example, a formulation (e.g., pharmaceutical formulation) will not produce an escape mutant when the cells are infected with the virus under prolonged or repeated exposure to the formulation (e.g., pharmaceutical formulation).

One exemplary method includes infection of cells (e.g., MDCK cells) with a fixed amount of influenza A viral particles in the presence of the antibody at a concentration known to attenuate infection rates by 50%. Viral progeny collected after each passaging is used to infect a fresh cell culture in the presence of the same or greater concentration of the antibody. After multiple cycles of infection, e.g., after 15 cycles, 12 cycles, 11 cycles, 10 cycles, 9 cycles, 8 cycles, 7 cycles, 6 cycles, or 5 cycles, of infection under these conditions, the HA nucleotide sequence extracted from 20 viral plaque picks is evaluated for enrichment for mutations that renders the viral isolate resistant to neutralization by the antibody (an escape mutant). If no mutants with reduced sensitivity to the antibody are detected after the multiple rounds of selection, e.g., after 11 rounds, 10 rounds, or 9 rounds of selection, the antibody is determined to be resistant to escape mutations (see e.g., Throsby et al. (2008) *PLoS One*, volume 3, e3942).

In another example, an assay that measures minimum inhibitory concentration (MIC) of the neutralizing antibody can be used to identify escape mutants. The MIC of an antibody molecule is the lowest concentration of an antibody molecule that can be mixed with virus to prevent infection of cell culture with influenza. If escape mutants arise within a viral population, then the MIC of a particular antibody will be observed to increase with increased rounds of propagation under the antibody selective pressure, as the proportion of the viral particles that carry the resistance mutation within the population increased. Influenza escape mutants rarely if ever evolve in response to an anti-HA antibody molecule described herein, and therefore the MIC will stay the same over time.

Another assay suitable for monitoring for the development of escape mutants is a Cytopathic Effect (CPE) assay. A CPE assay monitors the ability of an antibody to neutralize (e.g., prevent infection by) an influenza strain. A CPE assay provides the minimal concentration of antibody required in cell culture to neutralize the virus. If escape mutants arise, than the CPE of a particular antibody will increase over time, as the antibody becomes less effective at neutralizing the virus. Viral strains rarely if ever produce escape mutants in response to an anti-HA antibody molecule described herein, and therefore the CPE will stay essentially the same over time.

Quantitative polymerase chain reaction (qPCR) can also be used to monitor for the development of escape mutants. qPCR is useful to monitor the ability of an antibody to neutralize (e.g., prevent infection by) an influenza strain. If an antibody effectively neutralizes a virus, then qPCR performed on cell culture samples will not detect presence of viral genomic nucleic acid. If escape mutants arise, than over time, qPCR will amplify more and more viral genomic nucleic acid. Escape mutants rarely if ever develop in response to an anti-HA antibody molecule described herein, and therefore qPCR will rarely if ever detect viral genomic nucleic acid, even after the passage of time.

Binding and Affinity

In an embodiment, the binding agents, particularly antibody molecules, described herein bind to two or more of the following: at least one HA polypeptide from a Group 1 influenza strain (e.g., an H1, H2, H5, H6, H8, H9 H12, H11, H13, H16 or H17 polypeptide); at least one HA polypeptide from a Group 2 influenza strain (e.g., an H3, H4, H14, H7, H10, or H15 polypeptide); and at least one HA polypeptide from a influenza B strain.

In an embodiment, a binding agent, e.g., an antibody molecule, has a $K_D$ for an HA from a Group 1 influenza strain (e.g., an H1, H2, H5, H6, H8, H9 H12, H11, H13, H16 or H17 polypeptide) of equal to or less than $10^{-6}$, $10^{-7}$, $10^{-8}$, $10^{-9}$, $10^{-10}$, $10^{-11}$, or $10^{-12}$ nM. In an embodiment, a binding agent, e.g., an antibody molecule, has a $K_D$ for an HA from a Group 2 influenza strain (e.g., an H3, H4, H14, H7, H10, or H15 polypeptide) of equal to or less than $10^{-6}$, $10^{-7}$, $10^{-8}$, $10^{-9}$, $10^{-10}$, $10^{-11}$, or $10^{-12}$ nM. In an embodiment, a binding agent, e.g., an antibody molecule, has a $K_D$ for an influenza B HA of equal to or less than $10^{-6}$, $10^{-7}$, $10^{-8}$, $10^{-9}$, $10^{-10}$, $10^{-11}$, or $10^{-12}$ nM.

In an embodiment, a binding agent, e.g., an antibody molecule, has: a) a first $K_D$ (representing an affinity for an HA from a Group 1 influenza strain, e.g., an H1, H2, H5, H6, H8, H9 H12, H11, H13, H16 or H17 polypeptide); and b) a second $K_D$ (representing an affinity for an HA from a Group 2 influenza strain, e.g., an H3, H4, H14, H7, H10, or H15 polypeptide), wherein the first and second $K_D$ are one or both of: both equal to or less than $10^{-8}$ nM; and within 10 or 100 fold of each other.

In an embodiment, a binding agent, e.g., an antibody molecule, has: a) a first $K_D$ (representing an affinity for an H1, e.g., the H1 from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004); and b) a second $K_D$ (representing an affinity for an H3 polypeptide, e.g., the H3 from an H3N2 strain, e.g., A/Brisbane/59/2007), wherein the first and second $K_D$ are one or both of: both equal to or less than $10^{-8}$ nM; and within 10 or 100 fold of each other.

In an embodiment, a binding agent, e.g., an antibody molecule, has: a) a first $K_D$ (representing an affinity for an H1, e.g., the H1 from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004); and b) a second $K_D$ (representing an affinity for an H3 polypeptide, e.g., the H3 from an H3N2 strain, e.g., A/Brisbane/59/2007), wherein the first and second $K_D$ are one or both of: both equal to or less than $10^{-8}$ nM; and within 10 or 100 fold of each other.

In an embodiment, a binding agent, e.g., an antibody molecule, has: a) a first $K_D$ (representing an affinity for an HA from a Group 1 influenza strain, e.g., an H1, H2, H5, H6, H8, H9 H12, H11, H13, H16 or H17 polypeptide and/or an affinity for an HA from a Group 2 influenza strain, e.g., an H3, H4, H14, H7, H10, or H15 polypeptide); and b) a second $K_D$ (representing an affinity for an influenza B HA, e.g., from B/Wisconsin/1/2010), wherein the first and second $K_D$ are one or both of: both equal to or less than $10^{-8}$ nM; and within 10 or 100 fold of each other.

In an embodiment, a binding agent, e.g., an antibody molecule, has: a) a first $K_D$ (representing an affinity for an HA from a Group 1 influenza strain, e.g., an H1, e.g., the H1 from an H1N1 strain, e.g., A/South Carolina/1/1918, A/Puerto Rico/08/1934, or A/California/04/2009, or an H5N1 strain, e.g., A/Indonesia/5/2005 or A/Vietnam/1203/2004, and/or an affinity for an HA from a Group 2 influenza strain, e.g., an H3 polypeptide, from an H3N2 strain, e.g., from A/Brisbane/59/2007); and b) a second $K_D$ (an affinity for an influenza B HA), wherein the first and second $K_D$ are: one or both of: both equal to or less than $10^{-8}$ nM; and within 10 or 100 fold of each other.

In an embodiment, the antibody molecule binds to at least one HA polypeptide from a Group 1 influenza strain with a higher affinity than a reference anti-HA antibody, and to at least one HA polypeptide from a Group 2 influenza strain with a higher affinity than a reference anti-HA antibody. In another embodiment, the antibody molecule binds to at least one HA polypeptide from an influenza A strain with a higher affinity than a reference anti-HA antibody, and to at least one HA polypeptide from an influenza B strain with a higher affinity than a reference anti-HA antibody. Exemplary reference HA antibodies include Ab 67-11 (U.S. Provisional Application No. 61/645,453, U.S. Application Publication No. 2013/0302348, and International Application Publication No. WO 2013/169377), F16 (F16, as used herein, refers to any specifically disclosed F16 sequence in U.S. Published Application No. 2010/0080813, U.S. published application No. 2011/0274702, WO2013/011347 or Corti et al., Science 333:850-856, 2011, published online Jul. 28, 2011; FIG. 4), F128 (U.S. Published Application No. 2010/0080813), and C179 (Okuno et al., *J. Virol.* 67:2552-1558, 1993), F10 (Sui et al., *Nat. Struct. Mol. Biol.* 16:265, 2009), CR9114 (Dreyfus et al., *Science.* 2012; 337(6100):1343-1348; published online Aug. 9, 2012), and CR6261 (Ekiert et al., *Science* 324:246-251, 2009).

Affinity, or relative affinity or aviditiy, can be measured by methods known in the art, such as by ELISA assay (Enzyme Linked Immunosorbent Assay), Surface Plasmon Resonance (SPR, e.g., by a Biacore™ Assay), or KinExA® assay (Sapidyne, Inc.). Relative binding affinity is expressed herein according to ELISA assay. As used herein, an anti-HA antibody that binds with "high affinity" to a Group 1 HA, to a Group 2 HA, and to a influenza B HA, can bind a Group 1 HA with a Kd less than or equal to 200 pM, e.g., less than or equal to 100 pM, as measured by ELISA, can bind a Group 2 HA with a Kd less than or equal to 200 pM, e.g., less than or equal to 100 pM, as measured by ELISA, and can bind an influenza B HA with a Kd less than or equal to 200 pM, e.g., less than or equal to 100 pM, as measured by ELISA.

Exemplary Anti-HA Antibody Molecules

Provided herein are antibodies that have one or more CDR sequences and one or more framework (FR) sequences as shown in Table 2.

TABLE 2

Heavy and Light Chain CDR and FR Sequences for Anti-HA Antibodies

| CDR/FR Region | Amino Acid Sequence | SEQ ID NO: |
|---|---|---|
| HC CDR1 | [S/T]Y[A/G]MH | 1 |
| HC CDR2 | V[I/V/L]S[Y/F]DG[S/N][Y/N][K/R]YYADSVQG | 2 |
| HC CDR3 | D[S/T][R/K/Q]LR[S/T]LLYFEWLS[Q/S]G[Y/L/V][F/L][N/D][P/Y] | 3 |
| LC CDR1 | Q[S/T][V/L/I][T/S][Y/F/W][N/S/D]YKNYLA | 4 |
| LC CDR1 | Q[S/T][V/L/I][T/S][Y/F/W][N/S/D/Q/R/E]YKNYLA | 170 |
| LC CDR2 | W[A/G]S[T/A/Y/H/K/D][R/L]E[S/T] | 5 |
| LC CDR3 | QQ[Y/H]YRTPP[T/S] | 6 |
| HC FR1 | [E/Q]VQLLE[S/T]GGGLVKPGQSLKLSCAASGFTF[S/T] | 7 |
| HC FR2 | WVRQPPGKGLEWVA | 8 |
| HC FR3 | RFTISRDNSKNTLYLQMNSLRAEDTAVYYCAK | 9 |
| HC FR4 | WG[A/Q]G[T/A][T/M][L/V]TVSS | 10 |
| LC FR1 | [E/D]I[V/Q]MTQSP[D/S][S/T][L/V][A/S][V/A][S/T][L/V/R]G[E/D]R[A/V][T/S]I[N/T/Q/D/R/]C[K/R]SS | 11 |
| LC FR2 | WYQQKPG[Q/K][P/A]PKLLIY | 12 |
| LC FR3 | GVP[D/E/S]RFSGSGSGTDFTLTISSLQ[A/P]ED[V/F/K/D]A[V/T]YYC | 13 |
| LC FR4 | FG[G/Q/T/S/N]GTK[L/V][D/E]IK | 14 |

In an embodiment, the anti-HA antibody comprises a heavy chain and/or alight chain as defined in Table 3 below. The amino acid sequences of the variable heavy and light chains of Table 3 are provided in FIGS. 2, 3, respectively, or in FIG. 7.

TABLE 3

Heavy and Light Chain Amino Acid Sequence Designations for Anti-HA Antibodies

| | Antibody | HC | SEQ ID NO: | LC | SEQ ID NO: |
|---|---|---|---|---|---|
| 1. | Ab A18 | 15 | 15 | 28 | 28 |
| 2. | Ab 014 | 16 | 16 | 29 | 29 |

TABLE 3-continued Heavy and Light Chain Amino Acid Sequence Designations for Anti-HA Antibodies

| | Antibody | HC | SEQ ID NO: | LC | SEQ ID NO: |
|---|---|---|---|---|---|
| 3. | Ab 028 | 16 | 16 | 30 | 30 |
| 4. | Ab 001 | 17 | 17 | 31 | 31 |
| 5. | Ab 002 | 18 | 18 | 31 | 31 |
| 6. | Ab 003 | 19 | 19 | 31 | 31 |
| 7. | Ab 009 | 17 | 17 | 32 | 32 |
| 8. | Ab 010 | 18 | 18 | 32 | 32 |
| 9. | Ab 011 | 19 | 19 | 32 | 32 |
| 10. | Ab 017 | 17 | 17 | 33 | 33 |
| 11. | Ab B18 | 18 | 18 | 33 | 33 |
| 12. | Ab 019 | 19 | 19 | 33 | 33 |
| 13. | Ab 025 | 17 | 17 | 34 | 34 |
| 14. | Ab 026 | 18 | 18 | 34 | 34 |
| 15. | Ab 027 | 19 | 19 | 34 | 34 |
| 16. | Ab 086 | 20 | 20 | 34 | 34 |
| 17. | Ab 154 | 21 | 21 | 29 | 29 |
| 18. | Ab 155 | 21 | 21 | 30 | 30 |
| 19. | Ab 157 | 22 | 22 | 29 | 29 |
| 20. | Ab 159 | 22 | 22 | 35 | 35 |
| 21. | Ab 160 | 17 | 17 | 36 | 36 |
| 22. | Ab 186 | 17 | 17 | 37 | 37 |
| 23. | Ab 187 | 17 | 17 | 38 | 38 |
| 24. | Ab 188 | 17 | 17 | 39 | 39 |
| 25. | Ab 189 | 17 | 17 | 40 | 40 |
| 26. | Ab 190 | 17 | 17 | 41 | 41 |
| 27. | Ab 191 | 17 | 17 | 42 | 42 |
| 28. | Ab 192 | 17 | 17 | 43 | 43 |
| 29. | Ab 193 | 17 | 17 | 44 | 44 |
| 30. | Ab 194 | 19 | 19 | 37 | 37 |
| 31. | Ab 195 | 19 | 19 | 38 | 38 |
| 32. | Ab 196 | 19 | 19 | 39 | 39 |
| 33. | Ab 197 | 19 | 19 | 40 | 40 |
| 34. | Ab 198 | 19 | 19 | 41 | 41 |
| 35. | Ab 199 | 19 | 19 | 42 | 42 |
| 36. | Ab 200 | 19 | 19 | 43 | 43 |
| 37. | Ab 202 | 17 | 17 | 45 | 45 |
| 38. | Ab 203 | 18 | 18 | 45 | 45 |
| 39. | Ab 204 | 19 | 19 | 45 | 45 |
| 40. | Ab 210 | 23 | 23 | 45 | 45 |
| 41. | Ab 211 | 17 | 17 | 46 | 46 |
| 42. | Ab 212 | 18 | 18 | 46 | 46 |
| 43. | Ab 213 | 19 | 19 | 46 | 46 |
| 44. | Ab 219 | 23 | 23 | 46 | 46 |
| 45. | Ab A001 | 24 | 24 | 47 | 47 |
| 46. | Ab A002 | 24 | 24 | 48 | 48 |
| 47. | Ab A003 | 24 | 24 | 49 | 49 |
| 48. | Ab 004 | 25 | 25 | 47 | 47 |
| 49. | Ab 005 | 25 | 25 | 48 | 48 |
| 50. | Ab 006 | 25 | 25 | 49 | 49 |
| 51. | Ab 007 | 26 | 26 | 47 | 47 |
| 52. | Ab 008 | 26 | 26 | 48 | 48 |
| 53. | Ab A009 | 26 | 26 | 49 | 49 |
| 54. | Ab A010 | 24 | 24 | 50 | 50 |
| 55. | Ab A011 | 24 | 24 | 51 | 51 |
| 56. | Ab 012 | 25 | 25 | 50 | 50 |
| 57. | Ab 013 | 25 | 25 | 51 | 51 |
| 58. | Ab A14 | 26 | 26 | 50 | 50 |
| 59. | Ab 015 | 26 | 26 | 51 | 51 |
| 60. | Ab 016 | 27 | 27 | 47 | 47 |
| 61. | Ab A017 | 27 | 27 | 48 | 48 |
| 62. | Ab C18 | 27 | 27 | 49 | 49 |
| 63. | Ab A019 | 27 | 27 | 50 | 50 |
| 64. | Ab 031 | 24 | 24 | 45 | 45 |
| 65. | Ab 032 | 25 | 25 | 45 | 45 |
| 66. | Ab 033 | 26 | 26 | 45 | 45 |
| 67. | Ab 034 | 27 | 27 | 45 | 45 |
| 68. | Ab 037 | 24 | 24 | 46 | 46 |
| 69. | Ab 038 | 25 | 25 | 46 | 46 |
| 70. | Ab 039 | 26 | 26 | 46 | 46 |
| 71. | Ab 040 | 27 | 27 | 46 | 46 |
| 72. | Ab 043 | 25 | 25 | 60 | 60 |
| 73. | Ab 044 | 25 | 25 | 52 | 52 |
| 74. | Ab 045 | 25 | 25 | 57 | 57 |
| 75. | Ab 046 | 25 | 25 | 59 | 59 |
| 76. | Ab 047 | 25 | 25 | 55 | 55 |
| 77. | Ab 048 | 25 | 25 | 58 | 58 |
| 78. | Ab 049 | 25 | 25 | 54 | 54 |
| 79. | Ab 050 | 25 | 25 | 56 | 56 |
| 80. | Ab 051 | 25 | 25 | 53 | 53 |
| 81. | Ab 052 | 25 | 25 | 61 | 61 |
| 82. | Ab 067 | 25 | 25 | 153 | 153 |
| 83. | Ab 068 | 25 | 25 | 154 | 154 |
| 84. | Ab 069 | 25 | 25 | 155 | 155 |
| 85. | Ab 070 | 25 | 25 | 156 | 156 |
| 86. | Ab 071 | 162 | 162 | 52 | 52 |
| 87. | Ab 072 | 163 | 163 | 52 | 52 |
| 88. | Ab 073 | 25 | 25 | 165 | 165 |
| 89. | Ab 074 | 25 | 25 | 166 | 166 |
| 90. | Ab 075 | 25 | 25 | 167 | 167 |
| 91. | Ab 076 | 25 | 25 | 168 | 168 |
| 92. | Ab 077 | 25 | 25 | 169 | 169 |
| 93. | Ab 078 | 164 | 164 | 52 | 52 |
| 94. | Ab 079 | 164 | 164 | 155 | 155 |
| 95. | Ab 080 | 164 | 164 | 166 | 166 |
| 96. | Ab 081 | 164 | 164 | 169 | 169 |

Ab A18 is also sometimes known as Ab018 herein.

In an embodiment, the anti-HA antibody comprises a heavy chain as defined in Table 4A below, and/or a light chain as defined in Table 4A below.

TABLE 4A

Heavy and Light Chain Amino Acid Sequence Designations

| HC | SEQ ID NO: | LC | SEQ ID NO: |
|---|---|---|---|
| 15 | 15 | 28 | 28 |
| 16 | 16 | 29 | 29 |
| 17 | 17 | 30 | 30 |
| 18 | 18 | 35 | 35 |
| 19 | 19 | 31 | 31 |
| 21 | 21 | 32 | 32 |
| 22 | 22 | 33 | 33 |
| 20 | 20 | 34 | 34 |
| 23 | 23 | 36 | 36 |
| 24 | 24 | 45 | 45 |
| 25 | 25 | 46 | 46 |
| 26 | 26 | 37 | 37 |
| 27 | 27 | 38 | 38 |
| Hc consensus (HC161) | 161 | 39 | 39 |
| | | 40 | 40 |
| 162 | 162 | 41 | 41 |
| 163 | 163 | 42 | 42 |
| 164 | 164 | 43 | 43 |
| | | 44 | 44 |
| | | 47 | 47 |
| | | 48 | 48 |
| | | 49 | 49 |
| | | 50 | 50 |
| | | 51 | 51 |
| | | 52 | 52 |
| | | 53 | 53 |
| | | 54 | 54 |
| | | 55 | 55 |
| | | 56 | 56 |
| | | 57 | 57 |
| | | 58 | 58 |
| | | 59 | 59 |
| | | 60 | 60 |
| | | 61 | 61 |
| | | 153 | 153 |
| | | 154 | 154 |
| | | 155 | 155 |
| | | 156 | 156 |
| LC consensus (LC62) | | | 62 |
| | | 165 | 165 |
| | | 166 | 166 |

TABLE 4A-continued

Heavy and Light Chain Amino Acid Sequence Designations

| HC | SEQ ID NO: | LC | SEQ ID NO: |
|---|---|---|---|
|  |  | 167 | 167 |
|  |  | 168 | 168 |
|  |  | 169 | 169 |

In an embodiment, an antibody molecule described herein comprises a heavy chain sequence as defined in Table 4A and a light chain sequence as defined in Table 4A.

In an embodiment, an antibody molecule described herein comprises a heavy chain sequence as defined herein, e.g., in Table 4A, where a dipeptide is fused to the N-terminus. Typically, the dipeptide is isoleucine-aspartic acid (Ile-Asp). In another embodiment, an antibody molecule described herein comprises a light chain sequence as defined herein, e.g., in Table 4A, where a dipeptide is fused to the N-terminus. Typically, the dipeptide is Ile-Asp. In yet another embodiment, an antibody molecule described herein comprises a heavy chain comprising an N-terminal Ile-Asp dipeptide and a light chain comprising an Ile-Asp dipeptide. In the propeptide sequence of the heavy chain or light chain polypeptide, the Ile-Asp dipeptide occurs between the signal sequence and FR1. Heavy chain and light chain variable sequences comprising an Ile-Asp dipeptide at the N-terminus are identified in Table 4B.

TABLE 4B

Heavy and Light Chain Amino Acid Sequence Designations, where the Sequence Includes an N-terminal Ile-Asp Dipeptide

| HC | SEQ ID NO: | LC | SEQ ID NO: |
|---|---|---|---|
| 15-ID | 96 | 28-ID | 110 |
| 16-ID | 97 | 29-ID | 111 |
| 17-ID | 98 | 30-ID | 112 |
| 18-ID | 99 | 35-ID | 113 |
| 19-ID | 100 | 31-ID | 114 |
| 21-ID | 101 | 32-ID | 115 |
| 22-ID | 102 | 33-ID | 116 |
| 20-ID | 103 | 34-ID | 117 |
| 23-ID | 104 | 36-ID | 118 |
| 24-ID | 105 | 45-ID | 119 |
| 25-ID | 106 | 46-ID | 120 |
| 26-ID | 107 | 37-ID | 121 |
| 27-ID | 108 | 38-ID | 122 |
| Hc consensus ID (161-ID) | 109 | 39-ID | 123 |
|  |  | 40-ID | 124 |
|  |  | 41-ID | 125 |
|  |  | 42-ID | 126 |
|  |  | 43-ID | 127 |
|  |  | 44-ID | 128 |
|  |  | 47-ID | 129 |
|  |  | 48-ID | 130 |
|  |  | 49-ID | 131 |
|  |  | 50-ID | 132 |
|  |  | 51-ID | 133 |
|  |  | 52-ID | 134 |
|  |  | 53-ID | 135 |
|  |  | 54-ID | 136 |
|  |  | 55-ID | 137 |
|  |  | 56-ID | 138 |
|  |  | 57-ID | 139 |
|  |  | 58-ID | 140 |
|  |  | 59-ID | 141 |
|  |  | 60-ID | 142 |
|  |  | 61ID | 143 |
|  |  | 153-ID | 157 |
|  |  | 154-ID | 158 |

TABLE 4B-continued

Heavy and Light Chain Amino Acid Sequence Designations, where the Sequence Includes an N-terminal Ile-Asp Dipeptide

| HC | SEQ ID NO: | LC | SEQ ID NO: |
|---|---|---|---|
|  |  | 155-ID | 159 |
|  |  | 156-ID | 160 |
|  |  | LC consensus ID (62-ID) | 144 |

In another embodiment, an antibody molecule described herein is other than an antibody known in the art. For example, the antibody is not Ab 67-11 (U.S. Provisional Application No. 61/645,453, U.S. Application Publication No. 2013/0302348, and International Application Publication No. WO 2013/169377), F16 (F16, as used herein, refers to any specifically disclosed F16 sequence in U.S. Application Publication No. 2010/0080813, U.S. Application Publication No. 2011/0274702, WO2013/011347 or Corti et al., Science 333:850-856, 2011, published online Jul. 28, 2011; FIGS. 12A to 12C), F128 (U.S. Application Publication No. 2010/0080813), C179 (Okuno et al., J. Virol. 67:2552, 1993), F10 (Sui et al., Nat. Struct. Mol. Biol. 16:265, 2009), CR9114 (Dreyfus et al., Science 337:1343, 2012), or CR6261 (Ekiert et al., Science 324:246, 2009). In an embodiment, an antibody described herein is other than Ab 67-11 (U.S. Provisional Application No. 61/645,453, U.S. Application Publication No. 2013/0302348, and International Application Publication No. WO 2013/169377).

Variants

In an embodiment, an antibody molecule described herein has a variable heavy chain immunoglobulin domain that is at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to a heavy chain disclosed herein, e.g., from Table 3, Table 4A, Table 4B, FIG. 2, FIG. 5 or FIG. 7, e.g. consensus sequence of SEQ ID NO:161, and has a variable light chain immunoglobulin domain that is at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to a light chain disclosed herein, e.g., from Table 3, Table 4A, Table 4B, FIGS. 3A-3B, FIGS. 6A-6B or FIG. 7, e.g., the consensus sequence of SEQ ID NO:62. The consensus sequences were determined through the analysis of biochemical and biophysical properties of several hundred computationally designed VH/VL combinations. The consensus sequences represent the amino acid sequences in which each amino acid is the one that occurs most frequently at that site when multiple sequences comprising desirable biochemical and biophysical data are aligned.

An exemplary anti-HA binding antibody has one or more CDRs, e.g., all three HC CDRs and/or all three LC CDRs of a particular antibody disclosed herein, or CDRs that are, in sum, at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to such an antibody.

In an embodiment, the H1 and H2 hypervariable loops have the same canonical structure as those of an antibody described herein. In an embodiment, the L1 and L2 hypervariable loops have the same canonical structure as those of an antibody described herein.

In an embodiment, the amino acid sequence of the HC and/or LC variable domain sequence is at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to the amino acid sequence of the HC and/or LC variable domain of an antibody described herein. The amino acid sequence of the HC and/or LC variable domain sequence can differ by at least one amino acid, but no more than ten, eight, six, five, four, three, or two amino acids from the corresponding sequence of an antibody described herein. For example, the differences may be primarily or entirely in the framework regions.

In certain embodiments, the amino acid differences are conservative amino acid differences (e.g., conservative amino acid substitutions). A "conservative" amino acid substitution is one in which the amino acid residue is replaced with an amino acid residue comprising a similar side chain. Families of amino acid residues comprising similar side chains have been defined in the art. These families include, e.g., amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The amino acid sequences of the HC and LC variable domain sequences can be encoded by a nucleic acid sequence that hybridizes under high stringency conditions to a nucleic acid sequence described herein or one that encodes a variable domain or an amino acid sequence described herein.

In an embodiment, the amino acid sequences of one or more framework regions (e.g., FR1, FR2, FR3, and/or FR4) of the HC and/or LC variable domain are at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to corresponding framework regions of the HC and LC variable domains of an antibody described herein. In an embodiment, one or more heavy or light chain framework regions (e.g., HC FR1, FR2, and FR3) are at least 85%, 87%, 88%, 89%, 90%, 92%, 94%, 95%, 96%, 97%, 98%, or 99% homologous, or at least 85%, 87%, 88%, 89%, 90%, 92%, 94%, 95%, 96%, 97%, 98%, or 99% identical, to the sequence of corresponding framework regions from a human germline antibody.

Production of Binding Agents

Nucleic acids (e.g., the genes) encoding a binding agent, e.g., an antibody molecule, generated by a method described herein can be sequenced, and all or part of the nucleic acids can be cloned into a vector that expresses all or part of the nucleic acids. For example, the nucleic acids can include a fragment of the gene encoding the antibody, such as a single chain antibody (scFv), a F(ab')$_2$ fragment, a Fab fragment, or an Fd fragment.

The disclosure also provides host cells comprising the nucleic acids encoding an antibody or fragment thereof as described herein. The host cells can be, for example, prokaryotic or eukaryotic cells, e.g., mammalian cells, or yeast cells, e.g., *Pichia* (see e.g., Powers et al. (2001). *J. Immunol. Methods* 251:123-35), Hanseula, or *Saccharomyces*.

Antibody molecules, particularly full length antibody molecules, e.g., IgGs, can be produced in mammalian cells. Exemplary mammalian host cells for recombinant expression include Chinese Hamster Ovary (CHO) cells (including dhfr CHO cells, described in Urlaub and Chasin (1980) *Proc. Natl. Acad. Sci. USA* 77:4216-4220, used with a DHFR selectable marker, e.g., as described in Kaufman and Sharp (1982) *Mol. Biol.* 159:601-621), lymphocytic cell lines, e.g., NS0 myeloma cells and SP2 cells, COS cells, K562, and a cell from a transgenic animal, e.g., a transgenic mammal. For example, the cell is a mammary epithelial cell.

In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216; 4,634,665; and 5,179,017). Exemplary selectable marker genes include the dihydrofolate reductase (DHFR) gene (for use in dhfr host cells with methotrexate selection/amplification) and the neo gene (for G418 selection).

In an exemplary system for recombinant expression of an antibody molecule (e.g., a full length antibody or an antigen-binding portion thereof), a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody molecule is recovered from the culture medium. Standard molecular biology techniques are used to prepare the recombinant expression vector, to transfect the host cells, to select for transformants, to culture the host cells, and to recover the antibody from the culture medium. For example, some antibodies can be isolated by affinity chromatography with a Protein A or Protein G. For example, purified antibodies can be concentrated to about 100 mg/mL to about 200 mg/mL using protein concentration techniques that are known in the art.

Antibody molecules can also be produced by a transgenic animal. For example, U.S. Pat. No. 5,849,992 describes a method for expressing an antibody molecule in the mammary gland of a transgenic mammal. A transgene is constructed that includes a milk-specific promoter and nucleic acid sequences encoding the antibody molecule of interest, e.g., an antibody described herein, and a signal sequence for secretion. The milk produced by females of such transgenic mammals includes, secreted therein, the antibody of interest, e.g., an antibody described herein. The antibody molecule can be purified from the milk, or for some applications, used directly.

Antibody molecules can also be expressed in vivo, following administration of a vector containing nucleic acids encoding the antibody heavy chain and the antibody light chain. Vector mediated gene-transfer is then used to engineer secretion of the anti-HA antibody into circulation.

For example, an anti-HA antibody heavy chain and an anti-HA antibody light chain as described herein are cloned into an adeno-associated virus (AAV)-based vector, and each of the anti-HA antibody heavy chain and the anti-HA antibody light chain are under control of a promoter, such as a cytomegalovirus (CMV) promoter. Administration of the vector to a subject, such as to a patient, e.g., a human patient, such as by intramuscular injection, results in expression of an anti-HA antibody, and secretion into the circulation.

Modifications of Binding Agents

Binding, agents, e.g., antibody molecules, described herein, can be modified to have numerous properties, e.g., to have altered, e.g., extended half life, to be associated with, e.g., covalently bound to detectable moieties, e.g., labels, to be associated with, e.g., covalently bound to toxins, or to have other properties, e.g., altered immune functions.

Antibody molecules may include modifications, e.g., modifications that alter Fc function, e.g., to decrease or remove interaction with an Fc receptor or with Clq, or both. In one example, the human IgG1 constant region can be mutated at one or more residues.

For some antibody molecules that include an Fc domain, the antibody production system may be designed to synthesize antibody molecules in which the Fc region is glycosylated. The Fc domain can be produced in a mammalian expression system that appropriately glycosylates the residue corresponding to asparagine 297. The Fc domain can also include other eukaryotic post-translational modifications.

Other suitable Fc domain modifications include those described in WO2004/029207. For example, the Fc domain can be an XmAb® Fc (Xencor, Monrovia, CA). The Fc domain, or a fragment thereof, can have a substitution in an Fcγ Receptor (FcγR) binding region, such as the domains and fragments described in WO05/063815. In some embodiments, the Fc domain, or a fragment thereof, has a substitution in a neonatal Fc Receptor (FcRn) binding region, such as the domains and fragments described in WO05047327. In other embodiments, the Fc domain is a single chain, or fragment thereof, or modified version thereof, such as those described in W2008143954. Other suitable Fc modifications are known and described in the art.

Antibody molecules can be modified, e.g., with a moiety that improves its stabilization and/or retention in circulation, e.g., in blood, serum, lymph, bronchoalveolar lavage, or other tissues, e.g., by at least 1.5, 2, 5, 10, or 50 fold.

For example, an antibody molecule generated by a method described herein can be associated with a polymer, e.g., a substantially non-antigenic polymer, such as a polyalkylene oxide or a polyethylene oxide. Suitable polymers will vary substantially by weight. Polymers comprising molecular number average weights ranging from about 200 to about 35,000 daltons (or about 1,000 to about 15,000, and 2,000 to about 12,500) can be used.

For example, an antibody molecule generated by a method described herein can be conjugated to a water soluble polymer, e.g., a hydrophilic polyvinyl polymer, e.g. polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides that comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparan.

Binding agents, e.g., antibody molecules, as disclosed herein, can by conjugated to another entity or moiety (e.g., to a cytotoxic or cytostatic moiety, a label or detectable moiety, or a therapeutic moiety). Exemplary moieties include: a cytotoxic or cytostatic agent, e.g., a therapeutic agent, a drug, a compound emitting radiation, molecules of plant, fungal, or bacterial origin, or a biological protein (e.g., a protein toxin) or particle (e.g., a recombinant viral particle, e.g., via a viral coat protein), a detectable agent; a pharmaceutical agent, and/or a protein or peptide that can mediate association of the antibody or antibody portion with another molecule (such as a streptavidin core region or a polyhistidine tag). A binding agent, e.g., an antibody molecule, as disclosed herein, can be functionally linked by any suitable method (e.g., chemical coupling, genetic fusion, covalent binding, noncovalent association or otherwise) to one or more other molecular entities.

Binding agents, e.g., antibody molecules, disclosed herein can be conjugated with a detectable moiety, e.g., a label or imaging agent. Such moieties can include enzymes (e.g., horseradish peroxidase, beta-galactosidase, luciferase, alkaline phosphatase, acetylcholinesterase, glucose oxidase and the like), radiolabels (e.g., $^{3}$H, $^{14}$C, $^{15}$N, $^{35}$S, $^{90}$Y, $^{99}$Tc, $^{111}$In, $^{125}$I, $^{131}$I and the like), haptens, fluorescent labels (e.g., FITC, rhodamine, lanthanide phosphors, fluorescein, fluorescein isothiocyanate, rhodamine, 5-dimethylamine-1-napthalenesulfonyl chloride, phycoerythrin and the like), phosphorescent molecules, chemiluminescent molecules, chromophores, luminescent molecules, photoaffinity molecules, colored particles or affinity ligands, such as biotin, predetermined polypeptide epitopes recognized by a secondary reporter (e.g., leucine zipper pair sequences, or binding sites for secondary antibodies, metal binding domains, epitope tags). In some embodiments, a moiety, e.g., a detectable moiety, e.g., a label, is attached by spacer arms of various lengths to reduce potential steric hindrance.

In an embodiment, a binding agent, e.g., antibody molecule, disclosed herein, is derivatized with a detectable enzyme and is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. A binding agent, e.g., antibody molecule, disclosed herein, ay also be derivatized with a prosthetic group (e.g., streptavidin/biotin and avidin/biotin). For example, an antibody may be derivatized with biotin, and detected through indirect measurement of avidin or streptavidin binding.

In an embodiment, the moiety comprises paramagnetic ions and NMR-detectable substances, among others. For example, in some embodiments, a paramagnetic ion is one or more of chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III), erbium (III), lanthanum (III), gold (III), lead (II), and/or bismuth (III).

Binding agents, e.g., antibody molecules, as disclosed herein, can be modified to be associated with, e.g., conjugated to, a therapeutic agent, e.g., an agent comprising anti-viral activity, anti-inflammatory activity, or cytotoxic activity, etc. In some embodiments, therapeutic agents can treat symptoms or causes of influenza infection (e.g., for example, anti-viral, pain-relief, anti-inflammatory, immunomodulatory, sleep-inducing activities, etc.).

Treatment Methods and Administration

The binding agents, e.g., antibody molecules, or formulations thereof, featured in the disclosure, can be used to treat a subject, e.g., a subject, e.g., a human subject, infected with, or at risk for becoming infected with, an influenza virus.

Any human is candidate to receive an antibody molecule disclosed herein for treatment or prevention of an infection by an influenza virus. Humans at high risk of infection, such as immunocompromised individuals, and humans who are at high risk of exposure to influenza virus are particularly suited to receive treatment with the antibody molecule. Immunocompromised individuals include the elderly (65 years and older) and children (e.g., 6 months to 18 years old), and people with chronic medical conditions. People at high risk of exposure include heath care workers, teachers and emergency responders (e.g., firefighters, policemen).

The antibody molecules described herein can also be used to prevent or reduce (e.g., minimize) secondary infection (e.g., secondary bacterial infection) or a risk of comprising secondary infection associated with influenza, or any effects (e.g., symptoms or complications) thereof on a subject. Opportunistic secondary bacterial infections (e.g., secondary bacterial pneumonia, e.g., primarily with *Streptococcus pneumonia*) contribute significantly to the overall morbidity and mortality associated with seasonal and pandemic influenza infections. The antibody molecules described herein can be used to prevent or reduce (e.g., minimize) the complications from secondary, opportunistic infections (e.g., bacterial infections) in a subject.

An antibody molecule can be administered to a subject, e.g., a human subject, by a variety of methods. For many applications, the route of administration is one of: intravenous injection or infusion, subcutaneous injection, or intramuscular injection. An antibody molecule can be administered as a fixed dose, or in a mg/kg dose. The antibody molecule can be administered intravenously (IV) or subcutaneously (SC). For example, the antibody molecule can be administered at a fixed unit dose of between about 50-600 mg IV, e.g., every 4 weeks, or between about 50-100 mg SC (e.g., 75 mg), e.g., at least once a week (e.g., twice a week). In an embodiment, the antibody molecule is administered IV at a fixed unit dose of 50 mg to 10000 mg, e.g., 1000 mg to 5000 mg, 2000 mg to 5000 mg, 2000 mg to 3000 mg, 2300 to 4600 mg, or 4000 mg to 5000 mg, e.g., 50 mg, 60 mg, 80 mg, 100 mg, 120 mg, 130 mg, 140 mg, 150 mg, 160 mg, 180 mg, 200 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, 2600 mg, 2700 mg, 2800 mg, 2900 mg, 3000 mg, 3100 mg, 3200 mg, 3300 mg, 3400 mg, 3500 mg, 3600 mg, 3700 mg, 3800 mg, 3900 mg, 4000 mg, 4100 mg, 4200 mg, 4300 mg, 4400 mg, 4500 mg, or more. Administration of the IV dose can be once or twice or three times or more per week, or once every two, three, four, or five weeks, or less frequently.

In an embodiment, the antibody molecule is administered SC at a fixed unit dose of 50 mg, 60 mg, 70 mg, 75 mg, 80 mg, 100 mg, or 120 mg or more. Administration of the SC dose can be once or twice or three times or more per week, or once every two, three, four, or five weeks, or less frequently.

An anti-HA antibody molecule disclosed herein can also be administered by inhalation, such as by intranasal or by oral inhalation, such as at a fixed unit dose of 50 mg, 60 mg, 80 mg, 100 mg, 120 mg, 130 mg, 140 mg, 150 mg, 160 mg, 180 mg, 200 mg, 300 mg, 400 mg, 500 mg, or 600 mg or more.

In an embodiment, an anti-HA antibody is administered to a subject via vector-mediated gene transfer, such as through the delivery of a vector encoding the heavy chain and the light chain of an anti-HA antibody, and the antibody is expressed from the heavy chain and light chain genes in the body. For example, nucleic acids encoding a heavy chain and a light chain can be cloned in a AAV vector, such as a self-complementary AAV vector, the scAAV vector administered to a human by injection, such as by IM injection, and the antibody is expressed and secreted into the circulation of the human.

An antibody molecule can also be administered in a bolus at a dose of between about 1 and 50 mg/kg, e.g., between about 1 and 10 mg/kg, between about 1 and 25 mg/kg or about 25 and 50 mg/kg, e.g., about 50 mg/kg, 25 mg/kg, 10 mg/kg, 6.0 mg/kg, 5.0 mg/kg, 4.0 mg/kg, 3.0 mg/kg, 2.0 mg/kg, 1.0 mg/kg, or less. Modified dose ranges include a dose that is less than about 3000 mg/subject, about 1500 mg/subject, about 1000 mg/subject, about 600 mg/subject, about 500 mg/subject, about 400 mg/subject, about 300 mg/subject, about 250 mg/subject, about 200 mg/subject, or about 150 mg/subject, typically for administration every fourth week or once a month. The antibody molecule can be administered, for example, every three to five weeks, e.g., every fourth week, or monthly.

Dosing can be adjusted according to a patient's rate of clearance of a prior administration of the antibody. For example, a patient may not be administered a second or follow-on dose before the level of antibodies in the patient's system has dropped below a pre-determined level. In an embodiment, a sample from a patient (e.g., plasma, serum, blood, urine, or cerebrospinal fluid (CSF)) is assayed for the presence of antibodies, and if the level of antibodies is above a pre-determined level, the patient will not be administered a second or follow-on dose. If the level of antibodies in the patient's system is below a pre-determined level, then the patient is administered a second or follow-on dose. A patient whose antibody levels are determined to be too high (above the pre-determined level) can be tested again after one or two or three days, or a week, and if the level of antibody in the patient samples has dropped below the pre-determined level, the patient may be administered a second or follow-on dose of antibody.

In certain embodiments, the antibody may be prepared with a carrier that will protect the drug against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Controlled Drug Delivery (Drugs and the Pharmaceutical Sciences), Second Edition, J. Robinson and V. H. L. Lee, eds., Marcel Dekker, Inc., New York, 1987.

Pharmaceutical compositions can be administered with a medical device. For example, pharmaceutical compositions can be administered with a needleless hypodermic injection device, such as the devices disclosed in U.S. Pat. Nos.

5,399,163; 5,383,851; 5,312,335; 5,064,413; 4,941,880; 4,790,824; or 4,596,556. Examples of well-known implants and modules are discussed in, e.g., U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system comprising multi-chamber compartments; and U.S. Pat. No. 4,475,196, which discloses an osmotic drug delivery system. Of course, many other such implants, delivery systems, and modules are also known.

In an embodiment, the binding agent, e.g., an antibody molecule, is administered buccally, orally, or by nasal delivery, e.g., as a liquid, spray, or aerosol, e.g., by topical application, e.g., by a liquid or drops, or by inhalation.

An antibody molecule described herein can be administered with one or more additional therapeutic agents, e.g., a second drug, for treatment of a viral infection, or a symptom of the infection. The antibody molecule and the one or more second or additional agents can be formulated together, in the same formulation, or they can be in separate formulations, and administered to a patient simultaneously or sequentially, in either order.

Dosage regimens are adjusted to provide the desired response, such as a therapeutic response or a combinatorial therapeutic effect. Generally, any combination of doses (either separate or co-formulated) of an antibody molecule and a second or additional agent can be used in order to provide a subject with both agents in bioavailable quantities.

Dosage unit form or "fixed dose" as used herein refers to physically discrete units suited as unitary dosages for the subjects to be treated; each unit contains a predetermined quantity of active compound calculated to produce the desired therapeutic effect in association with the required pharmaceutical carrier and optionally in association with another agent.

A pharmaceutical composition may include a "therapeutically effective amount" of an agent described herein. In an embodiment, where the antibody molecule is administered in combination with a second or additional agent, such effective amounts can be determined based on the combinatorial effect of the administered first and second or additional agent. A therapeutically effective amount of an agent may also vary according to factors such as the disease state, age, sex, and weight of the individual, and the ability of the compound to elicit a desired response in the individual, such as amelioration of at least one infection parameter, or amelioration of at least one symptom of the infection, such as chills, fever, sore throat, muscle pain, headache, coughing, weakness, fatigue and general discomfort. A therapeutically effective amount is also one in which any toxic or detrimental effects of the composition are outweighed by the therapeutically beneficial effects.

In an embodiment, administration of a binding agent, e.g., antibody molecule, provided, e.g., as a pharmaceutical preparation, is by one of the following routes: oral, intravenous, intramuscular, intra-arterial, subcutaneous, intraventricular, transdermal, interdermal, rectal, intravaginal, intraperitoneal, topical (as by liquids, powders, ointments, creams, sprays, or drops), mucosal, nasal, buccal, enteral, sublingual; intratracheal instillation, bronchial instillation, and/or inhalation; and/or as an oral spray, nasal spray, and/or aerosol.

Combination Treatments and Exemplary Second or Additional Agents

Binding agents, e.g., antibody molecules, provided e.g., as formulations (e.g., pharmaceutical formulations), can be administered either alone or in combination with one or more other therapy, e.g., the administration of a second or additional therapeutic agent.

In an embodiment, the combination can result in a lower dose of the antibody molecule or of the other therapy being needed, which, in an embodiment can reduce side effects. In an embodiment, the combination can result in enhanced delivery or efficacy of one or both agents. The agents or therapies can be administered at the same time (e.g., as a single formulation that is administered to a patient or as two separate formulations administered concurrently) or sequentially in any order.

Such second or additional agents include vaccines, antiviral agents, and/or additional antibodies. In typical embodiments the second or additional agent is not co-formulated with the binding agent, e.g., antibody molecule, though in others it is.

In an embodiment, the binding agent, e.g., antibody molecule, and the second or additional agent are administered such that one or more of the following is achieved: therapeutic levels, or therapeutic effects, of one overlap the other; detectable levels of both are present at the same time; or the therapeutic effect is greater than what would be seen in the absence of either the binding agent, e.g., antibody molecule, or the second or additional agent. In an embodiment, each agent will be administered at a dose and on a time schedule determined for that agent.

The second or additional agent can be, for example, for treatment or prevention of influenza. For example, the binding agents, e.g., antibody molecules, e.g., therapeutic antibodies, provided herein can be administered in combination with a vaccine, e.g., a vaccine described herein or a mixture (a.k.a. a cocktail) of influenza peptides to stimulate the patient's immune system to prevent infection with particular strains of influenza A. In other examples, the second or additional agent is an anti-viral agent (e.g., an anti-NA or anti-M2 agent), a pain reliever, an anti-inflammatory, an antibiotic, a steroidal agent, a second therapeutic antibody molecule (e.g., an anti-HA antibody), an adjuvant, a protease or glycosidase (e.g., sialidase), etc.

Exemplary anti-viral agents include, e.g., vaccines, neuraminidase inhibitors or nucleoside analogs. Exemplary anti-viral agents can include, e.g., zidovudine, gangcyclovir, vidarabine, idoxuridine, trifluridine, foscarnet, acyclovir, ribavirin, amantadine, remantidine, saquinavir, indinavir, ritonavir, alpha-interferons and other interferons, a neuraminidase inhibitor (e.g., zanamivir (Relenza®), oseltamivir (Tamiflu®), laninamivir, peramivir), rimantadine. Exemplary second antibody molecules include, for example Ab 67-11 (U.S. Provisional Application No. 61/645,453, U.S. Application Publication No. 2013/0302348, and International Application Publication No. WO 2013/169377), F16 (U.S. Application Publication No. 2010/0080813), F128 (U.S. Application Publication No. 2010/0080813), C179 (Okuno et al., *J. Virol.* 67:2552-8, 1993), F10 (Sui et al., *Nat. Struct. Mol. Biol.* 16:265, 2009), CR9114 (Dreyfus et al., *Science* 337:1343, 2012), or CR6261 (see e.g., Ekiert et al., *Science* 324:246, 2009). Thus, Ab 044 can be used in combination of any of those antibodies. In other embodiments, two or more binding agents, e.g., antibody molecules disclosed herein, can be administered in combination, e.g., Ab 044 can be administered in combination with Ab 032. In the case of combinations, two agents can be administered as part of the same dosage unit or administered separately. Other exemplary agents useful for treating the symptoms associated with influenza infection are acetaminophen, ibuprofen, aspirin, and naproxen.

In an embodiment, the antibody molecule and the second or additional agent are provided as a co-formulation, and the co-formulation is administered to the subject. It is further possible, e.g., at least 24 hours before or after administering the co-formulation, to administer separately one dose of the antibody formulation and then one dose of a formulation containing a second or additional agent. In another implementation, the antibody molecule and the second or additional agent are provided as separate formulations, and the step of administering includes sequentially administering the antibody molecule and the second or additional agent. The sequential administrations can be provided on the same day (e.g., within one hour of one another or at least 3, 6, or 12 hours apart) or on different days.

In an embodiment, the antibody molecule and the second or additional agent are each administered as a plurality of doses separated in time. The antibody molecule and the second or additional agent are generally each administered according to a regimen. The regimen for one or both may have a regular periodicity. The regimen for the antibody molecule can have a different periodicity from the regimen for the second or additional agent, e.g., one can be administered more frequently than the other. In one implementation, one of the antibody molecule and the second or additional agent is administered once weekly and the other once monthly. In another implementation, one of the antibody molecule and the second or additional agent is administered continuously, e.g., over a period of more than 30 minutes but less than 1, 2, 4, or 12 hours, and the other is administered as a bolus. In an embodiment, sequential administrations are administered. The time between administration of the one agent and another agent can be minutes, hours, days, or weeks. The use of an antibody molecule described herein can also be used to reduce the dosage of another therapy, e.g., to reduce the side-effects associated with another agent that is being administered. Accordingly, a combination can include administering a second or additional agent at a dosage at least 10, 20, 30, or 50% lower than would be used in the absence of the antibody molecule. The antibody molecule and the second or additional agent can be administered by any appropriate method, e.g., subcutaneously, intramuscularly, or intravenously.

In some embodiments, each of the antibody molecule and the second or additional agent is administered at the same dose as each is prescribed for monotherapy. In other embodiments, the antibody molecule is administered at a dosage that is equal to or less than an amount required for efficacy if administered alone. Likewise, the second or additional agent can be administered at a dosage that is equal to or less than an amount required for efficacy if administered alone.

In some cases, the formulations described herein, e.g., formulations containing an antibody molecule described herein, include one or more second or additional agents, or are administered in combination with a formulation containing one or more second or additional agents.

In an embodiment, a binding agent, e.g., antibody molecule, provided, e.g., as a pharmaceutical preparation, is administered by inhalation or aerosol delivery of a plurality of particles, e.g., particles comprising a mean particle size of 4, 5, 6, 7, 8, 9, 10, 11, 12, or 13 microns.

In an embodiment, the formulation is used (e.g., administered) in combination with an immunogen or a vaccine. Exemplary immunogens and vaccines are described in International Application Publication No. WO 2013/170139, the content of which is incorporated by reference in its entirety.

Kits

A formulation (e.g., pharmaceutical formulation) disclosed herein, e.g., generated by the methods described herein, can be provided (e.g., packaged) in a kit. The kit can include one or more other components, e.g., containers, buffers or other diluents, delivery devices, and the like.

In an embodiment, the kit includes materials for administering a formulation (e.g., pharmaceutical formulation) to a subject, such as for treatment or prevention of infection by influenza viruses. For example, the kit can include one or more or all of: (a) a container that contains a formulation (e.g., pharmaceutical formulation) that includes an antibody molecule, optionally (b) a container that contains a second therapeutic agent, and optionally (c) informational material.

In another embodiment, the kit includes materials for using an antibody molecule in a diagnostic assay, such as for detection of HA in a biological sample. For example, the kit can include one or more or all of: (a) a container that contains a formulation (e.g., pharmaceutical formulation) that includes an antibody molecule, optionally (b) a container that contains a reagents, e.g., labeled with a detectable moiety, to detect the antibody, e.g., for use in an ELISA or immunohistochemistry assay, and optionally (c) informational material. In another embodiment, the kit comprises a formulation, e.g., a binding agent (e.g., antibody molecule) comprising a detectable moiety.

In an embodiment, the kit comprises a solid substrate, e.g., bead, dipstick, array, and the like, on which is disposed a formulation, e.g., a binding agent (e.g., antibody molecule).

The informational material can be descriptive, instructional, marketing or other material that relates to the methods described herein and/or the use of the agents for therapeutic benefit, or for a diagnostic assay.

The informational material of the kits is not limited in its form. In an embodiment, the informational material can include information about production of the antibody, concentration, date of expiration, batch or production site information, and so forth. In an embodiment, the informational material relates to methods of administering the formulation or antibody molecule, e.g., in a suitable dose, dosage form, or mode of administration (e.g., a dose, dosage form, or mode of administration described herein), to treat a subject who has an infection, e.g., viral infection or secondary infection (e.g., secondary bacterial infection).

In another embodiment, the informational material relates to methods for using the formulation or antibody molecule for a diagnostic assay, e.g., to detect the presence of influenza viruses in a biological sample.

The information can be provided in a variety of formats, including printed text, computer readable material, video recording, or audio recording, or information that provides a link or address to substantive material.

In addition to the binding agent (e.g., antibody molecule), the formulation in the kit can include other ingredients, such as a solvent or buffer, a stabilizer, or a preservative. The binding agent (e.g., antibody molecule) can be provided in any form, e.g., a liquid, dried or lyophilized form, and substantially pure and/or sterile. When the agents are provided in a liquid solution, the liquid solution typically is an aqueous solution. When the agents are provided as a dried form, reconstitution generally is by the addition of a suitable solvent. The solvent, e.g., sterile water or buffer, can optionally be provided in the kit.

The kit can include one or more containers for the formulation containing the binding agent. In an embodiment, the kit contains separate containers, dividers or compartments for the formulation and informational material. For example, the formulation can be contained in a bottle, vial, or syringe, and the informational material can be contained in a plastic sleeve or packet. In another embodiment, the separate elements of the kit are contained within a single, undivided container. For example, the formulation is contained in a bottle, vial or syringe that has attached thereto the informational material in the form of a label. In an embodiment, the kit includes a plurality (e.g., a pack) of individual containers, each containing one or more unit dosage forms (e.g., a dosage form described herein) of the binding agent (e.g., antibody molecule). The containers can include a combination unit dosage, e.g., a unit that includes both the antibody molecule and the second or additional agent, such as in a desired ratio. For example, the kit can include a plurality of syringes, ampoules, foil packets, blister packs, or medical devices each containing, for example, a single combination unit dose. The containers of the kits can be air tight, waterproof (e.g., impermeable to changes in moisture or evaporation), and/or light-tight.

In an embodiment, the kit comprises two containers, one of which contains the formulation (e.g., pharmaceutical formulation) and the other of which contains an adjuvant. In an embodiment, the kit comprises two containers, one of which contains the formulation (e.g., pharmaceutical formulation) as a lyophilized powder and the other of which contains a liquid for resuspending the formulation (e.g., pharmaceutical formulation). In an embodiment, the kit further includes instructions for use of the formulation. The kit may contain a notice as required by governmental agency regulating the manufacture, use, and sale of pharmaceuticals or biological products, the notice indicating that the formulation has been approved for manufacture, use, and/or sale for administration to humans. The formulation may be supplied in a hermetically-sealed container. The formulation may be provided as a liquid or as a lyophilized powder that can be reconstituted by the addition, e.g., of water or saline, to a concentration suitable for administration to a subject.

The kit optionally includes a device suitable for administering the formulation, e.g., a syringe or device for delivering particles or aerosols, e.g., an inhaler, a spray device, or a dropper or other suitable delivery device. The device can be provided pre-loaded with one or both of the agents or can be empty but suitable for loading.

Diagnostic Methods

The binding agents, e.g., antibody molecules, provided herein are useful for identifying the presence of influenza in a biological sample, e.g., a patient sample, such as a fluid sample, e.g., a blood, serum, saliva, mucous, or urine sample, or a tissue sample, such as a biopsy.

In an embodiment, a patient sample is contacted with a binding agent, e.g., an antibody molecule, disclosed herein, and binding is detected. Binding can be detected with a number of formats and means of detection, e.g., with an antigen capture assay, such as an ELISA assay or Western blot, or an immunohistochemistry assay. In an embodiment, the binding agent, e.g., an antibody molecule, is provided, e.g., coupled to an insoluble matrix, e.g., a bead or other substrate, and a detection molecule used to detect binding of HA.

Binding of binding agent, e.g., antibody molecule, to HA, can be detected with a reagent comprising a detectable moiety, e.g., a reagent, e.g., an antibody, which binds the binding agent, e.g., antibody molecule. In an embodiment, the binding agent, e.g., antibody molecule, has a detectable moiety. Suitable detectable moieties include enzymes (e.g., horseradish peroxidase, beta-galactosidase, luciferase, alkaline phosphatase, acetylcholinesterase, glucose oxidase and the like), radiolabels (e.g., $^{3}$H, $^{14}$C, $^{15}$N, $^{35}$S, $^{90}$Y, $^{99}$Tc, $^{111}$In, $^{125}$I, $^{131}$I), haptens, fluorescent labels (e.g., FITC, rhodamine, lanthanide phosphors, fluorescein, fluorescein isothiocyanate, rhodamine, 5-dimethylamine-1-napthalenesulfonyl chloride, phycoerythrin and the like), phosphorescent molecules, chemiluminescent molecules, chromophores, luminescent molecules, photoaffinity molecules, colored particles or affinity ligands, such as biotin, predetermined polypeptide epitopes recognized by a secondary reporter (e.g., leucine zipper pair sequences, or binding sites for secondary antibodies, metal binding domains, epitope tags). In some embodiments, labels are attached by spacer arms of various lengths to reduce potential steric hindrance.

In an embodiment, a human is tested for presence of influenza virus be a method described herein, and if the test is positive, a binding agents, e.g., antibody molecules, e.g., an antibody, provided herein, is administered.

The binding agents, e.g., antibody molecules, e.g., an antibody, provided herein can be used for cytology assays, such as to identify an HA in a cell. The assay can be a colorimetric assay. A biological sample from a normal (non-infected) individual is used as a control. The diagnostic assay can be performed in vitro.

The diagnostic assay can also be performed to determine infection of cells in culture, e.g., of mammalian cells in culture. The antibody molecules can be used in in vitro assays.

Because the antibody molecules disclosed herein bind a broad spectrum of HA subtypes, the diagnostic assays disclosed herein can detect the presence of influenza virus in patients infected with a variety of distinct strains of influenza. A patient sample can be further tested with subtype specific antibodies, or other assays (e.g., RFLP (Restriction Fragment Length Polymorphism), PCR (Polymerase Chain Reaction), RT-PCR (Reverse Transcription coupled to Polymerase Chain Reaction), Northern blot, Southern blot or DNA sequencing) to further determine the particular strain of virus.

In an embodiment, a patient determined to be infected with influenza A can be further administered an antibody molecule disclosed herein, to treat the infection.

Also provided are solid substrates, e.g., beads, dipsticks, arrays, and the like, on which is disposed a binding agent, e.g., antibody molecule.

The disclosure is further illustrated by the following examples, which should not be construed as further limiting.

Anti-HA antibody molecules described herein are also disclosed in International Publication No. WO2013/170139, U.S. Pat. Nos. 8,877,200, 9,096,657, and U.S. Patent Application Publication No. US 2013/0302349. The contents of the aforesaid publications are incorporated by reference in their entirety.

TABLE 4C

Nucleic acid and amino acid sequences

| SEQ ID NO. | Lab no. | Source | Comment | Sequence |
|---|---|---|---|---|
| 1 | n.a. | Table 2 | Consensus AA sequence of HC CDR1 | [S/T]Y[A/G]MH |
| 2 | n.a. | Table 2 | Consensus AA sequence of HC CDR2 | V[I/V/L]S[Y/F]DG[S/N][Y/N][K/R]YYADSVQG |
| 3 | n.a. | Table 2 | Consensus AA sequence of HC CDR3 | D[S/T][R/K/Q]LR[S/T]LLYFEWLS[Q/S]G[Y/L/V][F/L][N/D][P/Y] |
| 4 | n.a. | Table 2 | Consensus AA sequence of LC CDR1 | Q[S/T][V/L/I][T/S][Y/F/W][N/S/D]YKNYLA |
| 170 | n.a. | Table 2 | Consensus AA sequence of LC CDR1 | Q[S/T][V/L/I][T/S][Y/F/W][N/S/D/Q/R/E]YKNYLA |
| 5 | n.a. | Table 2 | Consensus AA sequence of LC CDR2 | W[A/G]S[T/A/Y/H/K/D][R/L]E[S/T] |
| 6 | n.a. | Table 2 | Consensus AA sequence of LC CDR3 | QQ[Y/H]YRTPP[T/S] |
| 7 | n.a. | Table 2 | Consensus AA sequence of HC FR1 | [E/Q]VQLLE[S/T]GGGLVKPGQSLKLSCAASGFTF[S/T] |
| 8 | n.a. | Table 2 | Consensus AA sequence of HC FR2 | WVRQPPGKGLEWVA |
| 9 | n.a. | Table 2 | Consensus AA sequence of HC FR3 | RFTISRDNSKNTLYLQMNSLRAEDTAVYYCAK |
| 10 | n.a. | Table 2 | Consensus AA sequence of HC FR4 | WG[A/Q]G[T/A][T/M][L/V]TVSS |
| 11 | n.a. | Table 2 | Consensus AA sequence of LC FR1 | [E/D]I[V/Q]MTQSP[D/S][S/T][L/V][A/S][V/A][S/T][L/V/R]G[E/D]R[A/V][T/S][I[N/T/Q/D/R/]C[K/R]SS |
| 12 | n.a. | Table 2 | Consensus AA sequence of LC FR2 | WYQQKPG[Q/K][P/A]PKLLIY |
| 13 | n.a. | Table 2 | Consensus AA sequence of LC FR3 | GVP[D/E/S]RFSGSGSGTDFTLTISSLQ[A/P]ED[V/F/K/D]A[V/T]YYC |
| 14 | n.a. | Table 2 | Consensus AA sequence of LC FR4 | FG[G/Q/T/S/N]GTK[L/V][D/E]IK |
| 15 VH15 | Table 3, Table 4A, FIG. 2 | AA sequence of HC VR of Ab A18; entire HC domain is in FIG. 1; ID version is in FIG. 5; NT sequence is in Example 1 | EVQLLESGGGLVKPGQSLKLSCAASGFTFTSYGMHWVRQPPGKGLEWVAVISYDGSYKYYADSVQGRFTISRDNSKNTLYLQMNSLRAEDTAVYYCAKDSRLRSLLYFEWLSQGYFNPWGAGTTLTVSS |
| 28 VL28 | Table 3, Table 4A FIG. 3A | AA sequence of LC VR of Ab A18; entire LC domain is in FIG. 1; ID version is in FIG. 6A; NT sequence is in Example 1 | EIVMTQSPDSLAVSLGERATINCKSSQSVTYNYKNYLAWYQQKPGQPPKLLIYWASTRESGVPDRFSGSGSGTDFTLTISSLQAEDVAVYYCQQYYRTPPTPFGGGTKLDIK |
| 16 VH16 | Table 3 Table 4A FIG. 2 | AA sequence of HC VR of Abs 014, 028; ID version is in FIG. 5, NT sequence is in Example 1 | EVQLLESGGGLVKPGQSLKLSCAASGFTFSSYGMHWVRQPPGKGLEWVAVVSYDGSNKYYADSVQGRFTISRDNSKNTLYLQMNSLRAEDTAVYYCAKDTKLRSLLYFEWLSSGLLDYWGQGAMVTVSS |

TABLE 4C-continued

Nucleic acid and amino acid sequences

| SEQ ID NO. | Lab no. | Source | Comment | Sequence |
|---|---|---|---|---|
| 29 | VL29 | Table 3 Table 4A FIG. 3A | AA sequence of LC VR of Abs 014, 154, 157; ID version is in FIG. 6A; NT sequence is in Example 1 | EIVMTQSPDSLAVSLGERATINCKSSQSVTFSYKNYLAWYQQKPGQPPKLLIYWAS TRESGVPDRFSGSGSGTDFTLTISSLQAEDVAVYYCQQYRTPPFTGGGTKLDIK |
| 30 | VL30 | Table 3 Table 4A FIG. 3A | AA sequence of LC VR of Abs 028, 155; ID version is in FIG. 6A; NT sequence is in Example 1 | EIVMTQSPDSLAVSLGERATINCKSSQSVTFDYKNYLAWYQQKPGQPPKLLIYWAS TRESGVPDRFSGSGSGTDFTLTISSLQAEDVAVYYCQQYRTPPFTGGGTKLDIK |
| 17 | VH17 | Table 3 Table 4A FIG. 2 | AA sequence of HC VR of Abs 001, 009, 017, 025, 160, 186, 187, 188, 189, 190, 191, 192, 193, 202, 211; ID version is in FIG. 5 | EVQLLESGGGLVKPGQSLKLSCAASGFTFTSYGMHWVRQPPGKGLEWVAVVSYDGN YKYYADSVQGRFTISRDNSKNTLYLQMNSLRAEDTAVYYCAKDSRLRSLLYFEWLS QGYFNPWGAGTTLTVSS |
| 31 | VL31 | Table 3 Table 4A FIG. 3A | AA sequence of LC VR of Abs 001, 002, 003; ID version is in FIG. 6A | EIVMTQSPDSLAVSLGERATINCKSSQTVTFNYKNYLAWYQQKPGQPPKLLIYWAS TRESGVPDRFSGSGSGTDFTLTISSLQAEDVAVYYCQQHYRTPPSFGGGTKLDIK |
| 18 | VH18 | Table 3 Table 4A FIG. 2 | AA sequence of HC VR of Abs 002, 010, B18, 026, 203, 212; ID version is in FIG. 5 | EVQLLESGGGLVKPGQSLKLSCAASGFTFTSYGMHWVRQPPGKGLEWVAVLSYDGN YKYYADSVQGRFTISRDNSKNTLYLQMNSLRAEDTAVYYCAKDSRLRSLLYFEWLS QGYFNPWGAGTTLTVSS |
| 19 | VH19 | Table 3 Table 4A FIG. 2 | AA sequence of HC VR of Abs 003, 011, 019, 027, 194, 195, 196, 197, 198, 199, 200, 204, 213; ID version is in FIG. 5 | EVQLLESGGGLVKPGQSLKLSCAASGFTFTTYAMHWVRQPPGKGLEWVAVLSYDGN YKYYADSVQGRFTISRDNSKNTLYLQMNSLRAEDTAVYYCAKDSRLRSLLYFEWLS QGYFNPWGAGTTLTVSS |
| 32 | VL32 | Table 3 Table 4A FIG. 3A | AA sequence of LC VR of Abs 009, 010, 011; ID version is in FIG. 6A | EIVMTQSPDSLAVSLGERATINCKSSQTLSFNYKNYLAWYQQKPGQPPKLLIYWAS TRESGVPDRFSGSGSGTDFTLTISSLQAEDVAVYYCQQHYRTPPSFGGGTKLDIK |
| 33 | VL33 | Table 3 Table 4A FIG. 3A | AA sequence of LC VR of Abs 017, B18, 019; ID version is in FIG. 6A | EIVMTQSPDSLAVSLGERATINCKSSQTVTFNYKNYLAWYQQKPGQPPKLLIYFAS TRESGVPDRFSGSGSGTDFTLTISSLQAEDVAVYYCQQHYRTPPSFGGGTKLDIK |
| 34 | VL34 | Table 3 Table 4A FIG. 3A | AA sequence of LC VR of Abs 025, 026, 027, 086; ID version is in FIG. 6A | EIVMTQSPDSLAVSLGERATINCKSSQTLSFNYKNYLAWYQQKPGQPPKLLIYFAS TRESGVPDRFSGSGSGTDFTLTISSLQAEDVAVYYCQQHYRTPPSFGGGTKLDIK |
| 20 | VH20 | Table 3 Table 4A FIG. 2 | AA sequence of HC VR of Ab 086; ID version is in FIG. 5 | EVQLLESGGGLVKPGQSLKLSCAASGFTFTTYAMHWVRQPPGKGLEWVAVVSFDGN NRYYADSVQGRFTISRDNSKNTLYLQMNSLRAEDTAVYYCAKDSQLRSLLYFEWLS SGVLDYWGQGAMVTVSS |
| 21 | VH21 | Table 3 Table 4A FIG. 2 | AA sequence of HC VR of Abs 154,155; ID version is in FIG. 5 | EVQLLESGGGLVKPGQSLKLSCAASGFTFSSYGMHWVRQPPGKGLEWVAVVSYDGN NKYYADSVQGRFTISRDNSKNTLYLQMNSLRAEDTAVYYCAKDSKLRSLLYFEWLS SGLLDYWGQGAMVTVSS |

TABLE 4C-continued

Nucleic acid and amino acid sequences

| SEQ ID NO. | Lab no. | Source | Comment | Sequence |
|---|---|---|---|---|
| 22 | VH22 | Table 3 Table 4A FIG. 2 | AA sequence of HC VR of Abs 157, 159; ID version is in FIG. 5 | EVQLLESGGGLVKPGQSLKLSCAASGFTFTYAMHWVRQPPGKGLEWVAVVSYDGN NKYYADSVQGRFTISRDNSKNTLYLQMNSLRAEDTAVYYCAKDSKLRSLLYFEWLS SGLLDYWGQGAMVTVSS |
| 35 | VL35 | Table 3 Table 4A FIG. 3A | AA sequence of LC VR of Ab 159; ID version is in FIG. 6A | EIVMTQSPDSLAVSLGERATINCKSSQSVTWSYKNYLAWYQQKPGQPPKLLIYWAS TRESGVPDRFSGSGSGTDFTLTISSLQAEDVAVYYCQQYYRTPPTPFGGGTKLDIK |
| 36 | VL36 | Table 3 Table 4A FIG. 3A | AA sequence of LC VR of Ab 160; ID version is in FIG. 6A | EIVMSQSPDTLAVTLGERASINCKSSQTVTFNYKNYLAWYQQKPGQPPKVLIYWAS ARETGVPERFSGSGSGTDFTLTISSLQAEDVAVYYCQQHYRTPPSFGQGTKLEIK |
| 37 | VL37 | Table 3 Table 4A FIG. 3A | AA sequence of LC VR of Abs 186, 194; ID version is in FIG. 6A | EIVMTQSPDSLAVSLGERATINCKSSQTVTFNYKNYLAWYQQKPGQPPKLLIYWAS TRESGVPDRFSGSGSGTDFTLTISSLQAEDVAVYYCQQHYRTPSFGTGTKLDIK |
| 38 | VL38 | Table 3 Table 4A FIG. 3A | AA sequence of LC VR of Abs 187, 195; ID version is in FIG. 6A | EIVMTQSPDSLAVSLGERATINCKSSQTVTFNYKNYLAWYQQKPGQPPKLLIYWAS TRESGVPDRFSGSGSGTDFTLTISSLQAEDVAVYYCQQHYRTPPSFGSGTKLDIK |
| 39 | VL39 | Table 3 Table 4A FIG. 3A | AA sequence of LC VR of Abs 188, 196; ID version is in FIG. 6A | EIVMTQSPDSLAVSLGERATINCKSSQTVTFNYKNYLAWYQQKPGQPPKLLIYWAS TRESGVPDRFSGSGSGTDFTLTISSLQAEDVAVYYCQQHYRTPPSFGQGTKLDIK |
| 40 | VL40 | Table 3 Table 4A FIG. 3A | AA sequence of LC VR of Abs 189, 197; ID version is in FIG. 6A | EIVMTQSPDSLAVSLGERATINCKSSQTVTFNYKNYLAWYQQKPGQPPKLLIYWAS TRESGVPDRFSGSGSGTDFTLTISSLQAEDVAVYYCQQHYRTPPSFGNGTKLDIK |
| 41 | VL41 | Table 3 Table 4A FIG. 3A | AA sequence of LC VR of Abs 190, 198; ID version is in FIG. 6A | EIVMTQSPDSLAVSLGERATINCKSSQTLSFNYKNYLAWYQQKPGQPPKLLIYWAS TRESGVPDRFSGSGSGTDFTLTISSLQAEDVAVYYCQQHYRTPPSFGTGTKLDIK |
| 42 | VL42 | Table 3 Table 4A FIG. 3A | AA sequence of LC VR of Abs 191, 199; ID version is in FIG. 6A | EIVMTQSPDSLAVSLGERATINCKSSQTLSFNYKNYLAWYQQKPGQPPKLLIYWAS TRESGVPDRFSGSGSGTDFTLTISSLQAEDVAVYYCQQHYRTPPSFGSGTKLDIK |
| 43 | VL43 | Table 3 Table 4A FIG. 3A | AA sequence of LC VR of Abs 192, 200; ID version is in FIG. 6A | EIVMTQSPDSLAVSLGERATINCKSSQTLSFNYKNYLAWYQQKPGQPPKLLIYWAS TRESGVPDRFSGSGSGTDFTLTISSLQAEDVAVYYCQQHYRTPPSFGQGTKLDIK |
| 44 | VL44 | Table 3 Table 4A FIG. 3A | AA sequence of LC VR of Abs 193; ID version is in FIG. 6A | EIVMTQSPDSLAVSLGERATINCKSSQTLSFNYKNYLAWYQQKPGQPPKLLIYWAS TRESGVPDRFSGSGSGTDFTLTISSLQAEDVAVYYCQQHYRTPPSFGNGTKLDIK |
| 45 | VL45 | Table 3 Table 4A FIG. 3A | AA sequence of LC VR of Abs 202, 203, 204, 210, 031, 032, 033, 034; ID version is in FIG. 6A; NT sequence is in Example 1 | DIQMTQSPSSLSASVGDRVTITCRSSQSITFNYKNYLAWYQQKPGKAPKLLIYWGS YLESGVPSRFSGSGSGTDFTLTISSLQPEDFATYYCQQHYRTPPSFGQGTKVEIK |

TABLE 4C-continued

Nucleic acid and amino acid sequences

| SEQ ID NO. | Lab no. | Source | Comment | Sequence |
|---|---|---|---|---|
| 46 | VL46 | Table 3, Table 4A, FIG. 3A | AA sequence of LC VR of Abs 211, 212, 213, 219, 037, 038, 039, 040; ID version is in FIG. 6A | DIQMTQSPSSLSASVGDRVIITCRSSQSIIFNYKNYLGWYQQKPGKAPKLLIYWGS YLESGVPSRFSGSGSGTDFTLTISSLQPEDFATYYCQQHYRTPPSFGQGTKVEIK |
| 23 | VH23 | Table 3, Table 4A, FIG. 2 | AA sequence of HC VR of Abs 210, 219; ID version is in FIG. 5 | EVQLLESGGGLVKPGQSLKLLSCAASGFTFTSYGMHWVRQPPGKGLEWVAVVSYDGN YKYYADSVQGRFTISRDNSKNTLYLQMNSLRAEDTAVYYCAKDSKLRSLLYFEWLS QGYFNPWGAGTTLTVSS |
| 24 | VH24 | Table 3, Table 4A, FIG. 2 | AA sequence of HC VR of Abs A001, A002, A003, A010, A011, A017, 031, 037; ID version is in FIG. 5; NT sequence is in Example 1 | EVQLLESGGGLVKPGQSLKLLSCAASGFTFTSYAMHWVRQPPGKGLEWVAVVSYDGN YKYYADSVQGRFTISRDNSKNTLYLQMNSLRAEDTAVYYCAKDSRLRSLLYFEWLS QGYFNPWGQGTTLTVSS |
| 47 | VL47 | Table 3, Table 4A, FIG. 3A | AA sequence of LC VR of Abs A001, 004, 007, 016; ID version is in FIG. 6A | DIVMTQSPDTLAVTLGERATIQCKSSQTVTFNYKNYLAWYQQKPGQPPKLLIYWAS TRESGVPDRFSGSGSGTDFTLTISSLQAEDVAVYYCQQHYRTPPSFGQGTKLDIK |
| 48 | VL48 | Table 3, Table 4A, FIG. 3A | AA sequence of LC VR of Abs 002, 005, 008, A017; ID version is in FIG. 6A | DIVMTQSPDTVAVTGERATINCKSSQTVTFNYKNYLAWYQQKPGQPPKLLIYWAS TRESGVPDRFSGSGSGTDFTLTISSLQAEDVAVYYCQQHYRTPPSFGQGTKLDIK |
| 25 | VH25 | Table 3, Table 4A, FIG. 2 | AA sequence of HC VR of Abs 004, 005, 006, 012, 013, 032, 038, 043, 044, 045, 046, 047, 048, 049, 050, 051, 052, 067, 068, 069, 070, 073, 074, 075, 076, 077; ID version is in FIG. 5; NT sequence is in Example 1 | QVQLLETGGGLVKPGQSLKLLSCAASGFTFTSYAMHWVRQPPGKGLEWVAVVSYDGN YKYYADSVQGRFTISRDNSKNTLYLQMNSLRAEDTAVYYCAKDSRLRSLLYFEWLS QGYFNPWGQGTTLTVSS |
| 49 | VL49 | Table 3, Table 4A, FIG. 3A | AA sequence of LC VR of Abs A003, 006, 009, C18; ID version is in FIG. 6A | DIVMTQSPDTVAVTLGERATIDCKSSQTVTFNYKNYLAWYQQKPGQPPKLLIYWAS TRESGVPDRFSGSGSGTDFTLTISSLQAEDVAVYYCQQHYRTPPSFGQGTKLDIK |
| 26 | VH26 | Table 3, Table 4A, FIG. 2 | AA sequence of HC VR of Abs 007, 008, A009, A14, 015, 033, 039; ID version is in FIG. 5 | EVQLLESGGGLVKPGQSLKLLSCAASGFTFTSYAMHWVRQPPGKGLEWVAVVSYDGN YKYYADSVQGRFTISRDNSKNTLYLQMNSLRAEDTAVYYCAKDSQLRTLLYFEWLS QGYFNPWGQGTTLTVSS |
| 50 | VL50 | Table 3, Table 4A, FIG. 3A | AA sequence of LC VR of Abs A010 012, A14, A019; ID version is in FIG. 6A | DIVMTQSPDTLAVTVGERATIRCKSSQTVTFNYKNYLAWYQQKPGQPPKLLIYWAS TRESGVPDRFSGSGSGTDFTLTISSLQAEDVAVYYCQQHYRTPSFGQGTKLDIK |
| 51 | VL51 | Table 3, Table 4A, FIG. 3A | AA sequence of LC VR of Ab A011, 013, 015; ID version is in FIG. 6A | DIVMTQSPDTLAVSRGERATIDCKSSQTVTFNYKNYLAWYQQKPGQPPKLLIYWAS TRESGVPDRFSGSGSGTDFTLTISSLQAEDEAVYYCQQHYRTPPSFGQGTKLDIK |
| 27 | VH27 | Table 3, Table 4A, FIG. 2 | AA sequence of HC VR of Abs 016, A019, C18, A019, 034, 040; ID version is in FIG. 5 | EVQLLESGGGLVKPGQSLKLLSCAASGFTFTSYAMHWVRQPPGKGLEWVAVVSYDGN YKYYADSVQGRFTISRDNSKNTLYLQMNSLRAEDTAVYYCAKDSRLRTLLYFEWLS QGYFDPWGQGTTLTVSS |

TABLE 4C-continued

Nucleic acid and amino acid sequences

| SEQ ID NO. | Lab no. | Source | Comment | Sequence |
|---|---|---|---|---|
| 60 | VL60 | Table 3 Table 4A FIG. 3B | AA sequence of LC VR of Ab 043; ID version is in FIG. 6B | DIQMTQSPSSLSASVGDRVTITCRSSQSITFDNYKNYLAWYQQKPGKAPKLLIYWGS YLESGVPSRFSGSGSGTDFTLTISSLQPEDFATYYCQQYRTPSFGQGTKVEIK |
| 52 | VL52 | Table 3 Table 4A FIG. 3B | AA sequence of LC VR of Abs 044, 071, 072, 078; ID version is in FIG. 6B; NT sequence is in Example 1 | DIQMTQSPSSLSASVGDRVTITCRSSQSITFDYKNYLAWYQQKPGKAPKLLIYWGS YLESGVPSRFSGSGSGTDFTLTISSLQPEDFATYYCQQHYRTPPSFGQGTKVEIK |
| 57 | VL57 | Table 3 Table 4A FIG. 3B | AA sequence of LC VR of Ab 045; ID version is in FIG. 6B | DIQMTQSPSSLSASVGDRVTITCRSSQSITFNYKNYLAWYQQKPGKAPKLLIYWGS YLESGVPSRFSGSGSGTDFTLTISSLQPEDVATYYCQQHYRTPPSFGQGTKVEIK |
| 59 | VL59 | Table 3 Table 4A FIG. 3B | AA sequence of LC VR of Ab 046; ID version is in FIG. 6B | DIQMTQSPSSLSASVGDRVTITCRSSQSITFNYKNYLAWYQQKPGKAPKLLIYWGS YLESGVPSRFSGSGSGTDFTLTISSLQPEDDATYYCQQHYRTPPSFGQGTKVEIK |
| 55 | VL55 | Table 3 Table 4A FIG. 3B | AA sequence of LC VR of Ab 047; ID version is in FIG. 6B | DIQMTQSPSSLSASVGDRVTITCRSSQSITFNYKNYLAWYQQKPGKAPKLLIYWGS KLESGVPSRFSGSGSGTDFTLTISSLQPEDFATYYCQQHYRTPPSFGQGTKVEIK |
| 58 | VL58 | Table 3 Table 4A FIG. 3B | AA sequence of LC VR of Ab 048; ID version is in FIG. 6B | DIQMTQSPSSLSASVGDRVTITCRSSQSITFNYKNYLAWYQQKPGKAPKLLIYWGS YLESGVPSRFSGSGSGTDFTLTISSLQPEDKATYYCQQHYRTPPSFGQGTKVEIK |
| 54 | VL54 | Table 3 Table 4A FIG. 3B | AA sequence of LC VR of Ab 049; ID version is in FIG. 6B | DIQMTQSPSSLSASVGDRVTITCRSSQSITFNYKNYLAWYQQKPGKAPKLLIYWGS HLESGVPSRFSGSGSGTDFTLTISSLQPEDFATYYCQQHYRTPPSFGQGTKVEIK |
| 56 | VL56 | Table 3 Table 4A FIG. 3B | AA sequence of LC VR of Ab 050; ID version is in FIG. 6B | DIQMTQSPSSLSASVGDRVTITCRSSQSITFNYKNYLAWYQQKPGKAPKLLIYWGS DLESGVPSRFSGSGSGTDFTLTISSLQPEDFATYYCQQHYRTPPSFGQGTKVEIK |
| 53 | VL53 | Table 3 Table 4A FIG. 3B | AA sequence of LC VR of Ab 051; ID version is in FIG. 6B | DIQMTQSPSSLSASVGDRVTITCRSSQSITFNYKNYLAWYQQKPGKAPKLLIYWGS TLESGVPSRFSGSGSGTDFTLTISSLQPEDFATYYCQQHYRTPPSFGQGTKVEIK |
| 61 | VL61 | Table 3 Table 4A FIG. 3B | AA sequence of LC VR of Ab 052; ID version is in FIG. 6B | DIQMTQSPSSLSASVGDRVTITCRSSQSITFNYKNYLAWYQQKPGKAPKLLIYWGS TRESGVPSRFSGSGSGTDFTLTISSLQPEDFATYYCQQHYRTPPSFGQGTKVEIK |
| 153 | VL153 | Table 3 Table 4A FIG. 3B | AA sequence of LC VR of Ab 067; ID version is in FIG. 6B | DIQMTQSPSSLSASVGDRVTITCRSSQSITFQYKNYLAWYQQKPGKAPKLLIYWGS YLESGVPSRFSGSGSGTDFTLTISSLQPEDFATYYCQQHYRTPPSFGQGTKVEIK |
| 154 | VL154 | Table 3 Table 4A FIG. 3B | AA sequence of LC VR of Ab 068; ID version is in FIG. 6B | DIQMTQSPSSLSASVGDRVTITCRSSQSITFRYKNYLAWYQQKPGKAPKLLIYWGS YLESGVPSRFSGSGSGTDFTLTISSLQPEDFATYYCQQHYRTPPSFGQGTKVEIK |

TABLE 4C-continued

Nucleic acid and amino acid sequences

| SEQ ID NO. | Lab no. | Source | Comment | Sequence |
|---|---|---|---|---|
| 155 | VL155 | Table 3 Table 4A FIG. 3B | AA sequence of LC VR of Abs 069, 079; ID version is in FIG. 6B | DIQMTQSPSSLSASVGDRVTITCRSSQSITFEYKNYLAWYQQKPGKAPKLLIYWGS YLESGVPSRFSGSGSGTDFTLTISSLQPEDFATYYCQQHYRTPPSFGQGTKVEIK |
| 156 | VL156 | Table 3 Table 4A FIG. 3B | AA sequence of LC VR of Ab 070; ID version is in FIG. 6B | DIQMTQSPSSLSASVGDRVTITCRSSQSITFDYKNYLAWYQQKPGKAPKLLIYWGS TRESGVPSRFSGSGSGTDFTLTISSLQPEDFATYYCQQHYRTPPSFGQGTKVEIK |
| 162 | VL162 | Table 3 Table 4A FIG. 7 | AA sequence of HC VR of Ab 071 | EVQLLESGGGLVKPGQSLKLSCAASGFSFSTYAMHWVRQPPGKGLEWVAVVSYDGN YKYYADTVQGRFTISRDNSKNTLYLQMNSLRAEDTAVYYCAKDSRLRSLLYFEWLS QGYFNPWGQGTTLTVSS |
| 163 | VL163 | Table 3 Table 4A FIG. 7 | AA sequence of HC VR of Ab 072 | EVQLLESGGGLRKPGQSLKLSCAASGFSFSTYAMHWVRQPPGKGLEWVAVVSYDGN YKYYADSVQGRFTISRDNSKNTLYLQMNSLRAEDTAVYYCAKDSRLRSLLYFEWLS QGYFNPWGQGTTLTVSS |
| 165 | VL165 | Table 3 Table 4A FIG. 7 | AA sequence of LC VR of Ab 073 | DIQMTQSPSSLSASVGDRVTITCRSSQSITWNYKNYLAWYQQKPGKAPKLLIYWGS YLESGVPSRFSGSGSGTDFTLTISSLQPEDFATYYCQQHYRTPPSFGQGTKVEIK |
| 166 | VL166 | Table 3 Table 4A FIG. 7 | AA sequence of LC VR of Abs 074, 080 | DIQMTQSPSSLSASVGDRVTITCRSSQSITWDYKNYLAWYQQKPGKAPKLLIYWGS YLESGVPSRFSGSGSGTDFTLTISSLQPEDFATYYCQQHYRTPPSFGQGTKVEIK |
| 167 | VL167 | Table 3 Table 4A FIG. 7 | AA sequence of LC VR of Ab 075 | DIQMTQSPSSLSASVGDRVTITCRSSQSITWQYKNYLAWYQQKPGKAPKLLIYWGS YLESGVPSRFSGSGSGTDFTLTISSLQPEDFATYYCQQHYRTPPSFGQGTKVEIK |
| 168 | VL168 | Table 3 Table 4A FIG. 7 | AA sequence of LC VR of Ab 076 | DIQMTQSPSSLSASVGDRVTITCRSSQSITWRYKNYLAWYQQKPGKAPKLLIYWGS YLESGVPSRFSGSGSGTDFTLTISSLQPEDFATYYCQQHYRTPPSFGQGTKVEIK |
| 169 | VL169 | Table 3 Table 4A FIG. 7 | AA sequence of LC VR of Abs 077, 081 | DIQMTQSPSSLSASVGDRVTITCRSSQSITWEYKNYLAWYQQKPGKAPKLLIYWGS YLESGVPSRFSGSGSGTDFTLTISSLQPEDFATYYCQQHYRTPPSFGQGTKVEIK |
| 164 | VL164 | Table 3 Table 4A FIG. 7 | AA sequence of HC VR of Abs 078, 079, 080, 081 | QVQLLETGGGLVKPGQSLKLSCAASGFTFSTYAMHWVRQPPGKGLEWVAVVSYDGN YKYYADSVQGRFTISRDNSKNTLYLQMNSLRAEDTAVYYCAKDSRLRSLLYFEWLS QGYFNPWGQGTTLTVSS |
| 161 | HC161 | Table 4A FIG. 2 | AA sequence of HC VR consensus; ID version is in FIG. 5 | EVQLLESGGGLVKPGQSLKLSCAASGFTFSSYGMHWVRQPPGKGLEWVAVVSYDGS NKYYADSVQGRFTISRDNSKNTLYLQMNSLRAEDTAVYYCAKDSKLRSLLYFEWLS SGLLDYWGQGAMVTVSS |
| 62 | LC62 | Table 4A FIG. 3B | AA sequence of LC VR consensus; ID version is in FIG. 6B | DIQMTQSPSSLSASVGDRVTITCRSSQSITFNYKNYLAWYQQKPGKAPKLLIYWGS YLESGVPSRFSGSGSGTDFTLTISSLQPEDFATYYCQQHYRTPPSFGQGTKVEIK |

TABLE 4C-continued

Nucleic acid and amino acid sequences

| SEQ ID NO. | Lab no. | Source | Comment | Sequence |
|---|---|---|---|---|
| 96 | 15-ID | Table 4B FIG. 5 | AA sequence of HC VR of Ab A18; non-ID version is in FIG. 2 | IDEVQLLESGGGLVKPGQSLKLSCAASGFTFTSYGMHWVRQPPGKGLEWVAVISYD GSYKYYADSVQGRFTISRDNSKNTLYLQMNSLRAEDTAVYYCAKDSRLRSLLYFEW LSQGYFNPWGAGTTLTVSS |
| 110 | 28-ID | Table 4B FIG. 6A | AA sequence of LC VR of Ab A18; non-ID version is in FIGS. 3A-3B | IDEIVMTQSPDSLAVSLGERATINCKSSQSVTYNYKNYLAWYQQKPGQPPKLLIYW ASTRESGVPDRFSGSGSGTDFTLTISSLQAEDVAVYYCQQYYRTPFTFGGGTKLDI K |
| 97 | 16-ID | Table 4B FIG. 5 | AA sequence of HC VR of Abs 014, 028; non-ID version is in FIG. 2 | IDEVQLLESGGGLVKPGQSLKLSCAASGFTFSSYGMHWVRQPPGKGLEWVAVVSYD GSNKYYADSVQGRFTISRDNSKNTLYLQMNSLRAEDTAVYYCAKDTKLRSLLYFEW LSSGLLDYWGQGAMVTVSS |
| 111 | 29-ID | Table 4B FIG. 5 | AA sequence of LC VR of Abs 014, 154, 157; non-ID version is in FIGS. 3A-3B | IDEIVMTQSPDSLAVSLGERATINCKSSQSVTFSYKNYLAWYQQKPGQPPKLLIYW ASTRESGVPDRFSGSGSGTDFTLTISSLQAEDVAVYYCQQYYRTPTPFGGGTKLDI K |
| 98 | 17-ID | Table 4B FIG. 5 | AA sequence of HC VR of Ab 001, 009, 017, 025, 160, 186, 187, 188, 189, 190, 191, 192, 193, 202, 211; non-ID version is in FIG. 2 | IDEVQLLESGGGLVKPGQSLKLSCAASGFTFTSYGMHWVRQPPGKGLEWVAVVSYD GNYKYYADSVQGRFTISRDNSKNTLYLQMNSLRAEDTAVYYCAKDSRLRSLLYFEW LSQGYFNPWGAGTTLTVSS |
| 112 | 30-ID | Table 4B FIG. 6A | AA sequence of LC VR of Abs 028, 155; non-ID version is in FIGS. 3A-3B | IDEIVMTQSPDSLAVSLGERATINCKSSQSVTFDYKNYLAWYQQKPGQPPKLLIYW ASTRESGVPDRFSGSGSGTDFTLTISSLQAEDVAVYYCQQYYRTPTPFGGGTKLDI K |
| 99 | 18-ID | Table 4B FIG. 5 | AA sequence of HC VR of Abs 002, 010, B18, 026, 203, 212; non-ID version is in FIG. 2 | IDEVQLLESGGGLVKPGQSLKLSCAASGFTFTSYGMHWVRQPPGKGLEWVAVLSYD GNYKYYADSVQGRFTISRDNSKNTLYLQMNSLRAEDTAVYYCAKDSRLRSLLYFEW LSQGYFNPWGAGTTLTVSS |
| 113 | 35-ID | Table 4B FIG. 6A | AA sequence of LC VR of Ab 159; non-ID version is in FIGS. 3A-3B | IDEIVMTQSPDSLAVSLGERATINCKSSQSVTWSYKNYLAWYQQKPGQPPKLLIYW ASTRESGVPDRFSGSGSGTDFTLTISSLQAEDVAVYYCQQYYRTPTPFGGGTKLDI K |
| 100 | 19-ID | Table 4B FIG. 5 | AA sequence of HC VR of Abs 003, 011, 019, 027, 194, 195, 196, 197, 198, 199, 200, 204, 213; non-ID version is in FIG. 2 | IDEVQLLESGGGLVKPGQSLKLSCAASGFTFTTYAMHWVRQPPGKGLEWVAVLSYD GNYKYYADSVQGRFTISRDNSKNTLYLQMNSLRAEDTAVYYCAKDSRLRSLLYFEW LSQGYFNPWGAGTTLTVSS |
| 114 | 31-ID | Table 4B FIG. 6A | AA sequence of LC VR of Abs 001, 002, 003; non-ID version is in FIGS. 3A-3B | IDEIVMTQSPDSLAVSLGERATINCKSSQTVTFNYKNYLAWYQQKPGQPPKLLIYW ASTRESGVPDRFSGSGSGTDFTLTISSLQAEDVAVYYCQQHYRTPPSFGGGTKLDI K |
| 101 | 21-ID | Table 4B FIG. 5 | AA sequence of HC VR of Abs 154,155; non-ID version is in FIG. 2 | IDEVQLLESGGGLVKPGQSLKLSCAASGFTFSSYGMHWVRQPPGKGLEWVAVVSYD GNNKYYADSVQGRFTISRDNSKNTLYLQMNSLRAEDTAVYYCAKDSKLRSLLYFEW LSSGLLDYWGQGAMVTVSS |

TABLE 4C-continued

Nucleic acid and amino acid sequences

| SEQ ID NO. | Lab no. | Source | Comment | Sequence |
|---|---|---|---|---|
| 115 | 32-ID | Table 4B FIG. 6A | AA sequence of LC VR of Abs 009, 010, 011; non-ID version is in FIGS. 3A-3B | IDEIVMTQSPDSLAVSLGERATINCKSSQTLSFNYKNYLAWYQQKPGQPPKLLIYW ASTRESGVPDRFSGSGSGTDFTLTISSLQAEDVAVYYCQQHRTPSFGGGTKLDI K |
| 102 | 22-ID | Table 4B FIG. 5 | AA sequence of HC VR of Abs 157, 159; non-ID version is in FIG. 2 | IDEVQLLESGGGLIVKPGQSLKLSCAASGFTFTTYAMHWVRQPPGKGLEWVAVVSYD GNNKYYADSVQGRFTISRDNSKNTLYLQMNSLRAEDTAVYYCAKDSKLRSLLYFEW LSSGLLDYWGQGAMVTVSS |
| 116 | 33-ID | Table 4B FIG. 6A | AA sequence of LC VR of Abs 017, B18, 019; non-ID version is in FIGS. 3A-3B | IDEIVMTQSPDSLAVSLGERATINCKSSQTVTFNYKNYLAWYQQKPGQPPKLLIYF ASTRESGVPDRFSGSGSGTDFTLTISSLQAEDVAVYYCQQHRTPSFGGGTKLDI K |
| 103 | 20-ID | Table 4B FIG. 5 | AA sequence of HC VR of Ab 086; non-ID version is in FIG. 2 | IDEVQLLESGGGLIVKPGQSLKLSCAASGFTFTTYAMHWVRQPPGKGLEWVAVVSFD GNNRYYADSVQGRFTISRDNSKNTLYLQMNSLRAEDTAVYYCAKDSQLRSLLYFEW LSSGVLDYWGQGAMVTVSS |
| 117 | 34-ID | Table 4B FIG. 6A | AA sequence of LC VR of Abs 025, 026, 027, 086; non-ID version is in FIGS. 3A-3B | IDEIVMTQSPDSLAVSLGERATINCKSSQTLSFNYKNYLAWYQQKPGQPPKLLIYF ASTRESGVPDRFSGSGSGTDFTLTISSLQAEDVAVYYCQQHRTPSFGGGTKLDI K |
| 104 | 23-ID | Table 4B FIG. 5 | AA sequence of HC VR of Abs 210, 219; non-ID version is in FIG. 2 | IDEVQLLESGGGLIVKPGQSLKLSCAASGFTFTSYGMHWVRQPPGKGLEWVAVVSYD GNYKYYADSVQGRFTISRDNSKNTLYLQMNSLRAEDTAVYYCAKDSKLRSLLYFEW LSQGYFNPWGAGTTLTVSS |
| 118 | 36-ID | Table 4B FIG. 6A | AA sequence of LC VR of Ab 160; non-ID version is in FIGS. 3A-3B | IDEIVMSQSPDTLAVTLGERASINCKSSQTVTFNYKNYLAWYQQKPGQPPKVLIYW ASARETGVPERFSGSGSGTDFTLTISSLQAEDVAVYYCQQHRTPSFGQGTKLEI K |
| 105 | 24-ID | Table 4B FIG. 5 | AA sequence of HC VR of Abs A001, A002, A003, A010, A011, A031, 037; non-ID version is in FIG. 2 | IDEVQLLESGGGLIVKPGQSLKLSCAASGFTFTSYAMHWVRQPPGKGLEWVAVVSYD GNYKYYADSVQGRFTISRDNSKNTLYLQMNSLRAEDTAVYYCAKDSRLRSLLYFEW LSQGYFNPWGQGTTLTVSS |
| 119 | 45-ID | Table 4B FIG. 6A | AA sequence of LC VR of Abs 202, 203, 204, 210, 031, 032, 033, 034; non-ID version is in FIGS. 3A-3B | IDDIQMTQSPSSLSASVGDRVTITCRSSQSITFNYKNYLGWYQQKPGKAPKLLIYW GSYLESGVPSRFSGSGSGTDFTLTISSLQPEDFATYYCQQHRTPSFGQGTKVEI K |
| 106 | 25-ID | Table 4B FIG. 5 | AA sequence of HC VR of Abs 004, 005, 006, 012, 013, 032, 038, 043, 044, 045, 046, 047, 048, 049, 050, 051, 052, 067, 068, 069, 070, 073, 074, 075, 076, 077; non-ID version is in FIG. 2 | IDQVQLLETGGGLIVKPGQSLKLSCAASGFTFTSYAMHWVRQPPGKGLEWVAVVSYD GNYKYYADSVQGRFTISRDNSKNTLYLQMNSLRAEDTAVYYCAKDSRLRSLLYFEW LSQGYFNPWGQGTTLTVSS |
| 120 | 46-ID | Table 4B FIG. 6A | AA sequence of LC VR of Abs 211, 212, 213, 219, 037, 038, 039, 040; non-ID version is in FIGS. 3A-3B | IDDIQMTQSPSSLSASVGDRVTITCRSSQSITFNYKNYLGWYQQKPGKAPKLLIYW GSYLESGVPSRFSGSGSGTDFTLTISSLQPEDFATYYCQQHRTPSFGQGTKVEI K |

TABLE 4C-continued

Nucleic acid and amino acid sequences

| SEQ ID NO. | Lab no. | Source | Comment | Sequence |
|---|---|---|---|---|
| 107 | 26-ID | Table 4B FIG. 5 | AA sequence of HC VR of Abs 007, 008, A009, A14, 015, 033, 039; non-ID version is in FIG. 2 | IDEVQLLESGGGLVKPGQSLKLSCAASGFTFTSYAMHWVRQPPGKGLEWVAVVSYDGNYKYYADSVQGRFTISRDNSKNTLYLQMNSLRAEDTAVYYCAKDSQLRTLLYFEWLSQGYFNPWGQGTTLTVSS |
| 121 | 37-ID | Table 4B FIG. 6A | AA sequence of LC VR of Abs 186, 194; non-ID version is in FIGS. 3A-3B | IDEIVMTQSPDSLAVSLGERATINCKSSQTVTFNYKNYLAWYQQKPGQPPKLLIYWASTRESGVPDRFSGSGSGTDFTLTISSLQAEDVAVYYCQQHYRTPPSFGTGTKLDIK |
| 108 | 27-ID | Table 4B FIG. 5 | AA sequence of HC VR of Abs 016, A017, C18, A019, 034, 040; non-ID version is in FIG. 2 | IDEVQLLESGGGLVKPGQSLKLSCAASGFTFTSYAMHWVRQPPGKGLEWVAVVSYDGNYKYYADSVQGRFTISRDNSKNTLYLQMNSLRAEDTAVYYCAKDSRLRTLLYFEWLSQGYFDPWGQGTTLTVSS |
| 122 | 38-ID | Table 4B FIG. 6A | AA sequence of LC VR of Abs 187, 195; non-ID version is in FIGS. 3A-3B | IDEIVMTQSPDSLAVSLGERATINCKSSQTVTFNYKNYLAWYQQKPGQPPKLLIYWASTRESGVPDRFSGSGSGTDFTLTISSLQAEDVAVYYCQQHYRTPPSFGSGTKLDIK |
| 109 | 161-ID | Table 4B FIG. 5 | AA sequence of HC VR consensus ID; non-ID version is in FIG. 2 | IDEVQLLESGGGLVKPGQSLKLSCAASGFTFSSYGMHWVRQPPGKGLEWVAVVSYDGSNKYYADSVQGRFTISRDNSKNTLYLQMNSLRAEDTAVYYCAKDSKLRSLLYFEWLSSGLLDYWGQGAMVTVSS |
| 123 | 39-ID | Table 4B FIG. 6A | AA sequence of LC VR of Abs 188, 196; non-ID version is in FIGS. 3A-3B | IDEIVMTQSPDSLAVSLGERATINCKSSQTVTFNYKNYLAWYQQKPGQPPKLLIYWASTRESGVPDRFSGSGSGTDFTLTISSLQAEDVAVYYCQQHYRTPSFGQTKLDIK |
| 124 | 40-ID | Table 4B FIG. 6A | AA sequence of LC VR of Abs 189, 197; non-ID version is in FIGS. 3A-3B | IDEIVMTQSPDSLAVSLGERATINCKSSQTVTFNYKNYLAWYQQKPGQPPKLLIYWASTRESGVPDRFSGSGSGTDFTLTISSLQAEDVAVYYCQQHYRTPPSFGNGTKLDIK |
| 125 | 41-ID | Table 4B FIG. 6A | AA sequence of LC VR of Abs 190, 198; non-ID version is in FIGS. 3A-3B | IDEIVMTQSPDSLAVSLGERATINCKSSQTLSFNYKNYLAWYQQKPGQPPKLLIYWASTRESGVPDRFSGSGSGTDFTLTISSLQAEDVAVYYCQQHYRTPPSFGTGTKLDIK |
| 126 | 42-ID | Table 4B FIG. 6A | AA sequence of LC VR of Abs 191, 199; non-ID version is in FIGS. 3A-3B | IDEIVMTQSPDSLAVSLGERATINCKSSQTLSFNYKNYLAWYQQKPGQPPKLLIYWASTRESGVPDRFSGSGSGTDFTLTISSLQAEDVAVYYCQQHYRTPPSFGSGTKLDIK |
| 127 | 43-ID | Table 4B FIG. 6A | AA sequence of LC VR of Abs 192, 200; non-ID version is in FIGS. 3A-3B | IDEIVMTQSPDSLAVSLGERATINCKSSQTLSFNYKNYLAWYQQKPGQPPKLLIYWASTRESGVPDRFSGSGSGTDFTLTISSLQAEDVAVYYCQQHYRTPPSFGQGTKLDIK |
| 128 | 44-ID | Table 4B FIG. 6A | AA sequence of LC VR of Abs 193; non-ID version is in FIGS. 3A-3B | IDEIVMTQSPDSLAVSLGERATINCKSSQTLSFNYKNYLAWYQQKPGQPPKLLIYWASTRESGVPDRFSGSGSGTDFTLTISSLQAEDVAVYYCQQHYRTPPSFGNGTKLDIK |
| 129 | 47-ID | Table 4B FIG. 6A | AA sequence of LC VR of Abs A001, 004, 007, 016 | IDDIVMTQSPDTLAVTLGERATIQCKSSQTLTITSLQAEDVAVYYCQQHYRTPPSFGQGTKLDIK |

TABLE 4C-continued

Nucleic acid and amino acid sequences

| SEQ ID NO. | Lab no. | Source | Comment | Sequence |
|---|---|---|---|---|
| 130 | 48-ID | Table 4B FIG. 6A | AA sequence of LC VR of Abs 002, 005, 008, A017; non-ID version is in FIGS. 3A-3B | IDDIVMTQSPDTVAVTVGERATINCKSSQTVTFNYKNYLAWYQQKPGQPPKLLIYW ASTRESGVPDRFSGSGSGTDFTLTISSLQAEDVAVYYCQQHRTPPSFGQGTKLDI K |
| 131 | 49-ID | Table 4B FIG. 6A | AA sequence of LC VR of Abs A003, 006, A009, C18; non-ID version is in FIGS. 3A-3B | IDDIVMTQSPDTVAVTLGERATIDCKSSQTVTFNYKNYLAWYQQKPGQPPKLLIYW ASTRESGVPDRFSGSGSGTDFTLTISSLQAEDVAVYYCQQHRTPPSFGQGTKLDI K |
| 132 | 50-ID | Table 4B FIG. 6A | AA sequence of LC VR of Abs A010 012, A14, A019; non-ID version is in FIGS. 3A-3B | IDDIVMTQSPDTLAVTVGERATIRCKSSQTVTFNYKNYLAWYQQKPGQPPKLLIYW ASTRESGVPDRFSGSGSGTDFTLTISSLQAEDVAVYYCQQHRTPPSFGQGTKLDI K |
| 133 | 51-ID | Table 4B FIG. 6A | AA sequence of LC VR of Ab A011, 013, 015; non-ID version is in FIGS. 3A-3B | IDDIVMTQSPDTLAVSRGERATIDCKSSQTVTFNYKNYLAWYQQKPGQPPKLLIYW ASTRESGVPDRFSGSGSGTDFTLTISSLQAEDEAVYYCQQHRTPPSFGQGTKLDI K |
| 134 | 52-ID | Table 4B FIG. 6A | AA sequence of LC VR of Abs 044, 071, 072, 078; non-ID version is in FIGS. 3A-3B | IDDIQMTQSPSSLSASVGDRVTITCRSSQSITFDYKNYLAWYQKPGKAPKLLIYW GSYLESGVPSRFSGSGSGTDFTLTISSLQPEDFATYYCQQHRTPPSFGQGTKVEI K |
| 135 | 53-ID | Table 4B FIG. 6B | AA sequence of LC VR of Ab 051; non-ID version is in FIGS. 3A-3B | IDDIQMTQSPSSLSASVGDRVTITCRSSQSITFNYKNYLAWYQKPGKAPKLLIYW GSTLESGVPSRFSGSGSGTDFTLTISSLQPEDFATYYCQQHRTPPSFGQGTKVEI K |
| 136 | 54-ID | Table 4B FIG. 6B | AA sequence of LC VR of Ab 049; non-ID version is in FIGS. 3A-3B | IDDIQMTQSPSSLSASVGDRVTITCRSSQSITFNYKNYLAWYQKPGKAPKLLIYW GSHLESGVPSRFSGSGSGTDFTLTISSLQPEDFATYYCQQHRTPPSFGQGTKVEI K |
| 137 | 55-ID | Table 4B FIG. 6B | AA sequence of LC VR of Ab 047; non-ID version is in FIGS. 3A-3B | IDDIQMTQSPSSLSASVGDRVTITCRSSQSITFNYKNYLAWYQKPGKAPKLLIYW GSKLESGVPSRFSGSGSGTDFTLTISSLQPEDFATYYCQQHRTPPSFGQGTKVEI K |
| 138 | 56-ID | Table 4B FIG. 6B | AA sequence of LC VR of Ab 050; non-ID version is in FIGS. 3A-3B | IDDIQMTQSPSSLSASVGDRVTITCRSSQSITFNYKNYLAWYQKPGKAPKLLIYW GSDLESGVPSRFSGSGSGTDFTLTISSLQPEDFATYYCQQHRTPPSFGQGTKVEI K |
| 139 | 57-ID | Table 4B FIG. 6B | AA sequence of LC VR of Ab 045; non-ID version is in FIGS. 3A-3B | IDDIQMTQSPSSLSASVGDRVTITCRSSQSITFNYKNYLAWYQKPGKAPKLLIYW GSYLESGVPSRFSGSGSGTDFTLTISSLQPEDVATYYCQQHRTPPSFGQGTKVEI K |
| 140 | 58-ID | Table 4B FIG. 6B | AA sequence of LC VR of Ab 048; non-ID version is in FIGS. 3A-3B | IDDIQMTQSPSSLSASVGDRVTITCRSSQSITFNYKNYLAWYQKPGKAPKLLIYW GSYLESGVPSRFSGSGSGTDFTLTISSLQPEDKATYYCQQHRTPPSFGQGTKVEI K |

TABLE 4C-continued

Nucleic acid and amino acid sequences

| SEQ ID NO. | Lab no. | Source | Comment | Sequence |
|---|---|---|---|---|
| 141 | 59-ID | Table 4B FIG. 6B | AA sequence of LC VR of Ab 046; non-ID version is in FIGS. 3A-3B | IDDIQMTQSPSSLSASVGDRVTITCRSSQSITFNYKNYLAWYQQKPGKAPKLLIYW GSYLESGVPSRFSGSGSGTDFTLTISSLQPEDDATYYCQQHYRTPPSFGQGTKVEI K |
| 142 | 60-ID | Table 4B FIG. 6B | AA sequence of LC VR of Ab 043; non-ID version is in FIGS. 3A-3B | IDDIQMTQSPSSLSASVGDRVTITCRSSQSITFNYKNYLAWYQQKPGKAPKLLIYW GSYLESGVPSRFSGSGSGTDFTLTISSLQPEDFATYYCQQYRTPPSFGQGTKVEI |
| 143 | 61-ID | Table 4B FIG. 6B | AA sequence of LC VR of Ab 052; non-ID version is in FIGS. 3A-3B | IDDIQMTQSPSSLSASVGDRVTITCRSSQSITFNYKNYLAWYQQKPGKAPKLLIYW GSTRESGVPSRFSGSGSGTDFTLTISSLQPEDFATYYCQQHYRTPPSFGQGTKVEI K |
| 157 | 153-ID | Table 4B FIG. 6B | AA sequence of LC VR of Ab 067; non-ID version is in FIGS. 3A-3B | IDDIQMTQSPSSLSASVGDRVTITCRSSQSITFQYKNYLAWYQQKPGKAPKLLIYW GSYLESGVPSRFSGSGSGTDFTLTISSLQPEDFATYYCQQHYRTPPSFGQGTKVEI K |
| 158 | 154-ID | Table 4B FIG. 6B | AA sequence of LC VR of Ab 068; non-ID version is in FIGS. 3A-3B | IDDIQMTQSPSSLSASVGDRVTITCRSSQSITFRYKNYLAWYQQKPGKAPKLLIYW GSYLESGVPSRFSGSGSGTDFTLTISSLQPEDFATYYCQQHYRTPPSFGQGTKVEI K |
| 159 | 155-ID | Table 4B FIG. 6B | AA sequence of LC VR of Abs 069, 079; non-ID version is in FIGS. 3A-3B | IDDIQMTQSPSSLSASVGDRVTITCRSSQSITFEYKNYLAWYQQKPGKAPKLLIYW GSYLESGVPSRFSGSGSGTDFTLTISSLQPEDFATYYCQQHYRTPPSFGQGTKVEI K |
| 160 | 156-ID | Table 4B FIG. 6B | AA sequence of LC VR of Ab 070; non-ID version is in FIGS. 3A-3B | IDDIQMTQSPSSLSASVGDRVTITCRSSQSITFDYKNYLAWYQQKPGKAPKLLIYW GSYLESGVPSRFSGSGSGTDFTLTISSLQPEDFATYYCQQHYRTPPSFGQGTKVEI K |
| 144 | 62-ID | Table 4B FIG. 6B | AA sequence of LC VR consensus ID; non-ID version is in FIGS. 3A-3B | IDDIQMTQSPSSLSASVGDRVTITCRSSQSITFNYKNYLAWYQQKPGKAPKLLIYW GSYLESGVPSRFSGSGSGTDFTLTISSLQPEDFATYYCQQHYRTPPSFGQGTKVEI K |
| 63 | VH16 | Example 1 | NT sequence of HC VR of Abs 014, 028 | GAGGTACAGCTCCTCGAATCGGGAGGGGACTGGTCAATCCGGTCAATGCTCAA ACTCTCGTGTGCAGCGTCAGGTTTACGTTCAGCTCATATGGGATCACTGGGTCC GCCAGCCTCCCGGAAAGGGACTGGAGTGGGTGGCAGTGCGTCGTGTATGACGGAGC AATAAGTACTACGCCGATTCAGTGCAAGGTCGGTTTACCATTTCGAGGATAACAG CAAGAACACGCTCTACTTGCAGATGAACAGCTCGATCCCTGTTGTACTTCGAATGGTTGTCC ACTATTGCGCCAAAGACACAAAGCTGGGGGACTATTGGGGACAGGGCCATGGTCACCAGTATCCAGCGCGTC TCGGGCTTGCTTGACTATTGGGGACAGGGCCATGGTCACCAGTATCCAGCGCGTC GACTAAGGGCCC |
| 64 | VL29 | Example 1 | NT sequence of LC VR of Abs 014, 154, 157 | GAGATCGTGATGACGCAGAGCCCCGATAGCCTCGCTGTCTCAGTGGGAACGGGC CACGATTAACTGCAAATCCTCACAGTCGGTGACTTTCAGCTATGAGAATTACCTGG CATGGTATCAGCAGAAGCCGGGTCAACCCCAAAACTGTTGATCTACTGGGCCTCC ACACGCGAGTCGGGAGTCCCGGACGATTTCGGGTTCAGGGTCCGGCACTGACTT TACCCCTCACAATTTCATCGCTTCAAGCGGAGGATGTAGCAGTGTACTATTGTCAGC |

TABLE 4C-continued

Nucleic acid and amino acid sequences

| SEQ ID NO. | Lab no. | Source | Comment | Sequence |
|---|---|---|---|---|
| 65 | VL30 | Example 1 | NT sequence of LC VR of Abs 028, 155 | AGTATTACAGAACACCTCCACTTCGGAGGGGAACGAAACTGACATCAAGGGA TCC |
| 66 | VH15 | Example 1 | NT sequence of HC VR of Ab A18 | GAGATCGTGATGACGCAGAGACCCGATAGCTCGTCTGTCTCATTGGGGAACGGGC CACGATTAACTGCAAATCCTCACAGTCGGTGACTTTGACTATAAGAATTACCTGG CATGGTATCAGCAGAAGCCGGGTCAACCCCCAAAACTGTTGATCTACTGGGCTCC ACACCGCAGTCGGGAGTCCCGGACCCGATTTTCGGGTTCAGGGTCCGCACTGACTT TACCCTCACAATTTCATCGCTTCAAGCGAGGATGTAGCAGTGACTATTGTCAGC AGTATTACAGAACACCTCCCACTTCGGAGGGGAACGAAACTTGACATCAAGGGA TCC |
| 66 | VH15 | Example 1 | NT sequence of HC VR of Ab A18 | GAAGTGCAACTCCTCCAGTCAGGAGGAGAGGTTTGGTGAAACCGGGTCAGTCCTTGAA ACTGAGCTGTGCAAGCGGGTTCACGTTTACGTTACGGCCATGCACTGGGTAC GGCAGCCTCCCGGAAGGACTTGAATGGGTCGCCCTCACAATTCATACGACCGGTCG TACAAATACTATGCGATAGCGTGCAAGGTCGCTTCACAATTTCCGGGACACGGTCT GAAGAATACACTGTATCTTCAGATGAACTCGCTCAGGGCTGAAGGACACGGCGGTCT ATTACTGCGCGAAGGATTCGCAGTCAGATCCCTTTTGTACTTTGGCTGGCTGTCG CAGGGGTATTTCAACCCATGGGAGCCGGAACCACTTGACCGTATCAAGCGCGTC AACAAAGGGCCC |
| 187 | V L28 | Example 1 | NT sequence of LC VR of Ab A18 | GAAATTGTAATGACCCAGAGCCCTGATAGCCTTGCCGTGCCGTCCCCTGGGTGAGAGGGC GACAATCAATTGTAAGTCACAGTCGGTCACGTACAACTCAAGAACTACTCCTGG CGTGGTATCAACAGAAACCGGGTGCCAGACCCTTCTCGGGTCAGGATCGGAACTGACTT CACGTTGACTATTCCTCCTCCAGCAGAGATGTAGCGTCTACTATTGCCAAC AGTATTACAGAACACCGCCCTCACATTTGGAGGCGGAACAAACTTGACATCAAGGGA TCCGTGCCGCCCCAGCGTGTGTCCTCTGAACAACTTCTACCCCCGAGGCGAAGG CACAGGCCAGCGTGTGTGCAAACCCTGCAGAGCGGAACAGCCAGGGTGACC GAGCAGGACTCGAAGGACTACAGCCTACAGCCTCAGCACCCTGACGCTGACAA GCCCGACTACGAGAAGCACAAGAGTCTACGCCTGCGAGGTGACCCACCAGGGCGTCT CGAGCCCCGTGACCAAGAGTTTCAACCGGGCGAGTG |
| 149 | VL52 | Example 1 | NT sequence of LC VR of Abs 044, 071, 072, 078 | GACATTCAGATGACTCAGTCGCCTTCGTCATTGTCCGCTCCGTGGGTGATAGGGT CACGATCACGTGCCGGAGCAGCCAGTCATCCATCCTTCAATTACAAAACTATTTGG CATGGTATCAACAGAAACCGGAAAGGCGCCGAAGCTCTGATCTACTGGGGTTCA TATCTTGAGTCGGGGGGTGCCGTCGAGATTTTCGGCAGCGGATCGGAACGGACGGATTT CACGCTGACCATTTGTCACTCAGCAGACCTTTGCGACATATATTACTGTCAAC AGCACTACAGGACACCCCCAGCGTCTTCATCTTTCGGACAGGGACTAAAGTAGAAATCAAGGGA TCCGTGGCCGCCCCAGCCGTGTGTCCTCTGAACAACTTCTACCCCCGAGGCGAGGCAGTGAAGTC TCCAGTGGAAGGTGGACAACGCCCTGCAGAGCGGAACAGCCAGGAGAGCGTGACC GAGCAGGACTCGAAGGACTACAGCCTCAGCAGCACCCTGACGCTGACAA GCCCGACTACGAGAAGCACAAGGTCTACGCCTGCGAGGTCACCACCACCGGGCGTCT CGAGCCCCGTGACCAAGAGTTTCAACCGGGGCGAGTGCTGA |

TABLE 4C-continued

Nucleic acid and amino acid sequences

| SEQ ID NO. | Lab no. | Source | Comment | Sequence |
|---|---|---|---|---|
| 150 | VL45 | Example 1 | NT sequence of LC VR of Abs 202, 203, 204, 210, 031, 032, 033, 034 | GACATTCAGATGACTCAGTGCCTTCGTCATTGTCCGCCTCGTGGTGATAGGGT<br>CACGATCACGTGCCGAGCAGCAGCCCGAAAGGCGCCGAAGTCCATCACCTTCAATTACAAAACTATTTGG<br>CATGGTATCAACAGAAACCCGGAAAGGCCGAAGTCCTGATCTACTGGGTTCA<br>TATCTTGAGTCGGGGGTCCGTGCAGATTTCGAGCAGCGATCAGGACGGATTT<br>CACGCTGACCATTCGTCACTCCAGCCCGAGGACTTTGCACATATTACTGTCAAC<br>AGCACTACAGGACACCCCATCTTTCGACAGGGGACTAAAGTAGAAATCAAGGGA<br>TCCGTGCCGCCCCAGCGTCTTCATCTTCCCGCCAGCGACGAGCAGCTGAAGTC<br>GGGCACGCAGCGTGTGCCTCCTGACAACTTCTACCCCGCAGGCGAAGG<br>TCCAGTGGAAGTGGACAACGCCCTGCAGAGCGGGAACAGCCAGGAGAGCCTGACC<br>GAGCAGGACTCGAAGGACAGCACTACAAGGTCTACGCCTGCGAGGTGACCCATGCGAGCAA<br>GGCCGACTACGAGAAGCACAAGGTTTCAACCGGGCGAGTGCTGAGAATTC |
| 151 | VH25 | Example 1 | NT sequence of HC VR of Abs 004, 005, 006, 012, 013, 032, 038, 043, 044, 045, 046, 047, 048, 049, 050, 051, 052, 067, 068, 069, 070, 073, 074, 075, 076, 077 | CAGGTACAATTGCTTGAGACAGGTGAAGCCAGGTCAGTCATTGAA<br>CTGAGCTGTGCCGCATCCGGGTTCACATTCACTTCCTACGGCATGCACTGGGTC<br>GCCAGCCTCCCGGAAAGGGACTTGAGTGGGTCGCTGTGTATCGTATGATGGGAAT<br>TACAAATACTATGCAGATCCCGTGCAAGGCCGGTTTACGATTAGCAGGGACACTC<br>GAAGAATACCCTTACTTCCAAATGAACTCGCTCCGAGCGAGGAACACGGCGGTGT<br>ATTACTGCGCGAAGGATTCACGGTTGAGATCGTGCTCTATTTGAATGGTTGTCA<br>CAGGGTACTTCAACCGTGGGGTGCTCTGACAACAACATCACCCGTCCAGCTCAGCCTC<br>GACTAAAGGGCCCAGCGTGTTCCCGTGGCCCTCAAGGACTACTTCCCGAGCCTGACCGTG<br>GGACCCGCCCTGCGCCAGCGCGCCTCACATCGAGCGGGTCCACACCTTCCCGCCGTGCTGCA<br>GAGCAGCGGCCTTACTCGTGACGTGAACGTGGTACGGCGTGAGGTGCATAA<br>GGACCCAGAACGTACATCTGCAACGTGAACCAAGCCCTCGAACACCAAGTCGAC<br>AAGAAGGTGGAGCCCCCGAAGAGCTGCACAAAACTCACACATGCCCCCAAGG<br>AGTACTGAACTGCAACCGACCGGACCCCTGAGGTCACATCGTGGTGGACGTGAGC<br>CACGAAGACCCCGAGGTCAAGTTCAACTGGTACGGCGTGGAGGTGCATAA<br>TGCCAAGACAAAGCCGGAGGAGCAGTACAACAGCACGTACCGTGTGGTCAGCG<br>TCCTCACCGTCCTGCACCAGGACTGGCTGAATGGCAAGGAGTACAAGTGCAAGGTC<br>TCCAACAAAGCCCTCCCAGCCCCCATCGAGAAAACCATCTCCAAAGCCAAAGGTGA<br>GCCCCAGAGAACCAGGTACACCCTGCCCCCATCCCGGGATGAGCTGACCAAGA<br>ACCAGGTCAGCCTGACCTGCCTGGTCAAAGGCTTCTATCCCAGCGACATCGCCGTG<br>GAGTGGGAGAGCAATGGCAGCCCGGAGAACAACTACAAGACCACGCCTCCCGTGCT<br>GGACTCCGACGGCTCCTTCTTCCTCTACAGCAAGCTCACCGTGGACAAGAGCAGGT<br>GGCAGCAGGGGAACGTCTTCTCATGCTCCGTGATGCATGAGGCTCTGCACAACCAC<br>TACACGCAGAAGAGCCTCTCCCTGTCTCCGGGTAAATGA |
| 152 | VH24 | Example 1 | NT sequence of HC VR of Abs A001, A002, A003, A010, A011, 031, 037 | GAAGTACAATTGCTTGAGTCGGTGGAGGACTGTGAAGCCAGGTCAGTCATTGAA<br>ACTGAGCTGTCCGCATCCGGGTTCACATTCACTTCCTACGGCATGCACTGGGTCC<br>GCCAGCCTCCCGGAAAGGGACTTGAGTGGGTCGCTGTGGTATCGTATGATGGGAAT<br>TACAAATACTATGCAGATCCCGTGCAAGGCCGGTTTACGATTAGCAGGGACAACTC<br>GAAGAATACCCTTACTTCCAAATGAACTCGCTCCGAGCGAGGAACACGGCGGTGT<br>ATTACTGCGCGAAGGATTCACGGTTGAGATCGTGCTCTATTTGAATGGTTGTCA<br>CAGGGTACTTCAACCGTGGGGTCAGGGAACAACACTGACCGTCAGCTCAGCCTC |

TABLE 4C-continued

Nucleic acid and amino acid sequences

| SEQ ID NO. | Lab no. | Source | Comment | Sequence |
|---|---|---|---|---|
| | | | | GACTAAAGGGCCCAGCGTGTTCCCGTGGCCCCAGCAGCAAGAGCACCAGCGCG |
| | | | | GGACCCGCCGCCTGGGCTGCCTGGTCAAGGACTACTTCCCCGAGCCCGTGACCGTG |
| | | | | TCGTGGAACAGCGGCGCGCTCACTGCGTGAGCACGTTCCCAGCCGTGCTGCA |
| | | | | GAGCAGCGGCCTCTACTCCCTGAGCAGCGTGGTCACCGTGCCCAGCAGCAGCCTGG |
| | | | | GGACCCAGACCTACATCTGCAACGTGAATCACAAGCCCTCGAACACCAAGGTGGAC |
| | | | | AAGAAGGTGGAGCCCAAATCTTGTGACAAAACCCACACATGCCCACCGTGCCC |
| | | | | AGTACTGAACTCATGATCTCCGGACCCCTGAGGTCACATGCGTGGTGGTGGACGTGAGC |
| | | | | CACGAAGACCCTGAGGTCAAGTTCAACTGGTACGTGGACGGCGTGGAGGTGCATAA |
| | | | | TGCCAAGACAAAGCCGCGGGAGGAGCAGTACAACAGCACGTACCGTGGTGGTCAGCG |
| | | | | TCCTCACCGTCCTGCACCAGGACTGGCTGAATGGCAAGGAGTACAAGTGCAAGGTC |
| | | | | TCCAACAAAGCCCTCCCAGCCCCCATCGAGAAAACCATCTCCAAAGCCAAAGGTGA |
| | | | | GCCCCGAGAACCACAGGTGTACACCCTGCCCCCATCCCGGGATGAGCTGACCAAGA |
| | | | | ACCAGGTCAGCCTGACCTGCCTGGTCAAAGGCTTCTATCCCAGCGACATCGCCGTG |
| | | | | GAGTGGGAGAGCAATGGGCAGCCGGAGAACAACTACAAGACCACGCCTCCCGTGCT |
| | | | | GGACTCCGACGGCTCCTTCTTCCTCTACAGCAAGCTCACCGTGGACAAGAGCAGGT |
| | | | | GGCAGCAGGGAACGTCTTCTCATGCTCCGTGATGCATGAGGCTCTGCACAACCAC |
| | | | | TACACGCAGAAGAGCCTCTCCCTGTCTCCGGGTAAATGA |
| 94 | 15 | FIG. 1 | AA sequence of HC of Ab A18 | EVQLLESGGGLVKPGQSLKLSCAASGFTFTSYGMHWVRQPPGKGLEWVAVISYDGS |
| | | | | YKYYADSVQGRFTISRDNSKNTLYLQMNSLRAEDTAVYYCAKDSRLRSLLYFEWLS |
| | | | | QGYFNPWGAGTTLTVSSASTKGPSVFPLAPSSKSTSGGTAALGCLVKDYFPEPVTV |
| | | | | SWNSGALTSGVHTFPAVLQSSGLYSLSSVVTVPSSSLGTQTYICNVNHKPSNTKVD |
| | | | | KKVEPPKSCDKTHTCPPCPAPELLGGPSVFLFPPKPKDTLMISRTPEVTCVVVDVS |
| | | | | HEDPEVKFNWYVDGVEVHNAKTKPREEQYNSTYRVVSVLTVLHQDWLNGKEYKCKV |
| | | | | SNKALPAPIEKTISKAKGQPREPQVYTLPPSRDELTKNQVSLTCLVKGFYPSDIAV |
| | | | | EWESNGQPENNYKTTPPVLDSDGSFFLYSKLTVDKSRWQQGNVFSCSVMHEALHNH |
| | | | | YTQKSLSLSPGK |
| 188 | 28 | FIG. 1 | AA sequence of LC of Ab A18 | EIVMTQSPDSLAVSLGERATINCKSSQSVTNYKNYLAWYQQKPGQPPKLLIYWAS |
| | | | | TRESGVPDRFSGSGSGTDFTLTISSLQAEDVAVYYCQQYYRTPTPFGGGTKLDIKG |
| | | | | SVAAPSVFIFPPSDEQLKSGTASVVCLLNNFYPREAKVQWKVDNALQSGNSQESVT |
| | | | | EQDSKDSTYSLSSTLTLSKADYEKHKVYACEVTHQGLSSPVTKSFNRGE |
| 145 | n.a. | see text | AA sequence of LC CDR1 of Ab 044 | QSITFDYKNYLA |
| 146 | n.a. | see text | AA sequence of LC CDR1 of F16 VK | KSSQSVTFNYKNYLA |
| 147 | n.a. | see text | AA sequence of LC CDR2 of F16 VK | WASARES |
| 148 | n.a. | see text | AA sequence of LC CDR3 of F16 VK | QQHYRTPPT |
| 68 | n.a. | see text | AA sequence of HC CDR1 of Abs 044, 069, 032, 031 | SYAMH |
| 69 | n.a. | see text | AA sequence of HC CDR2 of Abs 044, 069, 032, 031 | VVSYDGNYKYYADSVQG |

TABLE 4C-continued

Nucleic acid and amino acid sequences

| SEQ ID NO. | Lab no. | Source | Comment | Sequence |
|---|---|---|---|---|
| 70 | n.a. | see text | AA sequence of HC CDR3 of Abs 044, 069, 032, 031 | DSRLRSLLYFEWLSQGYFNP |
| 71 | n.a. | see text | AA sequence of LC CDR1 of Abs 032, 031 | QSITFNYKNYLA |
| 72 | n.a. | see text | AA sequence of LC CDR2 of Abs 044, 069, 032, 031 | WGSYLES |
| 73 | n.a. | see text | AA sequence of LC CDR3 of Abs 044, 069, 032, 031 | QQHYRTPPS |
| 74 | n.a. | see text | AA sequence of HC FR1 of Ab 069 | QVQLLETGGGLVKPGGSLKLSCAASGFTFT |
| 75 | n.a. | see text | AA sequence of HC FR2 of Ab 069 | WVRQPPGKGLEWVA |
| 76 | n.a. | see text | AA sequence of HC FR3 of Ab 069 | RFTISRDNSKNTLYLQMNSLRAEDTAVYYCAK |
| 77 | n.a. | see text | AA sequence of HC FR4 of Ab 069 | WGQGTTLTVSS |
| 78 | n.a. | see text | AA sequence of LC FR1 of Ab 069 | DIQMTQSPSSLSASVGDRVTITCRSS |
| 79 | n.a. | see text | AA sequence of LC FR2 of Ab 069 | WYQQKPGKAPKLLIY |
| 80 | n.a. | see text | AA sequence of LC FR3 of Ab 069 | GVPSRFSGSGSGTDFLTISSLQPEDFATYYC |
| 81 | n.a. | see text | AA sequence of LC FR4 of Ab 069 | FGQGTKVEIK |
| 82 | n.a. | see text | AA sequence of HC FR1 of Ab 031 | EVQLLESGGGLVKPGGSLKLSCAASGFTFT |
| 83 | n.a. | see text | AA sequence of LC CDR1 of Ab A18 et al. | KSSQSVTYNYKNYLA |
| 84 | n.a. | see text | AA sequence of LC CDR2 of Ab A18 et al. | WASTRES |
| 85 | n.a. | see text | AA sequence of LC CDR3 of Ab A18 et al. | QQYYRTPPT |
| 86 | n.a. | see text | AA sequence of HC CDR1 of Ab A18 et al. | SYGMH |
| 87 | n.a. | see text | AA sequence of HC CDR2 of Ab A18 et al. | VISYDGSYKYYADSVQG |
| 88 | n.a. | see text | AA sequence of an HC CDR3 | DSELRSLLYFEWLSQGYFNP |
| 89 | n.a. | see text | AA sequence of HC FR4 of Ab A18 et al. | WGAGTTLTVSS |
| 90 | n.a. | see text | AA sequence of LC FR1 of Ab A18 et al. | EIVMTQSPDSLAVSLGERATINC |
| 91 | n.a. | see text | AA sequence of LC FR2 of Ab A18 et al. | WYQQKPGQPPKLLIY |

TABLE 4C-continued

Nucleic acid and amino acid sequences

| SEQ ID NO. | Lab no. | Source | Comment | Sequence |
|---|---|---|---|---|
| 92 | n.a. | see text | AA sequence of LC FR3 of Ab A18 et al. | GVPDRFSGSGSGTDFTLTISSLQAEDVAVYYC |
| 93 | n.a. | see text | AA sequence of LC FR4 of Ab A18 et al. | FGGGTKLDIK |
| 171 | n.a. | see text | AA sequence of HC FR4 of Ab 078 et al | WGQGTTVTVSS |
| 172 | n.a. | see text | AA sequence of LC CDR1 of Ab 069 | QSITFEYKNYLA |
| 173 | n.a. | see text | AA sequence of H3 HA1 | QDLPGNDNSTATLCLGHHAVPNGTLVKTITDDQIEVTNATELVQSSSTGKICNNPHRILDGIDCTLIDALLGDPHCDVFQNETWDLFVERSKAFSNCYPYDVPDYASLRSLVASSGTLEFITEGFTWTGVTQNGGSNACKRGPGSGFFSRLNWLTKSGSTYPVLNVTMPNNDNFDKLYIWGIHHPSTNQEQTSLYVQASGRVTVSTRRSQQTIIPNIGSRPWVRGLSSRISIYWTIVKPGDVLVINSNGNLIAPRGYFKMRTGKSSIMRSDAPIDTCISECITPNGSIPNDKPFQNVNKITYGACPKYVKQNTLKLATGMRNVPEKQTR |
| 174 | n.a. | see text | AA sequence of H3 HA2 | GLFGAIAGFIENGWEGMIDGWYGFRHQNSEGTGQAADLKSTQAAIDQINGKLNRVIEKTNEKFHQIEKEFSEVEGRIQDLEKYVEDTKIDLWSYNAELLVALENQHTIDLTDSEMNKLFEKTRRQLRENAEEMGNGCFKIYHKCDNACIESIRNGTYDHDVYRDEALNNRFQIKG |
| 175 | n.a. | FIG. 4 | AA sequence of HC VR of F16 | QVQLVQSGGGVVQPGRSLRLSCVASGFTFSTYAMHWVRQAPGRGLEWVAVISYDGNYKYYADSVKGRFSISRDNSNNTLHLEMNTLRTEDTALYYCAKDSQLRSLLYFEWLSQGYFDPWGQGTLVTVTS |
| 176 | n.a. | FIG. 4 | AA sequence of HC VR of F1370 | QVQLVQSGGGVVPPGRSLRLSCAASGFTFSTYGMHWVRQAPGKGLEWVAVISYDGNYKYYADSVKGRFTISRDNSKNTLNLDMNSLRTEDTALYYCAKDSQLRSLLYFDWLSQGYFDHWGQGTLVTVSS |
| 177 | n.a. | FIG. 4 | AA sequence of HC VR of F16 variant 1 | QVQLVESGGGVVQPGRSLRLSCAASGFTFSSYGMHWVRQAPGKGLEWVAVISYDGSNKYYADSVKGRFTISRDNSKNTLYLQMNSLRAEDTAVYYCAKDTAVYYCAKDSQLRSLLYFDWLSQGYFDYWGQGTLVTVSS |
| 178 | n.a. | FIG. 4 | AA sequence of HC VR of F16 variant 3 | QVQLVESGGGVVQPGRSLRLSCAASGFTFSTYAMHWVRQAPGKGLEWVAVISYDANYKYYADSVKGRFTISRDNSKNTLYLQMNSLRAEDTAVYYCAKDTAVYYCAKDSQLRSLLYFEWLSQGYFDYWGQGTLVTVSS |
| 179 | n.a. | FIG. 4 | AA sequence of HC VR of F16/370 | QVQLVQSGGGVVQPGRSLRLSCAASGFTFSSYGMHWVRQAPGKGLEWVAVISYDGNYKYYADSVKGRFTISRDNSKNTLYLEMNSLRTEDTALYYCAKDSQLRSLLYFDWLSQGYFDHWGQGTLVTVSS |
| 180 | n.a. | FIG. 4 | AA sequence of kappa LC VR of F16 | DIQMTSQPDSLAVSLGARATINCKSSQSVTFNYKNYLAWYQQKPGQPPKVLIYWASARESGVPDRFSGSGSGTDFTLTISSLQAEDVAVYYCQQHYRTPPTFGQGTKVEIK |
| 181 | n.a. | See text | AA sequence of H1 HA1 | TNADTICIGYHANNSTDTVDTVLEKNVTVTHSVNLLEDSHNGKLCKLKGIAPLQLGKCNIAGWLLGNPECDLLLTASSWSYIVETSNSENGTCYPGDFIDYEELREQLSSVSSFEKFEIFPKTSSWPNHETTKGVTAACSYAGASSFYRNLLWLTKKGGSYPKLSKSY |

TABLE 4C-continued

Nucleic acid and amino acid sequences

| SEQ ID NO. | Lab no. | Source | Comment | Sequence |
|---|---|---|---|---|
| | | | | VNNKGKEVLVLWGVHHPPTGTDQQSLYQNADAYVSVGSSKYNRRFTPEIAARPKVR DQAGRMNYYWTLLEPGDTITFEATGNLIAPWYAFALNRGSGSGIITSDAPVHDCNT KCQTPHGAINSSLPFQNIHPVTIGECPKYVRSTKLRMATGLRNIPSIQS |
| 182 | | See text | AA sequence of H1 HA2 | GLFGAIAGFIEGGWTGMIDGWYGYHHQNEQGSGYAAD

EXAMPLES

Example 1. Designing of Anti-HA Antibodies

Human antibodies (IgG) targeting viral hemagglutinin (HA) were computationally designed. HA mediates viral binding to host cell surface receptor, and cell membrane fusion to the viral envelope, resulting in viral entry. The antibody molecules described herein were designed to block HA's fusogenic activity.

All antibody constructs were based on human IgG1 structure (γ1 heavy chain and κ light chain). Point mutations in the $V_H$ (variable heavy domain) and $V_L$ (variable light domain) were computationally designed. These mutations are located within or outside the CDRs (Complementarity Determining Regions). The mutations were designed, e.g., to modify antigen binding properties (e.g., for stronger or weaker binding affinity), or to stabilize structure, or to improve expression properties, etc.

The heavy and light chain sequences of one antibody, called A18 is provided in FIG. 1.

The heavy and light chain pairings for exemplary computationally designed antibodies are shown in Table 3, above in Detailed Description.

DNA sequences for the variable heavy chain and variable light chain for each of antibodies Ab A18, Ab 031, Ab 032, Ab 044, Ab 014 and Ab 028 are provided below.

```
VH16:
                                                     (SEQ ID NO: 63)
GAGGTACAGCTCCTCGAATCGGGAGGGGGACTGGTCAAACCCGGTCAATCGCTCAAACTCTCGTGTGC

AGCGTCAGGTTTTACGTTCAGCTCATATGGGATGCACTGGGTCCGCCAGCCTCCGGGAAAGGGACTGG

AGTGGGTGGCAGTCGTGTCGTATGACGGGAGCAATAAGTACTACGCCGATTCAGTGCAAGGTCGGTTT

ACCATTTCGAGGGATAACAGCAAGAACACGCTCTACTTGCAGATGAACTCACTTAGAGCGGAAGATAC

GGCTGTGTACTATTGCGCCAAAGACACAAAGCTGCGATCCCTGTTGTACTTCGAATGGTTGTCCTCGG

GCTTGCTTGACTATTGGGGCAGGGCGCCATGGTCACAGTATCCAGCGCGTCGACTAAGGGGCCC

VL29:
                                                     (SEQ ID NO: 64)
GAGATCGTGATGACGCAGAGCCCCGATAGCCTCGCTGTCTCATTGGGGGAACGGGCCACGATTAACTG

CAAATCCTCACAGTCGGTGACTTTCAGCTATAAGAATTACCTGGCATGGTATCAGCAGAAGCCGGGTC

AACCCCCAAAACTGTTGATCTACTGGGCCTCCACACGCGAGTCGGGAGTCCCGGACCGATTTTCGGGT

TCAGGGTCCGGCACTGACTTTACCCTCACAATTTCATCGCTTCAAGCGGAGGATGTAGCAGTGTACTA

TTGTCAGCAGTATTACAGAACACCTCCCACCTTCGGAGGGGGAACGAAACTTGACATCAAGGGATCC

VL30:
                                                     (SEQ ID NO: 65)
GAGATCGTGATGACGCAGAGCCCCGATAGCCTCGCTGTCTCATTGGGGAACGGGCCACGATTAACTG

CAAATCCTCACAGTCGGTGACTTTCGACTATAAGAATTACCTGGCATGGTATCAGCAGAAGCCGGGTC

AACCCCCAAAACTGTTGATCTACTGGGCCTCCACACGCGAGTCGGGAGTCCCGGACCGATTTTCGGGT

TCAGGGTCCGGCACTGACTTTACCCTCACAATTTCATCGCTTCAAGCGGAGGATGTAGCAGTGTACTA

TTGTCAGCAGTATTACAGAACACCTCCCACCTTCGGAGGGGGAACGAAACTTGACATCAAGGGATCC

VH15:
                                                     (SEQ ID NO: 66)
GAAGTGCAACTCCTCGAGTCAGGAGGAGGTTTGGTGAAACCGGGTCAGTCCTTGAAACTGAGCTGTGC

AGCAAGCGGGTTCACGTTTACGTCGTACGGCATGCACTGGGTACGGCAGCCTCCCGGGAAGGGACTTG

AATGGGTCGCCGTCATCTCATACGACGGGTCGTACAAATACTATGCGGATAGCGTGCAAGGTCGCTTC

ACAATTTCCCGGGACAATTCGAAGAATACACTGTATCTTCAGATGAACTCGCTCAGGGCTGAGGACAC

GGCGGTCTATTACTGCGCGAAGGATTCGCGACTCAGATCCCTTTTGTACTTTGAGTGGCTGTCGCAGG

GGTATTTCAACCCATGGGAGCCGGAACCACTTTGACCGTATCAAGCGCGTCAACAAAGGGGCCC

VL28:
                                                     (SEQ ID NO: 67)
GAAATTGTAATGACGCAGAGCCCTGATAGCCTTGCCGTGTCCCTGGGTGAGAGGGCGACAATCAATTG

TAAGTCATCACAGTCGGTCACGTACAACTACAAGAACTACCTGGCGTGGTATCAACAGAAACCCGGGC

AGCCGCCCAAATTGCTCATCTATTGGGCTTCGACACGGGAGTCGGGTGTGCCAGACCGCTTCTCCGGG

TCAGGATCGGGAACTGACTTCACGTTGACTATTTCGTCCCTCCAGGCAGAAGATGTAGCCGTCTACTA

TTGCCAACAGTATTACAGAACGCCGCCTACATTTGGAGGCGGGACCAAACTTGACATCAAGGGATCCG
```

```
TGGCCGCCCCCAGCGTCTTCATCTTCCCGCCCAGCGACGAGCAGCTGAAGTCGGGCACGGCCAGCGTG

GTGTGCCTCCTGAACAACTTCTACCCCCGCGAGGCGAAGGTCCAGTGGAAGGTGGACAACGCCCTGCA

GAGCGGGAACAGCCAGGAGAGCGTGACCGAGCAGGACTCGAAGGACAGCACCTACAGCCTCAGCAGCA

CCCTGACGCTGAGCAAGGCCGACTACGAGAAGCACAAGGTCTACGCCTGCGAGGTGACCCACCAGGGG

CTCTCGAGCCCCGTGACCAAGAGCTTCAACCGGGGCGAGTGC
```

VL52:
(SEQ ID NO: 149)
```
GACATTCAGATGACTCAGTCGCCTTCGTCATTGTCCGCCTCCGTGGGTGATAGGGTCACGATCACGTG

CCGGAGCAGCCAGTCCATCACCTTCAATTACAAAAACTATTTGGCATGGTATCAACAGAAACCCGGAA

AGGCGCCGAAGCTCCTGATCTACTGGGGTTCATATCTTGAGTCGGGGGTGCCGTCGAGATTTTCGGGC

AGCGGATCAGGGACGGATTTCACGCTGACCATTTCGTCACTCCAGCCCGAGGACTTTGCGACATATTA

CTGTCAACAGCACTACAGGACACCCCCATCTTTCGGACAGGGGACTAAAGTAGAAATCAAGGGATCCG

TGGCCGCCCCCAGCGTCTTCATCTTCCCGCCCAGCGACGAGCAGCTGAAGTCGGGCACGGCCAGCGTG

GTGTGCCTCCTGAACAACTTCTACCCCCGCGAGGCGAAGGTCCAGTGGAAGGTGGACAACGCCCTGCA

GAGCGGGAACAGCCAGGAGAGCGTGACCGAGCAGGACTCGAAGGACAGCACCTACAGCCTCAGCAGCA

CCCTGACGCTGAGCAAGGCCGACTACGAGAAGCACAAGGTCTACGCCTGCGAGGTGACCCACCAGGGG

CTCTCGAGCCCCGTGACCAAGAGCTTCAACCGGGGCGAGTGCTGA
```

VL45:
(SEQ ID NO: 150)
```
GACATTCAGATGACTCAGTCGCCTTCGTCATTGTCCGCCTCCGTGGGTGATAGGGTCACGATCACGTG

CCGGAGCAGCCAGTCCATCACCTTCAATTACAAAAACTATTTGGCATGGTATCAACAGAAACCCGGAA

AGGCGCCGAAGCTCCTGATCTACTGGGGTTCATATCTTGAGTCGGGGGTGCCGTCGAGATTTTCGGGC

AGCGGATCAGGGACGGATTTCACGCTGACCATTTCGTCACTCCAGCCCGAGGACTTTGCGACATATTA

CTGTCAACAGCACTACAGGACACCCCCATCTTTCGGACAGGGGACTAAAGTAGAAATCAAGGGATCCG

TGGCCGCCCCCAGCGTCTTCATCTTCCCGCCCAGCGACGAGCAGCTGAAGTCGGGCACGGCCAGCGTG

GTGTGCCTCCTGAACAACTTCTACCCCCGCGAGGCGAAGGTCCAGTGGAAGGTGGACAACGCCCTGCA

GAGCGGGAACAGCCAGGAGAGCGTGACCGAGCAGGACTCGAAGGACAGCACCTACAGCCTCAGCAGCA

CCCTGACGCTGAGCAAGGCCGACTACGAGAAGCACAAGGTCTACGCCTGCGAGGTGACCCACCAGGGG

CTCTCGAGCCCCGTGACCAAGAGCTTCAACCGGGGCGAGTGCTGAGAATTC
```

VH25:
(SEQ ID NO: 151)
```
CAGGTACAATTGCTTGAGACAGGTGGAGGACTCGTGAAGCCAGGTCAGTCATTGAAACTGAGCTGTGC

CGCATCCGGGTTCACATTCACTTCCTACGCGATGCACTGGGTCCGCCAGCCTCCCGGAAAGGGACTTG

AGTGGGTCGCTGTGGTATCGTATGATGGGAATTACAAATACTATGCAGACTCCGTGCAAGGCCGGTTT

ACGATTAGCAGGGACAACTCGAAGAATACCCTTTACCTCCAAATGAACTCGCTCCGAGCGGAGGACAC

GGCGGTGTATTACTGCGCGAAGGATTCACGGTTGAGATCGCTGCTCTATTTTGAATGGTTGTCACAGG

GGTACTTCAACCCGTGGGGTCAGGGAACAACACTGACCGTCAGCTCAGCCTCGACTAAAGGGCCCAGC

GTGTTCCCGCTGGCCCCCAGCAGCAAGAGCACCAGCGGCGGGACCGCCGCCCTGGGCTGCCTCGTCAA

GGACTACTTCCCCGAGCCCGTGACCGTGTCGTGGAACAGCGGCGCGCTGACGAGCGGGGTCCACACCT

TCCCGGCCGTGCTGCAGAGCAGCGGCCTCTACTCGCTGAGCAGCGTGGTCACCGTGCCCAGCAGCAGC

CTGGGGACCCAGACGTACATCTGCAACGTGAACCACAAGCCCTCGAACACCAAGGTCGACAAGAAGGT

GGAGCCCCCGAAGAGCTGCGACAAAACTCACACATGCCCACCGTGCCCAGGTACTGAACTCCTGGGGG

GACCGTCAGTCTTCCTCTTCCCCCCAAAACCCAAGGACACCCTCATGATCTCCCGGACCCCTGAGGTC
```

```
                                  -continued
ACATGCGTGGTGGTGGACGTGAGCCACGAAGACCCTGAGGTCAAGTTCAACTGGTACGTGGACGGCGT

GGAGGTGCATAATGCCAAGACAAAGCCGCGGGAGGAGCAGTACAACAGCACGTACCGTGTGGTCAGCG

TCCTCACCGTCCTGCACCAGGACTGGCTGAATGGCAAGGAGTACAAGTGCAAGGTCTCCAACAAAGCC

CTCCCAGCCCCCATCGAGAAAACCATCTCCAAAGCCAAAGGTGAGCCCCGAGAACCACAGGTGTACAC

CCTGCCCCCATCCCGGGATGAGCTGACCAAGAACCAGGTCAGCCTGACCTGCCTGGTCAAAGGCTTCT

ATCCCAGCGACATCGCCGTGGAGTGGGAGAGCAATGGGCAGCCGGAGAACAACTACAAGACCACGCCT

CCCGTGCTGGACTCCGACGGCTCCTTCTTCCTCTACAGCAAGCTCACCGTGGACAAGAGCAGGTGGCA

GCAGGGGAACGTCTTCTCATGCTCCGTGATGCATGAGGCTCTGCACAACCACTACACGCAGAAGAGCC

TCTCCCTGTCTCCGGGTAAATGA

VH24:
                                                     (SEQ ID NO: 152)
GAAGTACAATTGCTTGAGTCGGGTGGAGGACTCGTGAAGCCAGGTCAGTCATTGAAACTGAGCTGTGC

CGCATCCGGGTTCACATTCACTTCCTACGCGATGCACTGGGTCCGCCAGCCTCCCGGAAAGGGACTTG

AGTGGGTCGCTGTGGTATCGTATGATGGGAATTACAAATACTATGCAGACTCCGTGCAAGGCCGGTTT

ACGATTAGCAGGGACAACTCGAAGAATACCCTTTACCTCCAAATGAACTCGCTCCGAGCGGAGGACAC

GGCGGTGTATTACTGCGCGAAGGATTCACGGTTGAGATCGCTGCTCTATTTTGAATGGTTGTCACAGG

GGTACTTCAACCCGTGGGGTCAGGGAACAACACTGACCGTCAGCTCAGCCTCGACTAAAGGGCCCAGC

GTGTTCCCGCTGGCCCCCAGCAGCAAGAGCACCAGCGGCGGGACCGCCGCCCTGGGCTGCCTCGTCAA

GGACTACTTCCCCGAGCCCGTGACCGTGTCGTGGAACAGCGGCGCGCTGACGAGCGGGGTCCACACCT

TCCCGGCCGTGCTGCAGAGCAGCGGCCTCTACTCGCTGAGCAGCGTGGTCACCGTGCCCAGCAGCAGC

CTGGGGACCCAGACGTACATCTGCAACGTGAACCACAAGCCCTCGAACACCAAGGTCGACAAGAAGGT

GGAGCCCCCGAAGAGCTGCGACGGTACCCACACATGCCCACCGTGCCCAGGTACTGAACTCCTGGGGG

GACCGTCAGTCTTCCTCTTCCCCCCAAAACCCAAGGACACCCTCATGATCTCCCGGACCCCTGAGGTC

ACATGCGTGGTGGTGGACGTGAGCCACGAAGACCCTGAGGTCAAGTTCAACTGGTACGTGGACGGCGT

GGAGGTGCATAATGCCAAGACAAAGCCGCGGGAGGAGCAGTACAACAGCACGTACCGTGTGGTCAGCG

TCCTCACCGTCCTGCACCAGGACTGGCTGAATGGCAAGGAGTACAAGTGCAAGGTCTCCAACAAAGCC

CTCCCAGCCCCCATCGAGAAAACCATCTCCAAAGCCAAAGGTGAGCCCCGAGAACCACAGGTGTACAC

CCTGCCCCCATCCCGGGATGAGCTGACCAAGAACCAGGTCAGCCTGACCTGCCTGGTCAAAGGCTTCT

ATCCCAGCGACATCGCCGTGGAGTGGGAGAGCAATGGGCAGCCGGAGAACAACTACAAGACCACGCCT

CCCGTGCTGGACTCCGACGGCTCCTTCTTCCTCTACAGCAAGCTCACCGTGGACAAGAGCAGGTGGCA

GCAGGGGAACGTCTTCTCATGCTCCGTGATGCATGAGGCTCTGCACAACCACTACACGCAGAAGAGCC

TCTCCCTGTCTCCGGGTAAATGA
```

Each of the above sequences can be modified to include an ATCGAT nucleotide sequence at the 5' end, which will encode a variable heavy chain or light chain polypeptide comprising Ile-Asp at the amino terminus.

Example 2. Initial Formulation Study

This Example summarizes the initial formulation study results for an exemplary anti-HA antibody molecule described herein, e.g., Ab 044.

Procedure

Fourteen formulation matrices with different pH values with 40 mM sodium phosphate-citrate buffer and with different compositions were prepared. The antibody sample was prepared by a sequence of Protein A affinity chromatography, anion exchange chromatography, and cation exchange chromatography. The purified samples were formulated in the appropriate solutions using Ultrafiltration/Diafiltration. Aliquots of 4.0 mL of antibody at 10 mg/mL in 30 mM Sodium Phosphate, 8.6 mM Citric Acid, 50 m·M Histidine, 90 m·M NaCl, pH 6.0 were transferred into a 30K MWCO Amicon Ultra Centrifugal filter and centrifuged at 3600 RPM for 30 minutes. Additional 2.0 mL of antibody at concentration of 10 mg/mL was added into each 30K MWCO Amicon Ultra Centrifugal filter and centrifuge at 3600 RPM for 40 minutes. The solution volume in each Amicon Ultra Centrifugal filter was reduced to approximately 500 µL. Aliquots of 4.0 ml of formulation matrix per filter were added (see Table 5 for the formulation components with 40 mM sodium phosphate/citrate buffer) and centrifuged at 3600 RPM for 40 minutes. The solution volume in each Amicon Ultra Centrifugal filter was reduced to approximately 500 μL. Additional 4.0 ml of formulation matrix per filter were added and the filters were centrifuged at 3600 RPM for 45 minutes. The solution volume in each Amicon Ultra Centrifugal filter was reduced to approximately 400 μL. After completion of the two buffer exchanges, it can be assumed that to the final solution contained less than 1.5% of the original solution composition. The final retentate volume was reduced from 6.0 mL to approximately 400 μL, with a theoretical concentration of around 150 mg/ml assuming no protein was lost to the membrane or precipitated out.

The retentate was then filtered through a 0.22 μM membrane. A280 and DSC were conducted to measure protein concentrations and the conformational stability of the antibody in each formulation, respectively. Each sample was also divided into 4 portions in glass vials. The first 3 aliquots have 65 μL solution. The remaining sample is in the 4th aliquot, with sample volume ranged between 65 and 350 μL. The first 3 aliquots were stored at 5° C., 45° C., and −70° C., respectively; the 4th portion was stored at 5° C. The $1^{st}$ three aliquots was pulled on day 7 and frozen at −70° C. and shipped on dry ice for analysis. These samples were analyzed with size exclusion-high performance liquid chromatography (SEC-HPLC), and the results are summarized in Table 6. The Appearance test was conducted for all of the $1^{st}$ three aliquots on day 1 and day 7 except the −70° C. samples on day 7 which was not thawed before shipping. All of samples appeared clear without visible particles. The 4th aliquot was stored at 5° C. for later analysis.

Results and Discussion

Table 5 shows formulation information, protein concentration, differential scanning calorimetry (DSC) peak temperatures, and the final volume after buffer exchange, while, Table 6 summarizes the size exclusion chromatography (SEC) results.

FIGS. 8A-8G show the DSC profile for all of the 14 formulation samples. Significant differences were observed between the formulations by DSC. A front shoulder was clearly observed for formulation #5, 7, 12, and 13 at approximately 70° C. for low pH samples (pH 5-5.5), indicating the anti-HA antibody molecule at lower pH denatured sooner as the temperature increased.

Table 6 shows the summary of the overall protein recovery of the concentration step and the Size Exclusion Chromatography (SEC) results of the 14 formulations stored at 3 temperatures. The recovery of the concentration step (targeted 100 mg/ml) was calculated based on the amount of protein at the start and end of the process. The results of the SEC analytics are expressed as a main peak, containing the HA antibody monomer, as well as peaks containing High Molecular Weight (HMW) and Low Molecular Weight (LMW) species, consisting of aggregates and breakdown products. Data show that all 42 samples tested consist to a very large proportion of monomeric species, as expressed by % Main Peak above 98%, when stored at 2-8° C. However, % High Molecular Weight Species (% HMWS), and/or % Low Molecular Species (% LMWS) increased more in some of the formulation upon storage at 45° C. for 1 week (#1, 3, 4, 9, 10, 11, 12 and 14) in comparison with rest of the formulation buffers. The results indicated that the levels of stress-induced aggregation and degradation vary depending on the formulation buffer.

TABLE 6

Summary of % Recovery of Concentration Step and SEC Results

| # | % Recovery | Temp ° C. | % HMWS | % Main Peak | % LMWS |
|---|---|---|---|---|---|
| 1 | 48 | −70 | 0.5 | 99.5 | 0 |
|   |    | 5   | 0.7 | 99.3 | 0 |
|   |    | 45  | 1.2 | 98.8 | 0 |

TABLE 5

Formulation information with A280 and DSC Data

| Number | pH | NaCl mM | Tw80 % | Sucro % | Hist % | Arg % | Gly % | Front Peak ° C. | Main Peak ° C. | mg/mL | Volume uL |
|---|---|---|---|---|---|---|---|---|---|---|---|
| 1  | 5.5 | 150 | 0.05  | 2 | 0 | 0 | 2 | Minor | 77.9 | 75.0  | 385 |
| 2  | 6.0 | 50  | 0     | 2 | 2 | 0 | 2 | Minor | 78.1 | 90.0  | 410 |
| 3  | 6.0 | 150 | 0.05  | 0 | 0 | 0 | 0 | No    | 77.3 | 106.0 | 284 |
| 4  | 7.0 | 50  | 0     | 0 | 0 | 0 | 0 | No    | 76.3 | 72.0  | 262 |
| 5  | 5.5 | 50  | 0     | 0 | 0 | 2 | 0 | 67.5  | 75.5 | 78.0  | 510 |
| 6  | 7.0 | 150 | 0.05  | 2 | 2 | 2 | 2 | No    | 77.3 | 73.0  | 436 |
| 7  | 5.5 | 150 | 0     | 0 | 2 | 0 | 2 | 65.5  | 75.4 | 66.0  | 486 |
| 8  | 6.5 | 150 | 0     | 0 | 2 | 2 | 2 | No    | 77.3 | 80.0  | 382 |
| 9  | 6.0 | 50  | 0.05  | 0 | 0 | 0 | 0 | No    | 76.8 | 47.0  | 317 |
| 10 | 8.0 | 150 | 0.05  | 2 | 2 | 0 | 0 | No    | 76.2 | 66.0  | 406 |
| 11 | 8.0 | 50  | 0     | 0 | 0 | 2 | 2 | No    | 76.5 | 69.0  | 475 |
| 12 | 5.0 | 100 | 0.025 | 1 | 1 | 1 | 1 | 65.3  | 65.3 | 73.0  | 483 |
| 13 | 5.0 | 50  | 0.05  | 0 | 0 | 2 | 0 | 68.4  | 68.4 | 57.0  | 481 |
| 14 | 6.0 | 150 | 0.05  | 0 | 0 | 2 | 0 | No    | 76.8 | 59.0  | 588 |

Sucro = Sucrose;

His = Histindine;

Arg = Arginine;

Gly = Glycine

TABLE 6-continued

Summary of % Recovery of Concentration Step and SEC Results

| # | % Recovery | Temp ° C. | % HMWS | % Main Peak | % LMWS |
|---|---|---|---|---|---|
| 2 | 62 | −70 | 0 | 100 | 0 |
|   |   | 5 | 0.1 | 99.9 | 0 |
|   |   | 45 | 0.2 | 99.8 | 0 |
| 3 | 50 | −70 | 0.1 | 99.7 | 0.1 |
|   |   | 5 | 0.1 | 99.9 | 0 |
|   |   | 45 | 0.3 | 98.7 | 1.0 |
| 4 | 32 | −70 | 0.5 | 99.5 | 0 |
|   |   | 5 | 0.5 | 99.5 | 0 |
|   |   | 45 | 0.7 | 98.8 | 0.5 |
| 5 | 66 | −70 | 0.2 | 99.8 |   |
|   |   | 5 | 0.2 | 99.8 |   |
|   |   | 45 | Crystallized |   |   |
| 6 | 53 | −70 | 0.6 | 99.4 | 0 |
|   |   | 5 | 0.6 | 99.4 | 0 |
|   |   | 45 | 0.9 | 99.0 | 0 |
| 7 | 54 | −70 | 0.5 | 99.5 | 0 |
|   |   | 5 | 0.4 | 99.6 | 0 |
|   |   | 45 | 0.6 | 99.4 | 0 |
| 8 | 51 | −70 | 0.5 | 99.6 | 0 |
|   |   | 5 | 0.5 | 99.5 | 0 |
|   |   | 45 | 0.7 | 99.3 | 0 |
| 9 | 25 | −70 | 0.1 | 99.9 | 0.1 |
|   |   | 5 | 0.1 | 99.9 | 0.0 |
|   |   | 45 | 0.2 | 99.0 | 0.8 |
| 10 | 45 | −70 | 0.7 | 99.1 | 0.2 |
|   |   | 5 | 0.7 | 99.1 | 0.2 |
|   |   | 45 | 1.2 | 97.7 | 1.2 |
| 11 | 55 | −70 | 0.5 | 99.5 | 0 |
|   |   | 5 | 0.4 | 99.4 | 0.2 |
|   |   | 45 | 1.2 | 98.7 | 0.1 |
| 12 | 59 | −70 | 0.5 | 99.4 | 0 |
|   |   | 5 | 0.6 | 99.4 | 0 |
|   |   | 45 | 1.3 | 98.7 | 0 |
| 13 | 46 | −70 | 0.6 | 99.4 | 0 |
|   |   | 5 | 0.6 | 99.4 | 0 |
|   |   | 45 | 3.5 | 95.7 | 0.8 |
| 14 | 58 | −70 | 0.5 | 99.5 | 0 |
|   |   | 5 | 0.5 | 99.5 | 0 |
|   |   | 45 | 0.9 | 98.4 | 0.7 |

% HMWS = % High Molecular Weight Species and % LMWS = % Low Molecular Species

This initial evaluation indicates that the antibody can be formulated up to 106 mg/nm land is stable within a wide range of pH and buffer compositions at 2-8° C. Differential Scanning Calorimetry (DSC) data from unstressed samples and the SEC-HPLC data on stressed and unstressed samples revealed differences between the formulations. Notably, Formulation #3-38.6 mM Sodium Phosphate-Citrate, 150 mM Sodium Chloride, pH 6.0, 0.05% Tween-80 samples reached a concentration of 106 mg/ml, did not result in a front should by DSC and maintained >98% monomer upon heat stress by SEC-HPLC.

Example 3: Development of Stable Formulations for Antibody Drug Product

This Example summarizes the formulation development study for an exemplary anti-HA antibody molecule described herein, e.g., Ab 044, at 25 mg/ml. A short-term thermal stressed stability study, a freeze/thaw study, and an agitation study were performed to screen out the desired formulation.

Five formulations were prepared at concentration of 25 mg/mL. Each formulation was divided into several portions for different storage conditions, which include 4° C. and 45° C. for 2 weeks, freeze/thaw for 1 and 3 cycles, and agitation for 16 hours at speed of 30 RPM by a cP Cole-Parmer. Appearance, SEC, CE-SDS, A280, IEF and potency analyses were conducted to evaluate the stability of these samples. Table 7 lists the composition of the 5 formulations. It was found that the antibody molecule was stable for up to 3 freeze/thaw cycles and overnight agitation. Among the 5 formulations, Formulation 1 and 4 were most stable. Formulation 1 was chosen as the final formulation for the antibody molecule based on the potential long term benefit of Tween-80.

TABLE 7

Composition of Formulations

| Formulation # | Formulation Title |
|---|---|
| #1 | 40 mM Citrate-Sodium Phosphate, 150 mM Sodium Chloride, pH 6.0, 0.025% Tween-80 |
| #2 | 40 mM Citrate-Sodium Phosphate, 150 mM Sodium Chloride, pH 6..5, 0.025% Tween-80 |
| #3 | 40 mM Citrate-Sodium Phosphate, 1% Glycine, 75 mM Sodium Chloride, pH 6.5, 0.025% Tween-80 |
| #4 | 40 mM Citrate-Sodium Phosphate, 150 mM Sodium Chloride, pH 6.0. |
| #5 | 40 mM Citrate-Sodium Phosphate, 75 mM Sodium Chloride, pH 6.5, 0.025% Tween-80 |

Summary of the Formulation Procedure

Citric Acid (JT Baker, Lot K42466) 100 mM, Sodium Phosphate Dibasic Heptahydrate (Fisher, Lot 125720) 100 mM, and NaCl (JT Baker, Lot L10472) 1.0 N were prepared. pH 6.0 buffer (100 mM) was prepared by mixing Citric Acid 100 mM and Sodium Phosphate Dibasic Heptahydrate 100 mM at a proper ratio determined by a pH meter. pH 6.5 buffer (100 mM) was also prepared by mixing Citric Acid 100 mM and Sodium Phosphate Dibasic Heptahydrate 100 mM at a proper ratio determined by the pH meter. The 5 formulations were prepared without Tween-80 according to Table 8 and were QS to a final volume of 125 mL with water in a graduated cylinder.

TABLE 8

Recipe of Formulation Buffer without Tween-80

| Formulation # | 1 | 2 | 3 | 4 | 5 |
|---|---|---|---|---|---|
| NaCl, 1N, mL; Final Conc = 75 or 150 nM | 18.8 | 18.8 | 9.4 | 18.8 | 9.4 |
| pH 6.0 100 mM, mL; Final Conc = 40 mM | 50 | 0 | 0 | 50 | 0 |
| pH 6.5 100 mM, mL; Final Conc = 40 mM | 0 | 50 | 50 | 0 | 50 |
| Glycine, g; Final Conc = 0% or 1.0% | 0 | 0 | 1.25 | 0 | 0 |

After 125 mL of formulation buffers were prepared, the pH values were further adjusted by 5N NaOH or 5N HCl to pH 6.0 or 6.5. The antibody bulk drug substance (BDS) (4.5 mg/mL, 229.2 mL) was prepared by a sequence of Protein A affinity chromatography, anion exchange chromatography, and cation exchange chromatography. The purified samples were formulated in the appropriate solutions using Ultrafiltration/Diafiltration.

Amicon Ultracel 30K Lot R2AA64948 (Max mL=15 mL) ultrafiltration tubes were used to perform buffer exchange/concentration. Sample volumes were adjusted according to A280 results with target value of 25 mg/mL. Table 9 lists recoveries of the formulation samples. Formulation #1 and #4 were combined.

TABLE 9

Recoveries of Formulation

| Formulation # | Weight g | Concentration mg/mL | Total Loading mg | Recovery % |
|---|---|---|---|---|
| #1 and #4 | 5.61 g | 24.69 | 174.26 | 79.5% |
| #2 | 2.68 g | 24.76 | 87.13 | 76.2% |
| #3 | 2.71 g | 24.82 | 87.13 | 77.2% |
| #5 | 2.64 g | 24.97 | 87.13 | 75.7% |

The combined formulation sample #1 and #4 was divided into equal portions as Formulation #1 and Formulation #4, respectively. Diluted Tween-80 (JT Baker, Lot H35614) (3%) was spiked into the samples except Formulation #4 to reach a concentration of 0.025% Tween-80. Each formulation sample was divided into multiple portions for testing on different conditions of T=0, Agitation, 1 cycle of freeze/thaw, 3 cycles of freeze/thaw, and for 2 weeks at 45° C.

Results

During the study, all samples were colorless without precipitation or visible particles. Table 10 lists the A280 results. The protein concentration after storage at different conditions remained the same.

TABLE 10

A280 Results

| Sample ID | mg/mL | Sample ID | mg/mL | Sample ID | mg/mL |
|---|---|---|---|---|---|
| Formulation #1, T = 0 | 24.8 | #1 T = 2 weeks 4° C. | 24.5 | #1 T = 2 weeks 45° C. | 24.3 |
| Formulation #1 1 F/T, T = 0 | 24.9 | | | | |
| Formulation #1 3 F/T, T = 0 | 24.3 | | | | |
| Formulation #1 Agitate, T = 0 | 24.4 | | | | |
| Formulation #2, T = 0 | 24.6 | #2 T = 2 weeks 4° C. | 25.1 | #2 T = 2 weeks 45° C. | 24.3 |
| Formulation #2 1 F/T, T = 0 | 24.9 | | | | |
| Formulation #2 3 F/T, T = 0 | 25.0 | | | | |
| Formulation #2 Agitate, T = 0 | 24.5 | | | | |
| Formulation #3, T = 0 | 24.3 | #3 T = 2 weeks 4° C. | 24.9 | #3 T = 2 weeks 45° C. | 24.3 |
| Formulation #3 1 F/T, T = 0 | 24.7 | | | | |
| Formulation #3 3 F/T, T = 0 | 24.5 | | | | |
| Formulation #3 Agitate, T = 0 | 25.6 | | | | |
| Formulation #4, T = 0 | 23.8 | #4 T = 2 weeks 4° C. | 24.5 | #4 T = 2 weeks 45° C. | 24.7 |
| Formulation #4 1 F/T, T = 0 | 24.7 | | | | |
| Formulation #4 3 F/T, T = 0 | 23.8 | | | | |
| Formulation #4 Agitate, T = 0 | 24.9 | | | | |
| Formulation #5, T = 0 | 24.8 | #5 T = 2 weeks 4° C. | 25.2 | #5 T = 2 weeks 45° C. | 24.3 |
| Formulation #5 1 F/T, T = 0 | 24.9 | | | | |
| Formulation #5 3 F/T, T = 0 | 24.7 | | | | |
| Formulation #5 Agitate, T = 0 | 24.6 | | | | |

Figure 9:
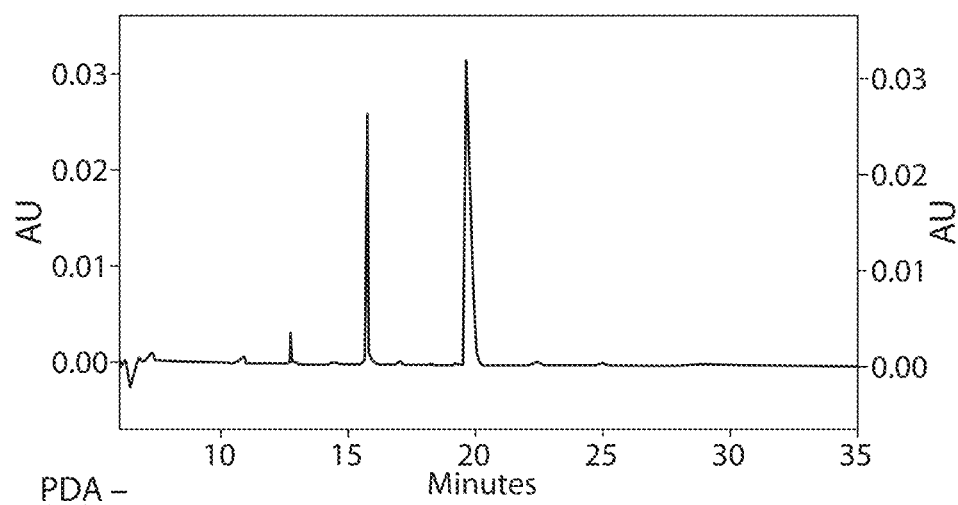
FIG. 9 depicts representative reduced CE-SDS electropherogram (Formulation #1, 45° C., 2 wks).

Table 11 lists capillary electrophoresis-SDS (CE-SDS) results for reduced samples. The antibody molecule was stable over freeze/thaw and agitation based on the reduced CE-SDS results. The combined (heavy chain and light chain) Main peak % area after storage at different conditions are listed. Formulations #1 and #4 showed improved stability as compared to the other 3 formulations. FIG. 9 shows a representative electropherogram of CE-SDS for a reduced sample.

TABLE 11

Combined (HC and LC) Main Peak % of CE-SDS for Reduced Samples

| | | Formulation # | | | | |
|---|---|---|---|---|---|---|
| | | #1 | #2 | #3 | #4 | #5 |
| CE Reduced | HC + LC, 4 C., 2 wks | 98.6 | 98.6 | 98.6 | 98.6 | 98.5 |
| CE Reduced | | 96.9 | 96.4 | 95.7 | 97.2 | 96.4 |
| Difference | T = 2 wks4 C. − T = 2 wks 45 C. | 1.7 | 2.2 | 2.9 | 1.4 | 2.1 |
| CE Reduced | HC + LC 4C 2 wks | 98.6 | 98.6 | 98.6 | 98.6 | 98.5 |
| CE Reduced | HC + LC 1 F/T 4 C. 2 wks | 98.7 | 98.6 | 98.7 | 98.4 | 98.6 |
| CE Reduced | HC + LC 3 F/T 4 C. 2 wks | 98.7 | 98.7 | 98.7 | 98.6 | 98.8 |
| CE Reduced | HC + LC Agitation 4 C. 2 wks | 98.7 | 98.7 | 98.7 | 98.8 | 98.6 |

Figure 10:
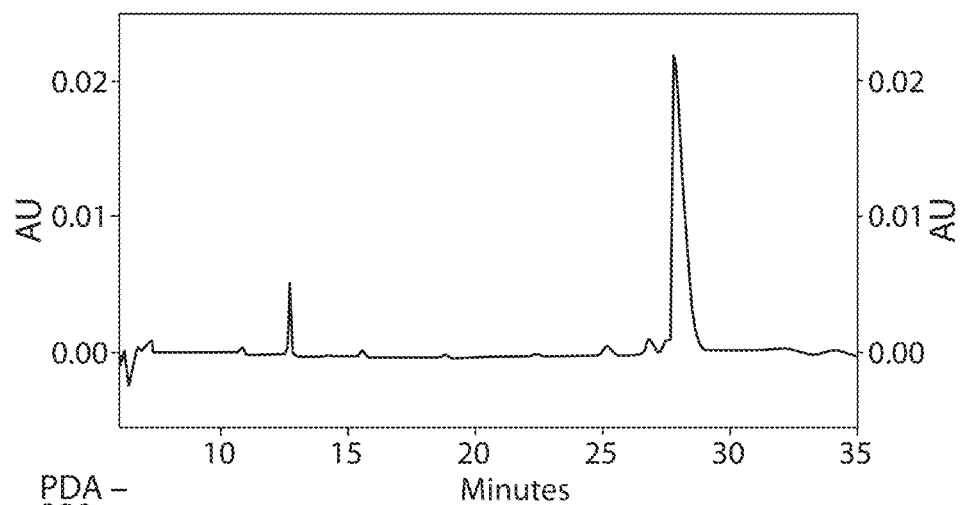
FIG. 10 depicts representative non-reduced CE-SDS electropherogram (Formulation #1, 45° C., 2 wks).

Table 12 lists CE-SDS results for non-reduced samples. The Main peak % area for IgG at different conditions are listed. The antibody molecule was stable over freeze/thaw and agitation based on non-reduced CE-SDS. Formulations #1 and #4 appeared to maintain stability better than the other 3 formulations as demonstrated by the % Purity difference between 4° C. and 45° C. storage for 2 weeks. FIG. 10 shows a representative electropherogram of CE-SDS for a non-reduced sample.

TABLE 12

Main Peak % of CE-SDS for Non-Reduced Samples

| | | Formulation # | | | | |
|---|---|---|---|---|---|---|
| | | #1 | #2 | #3 | #4 | #5 |
| CE Non-Reduced | IgG 4 C. 2 wks | 97.0 | 97.3 | 97.4 | 97.1 | 97.1 |
| CE Non-Reduced | IgG 45 C. 2 wks | 92.0 | 91.0 | 90.6 | 91.7 | 91.4 |
| Difference | T = 2 wks 4 C. − T = 2 wks 45 C. | 5.0 | 6.3 | 6.8 | 5.4 | 5.7 |
| CE Non-Reduced | IgG 1 F/T 4 C. 2 wks | 97.0 | 96.9 | 96.9 | 96.8 | 96.8 |
| CE Non-Reduced | IgG 3 F/T 4 C. 2 wks | 96.8 | 96.7 | 96.8 | 96.7 | 96.6 |
| CE Non-Reduced | IgG Agitation 4 C. 2 wks | 96.6 | 96.4 | 96.6 | 96.4 | 96.4 |

Figure 11:
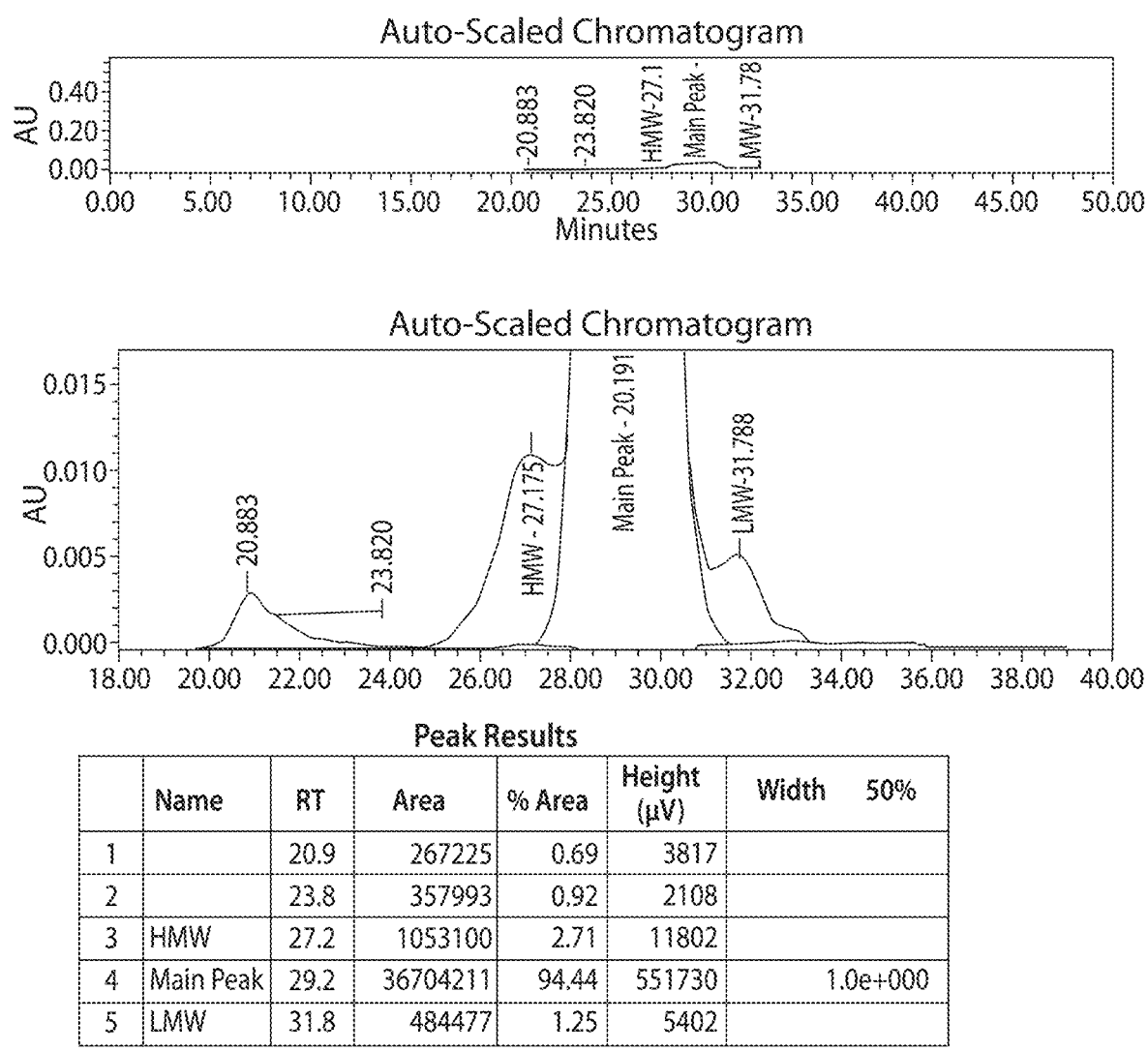
FIG. 11 depicts representative SEC chromatogram (Formulation #1, 45° C., 2 wks).

Table 13 lists SEC-HPLC results as % peak area for monomer peak, high molecular weight (HMW) peak and low molecular weight (LMW) peak from samples stored for 2 weeks at 4° C. and 45° C. The peak area % differences at 4° C. and 45° C. are also listed for different formulations. Formulation #2 and #3 showed the most change upon stress at 45° C. FIG. 11 shows a representative SEC chromatogram.

TABLE 13

SEC Result for 2 Week Samples at 4° C. and 45° C.

| Sample ID | HMW (%) | Monomer (%) | LMW (%) |
|---|---|---|---|
| Formulation #1, T = 0 | 1.57 | 98.43 | 0 |
| Formulation #1; 4 C. 2 wks | 1.90 | 98.10 | 0 |
| Formulation #1; 45 C. 2 wks | 4.31 | 94.44 | 1.25 |
| Formulation #2, T = 0 | 1.81 | 98.19 | 0 |
| Formulation #2; 4 C. 2 wks | 1.97 | 98.03 | 0 |
| Formulation #2; 45 C. 2 wks | 4.70 | 94.03 | 1.27 |
| Formulation #3, T = 0 | 1.53 | 98.47 | 0 |
| Formulation #3; 4 C. 2 wks | 1.76 | 98.24 | 0 |
| Formulation #3; 45 C. 2 wks | 4.70 | 94.21 | 1.09 |
| Formulation #4, T = 0 | 1.68 | 98.32 | 0 |
| Formulation #4; 4 C. 2 wks | 1.89 | 98.11 | 0 |
| Formulation #4; 45 C. 2 wks | 4.38 | 94.38 | 1.24 |
| Formulation #5, T = 0 | 1.64 | 98.36 | 0 |
| Formulation #5; 4 C. 2 wks | 1.96 | 98.04 | 0 |
| Formulation #5; 45 C. 2 wks | 4.29 | 94.54 | 1.17 |

Table 14 lists monomer % peak area from SEC for t=0 samples and after freeze/thaw (F/T) cycles or agitation. Minimal changes were observed for the different formulations after agitation, 1 cycle F/T, or 3 cycles F/T.

TABLE 14

SEC Result for T = 0 Samples

| Name | HMW (%) | Monomer (%) |
|---|---|---|
| Formulation #1; T = 0 | 1.57 | 98.43 |
| Formulation #1; 1 F/T | 1.64 | 98.36 |
| Formulation #1; 3 F/T | 1.61 | 98.39 |
| Formulation #1; Agitation | 1.77 | 98.23 |
| Formulation #2; T = 0 | 1.81 | 98.19 |
| Formulation #2; 1 F/T | 1.94 | 98.06 |
| Formulation #2; 3 F/T | 1.72 | 98.28 |
| Formulation #2; Agitation | 1.84 | 98.16 |
| Formulation #3; T = 0 | 1.53 | 98.47 |
| Formulation #3; 1 F/T | 1.55 | 98.45 |
| Formulation #3; 3 F/T | 1.65 | 98.35 |
| Formulation #3; Agitation | 1.63 | 98.37 |
| Formulation #4; T = 0 | 1.68 | 98.32 |
| Formulation #4; 1 F/T | 1.53 | 98.47 |
| Formulation #4; 3 F/T | 1.68 | 98.32 |
| Formulation #4; Agitation | 1.70 | 98.30 |
| Formulation #5; T = 0 | 1.64 | 98.36 |
| Formulation #5; 1 F/T | 1.65 | 98.35 |
| Formulation #5; 3 F/T | 1.79 | 98.21 |
| Formulation #5; Agitation | 1.65 | 98.35 |

Figure 12:
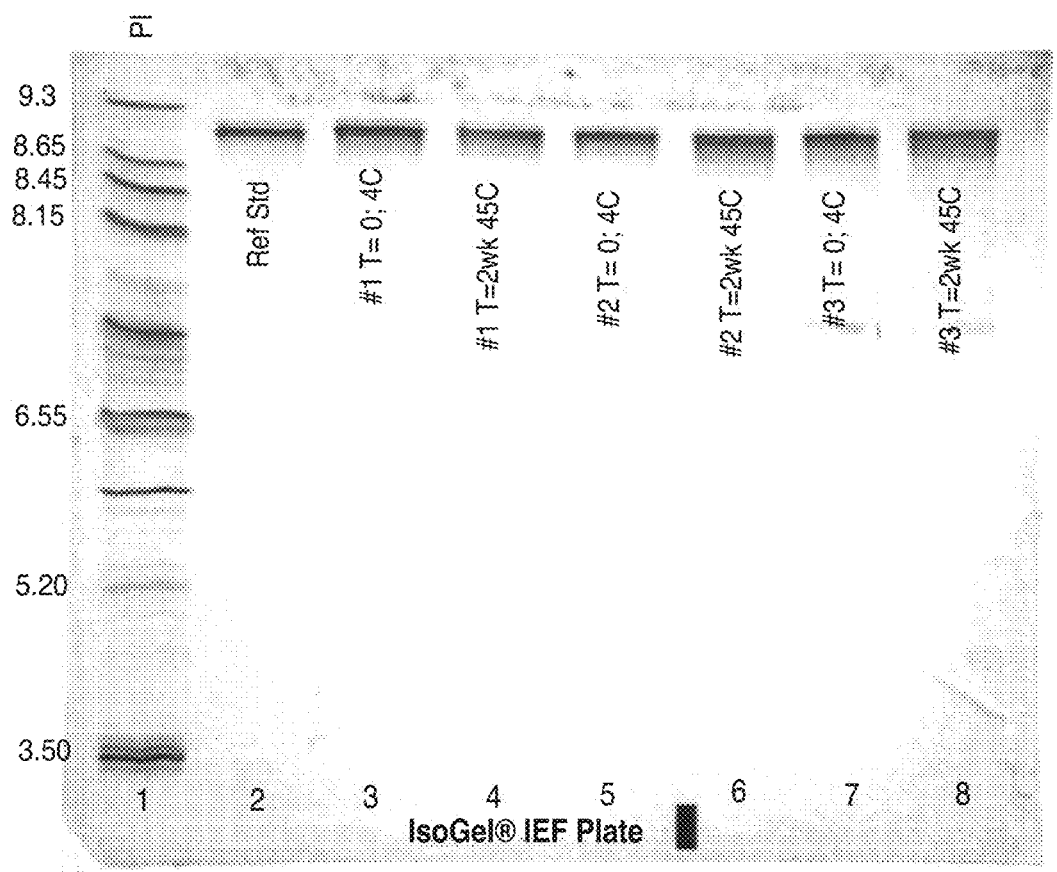
FIG. 12 depicts a representative IEF gel image.

Isoelectric focusing (IEF) was conducted to analyze all samples. A major band at the isoelectric point (pI) around 9.0 was observed for all of the samples. More degradation was observed for 45° C. samples (more acidic bands noted by eyes). No significant difference was observed among all the formulations. FIG. 12 shows a representative IEF gel image.

Based on the results of non-reduced CE-SDS and SEC, t=0 and t=2 wks 45° C. samples in formulation #3 were chosen to measure potency by Hemagglutinin (HA) binding ELISA since the antibody molecule in this formulation buffer had the most changes after storage at 45° C. for 2 weeks. The results are summarized in Table 15. The data indicated no significant changes in potency (% Activity) between t=0 and the stressed sample considering the assay precision. Therefore, it is reasonable to draw the similar conclusion of no change in the antibody molecule potency upon stress at 45° C. for 2 weeks in all of the formulations tested.

TABLE 15

Potency Result for t = 0 and 2 wks 45° C. Samples in Formulation #3

| Sample | % Activity |
|---|---|
| T = 0 | 123 |
| T = 2 wks 45 C. | 97 |

TABLE 15-continued

| Potency Result for t = 0 and 2 wks 45° C. Samples in Formulation #3 | |
| --- | --- |
| Sample | % Activity |
| Average % Activity | 110 |
| Standard Deviation (%) | 18.4 |
| % RSD | 16.7 |

The results indicate that the antibody molecule was stable up to 3 freeze/thaw cycles and overnight agitation. Among the 5 formulations, Formulation 1 and 4 were most stable. Formulation 1 was chosen as the final formulation for the antibody molecule based on the potential long term benefit of Tween-80. The formulation contains 40 mM Citrate-Sodium Phosphate, 150 mM sodium chloride, 0.025% polysorbate-80, pH 6.0.

Example 4: Population Pharmacokinetic and Viral Dynamic Modeling of VIS410 in a Human Challenge Model A population pharmacokinetic (popPK) and influenza viral dynamic model were developed to support the VIS410 clinical program (e.g., using a formulation described herein), integrating data from a Phase 1 healthy volunteer and a Phase 2a human influenza challenge study. VIS410 is also known as Ab 044 herein.

Methods

Nasal and serum PK data from a Phase 1 study (N=30, single IV doses 2-50 mg/kg) and a Phase 2a study (N=33, single IV doses of 2300 and 4600 mg) were used to develop the popPK model. In the Phase 2a study, volunteers were inoculated intranasally with an attenuated influenza A (H1N1) strain, and received placebo or VIS410 24 h post-inoculation. Frequent nasal viral load (qPCR and $TCID_5$), serum and nasal PK were measured. The pharmacodynamic analysis included viral load data from intent-to-treat infected subjects (ITT): placebo (n=7), 2300 mg (n=22), 4600 mg (n=4). All analyses were performed in NONMEM 7.3 and qPCR and $TCID50_{50}$ were modeled separately; BLQ data were handled using the M3 method, with predictive performance evaluated using NPDE (in R).

Results

A 3-compartment model adequately described PK with first-order distribution of VIS410 between nasal and central compartments (mean (% RSE) $CL_D$ serum-to-nasal 0.04 (19.5%) mL/h; and nasal-to-serum 1.95 (17.1%) mL/h). Body weight was the only covariate that was retained in the popPK model. Other covariates tested included gender, age and infection status, but were non-influential. A 92% reduction in viral load AUC by qPCR was observed at the 2300 mg dose compared to placebo (p<0.05). Viral dynamics in placebo and ITT subjects were well characterized by a modified viral dynamic model comprising virus, target epithelial cells, non-productive and productive infected cells; mAb drug effect was modeled as inhibiting membrane fusion in the nasal compartment, via an $E_{max}$ function (mean (% RSE) $EC_{50}$ qPCR=1.96 (13) g/mL and $EC_{50}$ $TCID_{50}$=18.4 (2.6) g/mL).

In summary, VIS410 demonstrated PK generally typical of IgG1 mAbs, and potent antiviral activity compared to placebo in the H1N1 human challenge model. A semi-mechanistic popPK model, which links mAb nasal concentrations to influenza viral dynamics based on the VIS410 mechanism of action was successfully developed. The model describes serum and nasal PK, with impact on viral load, and was used to support dose selection for future clinical development across a spectrum of populations. This approach may be extended to other mAbs targeted against influenza viral infections.

Additional examples are disclosed in International Application Publication No. WO2013/170139, U.S. Pat. Nos. 8,877,200, 9,096,657, and U.S. Patent Application Publication No. US 2013/0302349. The contents of the aforesaid publications are incorporated by reference in their entirety.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A pharmaceutical formulation comprising 100 mg/mL of an anti-hemagglutinin (HA) antibody molecule, amino acids consisting of 0.2% to 5% histidine and 0.5% to 5% arginine, and 0.02% polysorbate 80, wherein the formulation has a pH of 6, wherein the antibody molecule comprises:
   (a) a heavy chain (HC) immunoglobulin variable region segment comprising:
   an HC CDR1 comprising the sequence S-Y-A-M-H (SEQ ID NO: 68);
   an HC CDR2 comprising the sequence V-V-S-Y-D-G-N-Y-K-Y-Y-A-D-S-V-Q-G (SEQ ID NO: 69); and
   an HC CDR3 comprising the sequence D-S-R-L-R-S-L-L-Y-F-E-W-L-S-Q-G-Y-F-N-P (SEQ ID NO: 70); and
   (b) a light chain (LC) immunoglobulin variable region segment comprising:
   an LC CDR1 comprising the sequence Q-S-I-T-F-D-Y-K-N-Y-L-A (SEQ ID NO: 145);
   an LC CDR2 comprising the sequence W-G-S-Y-L-E-S (SEQ ID NO: 72); and
   an LC CDR3 comprising the sequence Q-Q-H-Y-R-T-P-P-S (SEQ ID NO: 73),
   wherein the antibody molecule is a human IgG1 antibody molecule, and
   wherein the purity of the antibody molecule in the formulation is at least 90% as determined by reduced or non-reduced CE-SDS.

2. The formulation of claim 1, wherein the antibody molecule comprises a heavy chain immunoglobulin variable region segment comprising SEQ ID NO: 25, or an amino acid sequence that differs by no more than 1, 2, 3, 4, or 5 amino acids in a framework region of SEQ ID NO: 25.

3. The formulation of claim 1, wherein the antibody molecule comprises a heavy chain immunoglobulin variable region segment comprising SEQ ID NO: 25.

4. The formulation of claim 1, wherein the antibody molecule comprises a light chain immunoglobulin variable region segment comprising SEQ ID NO: 52, or an amino acid sequence that differs by no more than 1, 2, 3, 4, or 5 amino acids in a framework region of SEQ ID NO: 52.

5. The formulation of claim 1, wherein the antibody molecule comprises a light chain immunoglobulin variable region segment comprising SEQ ID NO: 52.

6. The formulation of claim 1, wherein the antibody molecule comprises a heavy chain immunoglobulin variable region segment comprising SEQ ID NO: 25, and a light chain immunoglobulin variable region segment comprising SEQ ID NO: 52.

* * * * *

SEQUENCE LISTING

```
<160> NUMBER OF SEQ ID NOS: 188

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (3)..(3)
<223> OTHER INFORMATION: Ala or Gly

<400> SEQUENCE: 1
```

```
Xaa Tyr Xaa Met His
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ile, Val or Leu
<220> FEATURE:
<221> NAME/KEY: MOD_RES
<222> LOCATION: (4)..(4)
<223> OTHER INFORMATION: Tyr or Phe
<220> FEATURE:
<221> NAME/KEY: MOD_RES
<222> LOCATION: (7)..(7)
<223> OTHER INFORMATION: Ser or Asn
<220> FEATURE:
<221> NAME/KEY: MOD_RES
<222> LOCATION: (8)..(8)
<223> OTHER INFORMATION: Tyr or Asn
<220> FEATURE:
<221> NAME/KEY: MOD_RES
<222> LOCATION: (9)..(9)
<223> OTHER INFORMATION: Lys or Arg

<400> SEQUENCE: 2

Val Xaa Ser Xaa Asp Gly Xaa Xaa Xaa Tyr Tyr Ala Asp Ser Val Gln
1               5                   10                  15

Gly

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Arg, Lys or Gln
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (15)..(15)
<223> OTHER INFORMATION: Gln or Ser
<220> FEATURE:
<221> NAME/KEY: MOD_RES
<222> LOCATION: (17)..(17)
<223> OTHER INFORMATION: Tyr, Leu or Val
<220> FEATURE:
<221> NAME/KEY: MOD_RES
<222> LOCATION: (18)..(18)
<223> OTHER INFORMATION: Phe or Leu
<220> FEATURE:
<221> NAME/KEY: MOD_RES
<222> LOCATION: (19)..(19)
<223> OTHER INFORMATION: Asn or Asp
<220> FEATURE:
<221> NAME/KEY: MOD_RES
<222> LOCATION: (20)..(20)
```

<223> OTHER INFORMATION: Pro or Tyr

<400> SEQUENCE: 3

Asp Xaa Xaa Leu Arg Xaa Leu Leu Tyr Phe Glu Trp Leu Ser Xaa Gly
1               5                   10                  15

Xaa Xaa Xaa Xaa
            20

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Val, Leu or Ile
<220> FEATURE:
<221> NAME/KEY: MOD_RES
<222> LOCATION: (4)..(4)
<223> OTHER INFORMATION: Thr or Ser
<220> FEATURE:
<221> NAME/KEY: MOD_RES
<222> LOCATION: (5)..(5)
<223> OTHER INFORMATION: Tyr, Phe or Trp
<220> FEATURE:
<221> NAME/KEY: MOD_RES
<222> LOCATION: (6)..(6)
<223> OTHER INFORMATION: Asn, Ser or Asp

<400> SEQUENCE: 4

Gln Xaa Xaa Xaa Xaa Xaa Tyr Lys Asn Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Gly
<220> FEATURE:
<221> NAME/KEY: MOD_RES
<222> LOCATION: (4)..(4)
<223> OTHER INFORMATION: Thr, Ala, Tyr, His, Lys or Asp
<220> FEATURE:
<221> NAME/KEY: MOD_RES
<222> LOCATION: (5)..(5)
<223> OTHER INFORMATION: Arg or Leu
<220> FEATURE:
<221> NAME/KEY: MOD_RES
<222> LOCATION: (7)..(7)
<223> OTHER INFORMATION: Ser or Thr

<400> SEQUENCE: 5

Trp Xaa Ser Xaa Xaa Glu Xaa
1               5

<210> SEQ ID NO 6
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr or His
<220> FEATURE:
<221> NAME/KEY: MOD_RES
<222> LOCATION: (9)..(9)
<223> OTHER INFORMATION: Thr or Ser

<400> SEQUENCE: 6

Gln Gln Xaa Tyr Arg Thr Pro Pro Xaa
1               5

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Glu or Gln
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (30)..(30)
<223> OTHER INFORMATION: Ser or Thr

<400> SEQUENCE: 7

Xaa Val Gln Leu Leu Glu Xaa Gly Gly Gly Leu Val Lys Pro Gly Gln
1               5                   10                  15

Ser Leu Lys Leu Ser Cys Ala Ala Ser Gly Phe Thr Phe Xaa
            20                  25                  30

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Val Arg Gln Pro Pro Gly Lys Gly Leu Glu Trp Val Ala
1               5                   10

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 10
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ala or Gln
<220> FEATURE:
<221> NAME/KEY: MOD_RES
<222> LOCATION: (5)..(5)
<223> OTHER INFORMATION: Thr or Ala
<220> FEATURE:
<221> NAME/KEY: MOD_RES
<222> LOCATION: (6)..(6)
<223> OTHER INFORMATION: Thr or Met
<220> FEATURE:
<221> NAME/KEY: MOD_RES
<222> LOCATION: (7)..(7)
<223> OTHER INFORMATION: Leu or Val

<400> SEQUENCE: 10

Trp Gly Xaa Gly Xaa Xaa Xaa Thr Val Ser Ser
1               5                   10

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu or Asp
<220> FEATURE:
<221> NAME/KEY: MOD_RES
<222> LOCATION: (3)..(3)
<223> OTHER INFORMATION: Val or Gln
<220> FEATURE:
<221> NAME/KEY: MOD_RES
<222> LOCATION: (9)..(9)
<223> OTHER INFORMATION: Asp or Ser
<220> FEATURE:
<221> NAME/KEY: MOD_RES
<222> LOCATION: (10)..(10)
<223> OTHER INFORMATION: Ser or Thr
<220> FEATURE:
<221> NAME/KEY: MOD_RES
<222> LOCATION: (11)..(11)
<223> OTHER INFORMATION: Leu or Val
<220> FEATURE:
<221> NAME/KEY: MOD_RES
<222> LOCATION: (12)..(12)
<223> OTHER INFORMATION: Ala or Ser
<220> FEATURE:
<221> NAME/KEY: MOD_RES
<222> LOCATION: (13)..(13)
<223> OTHER INFORMATION: Val or Ala
<220> FEATURE:
<221> NAME/KEY: MOD_RES
<222> LOCATION: (14)..(14)
<223> OTHER INFORMATION: Ser or Thr
<220> FEATURE:
<221> NAME/KEY: MOD_RES
<222> LOCATION: (15)..(15)
<223> OTHER INFORMATION: Leu, Val or Arg
<220> FEATURE:
<221> NAME/KEY: MOD_RES
<222> LOCATION: (17)..(17)
<223> OTHER INFORMATION: Glu or Asp
<220> FEATURE:
<221> NAME/KEY: MOD_RES
<222> LOCATION: (19)..(19)
```

```
<223> OTHER INFORMATION: Ala or Val
<220> FEATURE:
<221> NAME/KEY: MOD_RES
<222> LOCATION: (20)..(20)
<223> OTHER INFORMATION: Thr or Ser
<220> FEATURE:
<221> NAME/KEY: MOD_RES
<222> LOCATION: (22)..(22)
<223> OTHER INFORMATION: Asn, Thr, Gln, Asp or Arg
<220> FEATURE:
<221> NAME/KEY: MOD_RES
<222> LOCATION: (24)..(24)
<223> OTHER INFORMATION: Lys or Arg

<400> SEQUENCE: 11

Xaa Ile Xaa Met Thr Gln Ser Pro Xaa Xaa Xaa Xaa Xaa Xaa Gly
1               5                   10                  15

Xaa Arg Xaa Xaa Ile Xaa Cys Xaa Ser Ser
            20                  25

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Gln or Lys
<220> FEATURE:
<221> NAME/KEY: MOD_RES
<222> LOCATION: (9)..(9)
<223> OTHER INFORMATION: Pro or Ala

<400> SEQUENCE: 12

Trp Tyr Gln Gln Lys Pro Gly Xaa Xaa Pro Lys Leu Leu Ile Tyr
1               5                   10                  15

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Asp, Glu or Ser
<220> FEATURE:
<221> NAME/KEY: MOD_RES
<222> LOCATION: (24)..(24)
<223> OTHER INFORMATION: Ala or Pro
<220> FEATURE:
<221> NAME/KEY: MOD_RES
<222> LOCATION: (27)..(27)
<223> OTHER INFORMATION: Val, Phe, Lys or Asp
<220> FEATURE:
<221> NAME/KEY: MOD_RES
<222> LOCATION: (29)..(29)
<223> OTHER INFORMATION: Val or Thr

<400> SEQUENCE: 13

Gly Val Pro Xaa Arg Phe Ser Gly Ser Gly Ser Gly Thr Asp Phe Thr
1               5                   10                  15

Leu Thr Ile Ser Ser Leu Gln Xaa Glu Asp Xaa Ala Xaa Tyr Tyr Cys
            20                  25                  30

<210> SEQ ID NO 14
```

-continued

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Gly, Gln, Thr, Ser or Asn
<220> FEATURE:
<221> NAME/KEY: MOD_RES
<222> LOCATION: (7)..(7)
<223> OTHER INFORMATION: Leu or Val
<220> FEATURE:
<221> NAME/KEY: MOD_RES
<222> LOCATION: (8)..(8)
<223> OTHER INFORMATION: Asp or Glu

<400> SEQUENCE: 14

Phe Gly Xaa Gly Thr Lys Xaa Xaa Ile Lys
1               5                   10

<210> SEQ ID NO 15
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Gly Met His Trp Val Arg Gln Pro Pro Gly Lys Gly Leu Glu Trp Val
        35                  40                  45

Ala Val Ile Ser Tyr Asp Gly Ser Tyr Lys Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Gly Trp Leu Ser
            100                 105                 110

Gln Gly Tyr Phe Asn Pro Trp Gly Ala Gly Thr Thr Leu Thr Val Ser
        115                 120                 125

Ser

<210> SEQ ID NO 16
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
```

```
                35                  40                  45
Ala Val Val Ser Tyr Asp Gly Ser Asn Lys Tyr Tyr Ala Asp Ser Val
 50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Thr Lys Leu Arg Ser Leu Leu Tyr Phe Glu Trp Leu Ser
                100                 105                 110

Ser Gly Leu Leu Asp Tyr Trp Gly Gln Gly Ala Met Val Thr Val Ser
            115                 120                 125

Ser

<210> SEQ ID NO 17
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Glu Val Gln Leu Leu Glu Ser Gly Gly Gly Leu Val Lys Pro Gly Gln
 1               5                  10                  15

Ser Leu Lys Leu Ser Cys Ala Ala Ser Gly Phe Thr Phe Thr Ser Tyr
                20                  25                  30

Gly Met His Trp Val Arg Gln Pro Pro Gly Lys Gly Leu Glu Trp Val
            35                  40                  45

Ala Val Val Ser Tyr Asp Gly Asn Tyr Lys Tyr Tyr Ala Asp Ser Val
 50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Arg Leu Arg Ser Leu Leu Tyr Phe Glu Trp Leu Ser
                100                 105                 110

Gln Gly Tyr Phe Asn Pro Trp Gly Ala Gly Thr Thr Leu Thr Val Ser
            115                 120                 125

Ser

<210> SEQ ID NO 18
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Glu Val Gln Leu Leu Glu Ser Gly Gly Gly Leu Val Lys Pro Gly Gln
 1               5                  10                  15

Ser Leu Lys Leu Ser Cys Ala Ala Ser Gly Phe Thr Phe Thr Ser Tyr
                20                  25                  30

Gly Met His Trp Val Arg Gln Pro Pro Gly Lys Gly Leu Glu Trp Val
            35                  40                  45

Ala Val Leu Ser Tyr Asp Gly Asn Tyr Lys Tyr Tyr Ala Asp Ser Val
 50                  55                  60
```

-continued

```
Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
        115                 120                 125

Ser

<210> SEQ ID NO 19
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Gln Leu Leu Glu Ser Gly Gly Gly Leu Val Lys Pro Gly Gln
  1               5                  10                  15

Ser Leu Lys Leu Ser Cys Ala Ala Ser Gly Phe Thr Phe Thr Thr Tyr
             20                  25                  30

Ala Met His Trp Val Arg Gln Pro Pro Gly Lys Gly Leu Glu Trp Val
         35                  40                  45

Ala Val Leu Ser Tyr Asp Gly Asn Tyr Lys Tyr Tyr Ala Asp Ser Val
     50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
        115                 120                 125

Ser

<210> SEQ ID NO 20
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Leu Glu Ser Gly Gly Gly Leu Val Lys Pro Gly Gln
  1               5                  10                  15

Ser Leu Lys Leu Ser Cys Ala Ala Ser Gly Phe Thr Phe Thr Thr Tyr
             20                  25                  30

Ala Met His Trp Val Arg Gln Pro Pro Gly Lys Gly Leu Glu Trp Val
         35                  40                  45

Ala Val Val Ser Phe Asp Gly Asn Asn Arg Tyr Tyr Ala Asp Ser Val
     50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

```
Ala Lys Asp Ser Gln Leu Arg Ser Leu Leu Tyr Phe Glu Trp Leu Ser
            100                 105                 110

Ser Gly Val Leu Asp Tyr Trp Gly Gln Gly Ala Met Val Thr Val Ser
            115                 120                 125

Ser
```

<210> SEQ ID NO 21
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Asn Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
            115                 120                 125

Ser
```

<210> SEQ ID NO 22
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Thr Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
            115                 120                 125
```

115                 120                 125
Ser

<210> SEQ ID NO 23
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
                20                  25                  30

Gly Met His Trp Val Arg Gln Pro Pro Gly Lys Gly Leu Glu Trp Val
            35                  40                  45

Ala Val Val Ser Tyr Asp Gly Asn Tyr Lys Tyr Tyr Ala Asp Ser Val
        50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Lys Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
        115                 120                 125

Ser

<210> SEQ ID NO 24
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
                20                  25                  30

Ala Met His Trp Val Arg Gln Pro Pro Gly Lys Gly Leu Glu Trp Val
            35                  40                  45

Ala Val Val Ser Tyr Asp Gly Asn Tyr Lys Tyr Tyr Ala Asp Ser Val
        50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Leu Thr Val Ser
        115                 120                 125

Ser

<210> SEQ ID NO 25
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Gln Val Gln Leu Leu Glu Thr Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Leu Thr Val Ser
        115                 120                 125

Ser

<210> SEQ ID NO 26
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Thr Leu Leu Tyr Phe Glu Trp Leu Ser
            100                 105                 110

Gln Gly Tyr Phe Asn Pro Trp Gly Gln Gly Thr Thr Leu Thr Val Ser
        115                 120                 125

Ser

<210> SEQ ID NO 27
<211> LENGTH: 129
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 27

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Thr Leu Leu Tyr Phe Glu Trp Leu Ser
            100                 105                 110

Gln Gly Tyr Phe Asp Pro Trp Gly Gln Gly Thr Thr Leu Thr Val Ser
        115                 120                 125

Ser

<210> SEQ ID NO 28
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Tyr Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys
            100                 105                 110

<210> SEQ ID NO 29
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Phe Ser
            20                  25                  30

```
Tyr Lys Asn Tyr Leu Ala Trp Tyr Gln Gln Lys Pro Gly Gln Pro Pro
            35                  40                  45

Lys Leu Leu Ile Tyr Trp Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Tyr Tyr
                 85                  90                  95

Arg Thr Pro Pro Thr Phe Gly Gly Gly Thr Lys Leu Asp Ile Lys
                100                 105                 110

<210> SEQ ID NO 30
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Thr Phe Asp
                 20                  25                  30

Tyr Lys Asn Tyr Leu Ala Trp Tyr Gln Gln Lys Pro Gly Gln Pro Pro
            35                  40                  45

Lys Leu Leu Ile Tyr Trp Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Tyr Tyr
                 85                  90                  95

Arg Thr Pro Pro Thr Phe Gly Gly Gly Thr Lys Leu Asp Ile Lys
                100                 105                 110

<210> SEQ ID NO 31
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Ile Val Met Thr Gln Ser Pro Asp Ser Leu Ala Val Ser Leu Gly
 1               5                  10                  15

Glu Arg Ala Thr Ile Asn Cys Lys Ser Ser Gln Thr Val Thr Phe Asn
                 20                  25                  30

Tyr Lys Asn Tyr Leu Ala Trp Tyr Gln Gln Lys Pro Gly Gln Pro Pro
            35                  40                  45

Lys Leu Leu Ile Tyr Trp Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                 85                  90                  95

Arg Thr Pro Pro Ser Phe Gly Gly Gly Thr Lys Leu Asp Ile Lys
                100                 105                 110
```

<210> SEQ ID NO 32
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gly Gly Thr Lys Leu Asp Ile Lys
            100                 105                 110

<210> SEQ ID NO 33
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Phe Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gly Gly Thr Lys Leu Asp Ile Lys
            100                 105                 110

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Phe Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gly Gly Thr Lys Leu Asp Ile Lys
                100                 105                 110

<210> SEQ ID NO 35
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Thr Trp Ser
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys
                100                 105                 110

<210> SEQ ID NO 36
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Ile Val Met Ser Gln Ser Pro Asp Thr Leu Ala Val Thr Leu Gly
 1               5                  10                  15

Glu Arg Ala Ser Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Val Leu Ile Tyr Trp Ala Ser Ala Arg Glu Thr Gly Val Pro Glu
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                85                  90                  95

-continued

Arg Thr Pro Pro Ser Phe Gly Gln Gly Thr Lys Leu Glu Ile Lys
                100                 105                 110

<210> SEQ ID NO 37
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Ser Gly Thr Lys Leu Asp Ile Lys
                100                 105                 110

<210> SEQ ID NO 38
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Ser Gly Thr Lys Leu Asp Ile Lys
                100                 105                 110

<210> SEQ ID NO 39
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Ile Val Met Thr Gln Ser Pro Asp Ser Leu Ala Val Ser Leu Gly

```
                1               5                  10                  15
Glu Arg Ala Thr Ile Asn Cys Lys Ser Ser Gln Thr Val Thr Phe Asn
                20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
                100                 105                 110

<210> SEQ ID NO 40
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Val Thr Phe Asn
                20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Asn Gly Thr Lys Leu Asp Ile Lys
                100                 105                 110

<210> SEQ ID NO 41
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
                20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
```

```
                85                  90                  95
Arg Thr Pro Pro Ser Phe Gly Thr Gly Thr Lys Leu Asp Ile Lys
            100                 105                 110

<210> SEQ ID NO 42
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Ser Gly Thr Lys Leu Asp Ile Lys
            100                 105                 110

<210> SEQ ID NO 43
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 44
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44
```

```
Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Thr Leu Ser Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Asn Gly Thr Lys Leu Asp Ile Lys
            100                 105                 110
```

<210> SEQ ID NO 45
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110
```

<210> SEQ ID NO 46
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Gly Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
50                  55                  60

Arg Phe Ser Gly Ser Gly Ser Gly Thr Asp Phe Thr Leu Thr Ile Ser
65                  70                  75                  80
```

```
Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 47
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Asp Ile Val Met Thr Gln Ser Pro Asp Thr Leu Ala Val Thr Leu Gly
1               5                   10                  15

Glu Arg Ala Thr Ile Gln Cys Lys Ser Ser Gln Thr Val Thr Phe Asn
            20                  25                  30

Tyr Lys Asn Tyr Leu Ala Trp Tyr Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Thr
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 48
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Asp Ile Val Met Thr Gln Ser Pro Asp Thr Val Ala Val Thr Val Gly
1               5                   10                  15

Glu Arg Ala Thr Ile Asn Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 49
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 49

Asp Ile Val Met Thr Gln Ser Pro Asp Thr Val Ala Val Thr Leu Gly
1               5                   10                  15

Glu Arg Ala Thr Ile Asp Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 50
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Ile Val Met Thr Gln Ser Pro Asp Thr Leu Ala Val Thr Val Gly
1               5                   10                  15

Glu Arg Ala Thr Ile Arg Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln His Tyr
                85                  90                  95

Arg Thr Pro Pro Ser Phe Gly Gln Gly Thr Lys Leu Asp Ile Lys
            100                 105                 110

<210> SEQ ID NO 51
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Val Met Thr Gln Ser Pro Asp Thr Leu Ala Val Ser Arg Gly
1               5                   10                  15

Glu Arg Ala Thr Ile Asp Cys Lys Ser Ser Gln Thr Val Thr Phe Asn
            20                  25                  30

Tyr Lys Asn Tyr Leu Ala Trp Tyr Gln Gln Lys Pro Gly Gln Pro Pro
        35                  40                  45

Lys Leu Leu Ile Tyr Trp Ala Ser Thr Arg Glu Ser Gly Val Pro Asp
    50                  55                  60

```
Arg Phe Ser Gly Ser Gly Ser Gly Thr Asp Phe Thr Leu Thr Ile Ser
 65                  70                  75                  80

Ser Leu Gln Ala Glu Asp Glu Ala Val Tyr Tyr Cys Gln Gln His Tyr
                 85                  90                  95

Arg Thr Pro Pro Ser Phe Gly Gln Gly Thr Lys Leu Asp Ile Lys
                100                 105                 110

<210> SEQ ID NO 52
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Thr Phe Asp
                20                  25                  30

Tyr Lys Asn Tyr Leu Ala Trp Tyr Gln Gln Lys Pro Gly Lys Ala Pro
             35                  40                  45

Lys Leu Leu Ile Tyr Trp Gly Ser Tyr Leu Glu Ser Gly Val Pro Ser
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
                100                 105                 110

<210> SEQ ID NO 53
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Thr Phe Asn
                20                  25                  30

Tyr Lys Asn Tyr Leu Ala Trp Tyr Gln Gln Lys Pro Gly Lys Ala Pro
             35                  40                  45

Lys Leu Leu Ile Tyr Trp Gly Ser Thr Leu Glu Ser Gly Val Pro Ser
     50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
                100                 105                 110

<210> SEQ ID NO 54
<211> LENGTH: 111
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser His Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 55
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Lys Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 56
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Asp Leu Glu Ser Gly Val Pro Ser

```
                    50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                     85                  90                  95

Arg Thr Pro Pro Ser Phe Gly Gln Gly Thr Lys Val Glu Ile Lys
                100                 105                 110

<210> SEQ ID NO 57
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Asp Ile Gln Met Thr Gln Ser Pro Ser Ser Leu Ser Ala Ser Val Gly
  1               5                  10                  15

Asp Arg Val Thr Ile Thr Cys Arg Ser Ser Gln Ser Ile Thr Phe Asn
                 20                  25                  30

Tyr Lys Asn Tyr Leu Ala Trp Tyr Gln Gln Lys Pro Gly Lys Ala Pro
             35                  40                  45

Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Val Ala Thr Tyr Tyr Cys Gln Gln His Tyr
                     85                  90                  95

Arg Thr Pro Pro Ser Phe Gly Gln Gly Thr Lys Val Glu Ile Lys
                100                 105                 110

<210> SEQ ID NO 58
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Ser Leu Ser Ala Ser Val Gly
  1               5                  10                  15

Asp Arg Val Thr Ile Thr Cys Arg Ser Ser Gln Ser Ile Thr Phe Asn
                 20                  25                  30

Tyr Lys Asn Tyr Leu Ala Trp Tyr Gln Gln Lys Pro Gly Lys Ala Pro
             35                  40                  45

Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Lys Ala Thr Tyr Tyr Cys Gln Gln His Tyr
                     85                  90                  95

Arg Thr Pro Pro Ser Phe Gly Gln Gly Thr Lys Val Glu Ile Lys
                100                 105                 110

<210> SEQ ID NO 59
<211> LENGTH: 111
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Asp Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 60
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Tyr Tyr
                85                  90                  95

Arg Thr Pro Pro Ser Phe Gly Gln Gly Thr Lys Val Glu Ile Lys
            100                 105                 110

<210> SEQ ID NO 61
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Asn
            20                  25                  30

Tyr Lys Asn Tyr Leu Ala Trp Tyr Gln Gln Lys Pro Gly Lys Ala Pro
        35                  40                  45

```
Lys Leu Leu Ile Tyr Trp Gly Ser Thr Arg Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
                100                 105                 110

<210> SEQ ID NO 62
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Thr Phe Asn
                 20                  25                  30

Tyr Lys Asn Tyr Leu Ala Trp Tyr Gln Gln Lys Pro Gly Lys Ala Pro
             35                  40                  45

Lys Leu Leu Ile Tyr Trp Gly Ser Thr Arg Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
                100                 105                 110

<210> SEQ ID NO 63
<211> LENGTH: 405
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
gaggtacagc tcctcgaatc gggaggggga ctggtcaaac ccggtcaatc gctcaaactc      60
tcgtgtgcag cgtcaggttt tacgttcagc tcatatggga tgcactgggt ccgccagcct    120
ccgggaaagg gactggagtg gtggcagtc gtgtcgtatg acgggagcaa taagtactac    180
gccgattcag tgcaaggtcg gtttaccatt tcgagggata acagcaagaa cacgctctac    240
ttgcagatga actcacttag agcggaagat acggctgtgt actattgcgc caaagacaca    300
aagctgcgat ccctgttgta cttcgaatgg ttgtcctcgg gcttgcttga ctattggggg    360
cagggcgcca tggtcacagt atccagcgcg tcgactaagg ggccc                    405

<210> SEQ ID NO 64
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 64

```
gagatcgtga tgacgcagag ccccgatagc ctcgctgtct cattggggga acgggccacg    60
attaactgca aatcctcaca gtcggtgact ttcagctata agaattacct ggcatggtat   120
cagcagaagc cgggtcaacc cccaaaactg ttgatctact gggcctccac acgcgagtcg   180
ggagtcccgg accgattttc gggttcaggg tccggcactg actttaccct cacaatttca   240
tcgcttcaag cggaggatgt agcagtgtac tattgtcagc agtattacag aacacctccc   300
accttcggag ggggaacgaa acttgacatc aagggatcc                          339
```

<210> SEQ ID NO 65
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 65

```
gagatcgtga tgacgcagag ccccgatagc ctcgctgtct cattggggga acgggccacg    60
attaactgca aatcctcaca gtcggtgact ttcgactata agaattacct ggcatggtat   120
cagcagaagc cgggtcaacc cccaaaactg ttgatctact gggcctccac acgcgagtcg   180
ggagtcccgg accgattttc gggttcaggg tccggcactg actttaccct cacaatttca   240
tcgcttcaag cggaggatgt agcagtgtac tattgtcagc agtattacag aacacctccc   300
accttcggag ggggaacgaa acttgacatc aagggatcc                          339
```

<210> SEQ ID NO 66
<211> LENGTH: 405
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

```
gaagtgcaac tcctcgagtc aggaggaggt ttggtgaaac cgggtcagtc cttgaaactg    60
agctgtgcag caagcgggtt cacgtttacg tcgtacggca tgcactgggt acggcagcct   120
cccgggaagg gacttgaatg ggtcgccgtc atctcatacg acgggtcgta caaatactat   180
gcggatagcg tgcaaggtcg cttcacaatt tcccgggaca attcgaagaa tacactgtat   240
cttcagatga actcgctcag ggctgaggac acggcggtct attactgcgc gaaggattcg   300
cgactcagat cccttttgta ctttgagtgg ctgtcgcagg ggtatttcaa cccatgggga   360
gccggaacca ctttgaccgt atcaagcgcg tcaacaaagg ggccc                   405
```

<210> SEQ ID NO 67
<211> LENGTH: 654
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
gaaattgtaa tgacgcagag ccctgatagc cttgccgtgt ccctgggtga gagggcgaca    60
atcaattgta agtcatcaca gtcggtcacg tacaactaca agaactacct ggcgtggtat   120
caacagaaac ccgggcagcc gcccaaattg ctcatctatt gggcttcgac acgggagtcg   180
```

```
ggtgtgccag accgcttctc cgggtcagga tcgggaactg acttcacgtt gactatttcg    240
tccctccagg cagaagatgt agccgtctac tattgccaac agtattacag aacgccgcct    300
acatttggag gcgggaccaa acttgacatc aagggatccg tggccgcccc cagcgtcttc    360
atcttcccgc ccagcgacga gcagctgaag tcgggcacgg ccagcgtggt gtgcctcctg    420
aacaacttct accccgcga ggcgaaggtc cagtggaagg tggacaacgc cctgcagagc    480
gggaacagcc aggagagcgt gaccgagcag gactcgaagg acagcaccta cagcctcagc    540
agcaccctga cgctgagcaa ggccgactac gagaagcaca aggtctacgc ctgcgaggtg    600
acccaccagg ggctctcgag ccccgtgacc aagagcttca ccggggcga gtgc          654
```

```
<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Tyr Ala Met His
1               5

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Val Val Ser Tyr Asp Gly Asn Tyr Lys Tyr Tyr Ala Asp Ser Val Gln
1               5                   10                  15

Gly

<210> SEQ ID NO 70
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Asp Ser Arg Leu Arg Ser Leu Leu Tyr Phe Glu Trp Leu Ser Gln Gly
1               5                   10                  15

Tyr Phe Asn Pro
            20

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Ser Ile Thr Phe Asn Tyr Lys Asn Tyr Leu Ala
1               5                   10

<210> SEQ ID NO 72
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Trp Gly Ser Tyr Leu Glu Ser
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Gln His Tyr Arg Thr Pro Pro Ser
1               5

<210> SEQ ID NO 74
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Gln Leu Leu Glu Thr Gly Gly Gly Leu Val Lys Pro Gly Gln
1               5                   10                  15

Ser Leu Lys Leu Ser Cys Ala Ala Ser Gly Phe Thr Phe Thr
            20                  25                  30

<210> SEQ ID NO 75
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Trp Val Arg Gln Pro Pro Gly Lys Gly Leu Glu Trp Val Ala
1               5                   10

<210> SEQ ID NO 76
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 77
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 77

Trp Gly Gln Gly Thr Thr Leu Thr Val Ser Ser
1               5                   10

<210> SEQ ID NO 78
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ser Ser
            20                  25

<210> SEQ ID NO 79
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Trp Tyr Gln Gln Lys Pro Gly Lys Ala Pro Lys Leu Leu Ile Tyr
1               5                   10                  15

<210> SEQ ID NO 80
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Phe Gly Gln Gly Thr Lys Val Glu Ile Lys
1               5                   10

<210> SEQ ID NO 82
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 82

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr
            20                  25                  30

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Lys Ser Ser Gln Ser Val Thr Tyr Asn Tyr Lys Asn Tyr Leu Ala
1               5                   10                  15

<210> SEQ ID NO 84
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Trp Ala Ser Thr Arg Glu Ser
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gln Gln Tyr Tyr Arg Thr Pro Pro Thr
1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Tyr Gly Met His
1               5

<210> SEQ ID NO 87
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Val Ile Ser Tyr Asp Gly Ser Tyr Lys Tyr Tyr Ala Asp Ser Val Gln
1               5                   10                  15

Gly

<210> SEQ ID NO 88
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Asp Ser Glu Leu Arg Ser Leu Leu Tyr Phe Glu Trp Leu Ser Gln Gly
1               5                   10                  15

Tyr Phe Asn Pro
            20

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Trp Gly Ala Gly Thr Thr Leu Thr Val Ser Ser
1               5                   10

<210> SEQ ID NO 90
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Glu Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 91
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Trp Tyr Gln Gln Lys Pro Gly Gln Pro Pro Lys Leu Leu Ile Tyr
1               5                   10                  15

<210> SEQ ID NO 92
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys

```
              20                  25                  30
```

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Phe Gly Gly Gly Thr Lys Leu Asp Ile Lys
1               5                   10

<210> SEQ ID NO 94
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr Ser Tyr
            20                  25                  30

Gly Met His Trp Val Arg Gln Pro Gly Lys Gly Leu Glu Trp Val
        35                  40                  45

Ala Val Ile Ser Tyr Asp Gly Ser Tyr Lys Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Ala Gly Thr Thr Leu Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro
225                 230                 235                 240

Pro Cys Pro Gly Thr Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe

```
                275                 280                 285
Asn Trp Tyr Val Asp Gly Val Glu Val His Asn Ala Lys Thr Lys Pro
    290                 295                 300
Arg Glu Glu Gln Tyr Asn Ser Thr Tyr Arg Val Val Ser Val Leu Thr
305                 310                 315                 320
Val Leu His Gln Asp Trp Leu Asn Gly Lys Glu Tyr Lys Cys Lys Val
                325                 330                 335
Ser Asn Lys Ala Leu Pro Ala Pro Ile Glu Lys Thr Ile Ser Lys Ala
            340                 345                 350
Lys Gly Gln Pro Arg Glu Pro Gln Val Tyr Thr Leu Pro Pro Ser Arg
            355                 360                 365
Asp Glu Leu Thr Lys Asn Gln Val Ser Leu Thr Cys Leu Val Lys Gly
        370                 375                 380
Phe Tyr Pro Ser Asp Ile Ala Val Glu Trp Glu Ser Asn Gly Gln Pro
385                 390                 395                 400
Glu Asn Asn Tyr Lys Thr Thr Pro Pro Val Leu Asp Ser Asp Gly Ser
                405                 410                 415
Phe Phe Leu Tyr Ser Lys Leu Thr Val Asp Lys Ser Arg Trp Gln Gln
            420                 425                 430
Gly Asn Val Phe Ser Cys Ser Val Met His Glu Ala Leu His Asn His
        435                 440                 445
Tyr Thr Gln Lys Ser Leu Ser Leu Ser Pro Gly Lys
    450                 455                 460

<210> SEQ ID NO 95
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Thr Tyr Asn
            20                  25                  30
Tyr Lys Asn Tyr Leu Ala Trp Tyr Gln Gln Lys Pro Gly Gln Pro Pro
        35                  40                  45
Lys Leu Leu Ile Tyr Trp Ala Ser Thr Arg Glu Ser Gly Val Pro Asp
    50                  55                  60
Arg Phe Ser Gly Ser Gly Ser Gly Thr Asp Phe Thr Leu Thr Ile Ser
65                  70                  75                  80
Ser Leu Gln Ala Glu Asp Val Ala Val Tyr Tyr Cys Gln Gln Tyr Tyr
                85                  90                  95
Arg Thr Pro Pro Thr Phe Gly Gly Gly Thr Lys Leu Asp Ile Lys Gly
            100                 105                 110
Ser Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
                165                 170                 175
```

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215

<210> SEQ ID NO 96
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Gly Met His Trp Val Arg Gln Pro Pro Gly Lys Gly Leu Glu
        35                  40                  45

Trp Val Ala Val Ile Ser Tyr Asp Gly Ser Tyr Lys Tyr Tyr Ala Asp
50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Ala Gly Thr Thr Leu Thr
            115                 120                 125

Val Ser Ser
    130

<210> SEQ ID NO 97
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Ser
            20                  25                  30

Ser Tyr Gly Met His Trp Val Arg Gln Pro Pro Gly Lys Gly Leu Glu
        35                  40                  45

Trp Val Ala Val Val Ser Tyr Asp Gly Ser Asn Lys Tyr Tyr Ala Asp
50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Thr Lys Leu Arg Ser Leu Leu Tyr Phe Glu Trp
            100                 105                 110
```

Leu Ser Ser Gly Leu Leu Asp Tyr Trp Gly Gln Gly Ala Met Val Thr
            115                 120                 125

Val Ser Ser
    130

<210> SEQ ID NO 98
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Gly Met His Trp Val Arg Gln Pro Pro Gly Lys Gly Leu Glu
        35                  40                  45

Trp Val Ala Val Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Ala Gly Thr Thr Leu Thr
            115                 120                 125

Val Ser Ser
    130

<210> SEQ ID NO 99
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Gly Met His Trp Val Arg Gln Pro Pro Gly Lys Gly Leu Glu
        35                  40                  45

Trp Val Ala Val Leu Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Ala Gly Thr Thr Leu Thr
            115                 120                 125

Val Ser Ser
    130

<210> SEQ ID NO 100
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Thr Tyr Ala Met His Trp Val Arg Gln Pro Pro Gly Lys Gly Leu Glu
        35                  40                  45

Trp Val Ala Val Leu Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Ala Gly Thr Thr Leu Thr
        115                 120                 125

Val Ser Ser
    130

<210> SEQ ID NO 101
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Ser
            20                  25                  30

Ser Tyr Gly Met His Trp Val Arg Gln Pro Pro Gly Lys Gly Leu Glu
        35                  40                  45

Trp Val Ala Val Val Ser Tyr Asp Gly Asn Asn Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Lys Leu Arg Ser Leu Leu Tyr Phe Glu Trp
            100                 105                 110

Leu Ser Ser Gly Leu Leu Asp Tyr Trp Gly Gln Gly Ala Met Val Thr
        115                 120                 125

Val Ser Ser
    130

<210> SEQ ID NO 102
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Thr Tyr Ala Met His Trp Val Arg Gln Pro Pro Gly Lys Gly Leu Glu
        35                  40                  45

Trp Val Ala Val Val Ser Tyr Asp Gly Asn Asn Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Lys Leu Arg Ser Leu Leu Tyr Phe Glu Trp
            100                 105                 110

Leu Ser Ser Gly Leu Leu Asp Tyr Trp Gly Gln Gly Ala Met Val Thr
        115                 120                 125

Val Ser Ser
    130

<210> SEQ ID NO 103
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Thr Tyr Ala Met His Trp Val Arg Gln Pro Pro Gly Lys Gly Leu Glu
        35                  40                  45

Trp Val Ala Val Val Ser Phe Asp Gly Asn Asn Arg Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Gln Leu Arg Ser Leu Leu Tyr Phe Glu Trp
            100                 105                 110

Leu Ser Ser Gly Val Leu Asp Tyr Trp Gly Gln Gly Ala Met Val Thr
        115                 120                 125

Val Ser Ser
    130

<210> SEQ ID NO 104
<211> LENGTH: 131

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Gly Met His Trp Val Arg Gln Pro Pro Gly Lys Gly Leu Glu
        35                  40                  45

Trp Val Ala Val Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Lys Leu Arg Ser Leu Leu Tyr Phe Glu Trp
            100                 105                 110

Leu Ser Gln Gly Tyr Phe Asn Pro Trp Gly Ala Gly Thr Thr Leu Thr
        115                 120                 125

Val Ser Ser
    130

<210> SEQ ID NO 105
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Ala Met His Trp Val Arg Gln Pro Pro Gly Lys Gly Leu Glu
        35                  40                  45

Trp Val Ala Val Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Gln Gly Thr Thr Leu Thr
        115                 120                 125

Val Ser Ser
    130

<210> SEQ ID NO 106
<211> LENGTH: 131
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 106

```
Ile Asp Gln Val Gln Leu Leu Glu Thr Gly Gly Leu Val Lys Pro
1               5                   10                  15

Gly Gln Ser Leu Lys Leu Ser Cys Ala Ala Ser Gly Phe Thr Phe Thr
                20                  25                  30

Ser Tyr Ala Met His Trp Val Arg Gln Pro Pro Gly Lys Gly Leu Glu
            35                  40                  45

Trp Val Ala Val Val Ser Tyr Asp Gly Asn Tyr Lys Tyr Tyr Ala Asp
        50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Ser Leu Leu Tyr Phe Glu Trp
            100                 105                 110

Leu Ser Gln Gly Tyr Phe Asn Pro Trp Gly Gln Gly Thr Thr Leu Thr
        115                 120                 125

Val Ser Ser
    130
```

<210> SEQ ID NO 107
<211> LENGTH: 131
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 107

```
Ile Asp Glu Val Gln Leu Leu Glu Ser Gly Gly Leu Val Lys Pro
1               5                   10                  15

Gly Gln Ser Leu Lys Leu Ser Cys Ala Ala Ser Gly Phe Thr Phe Thr
                20                  25                  30

Ser Tyr Ala Met His Trp Val Arg Gln Pro Pro Gly Lys Gly Leu Glu
            35                  40                  45

Trp Val Ala Val Val Ser Tyr Asp Gly Asn Tyr Lys Tyr Tyr Ala Asp
        50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Gln Leu Arg Thr Leu Leu Tyr Phe Glu Trp
            100                 105                 110

Leu Ser Gln Gly Tyr Phe Asn Pro Trp Gly Gln Gly Thr Thr Leu Thr
        115                 120                 125

Val Ser Ser
    130
```

<210> SEQ ID NO 108
<211> LENGTH: 131
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 108

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Thr
            20                  25                  30

Ser Tyr Ala Met His Trp Val Arg Gln Pro Pro Gly Lys Gly Leu Glu
        35                  40                  45

Trp Val Ala Val Val Ser Tyr Asp Gly Asn Tyr Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Arg Leu Arg Thr Leu Leu Tyr Phe Glu Trp
            100                 105                 110

Leu Ser Gln Gly Tyr Phe Asp Pro Trp Gly Gln Gly Thr Thr Leu Thr
            115                 120                 125

Val Ser Ser
    130

<210> SEQ ID NO 109
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Ile Asp Glu Val Gln Leu Leu Glu Ser Gly Gly Gly Leu Val Lys Pro
1               5                   10                  15

Gly Gln Ser Leu Lys Leu Ser Cys Ala Ala Ser Gly Phe Thr Phe Ser
            20                  25                  30

Ser Tyr Gly Met His Trp Val Arg Gln Pro Pro Gly Lys Gly Leu Glu
        35                  40                  45

Trp Val Ala Val Val Ser Tyr Asp Gly Ser Asn Lys Tyr Tyr Ala Asp
    50                  55                  60

Ser Val Gln Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Asp Ser Lys Leu Arg Ser Leu Leu Tyr Phe Glu Trp
            100                 105                 110

Leu Ser Ser Gly Leu Leu Asp Tyr Trp Gly Gln Gly Ala Met Val Thr
            115                 120                 125

Val Ser Ser
    130

<210> SEQ ID NO 110
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Ile Asp Glu Ile Val Met Thr Gln Ser Pro Asp Ser Leu Ala Val Ser

```
              1               5                  10                 15
Leu Gly Glu Arg Ala Thr Ile Asn Cys Lys Ser Ser Gln Ser Val Thr
              20                 25                 30

Tyr Asn Tyr Lys Asn Tyr Leu Ala Trp Tyr Gln Gln Lys Pro Gly Gln
              35                 40                 45

Pro Pro Lys Leu Leu Ile Tyr Trp Ala Ser Thr Arg Glu Ser Gly Val
              50                 55                 60

Pro Asp Arg Phe Ser Gly Ser Gly Ser Gly Thr Asp Phe Thr Leu Thr
 65               70                 75                 80

Ile Ser Ser Leu Gln Ala Glu Asp Val Ala Val Tyr Tyr Cys Gln Gln
                  85                 90                 95

Tyr Tyr Arg Thr Pro Pro Thr Phe Gly Gly Gly Thr Lys Leu Asp Ile
              100                105                110

Lys

<210> SEQ ID NO 111
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Ile Asp Glu Ile Val Met Thr Gln Ser Pro Asp Ser Leu Ala Val Ser
 1               5                  10                 15

Leu Gly Glu Arg Ala Thr Ile Asn Cys Lys Ser Ser Gln Ser Val Thr
              20                 25                 30

Phe Ser Tyr Lys Asn Tyr Leu Ala Trp Tyr Gln Gln Lys Pro Gly Gln
              35                 40                 45

Pro Pro Lys Leu Leu Ile Tyr Trp Ala Ser Thr Arg Glu Ser Gly Val
              50                 55                 60

Pro Asp Arg Phe Ser Gly Ser Gly Ser Gly Thr Asp Phe Thr Leu Thr
 65               70                 75                 80

Ile Ser Ser Leu Gln Ala Glu Asp Val Ala Val Tyr Tyr Cys Gln Gln
                  85                 90                 95

Tyr Tyr Arg Thr Pro Pro Thr Phe Gly Gly Gly Thr Lys Leu Asp Ile
              100                105                110

Lys

<210> SEQ ID NO 112
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Ile Asp Glu Ile Val Met Thr Gln Ser Pro Asp Ser Leu Ala Val Ser
 1               5                  10                 15

Leu Gly Glu Arg Ala Thr Ile Asn Cys Lys Ser Ser Gln Ser Val Thr
              20                 25                 30

Phe Asp Tyr Lys Asn Tyr Leu Ala Trp Tyr Gln Gln Lys Pro Gly Gln
              35                 40                 45

Pro Pro Lys Leu Leu Ile Tyr Trp Ala Ser Thr Arg Glu Ser Gly Val
              50                 55                 60
```

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Arg Thr Pro Pro Thr Phe Gly Gly Gly Thr Lys Leu Asp Ile
            100                 105                 110

Lys
```

<210> SEQ ID NO 113
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

```
Ile Asp Glu Ile Val Met Thr Gln Ser Pro Asp Ser Leu Ala Val Ser
 1               5                  10                  15

Leu Gly Glu Arg Ala Thr Ile Asn Cys Lys Ser Ser Gln Ser Val Thr
                20                  25                  30

Trp Ser Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Arg Thr Pro Pro Thr Phe Gly Gly Gly Thr Lys Leu Asp Ile
            100                 105                 110

Lys
```

<210> SEQ ID NO 114
<211> LENGTH: 113
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

```
Ile Asp Glu Ile Val Met Thr Gln Ser Pro Asp Ser Leu Ala Val Ser
 1               5                  10                  15

Leu Gly Glu Arg Ala Thr Ile Asn Cys Lys Ser Ser Gln Thr Val Thr
                20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Gly Gly Thr Lys Leu Asp Ile
            100                 105                 110

Lys
```

<210> SEQ ID NO 115
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
                20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gly Gly Thr Lys Leu Asp Ile
            100                 105                 110

Lys

<210> SEQ ID NO 116
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
                20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Phe Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gly Gly Thr Lys Leu Asp Ile
            100                 105                 110

Lys

<210> SEQ ID NO 117
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gly Gly Thr Lys Leu Asp Ile
            100                 105                 110

Lys

<210> SEQ ID NO 118
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Ile Asp Glu Ile Val Met Ser Gln Ser Pro Asp Thr Leu Ala Val Thr
1               5                   10                  15

Leu Gly Glu Arg Ala Ser Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Val Leu Ile Tyr Trp Ala Ser Ala Arg Glu Thr Gly Val
    50                  55                  60

Pro Glu Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Glu Ile
            100                 105                 110

Lys

<210> SEQ ID NO 119
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 120
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Gly Trp Tyr Gln Gln Lys Pro Gly Lys
            35                  40                  45

Ala Pro Lys Leu Leu Ile Tyr Trp Gly Ser Tyr Leu Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 121
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Thr Gly Thr Lys Leu Asp Ile
            100                 105                 110

Lys

<210> SEQ ID NO 122
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
                20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Ser Gly Thr Lys Leu Asp Ile
            100                 105                 110

Lys

<210> SEQ ID NO 123
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
                20                  25                  30

Phe Asn Tyr Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
            100                 105                 110

Lys

<210> SEQ ID NO 124
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Asn Gly Thr Lys Leu Asp Ile
            100                 105                 110

Lys

<210> SEQ ID NO 125
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Thr Gly Thr Lys Leu Asp Ile
            100                 105                 110

Lys

<210> SEQ ID NO 126
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Ile Asp Glu Ile Val Met Thr Gln Ser Pro Asp Ser Leu Ala Val Ser
1               5                   10                  15

Leu Gly Glu Arg Ala Thr Ile Asn Cys Lys Ser Ser Gln Thr Leu Ser
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val

```
              50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Ser Gly Thr Lys Leu Asp Ile
                100                 105                 110

Lys

<210> SEQ ID NO 127
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Ile Asp Glu Ile Val Met Thr Gln Ser Pro Asp Ser Leu Ala Val Ser
  1               5                  10                  15

Leu Gly Glu Arg Ala Thr Ile Asn Cys Lys Ser Ser Gln Thr Leu Ser
                 20                  25                  30

Phe Asn Tyr Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Gln Gly Thr Lys Leu Asp Ile
                100                 105                 110

Lys

<210> SEQ ID NO 128
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Ile Asp Glu Ile Val Met Thr Gln Ser Pro Asp Ser Leu Ala Val Ser
  1               5                  10                  15

Leu Gly Glu Arg Ala Thr Ile Asn Cys Lys Ser Ser Gln Thr Leu Ser
                 20                  25                  30

Phe Asn Tyr Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

His Tyr Arg Thr Pro Pro Ser Phe Gly Asn Gly Thr Lys Leu Asp Ile
                100                 105                 110
```

Lys

<210> SEQ ID NO 129
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Ile Asp Asp Ile Val Met Thr Gln Ser Pro Asp Thr Leu Ala Val Thr
1               5                   10                  15

Leu Gly Glu Arg Ala Thr Ile Gln Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Thr Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
            100                 105                 110

Lys

<210> SEQ ID NO 130
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Ile Asp Asp Ile Val Met Thr Gln Ser Pro Asp Thr Val Ala Val Thr
1               5                   10                  15

Val Gly Glu Arg Ala Thr Ile Asn Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
            100                 105                 110

Lys

<210> SEQ ID NO 131
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 131

Ile Asp Asp Ile Val Met Thr Gln Ser Pro Asp Thr Val Ala Val Thr
1               5                   10                  15

Leu Gly Glu Arg Ala Thr Ile Asp Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
            100                 105                 110

Lys

<210> SEQ ID NO 132
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Ile Asp Asp Ile Val Met Thr Gln Ser Pro Asp Thr Leu Ala Val Thr
1               5                   10                  15

Val Gly Glu Arg Ala Thr Ile Arg Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Arg Thr Pro Pro Ser Phe Gly Gln Gly Thr Lys Leu Asp Ile
            100                 105                 110

Lys

<210> SEQ ID NO 133
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Ile Asp Asp Ile Val Met Thr Gln Ser Pro Asp Thr Leu Ala Val Ser
1               5                   10                  15

Arg Gly Glu Arg Ala Thr Ile Asp Cys Lys Ser Ser Gln Thr Val Thr
            20                  25                  30

Phe Asn Tyr Lys Asn Tyr Leu Ala Trp Tyr Gln Gln Lys Pro Gly Gln
        35                  40                  45
```

```
Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Glu Ala Val Tyr Tyr Cys Gln Gln
                85                  90                  95

His Tyr Arg Thr Pro Pro Ser Phe Gly Gln Gly Thr Lys Leu Asp Ile
                100                 105                 110

Lys

<210> SEQ ID NO 134
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
                20                  25                  30

Phe Asp Tyr Lys Asn Tyr Leu Ala Trp Tyr Gln Gln Lys Pro Gly Lys
            35                  40                  45

Ala Pro Lys Leu Leu Ile Tyr Trp Gly Ser Tyr Leu Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
                100                 105                 110

Lys

<210> SEQ ID NO 135
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
                20                  25                  30

Phe Asn Tyr Lys Asn Tyr Leu Ala Trp Tyr Gln Gln Lys Pro Gly Lys
            35                  40                  45

Ala Pro Lys Leu Leu Ile Tyr Trp Gly Ser Thr Leu Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
                100                 105                 110
```

Lys

<210> SEQ ID NO 136
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser His Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Thr Pro Pro Ser Phe Gly Gln Gly Thr Lys Val Glu Ile
            100                 105                 110

Lys

<210> SEQ ID NO 137
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Lys Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Thr Pro Pro Ser Phe Gly Gln Gly Thr Lys Val Glu Ile
            100                 105                 110

Lys

<210> SEQ ID NO 138
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Asp Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 139
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 140
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

```
Ala Pro Lys Leu Leu Ile Tyr Trp Gly Ser Tyr Leu Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Lys Ala Thr Tyr Tyr Cys Gln Gln
                 85                  90                  95

His Tyr Arg Thr Pro Pro Ser Phe Gly Gln Gly Thr Lys Val Glu Ile
            100                 105                 110

Lys

<210> SEQ ID NO 141
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Ile Asp Asp Ile Gln Met Thr Gln Ser Pro Ser Ser Leu Ser Ala Ser
 1               5                  10                  15

Val Gly Asp Arg Val Thr Ile Thr Cys Arg Ser Ser Gln Ser Ile Thr
                 20                  25                  30

Phe Asn Tyr Lys Asn Tyr Leu Ala Trp Tyr Gln Gln Lys Pro Gly Lys
             35                  40                  45

Ala Pro Lys Leu Leu Ile Tyr Trp Gly Ser Tyr Leu Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Ala Thr Tyr Tyr Cys Gln Gln
                 85                  90                  95

His Tyr Arg Thr Pro Pro Ser Phe Gly Gln Gly Thr Lys Val Glu Ile
            100                 105                 110

Lys

<210> SEQ ID NO 142
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Ile Asp Asp Ile Gln Met Thr Gln Ser Pro Ser Ser Leu Ser Ala Ser
 1               5                  10                  15

Val Gly Asp Arg Val Thr Ile Thr Cys Arg Ser Ser Gln Ser Ile Thr
                 20                  25                  30

Phe Asn Tyr Lys Asn Tyr Leu Ala Trp Tyr Gln Gln Lys Pro Gly Lys
             35                  40                  45

Ala Pro Lys Leu Leu Ile Tyr Trp Gly Ser Tyr Leu Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Tyr Arg Thr Pro Pro Ser Phe Gly Gln Gly Thr Lys Val Glu Ile
```

Lys

<210> SEQ ID NO 143
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 144
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asn Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 145
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 145

Gln Ser Ile Thr Phe Asp Tyr Lys Asn Tyr Leu Ala
1               5                   10

<210> SEQ ID NO 146
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Lys Ser Ser Gln Ser Val Thr Phe Asn Tyr Lys Asn Tyr Leu Ala
1               5                   10                  15

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Trp Ala Ser Ala Arg Glu Ser
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gln Gln His Tyr Arg Thr Pro Pro Thr
1               5

<210> SEQ ID NO 149
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149

```
gacattcaga tgactcagtc gccttcgtca ttgtccgcct ccgtgggtga tagggtcacg      60
atcacgtgcc ggagcagcca gtccatcacc ttcaattaca aaaactattt ggcatggtat     120
caacagaaac ccggaaaggc gccgaagctc ctgatctact ggggttcata tcttgagtcg     180
ggggtgccgt cgagattttc gggcagcgga tcagggacgg atttcacgct gaccatttcg     240
tcactccagc ccgaggactt tgcgacatat tactgtcaac agcactacag gacccccca     300
tctttcggac aggggactaa agtagaaatc aagggatccg tggccgcccc cagcgtcttc     360
atcttcccgc ccagcgacga gcagctgaag tcgggcacgg ccagcgtggt gtgcctcctg     420
aacaacttct accccgcgcg aggcgaaggtc cagtggaagg tggacaacgc cctgcagagc     480
gggaacagcc aggagagcgt gaccgagcag gactcgaagg acagcaccta cagcctcagc     540
agcaccctga cgctgagcaa ggccgactac gagaagcaca aggtctacgc ctgcgaggtg     600
```

```
acccaccagg ggctctcgag ccccgtgacc aagagcttca accggggcga gtgctga      657
```

<210> SEQ ID NO 150
<211> LENGTH: 663
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150

```
gacattcaga tgactcagtc gccttcgtca ttgtccgcct ccgtgggtga tagggtcacg      60
atcacgtgcc ggagcagcca gtccatcacc ttcaattaca aaaactattt ggcatggtat     120
caacagaaac ccggaaaggc gccgaagctc ctgatctact ggggttcata tcttgagtcg     180
ggggtgccgt cgagattttc gggcagcgga tcagggacgg atttcacgct gaccatttcg     240
tcactccagc ccgaggactt tgcgacatat tactgtcaac agcactacag gacacccca     300
tctttcggac aggggactaa agtagaaatc aagggatccg tggccgcccc cagcgtcttc     360
atcttcccgc cagcgacga gcagctgaag tcgggcacgg ccagcgtggt gtgcctcctg     420
aacaacttct accccgcga gcgaaggtc cagtggaagg tggacaacgc cctgcagagc      480
gggaacagcc aggagagcgt gaccgagcag gactcgaagg acagcaccta cagcctcagc     540
agcaccctga cgctgagcaa ggccgactac gagaagcaca aggtctacgc ctgcgaggtg     600
acccaccagg ggctctcgag ccccgtgacc aagagcttca accggggcga gtgctgagaa     660
ttc                                                                  663
```

<210> SEQ ID NO 151
<211> LENGTH: 1383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 151

```
caggtacaat tgcttgagac aggtggagga ctcgtgaagc caggtcagtc attgaaactg      60
agctgtgccg catccgggtt cacattcact tcctacgcga tgcactgggt ccgccagcct     120
cccggaaagg gacttgagtg gtcgctgtg gtatcgtatg atgggaatta caaatactat     180
gcagactccg tgcaaggccg gttacgatt agcagggaca actcgaagaa tacccttac      240
ctccaaatga actcgctccg agcggaggac acggcggtgt attactgcgc gaaggattca     300
cggttgagat cgctgctcta ttttgaatgg ttgtcacagg ggtacttcaa cccgtggggt     360
cagggaacaa cactgaccgt cagctcagcc tcgactaaag gcccagcgt gttcccgctg      420
gcccccagca gcaagagcac cagcggcggg accgccgccc tgggctgcct cgtcaaggac     480
tacttccccg agcccgtgac cgtgtcgtgg aacagcggcg cgctgacgag cggggtccac     540
accttcccgg ccgtgctgca gagcagcggc ctctactcgc tgagcagcgt ggtcaccgtg     600
cccagcagca gcctggggac ccagacgtac atctgcaacg tgaaccacaa gccctcgaac     660
accaaggtcg acaagaaggt ggagcccccg aagagctgcg acaaaactca cacatgccca     720
ccgtgcccag gtactgaact cctgggggga ccgtcagtct tcctcttccc cccaaaaccc     780
aaggacaccc tcatgatctc ccggacccct gaggtcacat gcgtggtggt ggacgtgagc     840
cacgaagacc ctgaggtcaa gttcaactgg tacgtggacg gcgtggaggt gcataatgcc     900
```

| | |
|---|---|
| aagacaaagc cgcgggagga gcagtacaac agcacgtacc gtgtggtcag cgtcctcacc | 960 |
| gtcctgcacc aggactggct gaatggcaag gagtacaagt gcaaggtctc caacaaagcc | 1020 |
| ctcccagccc ccatcgagaa aaccatctcc aaagccaaag gtgagcccg agaaccacag | 1080 |
| gtgtacaccc tgcccccatc ccgggatgag ctgaccaaga accaggtcag cctgacctgc | 1140 |
| ctggtcaaag gcttctatcc cagcgacatc gccgtggagt gggagagcaa tgggcagccg | 1200 |
| gagaacaact acaagaccac gcctcccgtg ctggactccg acggctcctt cttcctctac | 1260 |
| agcaagctca ccgtggacaa gagcaggtgg cagcagggga acgtcttctc atgctccgtg | 1320 |
| atgcatgagg ctctgcacaa ccactacacg cagaagagcc tctccctgtc tccgggtaaa | 1380 |
| tga | 1383 |

<210> SEQ ID NO 152
<211> LENGTH: 1383
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 152

| | |
|---|---|
| gaagtacaat tgcttgagtc gggtggagga ctcgtgaagc caggtcagtc attgaaactg | 60 |
| agctgtgccg catccgggtt cacattcact tcctacgcga tgcactgggt ccgccagcct | 120 |
| cccggaaagg gacttgagtg ggtcgctgtg gtatcgtatg atgggaatta caaatactat | 180 |
| gcagactccg tgcaaggccg gtttacgatt agcagggaca actcgaagaa tacccttttac | 240 |
| ctccaaatga actcgctccg agcggaggac acggcggtgt attactgcgc gaaggattca | 300 |
| cggttgagat cgctgctcta tttgaatgg ttgtcacagg ggtacttcaa cccgtggggt | 360 |
| cagggaacaa cactgaccgt cagctcagcc tcgactaaag gcccagcgt gttcccgctg | 420 |
| gcccccagca gcaagagcac cagcggcggg accgccgccc tgggctgcct cgtcaaggac | 480 |
| tacttccccg agcccgtgac cgtgtcgtgg aacagcggcg cgctgaccag cggggtccac | 540 |
| accttcccgg ccgtgctgca gagcagcggc ctctactcgc tgagcagcgt ggtcaccgtg | 600 |
| cccagcagca gcctggggac ccagacgtac atctgcaacg tgaaccacaa gcctcgaac | 660 |
| accaaggtcg acaagaaggt ggagcccccg aagagctgcg acggtacccca cacatgccca | 720 |
| ccgtgcccag gtactgaact cctggggga ccgtcagtct tcctcttccc cccaaaaccc | 780 |
| aaggacaccc tcatgatctc ccggacccct gaggtcacat gcgtggtggt ggacgtgagc | 840 |
| cacgaagacc ctgaggtcaa gttcaactgg tacgtggacg gcgtggaggt gcataatgcc | 900 |
| aagacaaagc cgcgggagga gcagtacaac agcacgtacc gtgtggtcag cgtcctcacc | 960 |
| gtcctgcacc aggactggct gaatggcaag gagtacaagt gcaaggtctc caacaaagcc | 1020 |
| ctcccagccc ccatcgagaa aaccatctcc aaagccaaag gtgagcccg agaaccacag | 1080 |
| gtgtacaccc tgcccccatc ccgggatgag ctgaccaaga accaggtcag cctgacctgc | 1140 |
| ctggtcaaag gcttctatcc cagcgacatc gccgtggagt gggagagcaa tgggcagccg | 1200 |
| gagaacaact acaagaccac gcctcccgtg ctggactccg acggctcctt cttcctctac | 1260 |
| agcaagctca ccgtggacaa gagcaggtgg cagcagggga acgtcttctc atgctccgtg | 1320 |
| atgcatgagg ctctgcacaa ccactacacg cagaagagcc tctccctgtc tccgggtaaa | 1380 |
| tga | 1383 |

<210> SEQ ID NO 153

```
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Gln
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 154
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Arg
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 155
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Phe Glu
            20                  25                  30
```

```
Tyr Lys Asn Tyr Leu Ala Trp Tyr Gln Gln Lys Pro Gly Lys Ala Pro
            35                  40                  45

Lys Leu Leu Ile Tyr Trp Gly Ser Tyr Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
                100                 105                 110

<210> SEQ ID NO 156
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Ser Ile Thr Phe Asp
                20                  25                  30

Tyr Lys Asn Tyr Leu Ala Trp Tyr Gln Gln Lys Pro Gly Lys Ala Pro
            35                  40                  45

Lys Leu Leu Ile Tyr Trp Gly Ser Thr Arg Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln Gln His Tyr
                 85                  90                  95

Arg Thr Pro Pro Ser Phe Gly Gln Gly Thr Lys Val Glu Ile Lys
                100                 105                 110

<210> SEQ ID NO 157
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Ile Asp Asp Ile Gln Met Thr Gln Ser Pro Ser Ser Leu Ser Ala Ser
 1               5                  10                  15

Val Gly Asp Arg Val Thr Ile Thr Cys Arg Ser Ser Gln Ser Ile Thr
                20                  25                  30

Phe Gln Tyr Lys Asn Tyr Leu Ala Trp Tyr Gln Gln Lys Pro Gly Lys
            35                  40                  45

Ala Pro Lys Leu Leu Ile Tyr Trp Gly Ser Tyr Leu Glu Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

His Tyr Arg Thr Pro Pro Ser Phe Gly Gln Gly Thr Lys Val Glu Ile
                100                 105                 110
```

Lys

<210> SEQ ID NO 158
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Arg Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 159
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Glu Tyr Lys Asn Tyr Leu Ala Trp Tyr Gln Gln Lys Pro Gly Lys
        35                  40                  45

Ala Pro Lys Leu Leu Ile Tyr Trp Gly Ser Tyr Leu Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 160
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 160

Ile Asp Asp Ile Gln Met Thr Gln Ser Pro Ser Ser Leu Ser Ala Ser
1               5                   10                  15

Val Gly Asp Arg Val Thr Ile Thr Cys Arg Ser Ser Gln Ser Ile Thr
            20                  25                  30

Phe Asp Tyr Lys Asn Tyr Leu Ala Trp Tyr Gln Gln Lys Pro Gly Lys
        35                  40                  45

Ala Pro Lys Leu Leu Ile Tyr Trp Gly Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

His Tyr Arg Thr Pro Pro Ser Phe Gly Gln Gly Thr Lys Val Glu Ile
            100                 105                 110

Lys

<210> SEQ ID NO 161
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Ser Ser Tyr
            20                  25                  30

Gly Met His Trp Val Arg Gln Pro Pro Gly Lys Gly Leu Glu Trp Val
        35                  40                  45

Ala Val Val Ser Tyr Asp Gly Ser Asn Lys Tyr Tyr Ala Asp Ser Val
    50                  55                  60

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Lys Leu Arg Ser Leu Leu Tyr Phe Glu Trp Leu Ser
            100                 105                 110

Ser Gly Leu Leu Asp Tyr Trp Gly Gln Gly Ala Met Val Thr Val Ser
        115                 120                 125

Ser

<210> SEQ ID NO 162
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Ser Phe Ser Thr Tyr
            20                  25                  30
```

```
Ala Met His Trp Val Arg Gln Pro Pro Gly Lys Gly Leu Glu Trp Val
        35                  40                  45

Ala Val Val Ser Tyr Asp Gly Asn Tyr Lys Tyr Ala Asp Thr Val
 50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Arg Leu Arg Ser Leu Leu Tyr Phe Glu Trp Leu Ser
                100                 105                 110

Gln Gly Tyr Phe Asn Pro Trp Gly Gln Gly Thr Thr Leu Thr Val Ser
            115                 120                 125

Ser
```

<210> SEQ ID NO 163
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 163

```
Glu Val Gln Leu Leu Glu Ser Gly Gly Gly Leu Arg Lys Pro Gly Gln
 1               5                  10                  15

Ser Leu Lys Leu Ser Cys Ala Ala Ser Gly Phe Ser Phe Ser Thr Tyr
                20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Ala Asp Ser Val
 50                  55                  60

Gln Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Arg Leu Arg Ser Leu Leu Tyr Phe Glu Trp Leu Ser
                100                 105                 110

Gln Gly Tyr Phe Asn Pro Trp Gly Gln Gly Thr Thr Leu Thr Val Ser
            115                 120                 125

Ser
```

<210> SEQ ID NO 164
<211> LENGTH: 129
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 164

```
Gln Val Gln Leu Leu Glu Thr Gly Gly Gly Leu Val Lys Pro Gly Gln
 1               5                  10                  15

Ser Leu Lys Leu Ser Cys Ala Ala Ser Gly Phe Thr Phe Thr Ser Tyr
                20                  25                  30

Ala Met His Trp Val Arg Gln Pro Pro Gly Lys Gly Leu Glu Trp Val
        35                  40                  45

Ala Val Val Ser Tyr Asp Gly Asn Tyr Lys Tyr Ala Asp Ser Val
 50                  55                  60
```

Gln Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Arg Leu Arg Ser Leu Leu Tyr Phe Glu Trp Leu Ser
            100                 105                 110

Gln Gly Tyr Phe Asn Pro Trp Gly Gln Gly Thr Thr Val Thr Val Ser
                115                 120                 125

Ser

<210> SEQ ID NO 165
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Trp Asn
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 166
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Trp Asp
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

```
<210> SEQ ID NO 167
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Trp Gln
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 168
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Trp Arg
            20                  25                  30

Tyr Lys Asn Tyr Leu Ala Trp Tyr Gln Gln Lys Pro Gly Lys Ala Pro
        35                  40                  45

Lys Leu Leu Ile Tyr Trp Gly Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 169
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Thr Trp Glu
```

```
                    20                  25                  30

Tyr Lys Asn Tyr Leu Ala Trp Tyr Gln Gln Lys Pro Gly Lys Ala Pro
            35                  40                  45

Lys Leu Leu Ile Tyr Trp Gly Ser Tyr Leu Glu Ser Gly Val Pro Ser
        50                  55                  60

Arg Phe Ser Gly Ser Gly Ser Gly Thr Asp Phe Thr Leu Thr Ile Ser
 65                 70                  75                  80

Ser Leu Gln Pro Glu Asp Phe Ala Thr Tyr Tyr Cys Gln Gln His Tyr
                85                  90                  95

Arg Thr Pro Pro Ser Phe Gly Gln Gly Thr Lys Val Glu Ile Lys
            100                 105                 110

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Val, Leu or Ile
<220> FEATURE:
<221> NAME/KEY: MOD_RES
<222> LOCATION: (4)..(4)
<223> OTHER INFORMATION: Thr or Ser
<220> FEATURE:
<221> NAME/KEY: MOD_RES
<222> LOCATION: (5)..(5)
<223> OTHER INFORMATION: Tyr, Phe or Trp
<220> FEATURE:
<221> NAME/KEY: MOD_RES
<222> LOCATION: (6)..(6)
<223> OTHER INFORMATION: Asn, Ser, Asp, Gln, Arg or Glu

<400> SEQUENCE: 170

Gln Xaa Xaa Xaa Xaa Xaa Tyr Lys Asn Tyr Leu Ala
 1               5                  10

<210> SEQ ID NO 171
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Trp Gly Gln Gly Thr Thr Val Thr Val Ser Ser
 1               5                  10

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gln Ser Ile Thr Phe Glu Tyr Lys Asn Tyr Leu Ala
 1               5                  10
```

<210> SEQ ID NO 173
<211> LENGTH: 329
<212> TYPE: PRT
<213> ORGANISM: Influenza A virus

<400> SEQUENCE: 173

Gln Asp Leu Pro Gly Asn Asp Asn Ser Thr Ala Thr Leu Cys Leu Gly
1               5                   10                  15

His His Ala Val Pro Asn Gly Thr Leu Val Lys Thr Ile Thr Asp Asp
            20                  25                  30

Gln Ile Glu Val Thr Asn Ala Thr Glu Leu Val Gln Ser Ser Ser Thr
        35                  40                  45

Gly Lys Ile Cys Asn Asn Pro His Arg Ile Leu Asp Gly Ile Asp Cys
    50                  55                  60

Thr Leu Ile Asp Ala Leu Leu Gly Asp Pro His Cys Asp Val Phe Gln
65                  70                  75                  80

Asn Glu Thr Trp Asp Leu Phe Val Glu Arg Ser Lys Ala Phe Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Ile Thr Glu Gly Phe Thr Trp Thr
        115                 120                 125

Gly Val Thr Gln Asn Gly Gly Ser Asn Ala Cys Lys Arg Gly Pro Gly
    130                 135                 140

Ser Gly Phe Phe Ser Arg Leu Asn Trp Leu Thr Lys Ser Gly Ser Thr
145                 150                 155                 160

Tyr Pro Val Leu Asn Val Thr Met Pro Asn Asn Asp Asn Phe Asp Lys
                165                 170                 175

Leu Tyr Ile Trp Gly Ile His His Pro Ser Thr Asn Gln Glu Gln Thr
            180                 185                 190

Ser Leu Tyr Val Gln Ala Ser Gly Arg Val Thr Val Ser Thr Arg Arg
        195                 200                 205

Ser Gln Gln Thr Ile Ile Pro Asn Ile Gly Ser Arg Pro Trp Val Arg
    210                 215                 220

Gly Leu Ser Ser Arg Ile Ser Ile Tyr Trp Thr Ile Val Lys Pro Gly
225                 230                 235                 240

Asp Val Leu Val Ile Asn Ser Asn Gly Asn Leu Ile Ala Pro Arg Gly
                245                 250                 255

Tyr Phe Lys Met Arg Thr Gly Lys Ser Ser Ile Met Arg Ser Asp Ala
            260                 265                 270

Pro Ile Asp Thr Cys Ile Ser Glu Cys Ile Thr Pro Asn Gly Ser Ile
        275                 280                 285

Pro Asn Asp Lys Pro Phe Gln Asn Val Asn Lys Ile Thr Tyr Gly Ala
    290                 295                 300

Cys Pro Lys Tyr Val Lys Gln Asn Thr Leu Lys Leu Ala Thr Gly Met
305                 310                 315                 320

Arg Asn Val Pro Glu Lys Gln Thr Arg
                325

<210> SEQ ID NO 174
<211> LENGTH: 175
<212> TYPE: PRT
<213> ORGANISM: Influenza A virus

<400> SEQUENCE: 174

```
Gly Leu Phe Gly Ala Ile Ala Gly Phe Ile Glu Asn Gly Trp Glu Gly
1               5                   10                  15

Met Ile Asp Gly Trp Tyr Gly Phe Arg His Gln Asn Ser Glu Gly Thr
            20                  25                  30

Gly Gln Ala Ala Asp Leu Lys Ser Thr Gln Ala Ala Ile Asp Gln Ile
        35                  40                  45

Asn Gly Lys Leu Asn Arg Val Ile Glu Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asn Lys Leu Phe Glu Lys Thr Arg Arg Gln Leu Arg Glu
        115                 120                 125

Asn Ala Glu Glu Met Gly Asn Gly Cys Phe Lys Ile Tyr His Lys Cys
    130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly
                165                 170                 175
```

<210> SEQ ID NO 175
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

```
Gln Val Gln Leu Val Gln Ser Gly Gly Gly Val Val Gln Pro Gly Arg
1               5                   10                  15

Ser Leu Arg Leu Ser Cys Val Ala Ser Gly Phe Thr Phe Ser Thr Tyr
            20                  25                  30

Ala Met His Trp Val Arg Gln Ala Pro Gly Arg Gly Leu Glu Trp Val
        35                  40                  45

Ala Val Ile Ser Tyr Asp Gly Asn Tyr Lys Tyr Tyr Ala Asp Ser Val
    50                  55                  60

Lys Gly Arg Phe Ser Ile Ser Arg Asp Asn Ser Asn Thr Leu His
65                  70                  75                  80

Leu Glu Met Asn Thr Leu Arg Thr Glu Asp Thr Ala Leu Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Pro Trp Gly Gln Gly Thr Leu Val Thr Val Thr
        115                 120                 125

Ser
```

<210> SEQ ID NO 176
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gln Val Gln Leu Val Gln Ser Gly Gly Val Val Pro Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Tyr Lys Tyr Ala Asp Ser Val
    50                  55                  60

Arg Gly Arg Phe Thr Ile Ser Arg Asp Asn Ser Lys Asn Thr Leu Asn
65                  70                  75                  80

Leu Asp Met Asn Ser Leu Arg Thr Glu Asp Thr Ala Leu Tyr Tyr Cys
                85                  90                  95

Ala Lys Asp Ser Gln Leu Arg Ser Leu Leu Tyr Phe Asp Trp Leu Ser
            100                 105                 110

Gln Gly Tyr Phe Asp His Trp Gly Gln Gly Thr Leu Val Thr Val Ser
        115                 120                 125

Ser

<210> SEQ ID NO 177
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Asp Trp Leu Ser
            100                 105                 110

Gln Gly Tyr Phe Asp Tyr Trp Gly Gln Gly Thr Leu Val Thr Val Ser
        115                 120                 125

Ser

<210> SEQ ID NO 178
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gln Val Gln Leu Val Glu Ser Gly Gly Gly Val Val Gln Pro Gly Arg
1               5                   10                  15

```
Ser Leu Arg Leu Ser Cys Ala Ala Ser Gly Phe Thr Phe Ser Thr Tyr
            20                  25                  30

Ala Met His Trp Val Arg Gln Ala Pro Gly Lys Gly Leu Glu Trp Val
        35                  40                  45

Ala Val Ile Ser Tyr Asp Ala Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ser Gln Leu Arg Ser Leu Leu Tyr Phe Glu Trp Leu Ser
            100                 105                 110

Gln Gly Tyr Phe Asp Tyr Trp Gly Gln Gly Thr Leu Val Thr Val Ser
        115                 120                 125

Ser
```

```
<210> SEQ ID NO 179
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Ser Tyr Asp Gly Asn Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Thr Glu Asp Thr Ala Leu Tyr Tyr Cys
                85                  90                  95

Ala Lys Asp Ser Gln Leu Arg Ser Leu Leu Tyr Phe Asp Trp Leu Ser
            100                 105                 110

Gln Gly Tyr Phe Asp His Trp Gly Gln Gly Thr Leu Val Thr Val Ser
        115                 120                 125

Ser
```

```
<210> SEQ ID NO 180
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Asp Ile Gln Met Thr Ser Gln Pro Asp Ser Leu Ala Val Ser Leu Gly
1               5                   10                  15

Ala Arg Ala Thr Ile Asn Cys Lys Ser Ser Gln Ser Val Thr Phe Asn
            20                  25                  30

Tyr Lys Asn Tyr Leu Ala Trp Tyr Gln Gln Lys Pro Gly Gln Pro Pro
        35                  40                  45
```

```
Lys Val Leu Ile Tyr Trp Ala Ser Ala Arg Glu Ser Gly Val Pro Asp
             50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln His Tyr
                 85                  90                  95

Arg Thr Pro Pro Thr Phe Gly Gln Gly Thr Lys Val Glu Ile Lys
                100                 105                 110

<210> SEQ ID NO 181
<211> LENGTH: 329
<212> TYPE: PRT
<213> ORGANISM: Influenza A virus

<400> SEQUENCE: 181

Thr Asn Ala Asp Thr Ile Cys Ile Gly Tyr His Ala Asn Asn Ser Thr
  1               5                  10                  15

Asp Thr Val Asp Thr Val Leu Glu Lys Asn Val Thr Val Thr His Ser
                 20                  25                  30

Val Asn Leu Leu Glu Asp Ser His Asn Gly Lys Leu Cys Lys Leu Lys
             35                  40                  45

Gly Ile Ala Pro Leu Gln Leu Gly Lys Cys Asn Ile Ala Gly Trp Leu
 50                  55                  60

Leu Gly Asn Pro Glu Cys Asp Leu Leu Leu Thr Ala Ser Ser Trp Ser
 65                  70                  75                  80

Tyr Ile Val Glu Thr Ser Asn Ser Glu Asn Gly Thr Cys Tyr Pro Gly
                 85                  90                  95

Asp Phe Ile Asp Tyr Glu Glu Leu Arg Glu Gln Leu Ser Ser Val Ser
                100                 105                 110

Ser Phe Glu Lys Phe Glu Ile Phe Pro Lys Thr Ser Ser Trp Pro Asn
            115                 120                 125

His Glu Thr Thr Lys Gly Val Thr Ala Ala Cys Ser Tyr Ala Gly Ala
    130                 135                 140

Ser Ser Phe Tyr Arg Asn Leu Leu Trp Leu Thr Lys Lys Gly Ser Ser
145                 150                 155                 160

Tyr Pro Lys Leu Ser Lys Ser Tyr Val Asn Asn Lys Gly Lys Glu Val
                165                 170                 175

Leu Val Leu Trp Gly Val His His Pro Pro Thr Gly Thr Asp Gln Gln
            180                 185                 190

Ser Leu Tyr Gln Asn Ala Asp Ala Tyr Val Ser Val Gly Ser Ser Lys
            195                 200                 205

Tyr Asn Arg Arg Phe Thr Pro Glu Ile Ala Ala Arg Pro Lys Val Arg
    210                 215                 220

Asp Gln Ala Gly Arg Met Asn Tyr Tyr Trp Thr Leu Leu Glu Pro Gly
225                 230                 235                 240

Asp Thr Ile Thr Phe Glu Ala Thr Gly Asn Leu Ile Ala Pro Trp Tyr
                245                 250                 255

Ala Phe Ala Leu Asn Arg Gly Ser Gly Ser Gly Ile Ile Thr Ser Asp
            260                 265                 270

Ala Pro Val His Asp Cys Asn Thr Lys Cys Gln Thr Pro His Gly Ala
            275                 280                 285

Ile Asn Ser Ser Leu Pro Phe Gln Asn Ile His Pro Val Thr Ile Gly
    290                 295                 300

Glu Cys Pro Lys Tyr Val Arg Ser Thr Lys Leu Arg Met Ala Thr Gly
```

Leu Arg Asn Ile Pro Ser Ile Gln Ser
                325

<210> SEQ ID NO 182
<211> LENGTH: 222
<212> TYPE: PRT
<213> ORGANISM: Influenza A virus

<400> SEQUENCE: 182

Gly Leu Phe Gly Ala Ile Ala Gly Phe Ile Glu Gly Gly Trp Thr Gly
1               5                   10                  15

Met Ile Asp Gly Trp Tyr Gly Tyr His His Gln Asn Glu Gln Gly Ser
            20                  25                  30

Gly Tyr Ala Ala Asp Gln Lys Ser Thr Gln Asn Ala Ile Asp Gly Ile
        35                  40                  45

Thr Asn Lys Val Asn Ser Val Ile Glu Lys Met Asn Thr Gln Phe Thr
    50                  55                  60

Ala Val Gly Lys Glu Phe Asn Asn Leu Glu Arg Arg Ile Glu Asn Leu
65                  70                  75                  80

Asn Lys Lys Val Asp Asp Gly Phe Leu Asp Ile Trp Thr Tyr Asn Ala
                85                  90                  95

Glu Leu Leu Val Leu Leu Glu Asn Glu Arg Thr Leu Asp Phe His Asp
            100                 105                 110

Ser Asn Val Arg Asn Leu Tyr Glu Lys Val Lys Ser Gln Leu Lys Asn
        115                 120                 125

Asn Ala Lys Glu Ile Gly Asn Gly Cys Phe Glu Phe Tyr His Lys Cys
    130                 135                 140

Asp Asp Ala Cys Met Glu Ser Val Arg Asn Gly Thr Tyr Asp Tyr Pro
145                 150                 155                 160

Lys Tyr Ser Glu Glu Ser Lys Leu Asn Arg Glu Glu Ile Asp Gly Val
                165                 170                 175

Lys Leu Glu Ser Met Gly Val Tyr Gln Ile Leu Ala Ile Tyr Ser Thr
            180                 185                 190

Val Ala Ser Ser Leu Val Leu Leu Val Ser Leu Gly Ala Ile Ser Phe
        195                 200                 205

Trp Met Cys Ser Asn Gly Ser Leu Gln Cys Arg Ile Cys Ile
    210                 215                 220

<210> SEQ ID NO 183
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Glu Val Gln Leu Leu Glu Ser Gly Gly Gly Leu Val Lys Pro Gly Gln
1               5                   10                  15

Ser Leu Lys Leu Ser Cys Ala Ala Ser Gly Phe Thr Phe Thr
            20                  25                  30

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic

```
          peptide
<220> FEATURE:
<221> NAME/KEY: MOD_RES
<222> LOCATION: (5)..(6)
<223> OTHER INFORMATION: Ser or Thr
<220> FEATURE:
<221> NAME/KEY: MOD_RES
<222> LOCATION: (8)..(8)
<223> OTHER INFORMATION: Ala or Gly

<400> SEQUENCE: 184

Gly Phe Thr Phe Xaa Xaa Tyr Xaa Met His
1               5                   10

<210> SEQ ID NO 185
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Val, Leu or Ile
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (8)..(8)
<223> OTHER INFORMATION: Tyr, Phe or Trp
<220> FEATURE:
<221> NAME/KEY: MOD_RES
<222> LOCATION: (9)..(9)
<223> OTHER INFORMATION: Asn, Ser or Asp

<400> SEQUENCE: 185

Xaa Ser Ser Gln Xaa Xaa Xaa Xaa Xaa Tyr Lys Asn Tyr Leu Ala
1               5                   10                  15

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (5)..(5)
<223> OTHER INFORMATION: Ser or Thr
<220> FEATURE:
<221> NAME/KEY: MOD_RES
<222> LOCATION: (6)..(6)
<223> OTHER INFORMATION: Val, Leu or Ile
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
```

```
<222> LOCATION: (8)..(8)
<223> OTHER INFORMATION: Tyr, Phe or Trp
<220> FEATURE:
<221> NAME/KEY: MOD_RES
<222> LOCATION: (9)..(9)
<223> OTHER INFORMATION: Asn, Ser, Asp, Gln, Arg or Glu

<400> SEQUENCE: 186

Xaa Ser Ser Gln Xaa Xaa Xaa Xaa Xaa Tyr Lys Asn Tyr Leu Ala
1               5                   10                  15

<210> SEQ ID NO 187
<211> LENGTH: 653
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 187
gaaattgtaa tgacgcagag ccctgatagc cttgccgtgt ccctgggtga gagggcgaca      60
atcaattgta agtcatcaca gtcggtcacg tacaactaca gaactacct ggcgtggtat      120 caacagaaac ccgggcagcc gcccaaattg ctcatctatt gggcttcgac acgggagtcg      180
ggtgtgccag accgcttctc cgggtcagga tcgggaactg acttcacgtt gactatttcg      240
tccctccagg cagaagatgt agccgtctac tattgccaac agtattacag aacgccgcct      300
acatttggag gcgggaccaa acttgacatc aagggatccg tggccgcccc cagcgtcttc      360
atcttcccgc ccagcgacga gcagctgaag tcgggcacgg ccagcgtggt gtgcctcctg      420
aacaacttct accccgcga ggcgaaggtc cagtggaagg tggacaacgc cctgcagagc      480
gggaacagcc aggagagcgt gaccgagcag gactcgaagg acagcaccta cagcctcagc      540
agcaccctga cgctgagcaa ggccgactac gagaagcaca aggtctacgc ctgcgaggtg      600
acccaccagg ggctctcgag ccccgtgacc aagagcttca ccggggcga gtg             653

<210> SEQ ID NO 188
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Thr Tyr Asn
                20                  25                  30

Tyr Lys Asn Tyr Leu Ala Trp Tyr Gln Gln Lys Pro Gly Gln Pro Pro
            35                  40                  45

Lys Leu Leu Ile Tyr Trp Ala Ser Thr Arg Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Tyr Tyr
                85                  90                  95

Arg Thr Pro Pro Thr Phe Gly Gly Gly Thr Lys Leu Asp Ile Lys Gly
            100                 105                 110

Ser Val Ala Ala Pro Ser Val Phe Ile Phe Pro Pro Ser Asp Glu Gln
        115                 120                 125
```

```
Leu Lys Ser Gly Thr Ala Ser Val Val Cys Leu Leu Asn Asn Phe Tyr
    130             135             140

Pro Arg Glu Ala Lys Val Gln Trp Lys Val Asp Asn Ala Leu Gln Ser
145             150             155             160

Gly Asn Ser Gln Glu Ser Val Thr Glu Gln Asp Ser Lys Asp Ser Thr
            165             170             175

Tyr Ser Leu Ser Ser Thr Leu Thr Leu Ser Lys Ala Asp Tyr Glu Lys
        180             185             190

His Lys Val Tyr Ala Cys Glu Val Thr His Gln Gly Leu Ser Ser Pro
    195             200             205

Val Thr Lys Ser Phe Asn Arg Gly Glu
    210             215
```